(12) United States Patent
Kolb et al.

(10) Patent No.: US 8,318,132 B2
(45) Date of Patent: *Nov. 27, 2012

(54) IMAGING AGENTS FOR DETECTING NEUROLOGICAL DYSFUNCTION

(75) Inventors: Hartmuth C. Kolb, Playa Del Rey, CA (US); Joseph C. Walsh, Pacific Palisades, CA (US); Wei Zhang, Los Angeles, CA (US); Peter J. H. Scott, Marina-del-Rey, CA (US); Kai Chen, Los Angeles, CA (US); Vani P. Mocharla, Los Angeles, CA (US); Dhanalakshmi Kasi, Los Angeles, CA (US); Gang Chen, Los Angeles, CA (US); Eric Wang, San Diego, CA (US); Anjana Sinha, San Diego, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 91 days.

This patent is subject to a terminal disclaimer.

(21) Appl. No.: 12/372,717

(22) Filed: Feb. 17, 2009

(65) Prior Publication Data

US 2011/0091382 A1    Apr. 21, 2011

Related U.S. Application Data

(60) Provisional application No. 61/066,101, filed on Feb. 14, 2008.

(51) Int. Cl.
*A61K 51/00* (2006.01)
*A61M 36/14* (2006.01)
(52) U.S. Cl. ............... 424/1.11; 424/1.89; 424/1.85; 424/1.81; 424/1.65; 424/9.1
(58) Field of Classification Search .............. 424/1.11
See application file for complete search history.

(56) References Cited

U.S. PATENT DOCUMENTS

| | | | |
|---|---|---|---|
| 5,871,934 | A | 2/1999 | Lee et al. |
| 2003/0149250 | A1 | 8/2003 | Kung et al. |
| 2006/0110787 | A1 | 5/2006 | Walker |
| 2007/0060618 | A1 | 3/2007 | Cosford et al. |
| 2007/0258887 | A1 | 11/2007 | Tamagnan et al. |

FOREIGN PATENT DOCUMENTS

| | | |
|---|---|---|
| EP | 1655287 | 5/2006 |
| EP | 1 815 872 A | 8/2007 |
| EP | 1944281 | 7/2008 |
| EP | 2218464 | 8/2010 |
| JP | 9165378 A | 6/1997 |
| JP | 2001048786 | 2/2001 |
| JP | 2006100537 | 4/2006 |
| JP | 2007223952 A | 9/2007 |
| WO | WO 94/14477 A | 7/1994 |
| WO | WO 97/14679 A | 4/1997 |
| WO | 02085903 A2 | 10/2002 |
| WO | WO 2004/043496 A | 5/2004 |
| WO | 2004056399 A2 | 7/2004 |
| WO | WO 2007/014467 | 2/2007 |
| WO | WO 2007/057705 A | 5/2007 |
| WO | 2007063946 A1 | 6/2007 |
| WO | WO 2007/094718 A | 8/2007 |
| WO | 2008073350 A2 | 6/2008 |
| WO | WO 2008/083454 A | 7/2008 |
| WO | 2008124812 A1 | 10/2008 |
| WO | WO 2008/131148 A | 10/2008 |
| WO | WO 2008/132454 A | 11/2008 |
| WO | 2009004914 A1 | 1/2009 |
| WO | 2009045535 A2 | 4/2009 |
| WO | 2009055401 | 4/2009 |
| WO | 2010011964 | 1/2010 |
| WO | 2010/073719 | 7/2010 |

OTHER PUBLICATIONS

Gao et al. J. Med. Chem. 2007, 50, 3814-3824.*
Bergstrom, Mats et al.: "Synthesis of some 11C-labeled MAO-A inhibitors and their in vivo uptake kinetics in rhesus monkey brain", Nuclear Medicine and Biology, 24(5), 381-388 Coden: Nimbieo; ISSN: 0883-2897, 1997.
Sintas, Jose A. et al.: "Iodination, radioiodination and spectroscopic identification of beta.-carboline derivatives", Journal of Labelled Compounds & Radiopharmaceuticals, 42(5), 409-413 Coden: JLCRD4; ISSN: 0362-4803, 1999.
Karimi, Farhad et al.: "Synthesis of 11c-labelled amides by palladium-mediated carboxamination using [11C]carbon monoxide, in situ activated amines and 1,2,2,6,6-pentamethylpiperidine", European Journal of Organic Chemistry, (11), 2132-2137 Coden: Ejocfk; ISSN: 1434-193X, 2003
Baranowska-Kortylewicz J et al.: "Radioiodination of 7-Methoxy- and 6,7-Dimethoxy-4-Bromomethylcoumarins", Journal of Labelled Compounds and Radiopharmaceuticals, John Wiley, Chichester, DB, vol. 29, No. 12, Jan. 1, 1991, pp. 1301-1307, ISSN: 0362-4803.
Heike Radeke et al.: "Synthesis and biological evaluation of the mitochondrial complex 1 inhibitor 2-[4-(4-fluorobutyl) benzylsulfanyl]-3-meth ylchromene-4-one as a potential cardiac positron emission tomography tracer", J. Med. Chem., vol. 50, 2007, pp. 4304-4315.
Maria Graciela Barolli et al.: "Synthesis of [131I]-iodinated quercetin", J. Label. Compds. Radiopharm., vol. 32, No. 11, 1997, pp. 297-933.
Hollie I. Swanson et al.: "Use of [125I]4'-iodoflavone as a tool to characterize ligand-dependent differences in Ah receptor behavior", J. Biochem. Molecular Toxicology, vol. 16, No. 6, 2002, pp. 298-310.

(Continued)

*Primary Examiner* — Michael G Hartley
*Assistant Examiner* — Sean R Donohue
(74) *Attorney, Agent, or Firm* — Joshua Ryan

(57) ABSTRACT

Disclosed here in are compounds and methods of diagnosing Alzheimer's Disease or a predisposition thereto in a mammal, the method comprising administering to the mammal a diagnostically effective amount of a radiolabeled compound, wherein the compound is selected from the group consisting of radiolabeled flavones, coumarins, carbazoles, quinolinones, chromenones, imidazoles and triazoles derivatives, allowing the compound to distribute into the brain tissue, and imaging the brain tissue, wherein an increase in binding of the compound to the brain tissue compared to a normal control level of binding indicates that the mammal is suffering from or is at risk of developing Alzheimer's Disease.

9 Claims, 26 Drawing Sheets

OTHER PUBLICATIONS

Takahashi K et al.: "Imaging of aromatase distribution in rat and rhesus monkey brains with [<11>C]vorozole" Nuclear Medicine and Biology, Elsevier, NY, US, vol. 33, No. 5, Jul. 1, 2006, pp. 599-605, XP025103506 ISSN: 0969-8051.

Wenchao Qu et al.: "Quick Assembly of 2,24-diphenyltriazoles as probes targeting beta-amyloid aggregates in alzheimer's disease", J. Med. Chem., vol. 50, 2007, pp. 3380-3387.

Glaser M et al.: "Click Labeling with 2-[18F]Fluoroethylazide for Positron Emission Tomography" Bioconjugate Chemistry, ACS, Washington, DC, US, vol. 18, Apr. 13, 2007, pp. 989-993, ISSN: 1043-1802.

Sirion et al.: "An efficient F-18 labeling method for PET study: Huisgen 1,3-dipolar cycloaddition of bioactive substances and F-18-labeled compounds" Tetrahenron Letters, Elsevier, Amsterdam, vol. 48, No. 23, Jun. 4, 2007, pp. 3953-3957, ISSN: 0040-4039.

Mathias C. J. et al.: "Radiolebeled hypoxic cell sensitizers: Tracers for assessment of ischemia" Life Sciences, Pergamon Press, Oxford, GB, vol. 41, No. 2, Jul. 13, 1987, pp. 199-206, ISSN: 0024-3205.

Jerabek P.A. et al.: "Synthesis and biodistrubtion of <18>F-labeled fluoronitroimidazoles: Potential in vivo markers of hypoxic tissue", Applied Radiation and Isotopes, International Journal of Radiation Applications and Instrumentation, Part A, Pergamon Press, Ltd., GB, vol. 37, No. 7, Jan. 1, 1986, pp. 599-605, ISSN: 0883-2889.

Visser G.W. M. et al.: "THe preparation and stability of <211>At-astato-imidazoles" International Journal of Applied Radiation and Isotops, Pergamon Press, New York, NY, US, vol. 31, No. 5, May 1, 1980, pp. 275-278, ISSN: 0020-708X.

Miriko Tanaka et al.: "Radiosynthesis and evaluation of 11C-labeled diaryl-substituted imidazole and indole derivatives for mapping cyclooxygenase-2" Biological & Pharmaceutical Bulletin (of Japan)., vol. 29, No. 10, 2006, pp. 2087-2094, Pharmaceutical Society of Japan, Tokyo.

Gareth Getvoldsen et al.: Microwave-assisted cyclocondensation of 1,2-diaminobenzene with [4-18F]fluorobenzoic acid: microwave synthesis of 2-([4-18F]fluorophenyl) benzimidazole, Journal of Labelled Compounds and Radiopharmaceuticals, research article, J. Label Compd Radiopharm 2004; 47: 139-145.

Piotr Garnuszek et al.: "Synthesis and characterisation of platinum(II) complexes with histamine and iodohistamine", Inorganica Chimica Acta, vol. 338 (2002) 119-126.

Fumihiko Yamamoto et al.: "Synthesis and Evaluation of 4-Bromo-1-(3-[18F]fluoropropyl)-2-nitroimidazole with a Low Entergy LUMO Orbital Designed as Brain Hypoxia-Targeting Imaging Agent", Biol.Pharm. Bull. 25(5) 616-621 (2002), vol. 25, No. 5.

Fumihiko Yamamoto et al.: "Synthesis and Characterization of Lipohilic 1-[18F]Fluoralkyl-2Initroimidazoles for Imaging Hypoxia", Biol. Pharm. Bull. 22(6) 590-597 (1999), vol. 22, No. 6.

International Search Report of Application No. PCT/US2009/000961 dated Jul. 10, 2009.

Blom, Elisabeth et al.: "Synthesis and in vitro evaluation of 18F-.beta.-carboline alkaloids as PET ligands" Journal of Labelled Compounds and Radiopharmaceuticlas, 51(6), 277-282 Coden: JLCRD4, May 2008.

Dumont F. et al.: "Synthesis and In Vivo Evaluation of 7-chloro-5-[<123>I]iodo-4-oxo-1,4 dihydroquinoline-2-carboxylic Acid" Applied Radiation and Isotopes, Elsevier, Oxford, GB, vol. 48, No. 9, Sep. 1, 1997, pp. 1173-1177.

Livni E. et al.: "Synthesis and biodistribution of <18>F-labeled Fleroxacin" Nuclear Medicine and Biology, Elsevier, NY, US, vol. 20, No. 1, Jan. 1, 1993, pp. 81-87.

Zijlstra S et al.: "Synthesis and evaluation of fluorine-18 labelled compounds for imaging of bacterial infections with pet" Applied Radiation and Isotopes, Elsevier, Oxford, GB, vol. 64, No. 7, Jul. 1, 2006, pp. 802-807.

Chemical Abstracts Service, Columbus, Ohio, US: Choi, Osaku Wataru et al.: "Preparatoin of F-18 labeling benzyl N-containing heterocyclyl compounds as PET diagnostic remedies", Database accession No. 127:65770 abstract & JP 09 165378 A, Jun. 24, 1997.

Nordberg, A., "PET imaging of amyloid in Alzheimer's disease", Lancet Neurology, Lancet Publ. Group, London, GB, vol. 3, No. 9, Sep. 1, 2004, pp. 519-527.

Okamura, et al., "Quinoline and Benzimidazole Derivatives: Candidate Probes for In Vivo Imaging of Tau Pathology in Alzheimer's Disease.", Journal of Neuroscience, Nov. 23, 2005, 25(47):10857-10862.

Zheng, et al., "Biological Characters of [18F]0-FEt-PIB In a Rat Model of Alzheimer's Disease Using Micro-PET Imaging", Published in Acta Pharmacologica Sinica, vol. 29, No. 5, May 1, 2008 (pp. 548-554).

Wang, et al., "PET Imaging and Optical Imaging With D-Luciferin [<11>C]methyl Ester and D-Luciferin [11C]methyl Ether of Luciferase Gene Expression in Tumor Xenografts of Living Mice", Published in Bioorganic & Medicinal Chemistry Letters, vol. 16, No. 2, Jan. 15, 2006 (pp. 331-337).

Solbach, et al., "Efficient Radiosynthesis of Carbon-11 Labelled Uncharged Thioflavin T Derivatives Using [11C] methyl Triflate for Beta-Amyloid Imaging in Alzheimer's Disease With PET", Published in Applied Radiation and Isotopes, vol. 62, No. 4, Apr. 1, 2005 (pp. 591-595).

Mathis, et al., "Synthesis and Evaluation of 11C-Labeled 6-Substituted 2-Arylbenzothiazoles As Amyloid Imaging Agents", Published in Journal of Medicinal Chemistry, American Chemical Society, vol. 46, Jun. 19, 2003 (pp. 2740-2754).

Serdons, et al., "Synthesis and Evaluation of 18F-Labeled 2-Phenylbenzothiazoles As Positron Emission Tomography Imaging Agents for Amyloid Plaques in Alzheimer's Disease", Published in Journal of Medicinal Chemistry, American Cancer Society, vol. 52, Feb. 13, 2009 (pp. 1428-1437).

Johnson, et al., "AZD2184: A Radioligand for Sensitive Detection of Beta-Amyloid Deposits", Published in Journal of Neurochemistry, vol. 108, Mar. 1, 2009 (pp. 1177-1186).

Seneca, et al., "Brain and Whole-Body Imaging in Nonhuman Primates With [11C]MeS-IMPY, a Candidate Radioligand for Beta-Amyloid Plaques", Published in Nuclear Medicine and Biology, vol. 34, Aug. 6, 2007 (pp. 681-689).

Vasdev, et al., "Synthesis and Ex Vivo Evaluation of Carbon-11 Labelled N-(4-methoxybenzyl)-N'-(5-nitro-1,3-thiazol-2-yl)urea([11C]AR-A014418): A Radiolabelled Glycogen Synthase Kinase-3beta Specific Inhibitor for PET Studies", Published in Bioorganic & Medicinal Chemistry Letters, vol. 15, No. 23, Dec. 1, 2005 (pp. 5270-5273).

Aoyama, et al., "Polymethylated .gamma.-carbolines with potent anti-bovine viral diarrhea virus (BVDV) activity", Heterocycles (2009), 77(2), 779-785.

Sako, et al., "Gamma-carboline derivatives with anti-bovine viral diarrhea virus (BVDV) activity", Bioorg Med Chem Apr. 1, 2008, 16(7), 3780-3790.

Chen, et al., "Microwave-enhanced Fischer reaction: an efficient one-pot synthesis of y-carbolines", Synlett (2008), (1), 77-82.

Engler, et al., "Lewis Acid-Directed Cyclocondensation of Piperidone Enol Ethers with 2-Methoxy-4-(N-phenylsulfonyl)-1,4-benzoquinoneimine: A New Regioselective Synthesis of Oxygenated Carbolines", Journal of Organic Chemistry (2000), 65(8), 2444-2457.

Mehta, et al., "The elimination of an alkoxy group in the photo-Graebe-Ullmann conversion of 1-(2,5-dialkoxyphenyl) triazolopyridines into carbolines, and the preparation of $\alpha$-, $\gamma$- and $\sigma$-carboline quinones", J. Chem. Soc., Perkin Trans. 1, 1993, 1261-1267.

Parrick, et al., "Some carbazole and carboline quinones and an unexpected demethoxylation reaction", Journal of Chemical Research, Synopses (1990), 1.

Molina, et al., "Novel DNA Intercalators Based on the Pyridazino [1',6':1,2] pyrido [4,3-b] indol-5-inium System", J. Org. Chem, 1999, 64, 3907-3915.

Molina, et al., "Synthesis and DNA Binding Properties of y-Carbolinium Derivatives and Benzologues", J. Org. Chem, 1996, 61, 5587-5599.

PCT/US2010/028360 Search Report issued Nov. 22, 2010.

Kruglenko, et al.; "Condensed Imidazo-1,2,4-azines. 31. Synthesis and Chemical Transformations of Substituted 1,2,4-Triazepino[2,3-a]benzimidaloses"; Chemistry of Heterocyclic Compounds, vol. 38, No. 5, 2002—pp. 598-606.

Tseng, et al., "A Simple Regioselective Synthesis of Pyrimido[1,2-a]benzimidazoles"; vol. 24, May 1, 1987; Jun. 1, 1987, pp. 837-843.

Yousefi, et al., "Synthesis and Evaluation of 11C-Labeled Imidazo [2,1-b] benzothiazoles (IBTs) as PET Tracers for Imaging β-Amyloid Plaques in Alzheimer's Disease", J. Med. Chem., Article ASAP, DOI: 10.1021/jm101129a Publication Date (Web): Jan. 28, 2011.

Qu, et al., Radioiodinated Aza-Diphenylacetylenes As Potential SPECT Imaging Agents for Beta-Amyloid Plaque Detection, Published in Bioorganic & Medicinal Chemistry Letters, vol. 17, No. 13, Jul. 1, 2007 (pp. 3581-3584). Science Direct, Elsevier.

Invitation to Pay Additional Fees in PCT/US2010/028360, Date: Mar. 23, 2010.

* cited by examiner

Figure 4

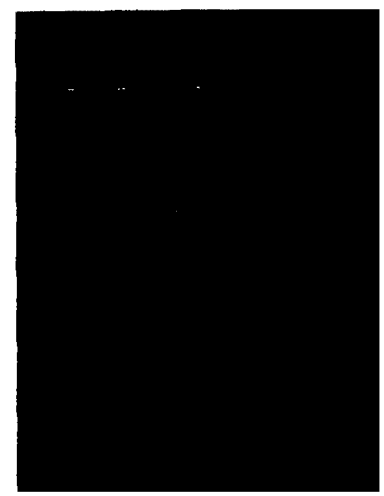
Figure 5

Figure 10
Healthy Control
[18F]-CB003 Stain
29072 (1x)
Alzheimer's Patient
[18F]-CB003 Stain
0801 (1x)
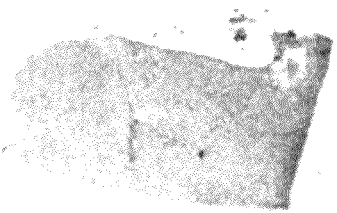
[18F]-CB003 100 µCi/slide
Incubation 30 min
PBS 5 min
30% EtOH/PBS 2 min
40% EtOH/PBS 2 min
20% EtOH/PBS 2 min
PBS 5 min
AD Patient 0801
80 year old male
5 µm slice thickness
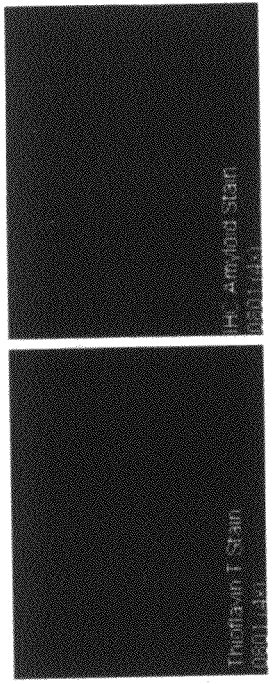
Healthy Patient 29072
77 year old female
5 µm slice thickness
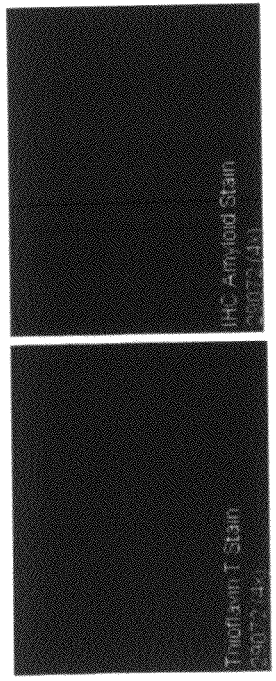

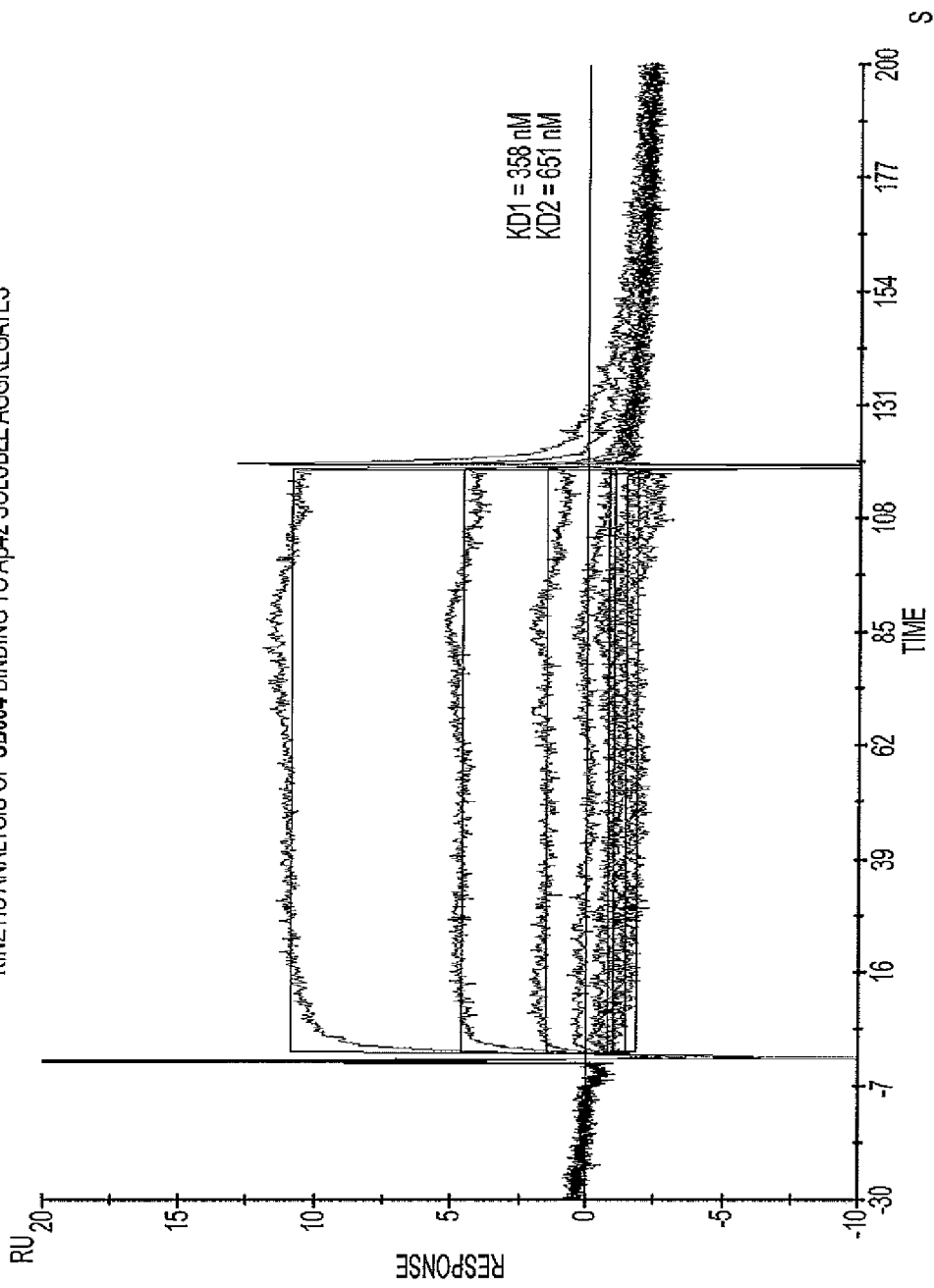

IMAGING AGENTS FOR DETECTING NEUROLOGICAL DYSFUNCTION

RELATED APPLICATIONS

The present application is based on and claims the priority of U.S. provisional application No. 60/066,101, filed Feb. 14, 2008, which is incorporated herein by reference.

Alzheimer's disease (AD), a leading cause of dementia, develops in one percent of the population between the ages 65 and 69, and increasing to 40-50% in those 95 years and older. AD patients exhibit telltale clinical symptoms that include cognitive impairment and deficits in memory function. In these patients, heavy senile plaque burden found in the cerebral cortex, verified by post mortem histopathological examination, confirms the presence of AD. The mature senile plaques consist of intracellular neurofibrillary tangles (NFT) derived from filaments of hyperphosphorylated tau proteins, and extracellular β-amyloid peptides derived from enzymatic processing of amyloid precursor protein. Interestingly, despite the development and presence of senile plaques in elderly persons with normal cognitive function, the severity of NFT and senile plaque deposition purportedly correlates with a loss of cognitive function and neuronal circuitry deterioration.

Despite Alzheimer's disease being the fourth leading cause of death in the United States, pharmaceutical intervention has yet to commercialize a curative therapy. Instead, clinicians currently prescribe cholinesterase inhibitors to cognitively impaired patients. Rivastigmine, a therapeutic treatment for both AD and Parkinson disease patients, inhibits both acetylcholinesterase and butyrylcholinesterase, preventing the breakdown of acetyl- and butyrylcholine. Galantamine, a naturally derived acetylcholinesterase inhibitor, increases nicotinic cholinergic receptors to release acetylcholine into the brain. As a final example, the acetylcholinesterase inhibitor Aricept slows progression of AD in patients by inhibiting acetylcholinesterase and thus increasing cortical acetylcholine. In a recent clinical trial, Aricept's effectiveness slowed AD progression in patients but the therapeutic effects disappeared after 36 months. The effect of treating AD patients with a therapeutic combination of both Aricept and memantine caused an increased cognitive function in those AD patients relative to those who just received only Aricept. Despite the usefulness of cholinesterase inhibitors, the current array of AD therapeutics can only delay full-onset AD by approximately two to three years, after which they are therapeutically ineffective in inhibiting cognitive decline. It has been reported that delaying AD onset by five years is sufficient to reduce the number of AD cases in half and, given the current shortcomings of cholinesterase inhibitors, further research efforts are required to meet that goal.

Neurological imaging of AD has seen the emergence of imaging tracers that appear to confirm the presence of AD based on plaque and fibril mediated tracer uptake and, subsequently, are currently undergoing extensive clinical examination. Many of these tracers contain chemotypes that derive from fluorescent dyes (Table 1). For example, increased uptake and binding of the napthylaniline derivative $^{18}$F-FDDNP in living brains correlates well with the presence of AD when compared to cognitively functional normals of similar age. [Liu, J., et al., *High-Yield, Automated Radiosynthesis of 2-(1-{6-[(2-[$^{18}$F]Fluoroethyl)(methyl)amino]-2-naphthyl}ethylidene)malonitrile ([$^{18}$F]FDDNP) Ready for Animal or Human Administration*. Molecular Imaging and Biology, 2007. 9: p. 6-16.] A competing compound, $^{11}$C-PIB, shows enhanced uptake in frontotemporal and hippocampal brain regions in AD patients when compared to healthy normals.

There are several issues, however, that question the validity of imaging senile plaques and tangles. First, the current array of AD imaging agents can only confirm the well-established manifestation of AD and this late stage diagnosis offers little defense against further disease progression past 36 months. Secondly, the detection of senile plaques and tangles may not correlate to development of the early stages of AD. Recent data suggests that the amyloid cascade model [Hardy, J. and D. Selkoe, *The Amyloid Hypothesis of Alzheimer's Disease: Progress and Problems on the Road to Therapeutics*. Science, 2002. 297: p. 353-356] does not accurately depict the primary factors leading to cognitive decline in AD patients and that other contributing factors, such as neuorotoxic soluble oligomers and aggregates may play a contributory role in neurodegeneration. [Talaga, P., *Inhibitors of beta-amyloid aggregation: still an issue of structure and function?* Drug Discovery Today: Therapeutic Strategies, 2004. 1: p. 7-12]. To date, FDDNP and PIB are not known to bind to neurotoxic soluble oligomers and aggregates and thus are not expected to differentiate accurately between the early stages of AD from the advanced stages of AD in patients.

As summarized from a recent discussion group on Dec. 5, 2006, (Biochemical Pharmacology Discussion Group, cosponsored by the American Chemical Society's New York section), researchers are now focusing on methods that target AD precursors by blocking either β-amyloid protein (BAP) production or by controlling mutant tau protein formation. Clearly, this focused research effort aims to control the formation of AD precursors that potentially lead to AD and this new strategy might delay full-onset AD more effectively that current therapeutics. In parallel, neurological imaging must mirror the therapeutic trend by identifying AD precursors in a duel effort to compliment both AD therapeutic development and, in addition, identify presymptomatic at-risk AD patients.

A number of medical diagnostic procedures, including PET and SPECT utilize radiolabeled compounds, are well known in the art. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}$C, $^{13}$N, $^{15}$O, $^{18}$F, $^{64}$Cu and $^{124}$I, or with a radionuclide useful for SPECT imaging, such as $^{99}$Tc, $^{77}$Br, $^{61}$Cu, $^{153}$Gd, $^{123}$I, $^{125}$I, $^{131}$I and $^{32}$P.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

DETAILED DESCRIPTION OF THE INVENTION

The present invention is directed to compounds having the structural Formula I where the radicals have the meanings given above.

"Halogen" or "halo" means F, Cl, Br and I.

"Alkyl" means a saturated monovalent hydrocarbon radical having straight or branched moieties. Examples of alkyl groups include, but are not limited to, methyl, ethyl, n-propyl, isopropyl and t-butyl.

"Alkenyl" means an alkyl moieties having at least one carbon-carbon double bond wherein alkyl is as defined above. Examples of alkenyl include, but are not limited to, ethenyl and propenyl.

"Alkynyl" means alkyl moieties having at least one carbon-carbon triple bond wherein alkyl is as defined above. Examples of alkynyl groups include, but are not limited to, ethynyl and 2-propynyl.

"Alkylene" or "alkenylenyl" means a saturated, divalent hydrocarbon radicals i.e., generally present as a bridging or linking group between two other groups, having straight or branched moieties. Examples of alkylene groups include —CH$_2$-(methylene); —CH$_2$CH$_2$-(ethylene); —CH$_2$CH$_2$CH$_2$-(propylene), —CH(CH$_3$)CH$_2$-(isopropylene) etc.

"Amino" means a nitrogen moiety having two further substituents where a hydrogen or carbon atom is attached to the nitrogen. For example, representative amino groups include —NH$_2$, —NHCH$_3$, —N(CH$_3$)$_2$, —NHC$_{2-3}$-alkyl, —N(C$_{2-3}$-alkyl)$_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl and the like.

"Aryl" means an organic radical derived from an aromatic hydrocarbon by removal of one hydrogen, such as phenyl, naphthyl, indenyl, indanyl and fluorenyl. "Aryl" encompasses fused ring groups wherein at least one ring is aromatic.

"Cycloalkyl" means non-aromatic saturated cyclic alkyl moieties consisting of one or more rings, wherein said rings (if more than one) share at least one carbon atom, wherein alkyl is as defined above. Examples of cycloalkyl include, but are not limited to, cyclopropyl, cyclobutyl, cyclopentyl, cyclohexyl, cycloheptyl, bicyclo-[3.1.0]-hexyl, bicyclo-[2.2.1]-hept-1-yl, norbornyl, spiro[4.5]decyl, spiro[4.4]nonyl, spiro[4.3]octyl, spiro[4.2]heptyl and adamantanyl.

"HaloC$_{1-6}$alkyl" means a C$_{1-6}$alkyl group that is substituted with at least one halogen atom on a carbon atom of the alkyl group. Non-exclusive, representative examples of such haloC$_{1-6}$alkyl include F—CH$_2$—, F—CH$_2$CH$_2$—, F—CH$_2$CH$_2$CH$_2$—, CHF$_2$—, CHF$_2$CH$_2$—, CHF$_2$CH$_2$CH$_2$—, Br—CH$_2$—, Br—CH$_2$CH$_2$—, Br—CH$_2$CH$_2$CH$_2$—, CHBr$_2$—, CHBr$_2$CH$_2$—, CHBr$_2$CH$_2$CH$_2$— and the like.

"Heterocyclic" or "heterocycloalkyl" means a non-aromatic cyclic groups consisting of one or more rings, wherein the rings (if more than one) share one or two atoms and each ring contains up to four heteroatoms (i.e. from zero to four heteroatoms, provided that at least one ring contains at least one heteroatom). The heterocyclic groups of this invention can also include ring systems substituted with one or more O, S(O)$_{0-2}$, and/or N—R$^{10}$ as heteroatoms, wherein R$^{10}$ is as defined herein, and wherein the subscript "0-2" of S(O)$_{0-2}$ represents an integer of 0, 1 or 2. Thus, S(O)$_2$ represents the group consisting of S, S(=O), and S(O)$_2$. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydropyranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydropyranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl and 1,4-dioxaspiro[4.2]heptyl.

"Heteroaryl" means an aromatic group containing one or more heteroatoms (O, S, or N), preferably from one to four heteroatoms. A heteroaryl may be a monocyclic or a polycyclic group. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, indazolyl, indolizinyl, phthalazinyl, triazinyl, 1,3,5-triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl and azaindolyl. In certain aspects of the present application, the heteroaryl is a 4-substituted-1H-1,2-3-triazol-1-yl.

As used herein, where a divalent group, such as a linker for example, is represented by a structure -A-B-, as shown below, it is intended to also represent a group that may be attached in both possible permutations, as noted in the two structures below.

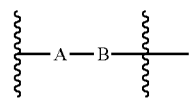

may also be

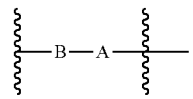

For example, when a divalent group such as the group "—N(R$^{10}$)C(O)—" is provided, for example, the group is intended to also include both the divalent group —N(R$^{10}$)C(O)— and also the divalent group —C(O)N(R$^{10}$)—.

The substituents or the groups C$_{1-6}$alkyl, C$_{3-6}$cycloalkyl, C$_{3-12}$cycloalkylC$_{1-5}$alkyl, C$_{6-14}$aryl, C$_{6-14}$aryloxy, C$_{6-10}$arylC$_{1-4}$alkyl, heteroaryl, heteroaryloxy etc. . . . of the variables R$^1$, R$^2$, R$^3$, R$^4$, R$^5$, R$^6$, R$^7$, R$^8$, R$^9$ and R$^{10}$ are also optionally further substituted by substituents selected from the group consisting of amino, halo, cyano, nitro, hydroxyl, —SH, —SC$_{1-6}$alkyl, —C(O)NH$_2$, —C(S)NH$_2$, halo C$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl.

For example, in certain aspect of the present application, the heteroaryl substituent is a 4-substituted-1H-1,2-3-triazol-1-yl. In the radiolabeled compounds of the present application, a radionuclide may be attached to an aryl group of the compound of Formulae I to VI, as in a 2-$^{18}$F-carbazole derivative such as the compound represented as:

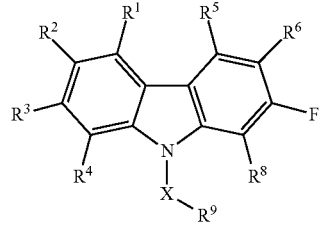

or a 2-($^{18}$F-fluoroethyl)-'carbazole, 2-($^{18}$F-fluoromethyl)-'carbazole, a $^{11}$C-methoxy-group, for example, and/or the radionuclide may be attached to any one or more of the variables R$^1$, R$^2$, R$^3$, R$^4$, R$^5$, R$^6$, R$^7$, R$^8$, R$^9$ and R$^{10}$ by way of a $^{18}$F-fluoroethyl-group, a $^{18}$F-fluoromethyl-group, a $^{11}$C-methoxy-group, 4-[($^{18}$F-fluoroethyl)-1H-1,2-3-triazol-1-yl]

ethoxy-group, 4-[($^{18}$F-fluoroethyl)-1H-1,2,3-triazol-1-yl]-propyloxy-group, a $^{123}$I, a $^{124}$I, a $^{125}$I or a $^{131}$I group, and the like. Unless otherwise noted, a compound represented as being substituted by an atom, such as the generic representation by the atom fluorine in F—CH$_2$CH$_2$—('carbazole) or F—CH$_2$CH$_2$O-('carbazole), for example, is intended to cover both the naturally occurring element $^{19}$F (fluorine-19) as well as the $^{18}$F (fluorine-18) isotope(s) of the element itself.

The term "optionally substituted" or "substituted" refers to the specific substituents or groups wherein one to four hydrogen atoms in the group may be replaced by one to four substituents, for example, independently selected from the substituents amino, halo, cyano, nitro, hydroxyl, —SH, —SC$_{1-6}$alkyl, —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl, or as specifically disclosed herein. In addition, the substituents may also include alkyl, aryl, alkylene-aryl, hydroxy, alkoxy, aryloxy, perhaloalkoxy, heterocyclyl, azido, amino, guanidino, amidino, halo, alkylthio, oxo, acylalkyl, carboxy esters, carboxyl, carboxamido, acyloxy, aminoalkyl, alkylaminoaryl, alkylaminoalkyl, alkoxyaryl, arylamino, phosphono, sulfonyl, carboxamidoaryl, hydroxyalkyl, haloalkyl, alkoxyalkyl and perhaloalkyl. In addition, the term "optionally substituted" or "substituted" in reference to the variables $R^1$, $R^2$, $R^3$, $R^4$, $R^5$, $R^6$, $R^7$, $R^8$, $R^9$ and $R^{10}$, includes groups substituted by one to four substituents, as identified above, that further comprise a positron or gamma emitter. Such positron emitters include, but are not limited to, $^{11}$C, $^{13}$N, $^{15}$O, $^{18}$F, $^{123}$I, $^{124}$I, $^{125}$I, $^{131}$I and $^{77}$Br.

The term "radiolabeled compound" as used herein refers to compounds having an atom or group that may provide a radiolabel or may be converted to a radiolabel, such as from a non-radioactive atom to a radionuclide that is active, such as for example, $^{11}$C, $^{13}$N, $^{15}$O, $^{18}$F, $^{123}$I, $^{124}$I, $^{125}$I, $^{131}$I and $^{77}$Br. In addition, for the purpose of the present application, such "radiolabeled compound" may also refer to an atom or a group, that comprises a non-active nuclide, such as a halogen, such as $^{19}$F for example, wherein the compound may be used and administered in a therapeutically effective amount.

Compounds of the Formula I to Formula VI may have optical centers and therefore may occur in different enantiomeric and diastereomeric configurations. The present invention includes all enantiomers, diastereomers, and other stereoisomers of such compounds of the Formula I to Formula VI, as well as racemic compounds and racemic mixtures and other mixtures of stereoisomers thereof. Pharmaceutically acceptable salts of the compounds of Formula I to Formula VI include the acid addition and base salts thereof. Suitable acid addition salts are formed from acids which form non-toxic salts. Examples include, but are not limited to, the acetate, adipate, aspartate, benzoate, besylate, bicarbonate/carbonate, bisulphate/sulphate, borate, citrate, formate, fumarate, gluconate, glucuronate, hydrochloride/chloride, hydrobromide/bromide, hydroiodide/iodide, lactate, malate, maleate, malonate, mesylate, methylsulphate, naphthylate, oxalate, palmitate, phosphate/hydrogen phosphate/dihydrogen phosphate, pyroglutamate, salicylate, stearate, succinate, sulfonate, tartrate, tosylate and trifluoroacetate salts. Suitable base salts are formed from bases which form non-toxic salts. Examples include, but are not limited to, the aluminum, arginine, benzathine, calcium, choline, diethylamine, diolamine, glycine, lysine, magnesium, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002). Pharmaceutically acceptable salts of compounds of Formula I to Formula VI may be prepared by one or more of three methods: (i) by reacting the compound of Formula I to Formula VI with the desired acid or base; (ii) by removing an acid- or base-labile protecting group from a suitable precursor of the compound of Formula I to Formula VI; or (iii) by converting one salt of the compound of Formula I to Formula VI to another salt by the reaction with an appropriate acid or base or by means of a suitable ion exchange column.

BRIEF DESCRIPTION OF DRAWINGS

FIG. 4 shows immunostaining of brain sections with thioflavin T, thioflavin T with tracer and no thioflavin T.

FIG. 5 shows immunostaining of brain sections with FDDNP, FDDNP with tracer and no FDDNP.

FIG. 10 shows [18F]-CB003 clearly distinguishes between Alzheimer's and normal brains.

FIG. 17 shows surface plasmon resonance assay results of CB004 binding to Aβ42 soluble aggregates.

SUMMARY OF THE INVENTION

Figure 1:
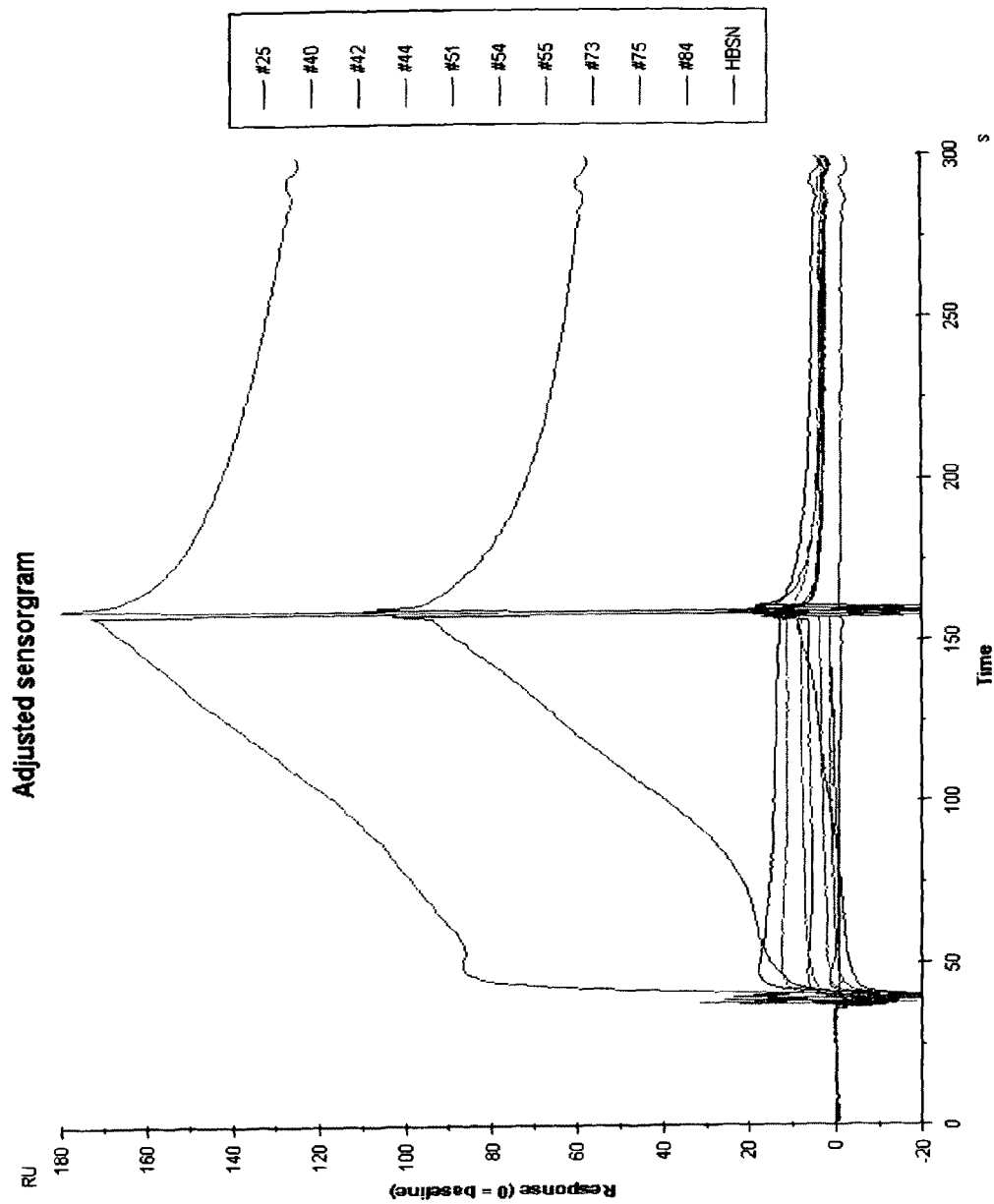
FIG. 1 shows Biacore binding assay results.

In one embodiment, there is provided a radiolabeled compound of the Formula I to Formula VI:

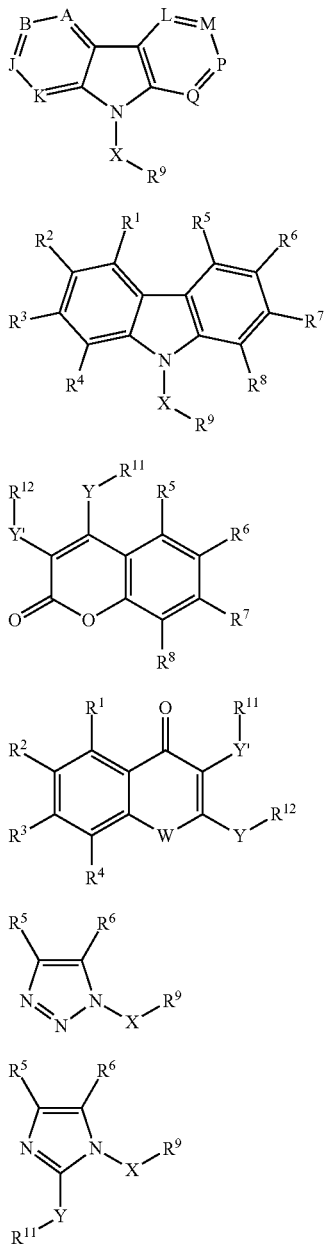

Formula I

Formula II

Formula III

Formula IV

Formula V

Formula VI wherein:
For Formula I:
A is N or $CR^1$; B is N or $CR^2$; J is N or $CR^3$; K is N or $CR^4$; L is N or $CR^5$; M is N or $CR^6$; P is N or $CR^7$; and Q is N or $CR^8$, provided that no more than two of A, B, J, K, L, M, P and Q can be N;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—;

$R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of $R^1$ and $R^2$, $R^2$ and $R^3$, $R^3$ and $R^4$, $R^5$ and $R^6$, $R^6$ and $R^7$, or $R^7$ and $R^8$ together with the carbon atoms to which they are attached to, form a substituted or unsubstituted aromatic or non-aromatic carbocyclic or heterocyclic ring;

provided that at least any two of $R^1$, $R^2$, $R^3$, $R^4$, $R^5$, $R^6$, $R^7$ and $R^8$ are hydrogens;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each $R^{10}$ is independently H or $C_{1-6}$alkyl;

provided that the compound of Formula I is not a compound selected from the group consisting of 2-fluoroethyl 6-fluoro-4-methoxy-9H-pyrido[3,4-b]indole-3-carboxylate, 2-fluoropropyl 6-fluoro-4-methoxy-9H-pyrido[3,4-b]indole-3-carboxylate, 9H-pyrido[3,4-b]indole-3-carboxylate, 9H-pyrido[3,4-b]indole-3-thiocarboxylate, 9H-pyrido[3,4-b]indole-3-carboxamide, 9H-pyrido[3,4-b]indole-3-carbimidate, β-carboline-3-carboxylate, β-carboline-3-thiocarboxylate, β-carboline-3-carboxamide, β-carboline-3-carbimidate; (S)-4-(3-(3-(2'-18F]-fluoroethylamino)-2-hydroxypropoxy)-carbazol, R, S, SS and SR-1'-[18F]-fluorocarazolol (FCAR) and [11C]-carazolol (CAR), (S)-(+ 4-(2-hydroxy-3-(1'-[18F]fluoroisopropyl)-aminopropoxy) carbazole, 7-(2-fluoroethoxy)-1-methyl-9H-β-carboline, 7-(2-fluoropropoxy)-1-methyl-9H-β-carboline, 7-[2-(2-fluoroethoxy)ethoxy]-1-methyl-9H-β-carboline, 7-{2-[2-(2-fluoroethoxy)ethoxy]ethoxy}-1-methyl-9H-β-carboline and carbazolyl-(4)-oxypropanolamine and their derivatives;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof;

For Formula II:
X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—;

$R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo- $CH_2CH_2O-$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of R$^1$ and R$^2$, R$^2$ and R$^3$, R$^3$ and R$^4$, R$^5$ and R$^6$, R$^6$ and R$^7$, or R$^7$ and R$^8$ together with the carbon atoms to which they are attached to, form a substituted or unsubstituted aromatic or non-aromatic carbocyclic or heterocyclic ring;

provided that at least any two of R$^1$, R$^2$, R$^3$, R$^4$, R$^5$, R$^6$, R$^7$ and R$^8$ are hydrogens;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each R$^{10}$ is independently H or $C_{1-6}$alkyl;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br.

and pharmaceutically acceptable salts thereof;

For Formula III:

Y and Y' are each independently a bond or are each independently selected from the group consisting of amino, halo, cyano, nitro, hydroxyl, —SR$^{10}$—C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, C$_{1-5}$alkoxy, H(OCH$_2$CH$_2$)$_{1-6}$O—, C$_{1-3}$alkyl(OCH$_2$CH$_2$)$_{1-6}$O—, halo-C$_{1-5}$alkoxy, halo-C$_{1-3}$alkyl(OCH$_2$CH$_2$)$_{1-6}$O—, halo-CH$_2$CH$_2$O—, C$_{3-6}$cycloalkoxy, C$_{3-12}$cycloalkylC$_{1-5}$alkoxy, heteroarylC$_{2-5}$alkoxy, C$_{6-14}$aryloxy, C$_{6-10}$arylC$_{1-4}$alkoxy and heteroaryloxy when R$^{11}$ and R$^{12}$ are absent;

R$^5$, R$^6$, R$^7$ and R$^8$ are each independently hydrogen or are each independently selected from the group consisting of amino, halo, cyano, nitro, hydroxyl, —SR$^{10}$—C(O)NH$_2$, —C(S)NH$_2$, halo-C$_{1-6}$alkyl, perhaloC$_{1-6}$alkyl, C$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, C$_{1-5}$alkoxy, H(OCH$_2$CH$_2$)$_{1-6}$O—, C$_{1-3}$alkyl(OCH$_2$CH$_2$)$_{1-6}$O—, halo-C$_{1-5}$alkoxy, halo-C$_{1-3}$alkyl(OCH$_2$CH$_2$)$_{1-6}$O—, halo-CH$_2$CH$_2$O—, C$_{3-6}$cycloalkoxy, C$_{3-12}$cycloalkylC$_{1-5}$alkoxy, heteroarylC$_{2-5}$alkoxy, C$_{6-14}$aryloxy, C$_{6-10}$arylC$_{1-4}$alkoxy, heteroaryloxy, C$_{1-5}$alkylNR$^{10}$C(O)—, (C$_{1-6}$alkyl)$_2$NC(O)CH(C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; or at least one of R$^5$ and R$^6$, R$^6$ and R$^7$ or R$^7$ and R$^8$ together with the carbon atoms to which they are attached to, form a substituted or unsubstituted aromatic or non-aromatic carbocyclic or heterocyclic ring;

provided that at least one of R$^5$, R$^6$, R$^7$ and R$^8$ is a hydrogen;

each R$^{10}$ is independently H or C$_{1-6}$alkyl;

R$^{11}$ and R$^{12}$ are each independently absent, a hydrogen or are each independently selected from the group consisting of halo, C$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, halo-(CH$_2$CH$_2$)$_{1-6}$—, halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br.

and pharmaceutically acceptable salts thereof;

For Formula IV:

W is O or —N—X—R$^9$;

X is a bond or is selected from the group consisting of C$_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y and Y' are each independently a bond or are each independently selected from the group consisting of amino, halo, cyano, nitro, hydroxyl, —SR$^{10}$—C(O)NH$_2$, —C(S)NH$_2$, halo-C$_{1-6}$alkyl, perhaloC$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, C$_{1-5}$alkoxy, H(OCH$_2$CH$_2$)$_{1-6}$O—, C$_{1-3}$ alkyl (OCH$_2$CH$_2$)$_{1-6}$O—, halo-C$_{1-5}$alkoxy, halo-C$_{1-3}$alkyl(OCH$_2$CH$_2$)$_{1-6}$O—, halo-CH$_2$CH$_2$O—, C$_{3-6}$cycloalkoxy, C$_{3-12}$cycloalkylC$_{1-5}$alkoxy, heteroarylC$_{2-5}$alkoxy, C$_{6-14}$aryloxy, C$_{6-10}$arylC$_{1-4}$alkoxy and heteroaryloxy when R$^{11}$ and R$^{12}$ are absent; or Y is

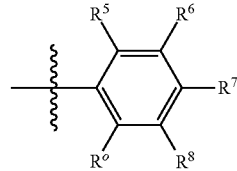

and R$^{12}$ is absent;

R$^1$, R$^2$, R$^3$ and R$^4$ are each independently hydrogen or are each independently selected from the group consisting of amino, halo, cyano, nitro, hydroxyl, —SR$^{10}$—C(O)NH$_2$, —C(S)NH$_2$, halo-C$_{1-6}$alkyl, perhaloC$_{1-6}$alkyl, C$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, C$_{1-5}$alkoxy, H(OCH$_2$CH$_2$)$_{1-6}$O—, C$_{1-3}$alkyl(OCH$_2$CH$_2$)$_{1-6}$O—, halo-C$_{1-5}$alkoxy, halo-C$_{1-3}$ alkyl(OCH$_2$CH$_2$)$_{1-6}$O—, halo-CH$_2$CH$_2$O—, C$_{3-6}$cycloalkoxy, C$_{3-12}$cycloalkylC$_{1-5}$alkoxy, heteroaryl C$_{2-5}$alkoxy, C$_{6-14}$aryloxy, C$_{6-10}$arylC$_{1-4}$alkoxy, heteroaryloxy, C$_{1-5}$alkylNR$^{10}$C(O)—, (C$_{1-6}$alkyl)$_2$NC(O)CH (C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; or at least one of R$^5$ and R$^6$, R$^6$ and R$^7$ or R$^7$ and R$^8$ together with the carbon atoms to which they are attached to, form a substituted or unsubstituted aromatic or non-aromatic carbocyclic or heterocyclic ring;

provided that at least one of R$^1$, R$^2$, R$^3$ and R$^4$ is a hydrogen;

R$^5$, R$^6$, R$^7$, R$^8$ and R$^o$ are each independently hydrogen or are each independently selected from the group consisting of amino, halo, cyano, nitro, hydroxyl, —SR$^{10}$—C(O)NH$_2$, —C(S)NH$_2$, halo-C$_{1-6}$alkyl, perhaloC$_{1-6}$alkyl, C$_{1-6}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, C$_{1-5}$alkoxy, H(OCH$_2$CH$_2$)$_{1-6}$O—, C$_{1-3}$alkyl(OCH$_2$CH$_2$)$_{1-6}$O—, halo-C$_{1-5}$alkoxy, halo-C$_{1-3}$alkyl(OCH$_2$CH$_2$)$_{1-6}$O—, halo-CH$_2$CH$_2$O—, C$_{3-6}$cycloalkoxy, C$_{3-12}$cycloalkylC$_{1-5}$alkoxy, heteroaryl C$_{2-5}$alkoxy, C$_{6-14}$aryloxy, C$_{6-10}$arylC$_{1-4}$alkoxy, heteroaryloxy, C$_{1-5}$alkylNR$^{10}$C(O)—, (C$_{1-6}$alkyl)$_2$NC(O)CH (C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C (O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each $R^{10}$ is independently H or $C_{1-6}$alkyl;

$R^{11}$ and $R^{12}$ are each independently absent, a hydrogen or are each independently selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br.

and pharmaceutically acceptable salts thereof;

For Formula V:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

$R^5$ and $R^6$ are each independently hydrogen or are each independently selected from the group consisting of amino, halo, cyano, nitro, hydroxyl, —SR$^{10}$—C(O)NH$_2$, —C(S)NH$_2$, halo-$C_{2-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl $C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$-alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or $R^5$ and $R^6$ together with the carbon atoms to which they are attached to, form a substituted or unsubstituted aromatic or non-aromatic carbocyclic or heterocyclic ring;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(O)—;

each $R^{10}$ is independently H or $C_{1-6}$alkyl;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof;

For Formula VI:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y is a bond or is selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl $C_{2-5}$alkoxy, $C_{6-14}$aryloxy, $C_{6-10}$aryl$C_{1-4}$alkoxy and heteroaryloxy;

$R^5$ and $R^6$ are each independently hydrogen or are each independently selected from the group consisting of amino, halo, cyano, nitro, hydroxyl, —SR$^{10}$—C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl $C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$-arylC(O)O—; or $R^5$ and $R^6$ together with the carbon atoms to which they are attached to, form a substituted or unsubstituted aromatic or non-aromatic carbocyclic or heterocyclic ring;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each $R^{10}$ is independently H or $C_{1-6}$alkyl;

$R^{11}$ is a hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$-aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

provided that at least one of $R^1$ to $R^{12}$ comprises a radiolabel, as defined herein;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In one variation of the above compound:

For Formula I:

A is N or CR$^1$; B is N or CR$^2$; J is N or CR$^3$; K is N or CR$^4$; L is N or CR$^5$; M is N or CR$^6$; P is N; and Q is N or CR$^8$;

X is a bond or is selected from the group consisting of $C_{1-6}$alkylenyl, —C(O)—, —C(S)—, —C(O)O— and —C(S)O—; and $R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —SR$^{10}$, —C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$-aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of $R^1$ and $R^2$, $R^2$ and $R^3$, $R^3$ and $R^4$, $R^5$ and $R^6$, $R^6$ and $R^7$, or $R^7$ and $R^8$ together with the carbon atoms to which they are attached to, form a substituted or unsubstituted aromatic or non-aromatic carbocyclic or heterocyclic ring;

For Formula II:

X is a bond or is selected from the group consisting of $C_{1-6}$alkylenyl, —C(O)—, —C(S)—, —C(O)— and —C(S)O—; and $R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)$NH_2$, —C(S)$NH_2$, halo$C_{1-6}$alkyl, perhalo$C_{1-6}$alkyl, $C_{1-6}$alkyl, $C_{3-6}$cycloallyl, $C_{3-12}$cycloalkyl$C_{1-5}$alkyl, $C_{6-10}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalicyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; or at least one of $R^1$ and $R^2$, $R^2$ and $R^3$, $R^3$ and $R^4$, $R^5$ and $R^6$, $R^6$ and $R^7$, or $R^7$ and $R^8$ together with the carbon atoms to which they are attached to, form a substituted or unsubstituted aromatic or non-aromatic carbocyclic or heterocyclic ring;

For Formula III:

Y and Y' are each independently selected from the group consisting of amino, halo, cyano, nitro, hydroxyl, —$SR^{10}$—C(O)$NH_2$, —C(S)$NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-10}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent;

$R^5$, $R^6$, $R^7$ and $R^8$ are each independently hydrogen or are each independently selected from the group consisting of amino, halo, cyano, nitro, hydroxyl, —$SR^{10}$—C(O)$NH_2$, —C(S)$NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{2-5}$alkoxy, halo-$C_{2-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-C$_{2-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; or at least one of $R^1$ and $R^2$, $R^2$ and $R^3$, $R^3$ and $R^4$, $R^5$ and $R^6$, $R^6$ and $R^7$, or $R^7$ and $R^8$ together with the carbon atoms to which they are attached to, form a substituted or unsubstituted aromatic or non-aromatic carbocyclic or heterocyclic ring;

For Formula IV:

W is O or —N—X—$R^9$;

$R^1$, $R^2$, $R^3$ and $R^4$ are each independently hydrogen or are each independently selected from the group consisting of amino, halo, cyano, nitro, hydroxyl, —$SR^{10}$—C(O)$NH_2$, —C(S)$NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; or at least one of $R^1$ and $R^2$, $R^2$ and $R^3$ or $R^3$ and $R^4$ together with the carbon atoms to which they are attached to, form a substituted or unsubstituted aromatic or non-aromatic carbocyclic or heterocyclic ring;

For Formula V:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

$R^5$ and $R^6$ are each independently hydrogen or are each independently selected from the group consisting of amino, halo, cyano, nitro, hydroxyl, —$SR^{10}$—C(O)$NH_2$, —C(S)$NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—; and $R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

For Formula VI:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y is a bond or is selected from the group consisting of amino, halo, cyano, nitro, hydroxyl, —$SR^{10}$—C(O)$NH_2$, —C(S)$NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy;

$R^5$ and $R^6$ are each independently hydrogen or are each independently selected from the group consisting of amino, halo, cyano, nitro, hydroxyl, —$SR^{10}$, —C(O)$NH_2$, —C(S)$NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-C$_{1-6}$alkylNR$^{10}$C(O)CH(C$_{1-5}$alkyl)-, halo-C$_{1-6}$alkylOC(O)CH(C$_{1-5}$alkyl)-, halo-C$_{1-5}$alkylNR$^{10}$C(O)—, C$_{1-5}$alkylNR$^{10}$C(O)O—, C$_{1-5}$alkylC(O)—, C$_{1-5}$alkylC(O)O—, C$_{6-10}$arylC(O)— and C$_{6-10}$arylC(O)O—;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$ $CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—; and $R^{11}$ is absent, a hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$(CH_2CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

and pharmaceutically acceptable salts thereof.

In another variation of the above compound:

For Formula I:

A is N or $CR^1$; B is N or $CR^2$; J is N or $CR^3$; K is N or $CR^4$; L is N or $CR^5$; M is N or $CR^6$; P is N or $CR^7$; and Q is N or $CR^8$, provided that no more than two of A, B, J, K, L, M, P and Q can be N;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

For Formula II:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-10}$aryl, $C_{6-10}$-aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

For Formula III:

Y and Y' are each independently a bond or are each independently selected from the group consisting of amino, halo, cyano, nitro, hydroxyl, —$SR^{10}$—C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-10}$aryloxy, $C_{6-10}$aryl$C_{1-4}$alkoxy and heteroaryloxy when $R^{11}$ and $R^{12}$ are absent; and $R^5$, $R^6$, $R^7$ and $R^8$ are each independently hydrogen or are each independently selected from the group consisting of amino, halo, cyano, nitro, hydroxyl, —$SR^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

For Formula IV:

W is O or —N—X—$R^9$;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—;

Y and Y' are each independently a bond or are each independently selected from the group consisting of amino, halo, cyano, nitro, hydroxyl, —$SR^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^1$, $R^2$, $R^3$ and $R^4$ are each independently hydrogen or are each independently selected from the group consisting of amino, halo, cyano, nitro, hydroxyl, —$SR^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

For Formula V:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^5$ and $R^6$ are each independently hydrogen or are each independently selected from the group consisting of amino, halo, cyano, nitro, hydroxyl, —$SR^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

For Formula VI:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—;

Y is a bond or is selected from the group consisting of amino, halo, cyano, nitro, hydroxyl, —$SR^{10}$, —C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ is absent; and $R^5$ and $R^6$ are each independently hydrogen or are each independently selected from the group consisting of amino, halo, cyano, nitro, hydroxyl, —$SR^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{1-5}$alkoxy, H(OCH$_2$CH$_2$)$_{1-6}$O— and $C_{1-3}$alkyl(OCH$_2$CH$_2$)$_{1-6}$O—;

wherein the radiolabel comprises a radionuclide selected from the group consisting of $^{11}C$, $^{13}N$, $^{15}O$, $^{18}F$, $^{123}I$, $^{124}I$, $^{125}I$, $^{131}I$ and $^{77}Br$;

and pharmaceutically acceptable salts thereof.

In another variation of the above compound:

For Formula I:

A is N or $CR^1$; B is N or $CR^2$; J is N or $CR^3$; K is N or $CR^4$; L is N or $CR^5$; M is N or $CR^6$; P is N or $CR^7$; and Q is N or $CR^8$, provided that no more than two of A, B, J, K, L, M, P and Q can be N;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of halo-$C_{1-5}$alkoxy, halo-$C_{1-3}$alkyl(OCH$_2$CH$_2$)$_{1-6}$O—, halo-CH$_2$CH$_2$O—, halo-$C_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

For Formula II:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of halo-$C_{2-5}$alkoxy, halo-$C_{1-3}$alkyl(OCH$_2$CH$_2$)$_{1-6}$O—, halo-CH$_2$CH$_2$O—, halo-CH$_2$CH$_2$—(OCH$_2$CH$_2$)$_{1-6}$O—, halo-$C_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

For Formula III:

Y and Y' are each independently a bond or are each independently selected from the group consisting of amino, halo, cyano, nitro, hydroxyl, —SR$^{10}$—C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^5$, $R^6$, $R^7$ and $R^8$ are each independently hydrogen or are each independently selected from the group consisting of halo-$C_{1-5}$alkoxy, halo-$C_{1-3}$alkyl(OCH$_2$CH$_2$)$_{1-6}$O—, halo-CH$_2$CH$_2$O—, FCH$_2$CH$_2$—(OCH$_2$CH$_2$)$_{1-6}$O—, haloC$_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

For Formula IV:

W is O or —N—X—$R^9$;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$) and —N($R^{10}$)S(O)$_2$—;

Y and Y' are each independently a bond or are each independently selected from the group consisting of amino, halo, cyano, nitro, hydroxyl, —SR$^{10}$—C(O)NH$_2$, —C(S)NH$_2$, halo-$C_{2-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^1$, $R^2$, $R^3$ and $R^4$ are each independently selected from the group consisting of halo-$C_{1-5}$alkoxy, halo-$C_{1-3}$alkyl(OCH$_2$CH$_2$)$_{1-6}$O—, halo-CH$_2$CH$_2$O—, halo-$C_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

For Formula V:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^5$ and $R^6$ are each independently hydrogen or are each independently selected from the group consisting of halo-$C_{1-5}$alkoxy, halo-$C_{1-3}$alkyl(OCH$_2$CH$_2$)$_{1-6}$O—, halo-CH$_2$CH$_2$O—, halo-$C_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

For Formula VI:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—;

Y is a bond or is selected from the group consisting of amino, halo, cyano, nitro, hydroxyl, —SR$^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ is absent; and $R^5$ and $R^6$ are each independently hydrogen or are each independently selected from the group consisting of halo-$C_{1-5}$alkoxy, halo-$C_{1-3}$alkyl(OCH$_2$CH$_2$)$_{1-6}$O—, halo-CH$_2$CH$_2$O—, halo-CH$_2$CH$_2$—(OCH$_2$CH$_2$)$_{1-6}$O—, halo-$C_{1-6}$alkylNR$^{10}$C(O)CH($C_{1-5}$alkyl)-, halo-$C_{1-6}$alkylOC(O)CH($C_{1-5}$alkyl)- and halo-$C_{1-5}$alkylNR$^{10}$C(O)—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In one variation of the above compound:

For Formula I:

A is N or CR$^1$; B is N or CR$^2$; J is N or CR$^3$; K is N or CR$^4$; L is N or CR$^5$; M is N or CR$^6$; P is N or CR$^7$; and Q is N or CR$^8$, provided that no more than two of A, B, J, K, L, M, P and Q can be N;

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$) and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$ alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula II:

X is a bond or is selected from the group consisting of $C_{1-6}$alkylenyl, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$—; and $R^1$, $R^2$, $R^3$, $R^4$, $R^5$, $R^6$, $R^7$ and $R^8$ are each independently hydrogen or are each independently selected from the group consisting of $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$arylC alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula III:

Y and Y' are each independently a bond or are each independently selected from the group consisting of amino, halo, cyano, nitro, hydroxyl, $-SR^{10}-C(O)NH_2$, $-C(S)NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O-$, $C_{1-3}$alkyl$(OCH_2CH_2)_{1-6}O-$, halo-$C_{2-5}$alkoxy, halo-$C_{1-3}$alkyl$(OCH_2CH_2)_{1-6}O-$, halo-$CH_2CH_2O-$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$-aryl$C_{1-4}$alkoxy and heteroaryloxy when $R^{11}$ and $R^{12}$ are absent; and $R^5$, $R^6$, $R^7$ and $R^8$ are each independently hydrogen or are each independently selected from the group consisting of $C_{3-6}$cycloalkoxy, $C_{3-12}$cycloalkyl$C_{1-5}$alkoxy, heteroaryl $C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula IV:

W is O or $-N-X-R^9$;

X is a bond or is selected from the group consisting of $C_{1-6}$alkylenyl, $-C(O)-$, $-C(S)-$, $-C(O)O-$, $-C(S)O-$, $-N(R^{10})C(O)-$, $-N(R^{10})C(S)-$, $-S(O)N(R^{10})-$ and $-N(R^{10})S(O)_2-$;

Y and Y' are each independently a bond or are each independently selected from the group consisting of amino, halo, cyano, nitro, hydroxyl, $-SR^{10}-C(O)NH_2$, $-C(S)NH_2$, halo-$C_{2-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O-$, $C_{1-3}$alkyl$(OCH_2CH_2)_{1-6}O-$, halo-$C_{1-5}$alkoxy, halo-$C_{1-3}$alkyl$(OCH_2CH_2)_{1-6}O-$, halo-$CH_2CH_2O-$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^1$, $R^2$, $R^3$ and $R^4$ are each independently hydrogen or are each independently selected from the group consisting of $C_{3-6}$cycloalkoxy, $C_{3-12}$cycloalkyl$C_{1-5}$alkoxy, heteroaryl $C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, $C_{1-5}$alkylNR$^{10}$C(O)O—, $C_{1-5}$alkylC(O)—, $C_{1-5}$alkylC(O)O—, $C_{6-10}$-arylC(O)— and $C_{6-10}$-arylC(O)O—;

For Formula V:

X is a bond or is selected from the group consisting of $C_{1-6}$alkylenyl, $-C(O)-$, $-C(S)-$, $-C(O)O-$, $-C(S)O-$, $-N(R^{10})C(O)-$, $-N(R^{10})C(S)-$, $-S(O)N(R^{10})-$ and $-N(R^{10})S(O)_2-$; and $R^5$ and $R^6$ are each independently hydrogen or are each independently selected from the group consisting of $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula VI:

X is a bond or is selected from the group consisting of $C_{1-6}$alkylenyl, $-C(O)-$, $-C(S)-$, $-C(O)O-$, $-C(S)O-$, $-N(R^{10})C(O)-$, $-N(R^{10})C(S)-$, $-S(O)N(R^{10})-$ and $-N(R^{10})S(O)_2-$;

Y is a bond or is selected from the group consisting of amino, halo, cyano, nitro, hydroxyl, $-SR^{10}-C(O)NH_2$, $-C(S)NH_2$, halo-$C_{2-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O-$, $C_{1-3}$alkyl$(OCH_2CH_2)_{1-6}O-$, halo-$C_{1-5}$alkoxy, halo-$C_{1-3}$alkyl$(OCH_2CH_2)_{1-6}O-$, halo-$CH_2CH_2O-$, $C_{3-6}$cycloalkoxy, $C_{3-12}$cycloalkyl$C_{1-5}$alkoxy, heteroaryl $C_{2-5}$alkoxy, $C_{6-14}$aryloxy, $C_{6-10}$aryl$C_{1-4}$alkoxy and heteroaryloxy when $R^{11}$ is absent; and $R^5$ and $R^6$ are each independently hydrogen or are each independently selected from the group consisting of $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$-arylC(O)O—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In another variation of the above compound:

For Formula I and Formula II:

X is a bond or is selected from the group consisting of $C_{1-6}$alkylenyl, $-C(O)-$, $-C(S)-$, $-C(O)O-$, $-C(S)O-$, $-N(R^{10})C(O)-$, $-N(R^{10})C(S)-$, $-S(O)N(R^{10})-$ and $-N(R^{10})S(O)_2-$;

$R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, $-SR^{10}$, $-C(O)NH_2$, $-C(S)NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O-$, $C_{1-3}$alkyl$(OCH_2CH_2)_{1-6}O-$, halo-$C_{1-5}$alkoxy, halo-$C_{1-3}$alkyl$(OCH_2CH_2)_{1-6}O-$, halo-$CH_2CH_2O-$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, halo-$C_{1-6}$alkylNR$^{10}$C(O)CH$(C_{1-5}$alkyl)-, halo-$C_{1-6}$alkylOC(O)CH$(C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of $R^1$ and $R^2$, $R^2$ and $R^3$, $R^3$ and $R^4$, $R^5$ and $R^6$, $R^6$ and $R^7$, or $R^7$ and $R^8$ together with the carbon atoms to which they are attached to, form a substituted or unsubstituted aromatic or non-aromatic carbocyclic or heterocyclic ring;

provided that at least any two of $R^1$, $R^2$, $R^3$, $R^4$, $R^5$, $R^6$, $R^7$ and $R^8$ are hydrogens;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo$(CH_2CH_2)_{1-6}-$; halo$CH_2CH_2-(OCH_2CH_2)_{1-6}-$, halo$CH_2CH_2-(OCH_2CH_2)_{1-6}O(CO)-$ and halo$CH_2CH_2-(OCH_2CH_2)_{1-6}(CO)-$; and each $R^{10}$ is independently H or $C_{1-6}$alkyl;

For Formula III:

Y and Y' are each independently a bond or are each independently selected from the group consisting of amino, halo, cyano, nitro, hydroxyl, $-SR^{10}-C(O)NH_2$, $-C(S)NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O-$, $C_{1-3}$alkyl$(OCH_2CH_2)_{1-6}O-$, halo-$C_{1-5}$alkoxy, halo-$C_{1-3}$alkyl$(OCH_2CH_2)_{1-6}O-$, halo-$CH_2CH_2O-$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^5$, $R^6$, $R^7$ and $R^8$ are each independently hydrogen or are each independently selected from the group consisting of amino, halo, cyano, nitro, hydroxyl, $-SR^{10}-C(O)NH_2$, $-C(S)NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo$C_{1-6}$alkylNR$^{10}$C(O)CH($C_{1-5}$alkyl)-, halo$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of R$^1$ and R$^2$, R$^2$ and R$^3$, R$^3$ and R$^4$, R$^5$ and R$^6$, R$^6$ and R$^7$, or R$^7$ and R$^8$ together with the carbon atoms to which they are attached to, form a substituted or unsubstituted aromatic or non-aromatic carbocyclic or heterocyclic ring;

provided that at least any two of R$^5$, R$^6$, R$^7$ and R$^8$ are hydrogens;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—; and each R$^{10}$ is independently H or $C_{1-6}$alkyl;

For Formula IV:

W is O or —N—X—R$^9$;

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y and Y' are each independently a bond or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when R$^{11}$ and R$^{12}$ are absent; and R$^1$, R$^2$, R$^3$ and R$^4$ are each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo$C_{1-6}$alkylNR$^{10}$C(O)CH($C_{1-5}$alkyl)-, halo$C_{1-6}$alkylOC(O)CH($C_{1-5}$alkyl)-, halo$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$-arylC(O)O—; or at least one of R$^1$ and R$^2$, R$^2$ and R$^3$ or R$^3$ and R$^4$ together with the carbon atoms to which they are attached to, form a substituted or unsubstituted aromatic or non-aromatic carbocyclic or heterocyclic ring;

provided that at least any two of R$^1$, R$^2$, R$^3$ and R$^4$ are hydrogens;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—; and each R$^{10}$ is independently H or $C_{1-6}$alkyl;

For Formula V:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—; and R$^5$ and R$^6$ are each independently each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$-arylC(O)— and $C_{6-10}$arylC(O)O—;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—; and each R$^{10}$ is independently H or $C_{1-6}$alkyl;

For Formula VI:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y is a bond or is selected from the group consisting of amino, halo, cyano, nitro, hydroxyl, —SR$^{10}$—C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{2-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when R$^{11}$ is absent; and R$^5$ and R$^6$ are each independently each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{16}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—; and each R$^{10}$ is independently H or $C_{1-6}$alkyl;

wherein the radiolabel comprises a radionuclide selected from the group consisting of $^{11}$C, $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In another variation of the above compound:

For Formula I and Formula II:

$R^1$, $R^2$, $R^3$, $R^4$, $R^5$, $R^6$, $R^7$ and $R^8$ are each independently hydrogen or are each independently selected from the group consisting of amino, halo, cyano, nitro, hydroxyl, —$SR^{10}$, —C(O)NH$_2$, —C(S)NH$_2$, $C_{1-5}$alkoxy, H(OCH$_2$CH$_2$)$_{1-6}$O— and $C_{1-3}$alkyl(OCH$_2$CH$_2$)$_{1-6}$O—;

For Formula III:

$R^5$, $R^6$, $R^7$ and $R^8$ are each independently hydrogen or are each independently selected from the group consisting of amino, halo, cyano, nitro, hydroxyl, —$SR^{10}$—C(O)NH$_2$, —C(S)NH$_2$, $C_{1-5}$alkoxy, H(OCH$_2$CH$_2$)$_{1-6}$O— and $C_{1-3}$alkyl(OCH$_2$CH$_2$)$_{1-6}$O—;

For Formula IV:

$R^1$, $R^2$, $R^3$ and $R^4$ are each independently hydrogen or are each independently selected from the group consisting of amino, halo, cyano, nitro, hydroxyl, —$SR^{10}$—C(O)NH$_2$, —C(S)NH$_2$, $C_{1-5}$alkoxy, H(OCH$_2$CH$_2$)$_{1-6}$O— and $C_{1-3}$alkyl(OCH$_2$CH$_2$)$_{1-6}$O—.

For Formula V and Formula VI:

$R^5$ and $R^6$ are each independently hydrogen or are each independently selected from the group consisting of amino, halo, cyano, nitro, hydroxyl, —$SR^{10}$—C(O)NH$_2$, —C(S)NH$_2$, $C_{1-5}$alkoxy, H(OCH$_2$CH$_2$)$_{1-6}$O— and $C_{1-3}$alkyl(OCH$_2$CH$_2$)$_{1-6}$O—, wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In a particular variation of each of the above compounds, the halo-moiety of the group selected from halo-$C_{1-6}$alkyl, halo-$C_{2-5}$alkoxy, halo-$C_{2-3}$alkyl(OCH$_2$CH$_2$)$_{1-6}$O—, halo-CH$_2$CH$_2$O—, halo-CH$_2$CH$_2$—(OCH$_2$CH$_2$)$_{1-6}$O—, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)—, halo-CH$_2$CH$_2$—(OCH$_2$CH$_2$)$_{1-6}$(CO)—, halo-$C_{2-6}$alkylNR$^{10}$C(O)CH($C_{1-5}$alkyl)-, halo-$C_{2-6}$alkylOC(O)CH($C_{1-5}$alkyl)- and halo$C_{1-5}$alkylNR$^{10}$C(O)— is selected from the group consisting of fluoro, iodo and bromo. In another variation of the above:

For Formula I and Formula II:

$R^1$, $R^2$, $R^3$, $R^4$, $R^5$, $R^6$, $R^7$ and $R^8$ are each independently hydrogen or are each independently selected from the group consisting of halo-$C_{2-5}$alkoxy, halo$C_{1-6}$alkyl, perhalo$C_{1-6}$alkyl, halo-$C_{2-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, halo$C_{2-6}$alkylNR$^{10}$C(O)CH($C_{1-5}$alkyl)-, halo$C_{2-6}$alkylOC(O)CH($C_{1-5}$alkyl)- and halo$C_{2-5}$alkylNR$^{10}$C(O)—;

For Formula III:

$R^5$, $R^6$, $R^7$ and $R^8$ are each independently hydrogen or are each independently selected from the group consisting of halo-$C_{1-5}$alkoxy, halo$C_{1-6}$alkyl, perhalo$C_{1-6}$alkyl, halo-$C_{2-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, halo$C_{2-6}$alkylNR$^{10}$C(O)CH($C_{1-5}$alkyl)-, halo$C_{2-6}$alkylOC(O)CH($C_{1-5}$alkyl)- and halo$C_{2-5}$alkylNR$^{10}$C(O)—;

For Formula IV:

$R^1$, $R^2$, $R^3$ and $R^4$ are each independently hydrogen or are each independently selected from the group consisting of halo-$C_{1-5}$alkoxy, halo$C_{1-6}$alkyl, perhalo$C_{1-6}$alkyl, halo-$C_{2-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, halo$C_{2-6}$alkylNR$^{10}$C(O)CH($C_{1-5}$alkyl)-, halo$C_{2-6}$alkylOC(O)CH($C_{1-5}$alkyl)- and halo$C_{2-5}$alkylNR$^{10}$C(O)—;

For Formula V and Formula VI:

$R^5$ and $R^6$ are each independently hydrogen or are each independently selected from the group consisting of halo-$C_{1-5}$alkoxy, halo$C_{1-6}$alkyl, perhalo$C_{1-6}$alkyl, halo-$C_{2-3}$alkyl (OCH$_2$CH$_2$)$_{1-6}$O—, F—CH$_2$CH$_2$O—, F—CH$_2$CH$_2$—(OCH$_2$CH$_2$)$_{1-6}$O—, halo$C_{2-6}$alkylNR$^{10}$C(O)CH($C_{1-5}$alkyl)-, halo$C_{2-6}$alkylOC(O)CH($C_{1-5}$alkyl)- and halo$C_{2-5}$alkylNR$^{10}$C(O)—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In yet another variation:

For Formula I and Formula II:

$R^1$, $R^2$, $R^3$, $R^4$, $R^5$, $R^6$, $R^7$ and $R^8$ are each independently hydrogen or are each independently selected from the group consisting of $C_{1-6}$alkyl, $C_{3-6}$cycloalkyl, $C_{3-12}$cycloalkyl$C_{1-5}$alkyl, heteroaryl $C_{2-5}$alkoxy, $C_{6-14}$aryl, $C_{6-10}$aryl$C_{1-4}$alkyl, heteroaryl, $C_{3-6}$cycloalkoxy, $C_{3-12}$cycloalkyl$C_{1-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula III:

$R^5$, $R^6$, $R^7$ and $R^8$ are each independently hydrogen or are each independently selected from the group consisting of $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{3-6}$cycloalkoxy, $C_{3-12}$cycloalkyl$C_{1-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula IV:

$R^1$, $R^2$, $R^3$ and $R^4$ are each independently hydrogen or are each independently selected from the group consisting of $C_{1-6}$alkyl, $C_{3-6}$cycloalkyl, $C_{3-12}$cycloalkyl$C_{1-5}$alkyl, heteroaryl $C_{2-5}$alkoxy, $C_{6-14}$aryl, $C_{6-10}$aryl$C_{1-4}$alkyl, heteroaryl, $C_{3-6}$cycloalkoxy, $C_{3-12}$cycloalkyl$C_{1-5}$alkoxy, $C_{6-14}$aryloxy, $C_{6-10}$aryl$C_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

For Formula V and Formula VI:

$R^5$ and $R^6$ are each independently hydrogen or are each independently selected from the group consisting of $C_{1-6}$alkyl, $C_{3-6}$cycloalkyl, $C_{3-12}$cycloalkyl$C_{1-5}$alkyl, heteroaryl$C_{2-5}$alkoxy, $C_{6-14}$aryl, $C_{6-10}$aryl$C_{1-4}$alkyl, heteroaryl, $C_{3-6}$cycloalkoxy, $C_{3-12}$cycloalicyl$C_{1-5}$alkoxy, $C_{6-14}$aryloxy, $C_{6-10}$aryl$C_{1-4}$ alkoxy, heteroaryloxy, $C_{1-5}$alkylNR$^{10}$C(O)—, ($C_{1-6}$alkyl)$_2$NC(O)CH($C_{1-5}$alkyl)-, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In yet another variation:

For Formula I and Formula II:

$R^1$, $R^2$, $R^3$, $R^4$, $R^5$, $R^6$, $R^7$ and $R^8$ are each independently hydrogen or selected from the group consisting of F—$C_{1-6}$alkyl, F—$C_{1-5}$alkoxy, F—$C_{1-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, 4-(F—$C_{1-6}$alkyl)-1H-1,2,3-triazol-1-yl-($C_{2-5}$alkoxy), F—$C_{2-6}$alkylNR$^{10}$C(O)CH($C_{1-5}$alkyl)-, F—$C_{1-6}$alkylOC(O)CH($C_{1-5}$alkyl)- and F—$C_{1-5}$alkylNR$^{10}$C(O)—;

For Formula III:

$R^5$, $R^6$, $R^7$ and $R^8$ are each independently hydrogen or selected from the group consisting of F—$C_{1-6}$alkyl, F—$C_{1-5}$alkoxy, F—$C_{1-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, 4-(F—$C_{1-6}$alkyl)-1H-1,2,3-triazol-1-yl-($C_{2-5}$alkoxy), F—$C_{2-6}$alkylNR$^{10}$C(O)CH($C_{1-5}$alkyl)-, F—$C_{1-6}$alkylOC(O)CH($C_{1-5}$alkyl)- and F—$C_{1-5}$alkylNR$^{10}$C(O)—;

For Formula IV:

$R^1$, $R^2$, $R^3$ and $R^4$ are each independently hydrogen or selected from the group consisting of F—$C_{1-6}$alkyl, F—$C_{1-5}$alkoxy, F—$C_{1-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, 4-(F—$C_{1-6}$alkyl)-1H-1,2,3-triazol-1-yl-($C_{2-5}$alkoxy), F—$C_{1-6}$alkylNR$^{10}$C(O)CH($C_{1-5}$alkyl)-, F—$C_{1-6}$alkylOC(O)CH($C_{1-5}$alkyl)- and F—$C_{1-5}$alkylNR$^{10}$C(O)—;

For Formula V and Formula VI:

$R^5$ and $R^6$ are each independently hydrogen or selected from the group consisting of F—$C_{1-6}$alkyl, F—$C_{1-5}$alkoxy, F—$C_{1-3}$alkyl(OCH$_2$CH$_2$)$_{1-6}$O—, F—CH$_2$CH$_2$O—, F—CH$_2$CH$_2$—(OCH$_2$CH$_2$)$_{1-6}$O—, 4-(F—$C_{1-6}$alkyl)-1H-1,2,3-triazol-1-yl-($C_{2-5}$alkoxy), F—$C_{1-6}$alkylNR$^{10}$C(O)CH($C_{1-5}$alkyl)-, F—$C_{1-6}$alkylOC(O)CH($C_{1-5}$alkyl)- and F—$C_{1-5}$alkylNR$^{10}$C(O)—;

wherein the radiolabel comprises a radionuclide selected from the group consisting of $^{11}$C, $^{11}$C, $^{13}$N, $^{15}$O, $^{18}$F, $^{123}$I, $^{124}$I, $^{125}$I, $^{131}$I and $^{77}$Br;

and pharmaceutically acceptable salts thereof.

In another particular variation of the above:

For Formula I and Formula II:

at least four of $R^1$, $R^2$, $R^3$, $R^4$, $R^5$, $R^6$, $R^7$ and $R^8$ are hydrogens;

For Formula III:

at least two of $R^5$, $R^6$, $R^7$ and $R^8$ are hydrogens;

For Formula IV:

at least two of $R^1$, $R^2$, $R^3$ and $R^4$ are hydrogens;

For Formula V and Formula VI:

at least one of $R^5$ or $R^6$ is a hydrogen;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br; and pharmaceutically acceptable salts thereof.

In yet another variation of each of the above, the amino group is selected from the group consisting of NH$_2$—, CH$_3$NH—, (CH$_3$)$_2$N—, $C_{1-3}$-alkylNH—, F—$C_{2-3}$-alkylNH—, F—($C_{2-3}$-alkylO)$_{1-4}$-alkyl-NH—, ($C_{1-3}$-alkyl)$_2$N—, $C_{1-6}$alkylNH—, ($C_{1-6}$alkyl)$_2$N—, $C_{3-6}$cycloalkylNH—, ($C_{3-6}$cycloalkyl)$_2$N—, $C_{3-12}$cycloalkylC$_{1-5}$alkylNH—, $C_{6-14}$arylNH—, $C_{6-10}$arylC$_{1-4}$alkylNH—, heteroarylNH—, $C_{6-14}$aryloxyNH—, $C_{6-10}$-arylC$_{1-4}$alkoxyNH— and heteroaryloxyNH—. In a particular variation of the Formula I, II, V and VI, X is a bond and $R^9$ is hydrogen.

In another aspect of each of the above compound, the compound comprises at least one radionuclide selected from the group consisting of $^{11}$C, $^{15}$O, $^{18}$F, $^{123}$I, $^{125}$I, $^{131}$I and $^{77}$Br.

In another aspect, there is provided a radiolabeled compound wherein the compound is selected from 2-(2-fluoroethoxy)-9H-carbazole; 9-(2-fluoroethyl)-9H-carbazol-2-ol; N-(2-fluoroethyl)-7-(2-(2-(2-methoxyethoxy)ethoxy)ethoxy)-9H-carbazol-3-amine; 7-(2-fluoroethoxy)-N,N-dimethyl-9H-carbazol-2-amine; 7-(2-(2-(2-fluoroethoxy)ethoxy)ethoxy)-N-methyl-9H-carbazol-3-amine; 1-(3,6-diamino-9H-carbazol-9-yl)-3-(2-(2-(2-fluoroethoxy)ethoxy)ethoxy)propan-1-one; N-(2-fluoroethyl)-2-hydroxy-11H-benzo[a]carbazole-3-carboxamide; 2-(6-chloro-9H-carbazol-2-yl)-N-(2-fluoroethyl)propanamide; 2-(6-fluoro-9H-carbazol-2-yl)-N,N-dimethylpropanamide; 2-methoxy-9H-carbazole; 6-iodo-2-methoxy-9H-carbazole; 2-(2-fluoroethoxy)-9H-carbazole; 9-(2-fluoroethyl)-9H-carbazol-2-ol; N-(2-fluoroethyl)-7-(2-(2-(2-methoxyethoxy)ethoxy)ethoxy)-9H-carbazol-3-amine; 7-(2-fluoroethoxy)-N,N-dimethyl-9H-carbazol-2-amine; 7424242-fluoroethoxy)ethoxy)ethoxy)-N-methyl-9H-carbazol-3-amine; 1-(3,6-diamino-9H-carbazol-9-yl)-3-(2-(2-(2-fluoroethoxy)ethoxy)ethoxy)propan-1-one; N-(2-fluoroethyl)-2-hydroxy-11H-benzo[a]carbazole-3-carboxamide; 2-(6-chloro-9H-carbazol-2-yl)-N-(2-fluoroethyl)propanamide; and 2-(6-fluoro-9H-carbazol-2-yl)-N,N-dimethylpropanamide.

In another embodiment, there is provided a radiolabeled compound of the formula IIa:

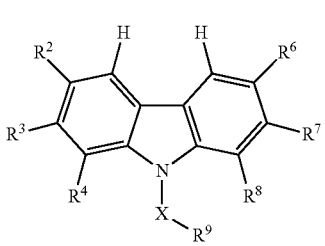

wherein:

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$;

$R^2$, $R^3$, $R^4$, $R^6$, $R^7$ and $R^8$ are each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkylC$_{1-5}$alkyl, $C_{6-14}$aryl, $C_{6-10}$arylC$_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$—(OCH$_2$CH$_2$)$_{1-6}$O—, $C_{3-6}$cycloalkoxy, $C_{3-12}$cycloalkylC$_{1-5}$alkoxy, heteroarylC$_{2-5}$alkoxy, $C_{6-14}$aryloxy, $C_{6-10}$arylC$_{1-4}$alkoxy, heteroaryloxy, $C_{1-5}$alkylNR$^{10}$C(O)—, ($C_{1-6}$alkyl)$_2$NC(O)CH($C_{1-5}$alkyl)-, halo-$C_{1-6}$alkylNR$^{10}$C(O)CH($C_{1-5}$alkyl)-, halo-$C_{1-6}$alkylOC(O)CH($C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

provided that at least any two of $R^2$, $R^3$, $R^4$, $R^6$, $R^7$ and $R^8$ are hydrogens, and at least one of $R^2$, $R^3$, $R^4$, $R^6$, $R^7$, $R^8$ and $R^9$ comprises the radiolabel;

$R^9$ is hydrogen or is selected from the group consisting of halo, $C_{1-6}$alkyl, $C_{3-6}$cycloalkyl, $C_{3-12}$cycloalkylC$_{1-5}$alkyl, $C_{6-14}$aryl, $C_{6-10}$arylC$_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each R$^{10}$ is independently H or $C_{1-6}$alkyl;

wherein the radiolabel comprises a radionuclide selected from the group consisting of $^{11}$C, $^{13}$N, $^{15}$O, $^{18}$F, $^{123}$I, $^{124}$I, $^{125}$I, $^{131}$I and $^{77}$Br; and pharmaceutically acceptable salts thereof.

In one variation of the above, X is a bond or is selected from the group consisting of $C_{1-6}$alkylenyl, —C(O)—, —C(O)O— and —N(R$^{10}$)C(O)—;

$R^2$, $R^3$, $R^4$, $R^6$, $R^7$ and $R^8$ are each independently hydrogen or are each independently selected from the group consisting of $C_{1-3}$alkylNH—, halo, cyano, hydroxyl, —SR$^{10}$, —C(O)NH$_2$, halo-$C_{1-6}$alkyl, perhalo$C_{1-6}$alkyl, $C_{1-6}$alkyl, $C_{3-6}$cycloalkyl, $C_{3-12}$cycloallylC$_{1-5}$alkyl, $C_{6-14}$aryl, $C_{6-10}$aryl- $C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, $C_{6-14}$aryloxy, $C_{6-10}$aryl$C_{1-4}$alkoxy, heteroaryloxy, heteroaryl$C_{2-5}$alkoxy, $C_{1-5}$alkylNR$^{10}$C(O)—, $(C_{1-6}$alkyl$)_2$NC(O)CH$(C_{1-5}$alkyl)-, halo-$C_{1-6}$alkylNR$^{10}$C(O)CH$(C_{1-5}$alkyl)-, halo-$C_{1-6}$alkylOC(O)CH$(C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; and $R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl $C_{1-4}$alkyl, heteroaryl, halo-$(CH_2CH_2)_{1-6}$—; halo-$CH_2CH_2$—$(OCH_2CH_2)_{1-6}$—, halo-$CH_2CH_2$—$(OCH_2CH_2)_{1-6}$O(CO)— and halo-$CH_2CH_2$—$(OCH_2CH_2)_{1-6}$(CO)—. In another variation of the above, X is a bond or is selected from the group consisting of $C_{1-6}$alkylenyl, —C(O)—, —C(O)O— and —N(R$^{10}$)C(O)—;

$R^2$, $R^4$, $R^6$ and $R^8$ are each hydrogen;

$R^3$ and $R^7$ are each independently selected from the group consisting of $C_{1-3}$alkylNH—, $(C_{1-3}$alkyl$)_2$N—, (halo-$C_{1-6}$alkyl)N$(C_{1-3}$alkyl)-, halo-$CH_2CH_2$—$(OCH_2CH_2)_{1-6}$N$(C_{1-3}$alkyl)-, halo, hydroxyl, halo-$C_{1-6}$alkyl, $C_{6-10}$-aryl$C_{1-4}$alkyl, 4-(halo-$C_{1-6}$alkyl)-triazol-1-yl)$C_{2-5}$alkoxy, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, halo-$C_{1-6}$alkylNR$^{10}$C(O)CH$(C_{1-5}$alkyl)-, halo-$C_{1-6}$alkylOC(O)CH$(C_{1-5}$alkyl)-, halo-$C_{1-5}$alkylNR$^{10}$C(O)—, $C_{1-5}$alkylC(O)—; and $R^9$ is hydrogen or is selected from the group consisting of halo, $C_{3-12}$cycloalkyl$C_{1-5}$alkyl, $C_{6-14}$aryl, $C_{6-10}$aryl$C_{1-4}$alkyl, heteroaryl, halo-$(CH_2CH_2)_{1-6}$—; halo-$CH_2CH_2$—$(OCH_2CH_2)_{1-6}$—, halo-$CH_2CH_2$—$(OCH_2CH_2)_{1-6}$O(CO)— and halo-$CH_2CH_2$—$(OCH_2CH_2)_{1-6}$(CO)—.

In another embodiment, there is provided a radiolabeled compound of the formula III:

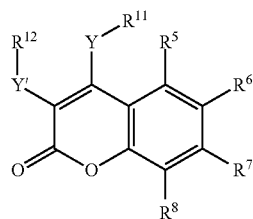

III wherein: Y and Y' are each independently a bond or are each independently selected from the group consisting of amino, halo, cyano, nitro, hydroxyl, —SR$^{10}$, —C(O)NH$_2$, —C(S)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent;

$R^5$, $R^6$, $R^7$ and $R^8$ are each independently hydrogen or are each independently selected from the group consisting of amino, halo, cyano, nitro, hydroxyl, —SR$^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, $(C_{1-6}$alkyl$)_2$NC(O)CH$(C_{1-5}$alkyl)-, halo-$C_{1-6}$alkylNR$^{10}$C(O)CH$(C_{1-5}$alkyl)-, halo-$C_{1-6}$alkylOC(O)CH$(C_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of $R^5$ and $R^6$, $R^6$ and $R^7$ or $R^7$ and $R^8$ together with the carbon atoms to which they are attached to, form a substituted or unsubstituted aromatic or non-aromatic carbocyclic or heterocyclic ring;

provided that at least one of $R^5$, $R^6$, $R^7$ and $R^8$ is a hydrogen;

each $R^{10}$ is independently H or $C_{1-6}$alkyl;

$R^{11}$ and $R^{12}$ are each independently absent, a hydrogen or are each independently selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$(CH_2CH_2)_{1-6}$—, halo-$CH_2CH_2$—$(OCH_2CH_2)_{1-6}$—, halo-$CH_2CH_2$—$(OCH_2CH_2)_{1-6}$O(CO)— and halo-$CH_2CH_2$—$(OCH_2CH_2)_{1-6}$(CO)—;

provided that at least one of $R^5$ to $R^{12}$ comprises a radiolabel;

wherein the radiolabel comprises a radionuclide selected from the group consisting of $^{11}C$, $^{11}C$, $^{13}N$, $^{15}O$, $^{18}F$, $^{123}I$, $^{124}I$, $^{125}I$, $^{131}I$ and $^{77}Br$; and pharmaceutically acceptable salts thereof. In one variation of the above, Y and Y' are each independently selected from the group consisting of amino, halo, hydroxyl, —SR$^1$—C(O)NH$_2$, —C(S)NH$_2$, halo-$C_{1-6}$alkyl, perhalo$C_{1-6}$alkyl, $C_{1-6}$alkyl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$— and halo-$CH_2CH_2O$— when $R^{11}$ and $R^{12}$ are absent; and $R^5$, $R^6$, $R^7$ and $R^8$ are each independently hydrogen or are each independently selected from the group consisting of amino, halo, hydroxyl, —SR$^{10}$—C(O)NH$_2$, halo$C_{1-6}$alkyl, perhalo$C_{1-6}$alkyl, $C_{1-6}$alkyl, $C_{3-6}$cycloalkyl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{2-5}$alkoxy, halo-$C_{2-3}$alkyl$(OCH_2CH_2)_{1-6}O$—, halo-$CH_2CH_2O$—, $C_{3-6}$cycloalkoxy, $C_{1-5}$alkylNR$^{10}$C(O)—, $(C_{1-6}$alkyl$)_2$NC(O)CH$(C_{1-5}$alkyl)-, halo-$C_{2-6}$alkylNR$^{10}$C(O)CH$(C_{1-5}$alkyl)-, halo-$C_{1-6}$alkylOC(O)CH$(C_{1-5}$alkyl)- and halo-$C_{1-5}$alkylNR$^{10}$C(O)—.

In another variation of the above, Y and Y' are each independently a bond or are each independently selected from the group consisting of amino, halo, hydroxyl, —C(O)NH$_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$— and halo-$CH_2CH_2O$— when $R^{11}$ and $R^{12}$ are absent; and $R^5$, $R^6$, $R^7$ and $R^8$ are each independently hydrogen or are each independently selected from the group consisting of halo-$C_{1-5}$alkoxy, halo-$C_{1-3}$ alkyl$(OCH_2CH_2)_{1-6}O$—, halo-$CH_2CH_2O$—, $FCH_2CH_2$—$(OCH_2CH_2)_{1-6}O$—, halo$C_{1-6}$alkylNR$^{10}$C(O)CH$(C_{1-5}$alkyl)-, halo-$C_{1-6}$alkylOC(O)CH$(C_{1-5}$alkyl)- and halo-$C_{1-5}$alkylNR$^{10}$C(O)—.

In yet another variation of the above, Y and Y' are each independently a bond or are each independently selected from the group consisting of amino, halo, hydroxyl, —SR$^{10}$—C(O)NH$_2$, —C(S)NH$_2$, halo$C_{1-6}$alkyl, perhalo-$C_{1-6}$alkyl, $C_{1-5}$alkoxy, $H(OCH_2CH_2)_{1-6}O$—, $C_{1-3}$alkyl$(OCH_2CH_2)_{1-6}O$—, halo-$C_{2-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^5$, $R^6$, $R^7$ and $R^8$ are each independently hydrogen or are each independently selected from the group consisting of $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, $C_{1-5}$alkylC(O)—, $C_{1-5}$alkylC(O)O—, $C_{6-10}$arylC(O)— and $C_{6-10}$arylC(O)O—.

In another embodiment, there is provided a radiolabeled compound of the formula IV:

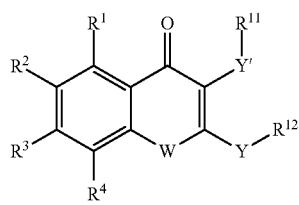

IV wherein:

W is O or —N—X—R$^9$;

X is a bond or is selected from the group consisting of $C_{1-6}$alkylenyl, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$—;

Y and Y' are each independently a bond or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; or Y is

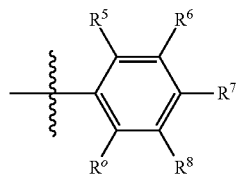

and R$^{12}$ is absent;

$R^1$, $R^2$, $R^3$ and $R^4$ are each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkoxy, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-$C_{1-6}$alkylNR$^{10}$C(O)CH(C$_{1-5}$alkyl)-, halo-$C_{1-6}$alkylOC(O)CH(C$_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—; or at least one of R$^5$ and R$^6$, R$^6$ and R$^7$ or R$^7$ and R$^8$ together with the carbon atoms to which they are attached to, form a substituted or unsubstituted aromatic or non-aromatic carbocyclic or heterocyclic ring;

provided that at least one of R$^1$, R$^2$, R$^3$ and R$^4$ is a hydrogen;

R$^5$, R$^6$, R$^7$, R$^8$ and R$^o$ are each independently hydrogen or are each independently selected from the group consisting of amino, halo, cyano, nitro, hydroxyl, —SR$^{10}$, —C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$ alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkylNR$^{10}$C(O)—, (C$_{1-6}$alkyl)$_2$NC(O)CH(C$_{1-5}$alkyl)-, halo-$C_{1-6}$alkylNR$^{10}$C(O)CH(C$_{1-5}$alkyl)-, halo-$C_{1-6}$alkylOC(O)CH(C$_{1-5}$alkyl)-, halo-$C_{1-5}$alkylNR$^{10}$C(O)—, $C_{1-5}$alkylNR$^{10}$C(O)O—, $C_{1-5}$alkylC(O)—, $C_{1-5}$alkylC(O)O—, $C_{6-10}$arylC(O)— and $C_{6-10}$arylC(O)O—;

R$^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

each R$^{10}$ is independently H or C$_{1-6}$alkyl; and

R$^{11}$ and R$^{12}$ are each independently absent, a hydrogen or are each independently selected from the group consisting of halo, $C_{1-6}$alkyl, $C_{3-6}$cycloalkyl, $C_{3-12}$cycloalkyl$C_{1-5}$alkyl, $C_{6-10}$aryl, $C_{6-10}$aryl$C_{1-4}$alkyl, heteroaryl, halo-(CH$_2$CH$_2$)$_{1-6}$—; halo-CH$_2$CH$_2$—(OCH$_2$CH$_2$)$_{1-6}$—, halo-CH$_2$CH$_2$—(OCH$_2$CH$_2$)$_{1-6}$O(CO)— and halo-CH$_2$CH$_2$—(OCH$_2$CH$_2$)$_{1-6}$(CO)—;

provided that at least one of R$^{11}$ to R$^{12}$ comprises a radiolabel, as defined herein;

wherein the radiolabel comprises a radionuclide selected from the group consisting of $^{11}$C, $^{11}$C, $^{13}$N, $^{15}$O, $^{18}$F, $^{123}$I, $^{124}$I, $^{125}$I, $^{131}$I and $^{77}$Br; and pharmaceutically acceptable salts thereof.

In one variation of the above compound, W is O or —N—X—R$^9$;

X is a bond or is selected from the group consisting of $C_{1-6}$alkylenyl, —C(O)—, —C(S)—, —C(O)O—, —C(S)O—, —N(R$^{10}$)C(O)—; and $R^1$, $R^2$, $R^3$ and $R^4$ are each independently hydrogen or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, $C_{1-5}$alkylC(O)—, $C_{1-5}$alkylC(O)O—, $C_{6-10}$arylC(O)— and $C_{6-10}$arylC(O)O—.

In one variation of the above compound, W is O or —N—X—R$^9$;

X is a bond or is selected from the group consisting of $C_{1-6}$alkylenyl, —C(O)—, —C(O)O— and —N(R$^{10}$)C(O)—;

Y and Y' are each independently a bond or are each independently selected from the group consisting of amino, halo, cyano, nitro, hydroxyl, —SR$^{10}$—C(O)NH$_2$, —C(S)NH$_2$, halo-$C_{1-6}$alkyl, perhalo$C_{1-6}$alkyl, $C_{1-5}$alkoxy, H(OCH$_2$CH$_2$)$_{1-6}$O—, $C_{1-3}$alkyl(OCH$_2$CH$_2$)$_{1-6}$O—, halo-$C_{1-5}$alkoxy, halo-$C_{1-3}$alkyl(OCH$_2$CH$_2$)$_{1-6}$O—, halo-CH$_2$CH$_2$O—, $C_{6-14}$aryloxy, $C_{6-10}$-aryl$C_{1-4}$alkoxy and heteroaryloxy when $R^{11}$ and $R^{12}$ are absent; and R$^1$, R$^2$, R$^3$ and R$^4$ are each independently hydrogen or are each independently selected from the group consisting of amino, halo, hydroxyl, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, heteroaryl$C_{2-5}$alkoxy, $C_{1-5}$alkoxy, $H(OCH_2CH_2)_{1-6}O$— and $C_{1-3}$alkyl$(OCH_2CH_2)_{1-6}O$—, In another variation of the above compound, W is O;

Y and Y' are each independently a bond or are each independently selected from the group consisting of amino, halo, hydroxyl, —$SR^{10}$, —$C(O)NH_2$, halo-$C_{2-6}$alkyl, perhalo $C_{1-6}$alkyl, $C_{1-6}$alkyl, $C_{3-6}$cycloalkyl, $C_{3-12}$cycloalkyl$C_{1-5}$ alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy and heteroaryloxy when $R^{11}$ and $R^{12}$ are absent; and $R^1$, $R^2$, $R^3$ and $R^4$ are each independently hydrogen or are each independently selected from the group consisting of halo-$C_{1-5}$alkoxy, halo-$C_{1-3}$alkyl$(OCH_2CH_2)_{1-6}O$—, halo-$CH_2CH_2O$—, halo-$C_{1-6}$alkyl$NR^{10}C(O)CH(C_{1-5}$alkyl)-, halo-$C_{1-6}$alkylOC(O)CH$(C_{1-5}$alkyl)- and halo-$C_{1-5}$alkyl $NR^{10}C(O)$—.

In yet another variation of the above compound, W is O;

X is a bond or is selected from the group consisting of $C_{1-6}$alkylenyl, —$C(O)$—, —$C(O)O$—;

Y and Y' are each independently a bond or are each independently selected from the group consisting of amino, halo, hydroxyl, —$C(O)NH_2$, —$C(S)NH_2$, halo-$C_{1-6}$alkyl, perhalo$C_{1-6}$alkyl, $C_{1-6}$alkyl, $C_{3-6}$cycloalkyl, $C_{3-12}$cycloalkyl $C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2 CH_2)_{1-6}O$—, halo-$C_{1-5}$alkoxy, halo-$C_{1-3}$alkyl$(OCH_2 CH_2)_{1-6}O$— and halo-$CH_2CH_2O$— when $R^{11}$ and $R^{12}$ are absent; and $R^1$, $R^2$, $R^3$ and $R^4$ are each independently hydrogen or are each independently selected from the group consisting of amino, halo, hydroxyl, —$SR^{10}$, —$C(O)NH_2$, —$C(S)NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl $(OCH_2CH_2)_{1-6}O$—, halo-$C_{1-5}$alkoxy, halo-$C_{1-3}$alkyl $(OCH_2CH_2)_{1-6}O$— and halo-$CH_2CH_2O$—; or at least one of $R^1$ and $R^2$, $R^2$ and $R^3$ or $R^3$ and $R^4$ together with the carbon atoms to which they are attached to, form a substituted or unsubstituted aromatic or non-aromatic carbocyclic or heterocyclic ring;

provided that at least any two of $R^1$, $R^2$, $R^3$ and $R^4$ are hydrogens;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$(CH_2 CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—; and each $R^{10}$ is independently H or $C_{1-6}$alkyl.

In another embodiment, there is provided a radiolabel compound of the formula VI:

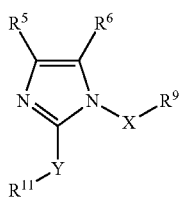

VI wherein:

X is a bond or is selected from the group consisting of $C_{1-6}$alkylenyl, —$C(O)$—, —$C(S)$—, —$C(O)O$—, —$C(S)O$—, —$N(R^{10})C(O)$—, —$N(R^{10})C(S)$—, —$S(O)N(R^{10})$— and —$N(R^{10})S(O)_2$—;

Y is a bond or is selected from the group consisting of amino, halo, cyano, nitro, hydroxyl, —$SR^{10}$, —$C(O)NH_2$, —$C(S)NH_2$, halo-$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2 CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$cycloalkyl$C_{1-5}$alkoxy, heteroaryl $C_{2-5}$alkoxy, $C_{6-14}$aryloxy, $C_{6-10}$aryl$C_{1-4}$alkoxy and heteroaryloxy;

$R^5$ and $R^6$ are each independently hydrogen or are each independently selected from the group consisting of amino, halo, cyano, nitro, hydroxyl, —$SR^{10}$—$C(O)NH_2$, —$C(S) NH_2$, halo$C_{1-6}$alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl $C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$—, halo-$CH_2CH_2O$—, $C_{3-6}$cycloalkoxy, $C_{3-12}$ cycloalkyl $C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkyl$NR^{10}C(O)$—, $(C_{1-6}$alkyl$)_2NC(O)CH(C_{1-5}$alkyl)-, halo-$C_{1-6}$alkyl$NR^{10}C(O)CH(C_{1-5}$alkyl)-, halo-$C_{1-6}$alkyl$OC (O)CH(C_{1-5}$alkyl)-, halo-$C_{1-5}$alkyl$NR^{10}C(O)$—, $C_{1-5}$alkyl$NR^{10}C(O)O$—, $C_{1-5}$alkyl$C(O)$—, $C_{1-5}$alkyl$C(O) O$—, $C_{6-10}$aryl$C(O)$— and $C_{6-10}$aryl$C(O)O$—; or $R^5$ and $R^6$ together with the carbon atoms to which they are attached to, form a substituted or unsubstituted aromatic or non-aromatic carbocyclic or heterocyclic ring;

$R^9$ is hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$(CH_2 CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—;

each $R^{10}$ is independently H or $C_{1-6}$alkyl;

$R^{11}$ is a hydrogen or is selected from the group consisting of halo, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$(CH_2 CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—;

provided that at least one of $R^1$ to $R^{11}$ comprises a radiolabel, as defined herein;

wherein the radiolabel comprises a radionuclide selected from the group consisting of $^{11}C$, $^{11}C$, $^{13}N$, $^{15}O$, $^{18}F$, $^{123}I$, $^{124}I$, $^{125}I$, $^{131}I$ and $^{77}Br$; and pharmaceutically acceptable salts thereof.

In one variation of the above compound, X is a bond or is selected from the group consisting of $C_{1-6}$alkylenyl, —$C(O)$—, —$C(O)O$—;

Y is a bond or is selected from the group consisting of amino, halo, —$SR^{10}$—$C(O)NH_2$, —$C(S)NH_2$, halo$C_{1-6}$ alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$-aryl$C_{1-4}$alkyl, heteroaryl, $C_{1-5}$alkoxy, $H(OCH_2CH_2)_{1-6}O$—, $C_{1-3}$alkyl$(OCH_2CH_2)_{1-6}O$—, halo-$C_{1-5}$alkoxy, halo-$C_{1-3}$alkyl$(OCH_2CH_2)_{1-6}O$— and halo-$CH_2CH_2O$—;

$R^5$ and $R^6$ are each independently hydrogen or are each independently selected from the group consisting of amino, halo, hydroxyl, —$SR^{10}$—$C(O)NH_2$, —$C(S)NH_2$, halo-$C_{1-6}$ alkyl, perhalo$C_{1-6}$alkyl, $C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $C_{1-5}$alkoxy, $H(OCH_2CH_2)_{1-6}O$—, $C_{1-3}$alkyl$(OCH_2 CH_2)_{1-6}O$—, halo-$C_{1-5}$alkoxy, halo-$C_{1-3}$alkyl$(OCH_2 CH_2)_{1-6}O$—, halo-$CH_2CH_2O$—, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, heteroaryloxy, $C_{1-5}$alkyl$NR^{10}C(O)$—, $(C_{1-6}alkyl)_2NC(O)CH(C_{1-5}alkyl)$-, halo-$C_{1-6}alkylNR^{10}C(O)$ $CH(C_{1-5}alkyl)$-, halo-$C_{1-6}alkylOC(O)CH(C_{1-5}alkyl)$-, halo-$C_{1-5}alkylNR^{10}C(O)$—, $C_{1-5}alkylNR^{10}C(O)O$—, $C_{1-5}alkylC(O)$—, $C_{1-5}alkylC(O)O$—, $C_{6-10}arylC(O)$— and $C_{6-10}arylC(O)O$—;

$R^9$ is hydrogen or is selected from the group consisting of halo, $C_{1-6}alkyl$, $C_{3-6}cycloalkyl$, $C_{3-12}cycloalkylC_{1-5}alkyl$, $C_{6-14}aryl$, $C_{6-10}$-$arylC_{1-4}alkyl$, halo-$(CH_2CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—; and $R^{11}$ is absent, a hydrogen or is selected from the group consisting of halo, $C_{1-6}alkyl$, $C_{3-6}cycloalkyl$, $C_{3-12}cycloalkylC_{1-5}alkyl$, $C_{6-14}aryl$, $C_{6-10}arylC_{1-4}alkyl$, halo-$(CH_2CH_2)_{1-6}$—; halo-$CH_2CH_2$—$(OCH_2CH_2)_{1-6}$—, halo-$CH_2CH_2$—$(OCH_2CH_2)_{1-6}O(CO)$— and halo-$CH_2CH_2$—$(OCH_2CH_2)_{1-6}(CO)$—.

In another variation of the above, X is a bond or is selected from the group consisting of $C_{1-6}alkylenyl$, —C(O)—, —C(O)O—;

Y is a bond or is selected from the group consisting of amino, halo, hydroxyl, —$SR^{10}$, —$C(O)NH_2$, —$C(S)NH_2$, halo-$C_{1-6}alkyl$, perhalo$C_{1-6}alkyl$, $C_{1-6}alkyl$, $C_{3-6}cycloalkyl$, $C_{3-12}cycloalkylC_{1-5}alkyl$, $C_{6-14}aryl$, $C_{6-10}$-$arylC_{1-4}alkyl$, heteroaryl, $C_{1-5}alkoxy$, $H(OCH_2CH_2)_{1-6}O$—, $C_{1-3}alkyl(OCH_2CH_2)_{1-6}O$—, halo-$C_{1-5}alkoxy$, halo-$C_{1-3}alkyl(OCH_2CH_2)_{1-6}O$—, halo-$CH_2CH_2O$—, $C_{3-6}cycloalkoxy$, $C_{3-12}cycloalkylC_{1-5}alkoxy$, heteroaryl$C_{2-5}alkoxy$, $C_{6-14}aryloxy$, $C_{6-10}arylC_{1-4}alkoxy$ and heteroaryloxy when $R^{11}$ is absent; and $R^5$ and $R^6$ are each independently hydrogen or are each independently selected from the group consisting of halo-$C_{1-5}alkoxy$, halo-$C_{1-3}alkyl(OCH_2CH_2)_{1-6}O$—, halo-$CH_2CH_2O$—, halo-$CH_2CH_2$—$(OCH_2CH_2)_{1-6}O$—, halo-$C_{1-6}alkylNR^{10}C(O)CH(C_{1-5}alkyl)$-, halo-$C_{1-6}alkylOC(O)CH(C_{1-5}alkyl)$- and halo-$C_{1-5}alkylNR^{10}C(O)$—.

In a particular variation of each of the above embodiments, aspects and variations, all of the variables $R^1$ to $R^{12}$ are not all hydrogens. In a particular variation of each of the above, the halo group is fluorine. In another variation of each of the above, the radionuclide is $^{18}F$ or $^{11}C$.

In another embodiment, there is provided a pharmaceutical composition for in vivo imaging of amyloid deposits, comprising (a) a compound of any one of the above, and (b) a pharmaceutically acceptable carrier. In another embodiment, there is provided a method of diagnosing Alzheimer's Disease or a predisposition thereto in a mammal, the method comprising: a) administering to the mammal a diagnostically effective amount of a radiolabeled compound, wherein the compound passes the blood-brain barrier and preferentially binds to a soluble AD oligomers, polymers and fibrils in a brain tissue and wherein the compound is selected from the group consisting of radiolabeled flavones, coumarins, carbazoles, quinolinones, chromenones, imidazoles and triazoles and their derivatives; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease. In one variation of the above method, the compound is a compound of any one of the above disclosed compounds.

In another embodiment, there is provided a method of diagnosing Alzheimer's Disease or a predisposition thereto in a mammal, the method comprising: a) administering to the mammal a diagnostically effective amount of a radiolabeled compound or composition of any one of the above, wherein the compound passes the blood-brain barrier and preferentially binds to a soluble AD oligomers, polymers and fibrils in a brain tissue; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease. In one variation of the above method, wherein the radiolabeled compound preferentially binds to fibrils. In another variation of the above, the brain tissue comprises a frontotemporal region or the hippocampal region. In a particular variation of the above method, the increase in binding is at least 10% greater than said normal control value. In another variation of each of the above methods, the compound is administered by intravenous injection.

In another embodiment, there is provided a method for detecting Alzheimer's Disease or a predisposition thereto in a living brain of a mammal, the method comprising: a) administering the mammal with a diagnostically effective amount of a radiolabeled compound that passes the blood-brain barrier and preferentially binds to a soluble AD oligomers, polymers and fibrils in the brain, wherein the detectably-labeled compound is a compound of any one of the above; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, there is provided a method for detecting Alzheimer's Disease or a predisposition thereto in a living brain of a mammal, the method comprising: a) administering the mammal with a diagnostically effective amount of a radiolabeled compound of any one of the above, wherein the compound passes the blood-brain barrier and preferentially binds to a soluble AD oligomers, polymers and fibrils in the brain; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, there is provided a method of diagnosing Alzheimer's Disease or a predisposition thereto in a mammal, the method comprising: a) administering to the mammal a diagnostically effective amount of a radiolabeled compound, wherein the compound passes the blood-brain barrier and preferentially binds to a soluble or insoluble AD oligomers, polymers, fibrils, hyperphosphorylated tau, neurofibrillary tangles, paired helical filaments and/or neurotoxic soluble oligomers in a brain, and wherein the radiolabeled compound is a compound as disclosed herein; and (b) employing a nuclear imaging technique selected from the group consisting of positron emission tomography (PET) and single photon emission computed tomography (SPECT) for monitoring or visualizing a distribution of the radiolabeled compound within the brain or within a portion thereof. In one variation of the above method, the radiolabeled compound or a derivative thereof, is a compound of any one of the above compounds. In yet another embodiment, there is provided a method for treating a disease or condition, in a mammal in need thereof, selected from the group consisting of anxiety, depression, schizophrenia, Alzheimer's Disease, stress-related disease, panic, a phobia, obsessive compulsive disorder, obesity, post-traumatic stress syndrome, or epilepsy comprising administering to the mammal a therapeutically effective amount of a compound of any one of the above. In one variation, the compound is a non-radiolabeled compound of any one of the above compounds. In another variation, the compound is administered rectally, topically, orally, sublingually or parenterally. In one variation, the compound is administered from about 0.001 to about 100 mg/kg of body weight of the mammal per day. In another variation, the compound is administered from about 0.1 to about 50 mg/kg of body weight of the mammal per day. In another variation of each of the above methods, the compound is selected from the group consisting of flavones, coumarins, carbazoles, quinolinones, chromenones, imidazoles and triazoles and their derivatives.

In one aspect, for the methods of detection that accurately detect early onset AD prior to clinical symptomology, the focus may be directed to targeting senile plaque precursors, rather than the plaques and/or fibrils themselves. Accordingly, a potentially more effective strategy for detecting and possibly treating AD, would rely on the detection of biomarkers such as neurotoxic soluble oligomers, which are linked to AD-related synaptic and neuronal damage, rather than the late-stage plaque, and fibril biomarkers associated with fully advanced AD.

TABLE 1

Known AD positive fluorescent dyes and imaging agents

| Name | Compound and Reference | Target | Binding Affinity |
|---|---|---|---|
| Congo Red | 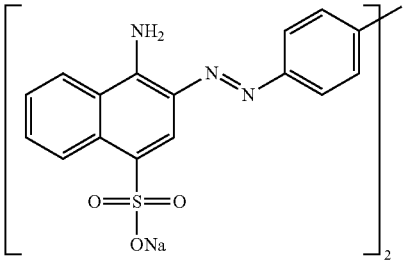<br>*Anal. Biochem.* 2006, 356, 265-272;<br>*J. Biol. Chem.* 2005, 280, 5892-5901 | Aβ monomer | $IC_{50}$: 2-10 uM |
| Curcumin | 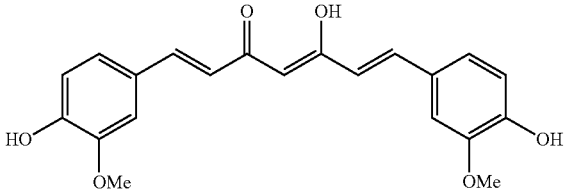<br>*Anal. Biochem.* 2006, 356, 265-272;<br>*J. Biol. Chem.* 2005, 280, 5892-5901 | Aβ monomer | $IC_{50}$: 10-20 uM |
| ANS | 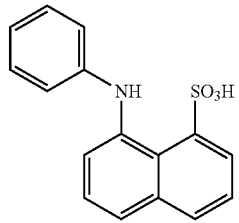<br>*Anal. Biochem.* 2006, 356, 265-272 | Aβ monomer | $IC_{50}$: >100 uM |
| Thioflavin T | 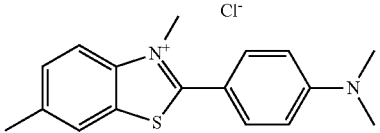<br>*Anal. Biochem.* 2006, 356, 265-272 | Aβ monomer | $IC_{50}$: >500 uM |

TABLE 1-continued

Known AD positive fluorescent dyes and imaging agents

| Name | Compound and Reference | Target | Binding Affinity |
|---|---|---|---|
| Iodinated Flavone | 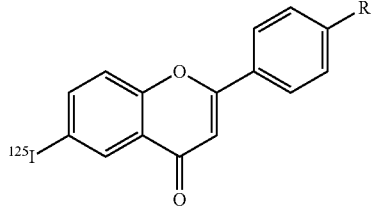<br>*J. Med. Chem.* 2005, 48, 7253-7260<br>R = NHMe, NMe$_2$, OMe, OH | Aβ40 aggregates | Ki = 13 nM (—NMe2) to 72 nM (—OH) |
| Pyridyl Styrene | 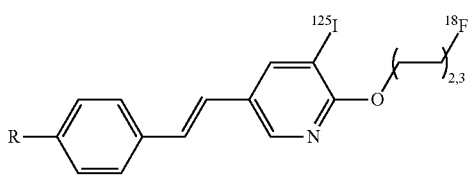<br>*J. Med. Chem.* 2007, 50, 2157-2165<br>R = NHMe, NMe$_2$ | Aβ fibrils | Kd = 7.5-9 nM |
| Diaryl acetylenes | 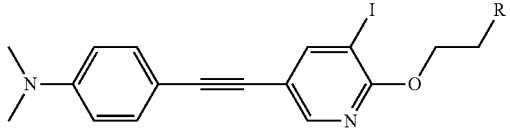<br>*Bioorg. Med. Chem.* 2007, 17, 3581-3584<br>R = —OH, —OCH$_2$CH$_2$—O—CH$_2$CH$_2$F | Aβ plaques | Kd = ~10 nM |
| Thiophene chalcones | 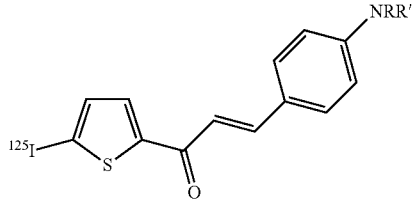<br>*Bioorg. Med. Chem.* 2007, 15, 6802-6809<br>R,R' = H, Me | Aβ 1-42 aggregates | Ki = 3.9-14 nM |
| Aurones | 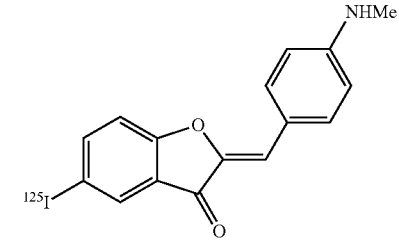<br>*Biochem. Biophys. Res. Commun.* 2007, 361, 116-121 | Aβ 1-42 aggregates | Ki = 1.24 nM |
| PIB | 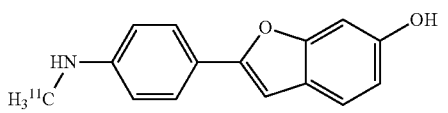<br>*J. Med. Chem.* 2006, 49, 2725-2730 | Aβ fibrils | Ki = 2.8 nM |

An assay was developed using a Biacore instrument that introduced screening ligands over gold-surface immobilized target proteins and measured the resultant rates of association and disassociation in order to screen various compounds that bind to soluble AD oligomers, polymers and fibrils. In FIG. 1, the left hand portion of the curve represents the binding of ligands to a specific substrate. The right portion of the curve represents the dissociation of the ligand from the substrate. Ligands that associated quickly and dissociated slowly, relative to a control ligand, were considered hits.

Figure 2:
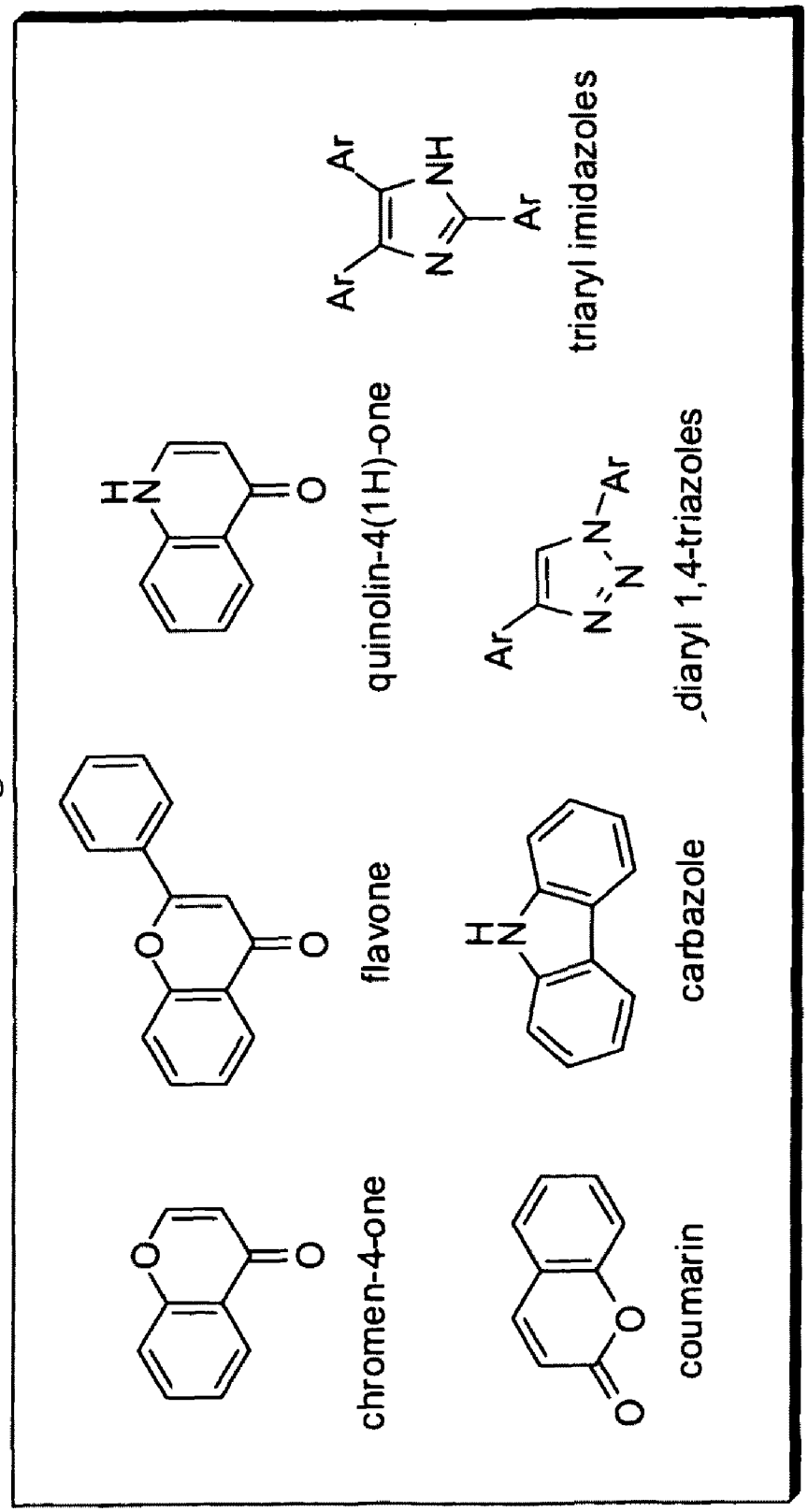
FIG. 2 shows representative scaffolds for compounds found to bind oligomer, polymers and/or fibrils.

Several hundred compounds were screened in a similar fashion and several common classes of compounds were identified as hits falling into seven common chemotypes: flavones, coumarins, carbazoles, quinolinones, chromenones, imidazoles and triazoles (FIG. 2).

From the screening library, 38 compounds were identified as binders to Aβ42 oligomers/soluble polymers (Table 2). Among these 38 compounds, 23 compounds bound to Aβ42 synthetic fibrils. Several compounds belonging to the flavone and coumarin architectures, bound very strongly to oligomers, polymers and fibrils. Chromenes, carbazoles and diaryl triazoles were found to bind to oligomers and polymers preferentially over fibrils. Several of these compounds can be prepared as radiolabeled analogs for use in detecting biomarkers in patients with AD.

TABLE 2

Compounds identified as binders to oligomers, polymers and/or fibrils.

| | BINDING LEVELS TO | |
|---|---|---|
| | $A\beta_{(1-42)}$ Oligomers/Polymers | $A\beta_{(1-42)}$ Fibrils |
| #25: 5-Amino-2-(trifluoromethyl)benzimidazole | ++ | + |
| #40: 6-Hydroxyflavone | ++ | + |
| #41: 7-Hydroxyflavone | + | + |
| #42: 3,6-Dihydroxyflavone | +++ | ++ |
| #44: Fisetin | ++++++ | +++++ |

TABLE 2-continued

Compounds identified as binders to oligomers, polymers and/or fibrils.

| | BINDING LEVELS TO | |
|---|---|---|
| | $A\beta_{(1-42)}$ Oligomers/Polymers | $A\beta_{(1-42)}$ Fibrils |
| #51: 5-methoxyflavone | + | − |
| #54: Harmol | ++ | + |
| #55: 2-Hydroxycarbazole | +++ | + |
| #73: 7,8-Dihydroxy-4-phenylcoumarin | +++++ | +++ |
| #75: 7-Hydroxy-4-methyl-3-phenylcoumarin | + | − |
| #84: 1-Chloro-4-hydroxyisoquinoline | + | − |

TABLE 2-continued

Compounds identified as binders to oligomers, polymers and/or fibrils.

| | BINDING LEVELS TO | |
|---|---|---|
| | $A\beta_{(1-42)}$ Oligomers/Polymers | $A\beta_{(1-42)}$ Fibrils |
| #89: 2-(5-Isoxazolyl)-4-methylphenol | + | + |
| #97: 1-Methyl-6,7-dihydroxy-1,2,3,4-tetrahydroisoquinol | ++ | + |
| #162: 5-Amino-8-hydroxyquinoline | ++ | + |
| #194: 7-Hydroxy-2-methyl-3-(4-phenyl-4H-1,2,4-triazol-3- | ++ | + |
| #197: 7-Ethoxy-2-methyl-3-phenoxy-4H-chromen-4-one | + | + |
| #199: 3-(4-Ethoxyphenoxy)-7-hydroxy-2-methyl-4H-chromen- | + | − |
| #200: 6-Ethyl-3-(4-fluorophenyl)-7-hydroxy-2-methyl-4H-c | + | − |

TABLE 2-continued
Compounds identified as binders to oligomers, polymers and/or fibrils.
| | BINDING LEVELS TO | |
|---|---|---|
| | $A\beta_{(1-42)}$ Oligomers/Polymers | $A\beta_{(1-42)}$ Fibrils |
201: 7,8-Dimethoxy-2-methyl-3-phenyl-4H-chromen-4-one
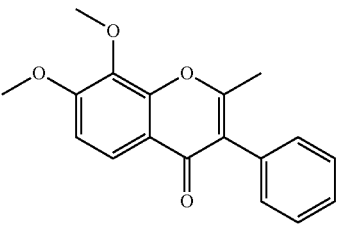
+ / −
202: 7-Hydroxy-2,8-dimethyl-3-(4-phenyl-4H-1,2,4-triazo
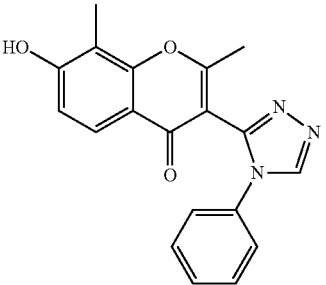
++ / −
203: 3-Hydroxy-2-phenylquinolin-4(1H)-one
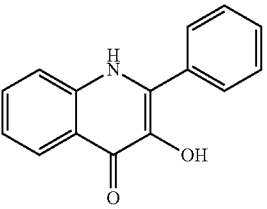
++++ / ++
204: 7-Hydroxy-3-methyl-2-phenyl-4H-chromen-4-one
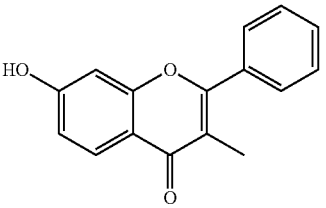
+ / +
205: 2-(3,4-Dimethoxyphenyl)-3,6-dimethoxy-4H-chromen-4
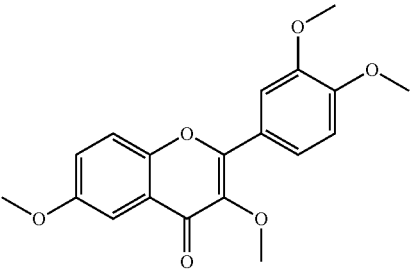
+++ / +

TABLE 2-continued

Compounds identified as binders to oligomers, polymers and/or fibrils.

| | BINDING LEVELS TO | |
|---|---|---|
| | $A\beta_{(1-42)}$ Oligomers/Polymers | $A\beta_{(1-42)}$ Fibrils |
| #206: 3,7-Dimethoxy-2-(3-methoxyphenyl)-4H-chromen-4-one | + | − |
| #207: 3,6-Dihydroxy-2-(3-hydroxyphenyl)-4H-chromen-4-one | ++++ | ++ |
| #209: 3-(4-Fluorophenyl)-7-hydroxy-2-methyl-4H-chromen-4 | + | + |
| #214: 2-(Furan-2-yl)-3-methoxy-4H-chromen-4-one | + | + |
| #216: 2-(Furan-2-yl)-3-hydroxy-6,8-dimethyl-4H-chromen-4 | + | − |
| #217: 3-Hydroxy-6,8-dimethyl-2-(thiophen-2-yl)-4H-chrome | + | − |

TABLE 2-continued
Compounds identified as binders to oligomers, polymers and/or fibrils.
| | BINDING LEVELS TO | |
|---|---|---|
| | $A\beta_{(1-42)}$ Oligomers/Polymers | $A\beta_{(1-42)}$ Fibrils |
| #236: A4B6 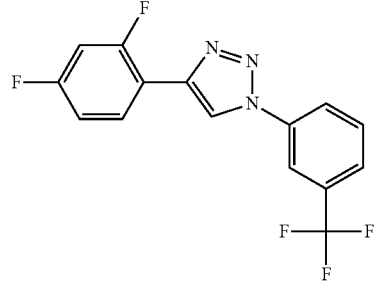 | + | + |
| #237: A4B7 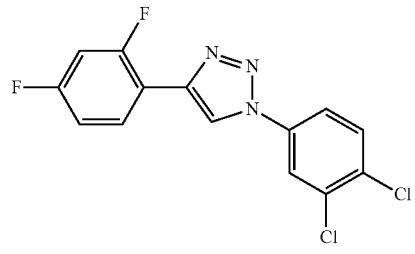 | + | − |
| #238: A5B2 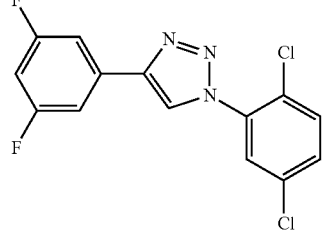 | + | − |
| #239: A5B4 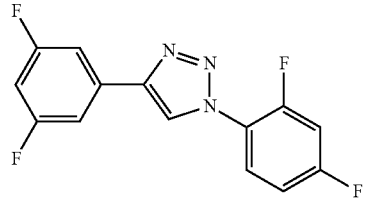 | ++++ | − |
| #6: A2B5 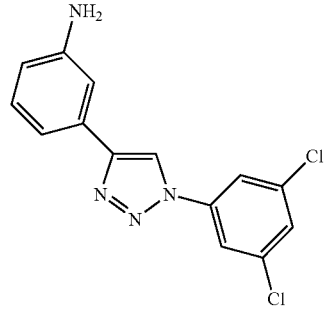 | + | + |

TABLE 2-continued

Compounds identified as binders to oligomers, polymers and/or fibrils.

| | BINDING LEVELS TO | |
|---|---|---|
| | Aβ$_{(1-42)}$ Oligomers/Polymers | Aβ$_{(1-42)}$ Fibrils |
| #261: 4-(4-(4-Fluorophenyl)-2-(4-nitrophenyl)-1H-imidazo | + | − |
| #262: 4-(4-(4-Fluorophenyl)-2-(4-(methylsulfinyl)phenyl) | ++ | + |
| #263: 4-(5-(4-Fluorophenyl)-4-(pyridin-4-yl)-1H-imidazol | ++ | ++ |
| #268: 2-(4-Fluorophenyl)-4,5-diphenyl-1H-imidazole | +/− | − |

A "+" sign represents a hit and the increase in "+" signs relates to increasing binding affinity.
A "−" sign represents no binding.

Table 3 provides examples of imaging agents derived from the hit scaffolds. Fluorides are shown in the structures as equivalent to $^{18}$F-fluoride and methyl groups are equivalent to $^{11}$C-carbon methyl groups.

TABLE 3

Examples of radiolabeled analogs useful for detecting AD biomarkers in vivo.

| Name | Structure | Chemical Formula | MW | Code |
|---|---|---|---|---|
| 2-(2-fluoroethoxy)-9H-carbazole | 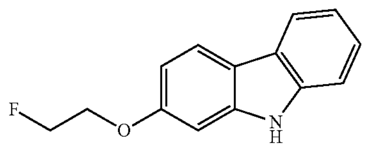 | $C_{14}H_{12}FNO$ | 229.25 | CB-001 |
| 9-(2-fluoroethyl)-9H-carbazole-2-ol | 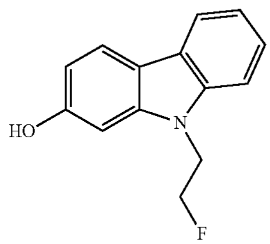 | $C_{14}H_{12}FNO$ | 229.25 | |
| N-(2-fluoroethyl-7-(2-(2-(2-methoxyethoxy)ethoxy)ethoxy)-9H-carbazol-3-amine | 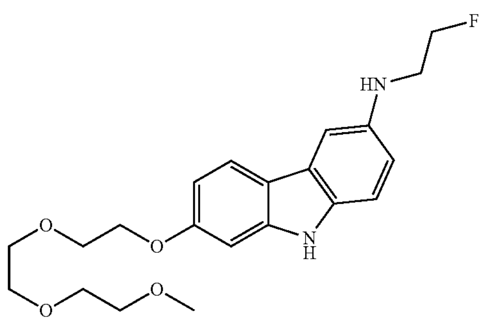 | $C_{21}H_{27}FN_2O_4$ | 390.45 | |
| 7-(2-fluoroethoxy)-N,N-dimethyl-9H-carbazol-2-amine | 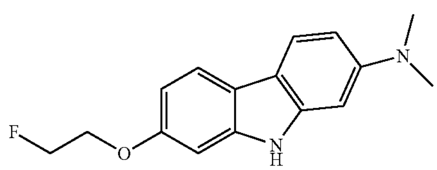 | $C_{16}H_{17}FN_2O$ | 272.32 | |
| 7-(2-(2-(2-fluoroethoxy)ethoxy)ethoxy)-N-methyl-9H-carbazol-3-amine | | $C_{19}H_{23}FN_2O_3$ | 346.40 | CB-008 |
| 1-(3,6-diamino-9H-carbazol-9-yl)-3-(2-(2-(2-fluoroethoxy)ethoxy)ethoxy)-propan-1-one | | $C_{21}H_{26}FN_3O_4$ | 403.45 | |

TABLE 3-continued

Examples of radiolabeled analogs useful for detecting AD biomarkers in vivo.

| Name | Structure | Chemical Formula | MW | Code |
|---|---|---|---|---|
| N-(2-fluroethyl)-2-hydroxy-11H-benzo[a]carbazole-3-carboxamide | 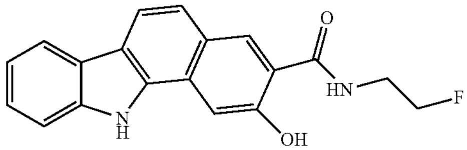 | $C_{19}H_{15}FN_2O_2$ | 322.33 | |
| 2-(6-chloro-9H-carbazol-2-yl)-N-(2-fluoro-ethyl)propanamide | 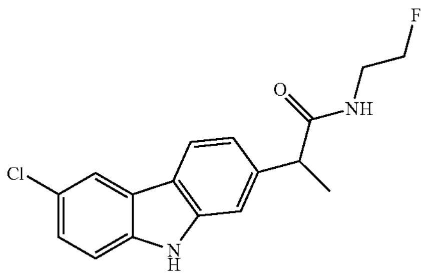 | $C_{17}H_{16}ClFN_2O$ | 318.77 | |
| 2-(6-fluoro-9H-carbazol-2-yl)-N,N-dimethyl-propanamide | 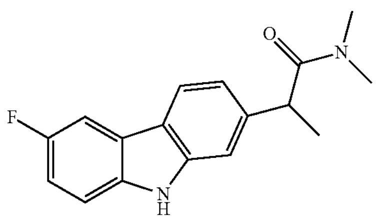 | $C_{17}H_{17}FN_2O$ | 284.33 | |
| 2-methoxy-9H-carbazole | 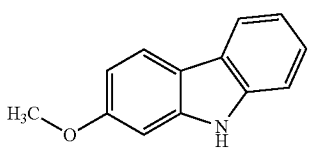 | $C_{13}H_{11}NO$ | 197.23 | |
| 6-iodo-2-methoxy-9H-carbazole | 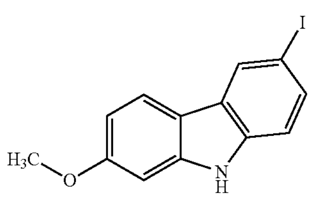 | $C_{13}H_{10}INO$ | 323.13 | |
| 7-(2-fluoroethoxy)-N,N-dimethyl-9H-carbazol-2-amine | 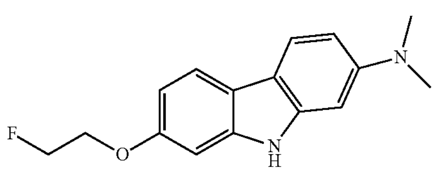 | $C_{16}H_{17}FN_2O$ | 272.32 | |
| tert-butyl 2-(2-(2-(2-fluoroethoxy)-ethoxy)ethoxy)-9H-carbazole-9-carboxylate | 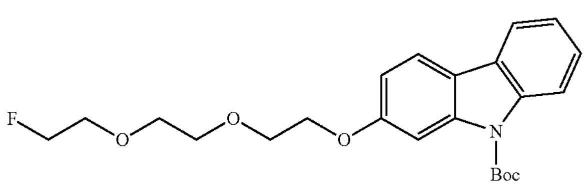 | $C_{23}H_{28}FNO_5$ | 417.47 | CB-005 |
| 2-(2-(2-(2-fluoroethoxy)-ethoxy)ethoxy)-9-methyl-9H-carbazole | 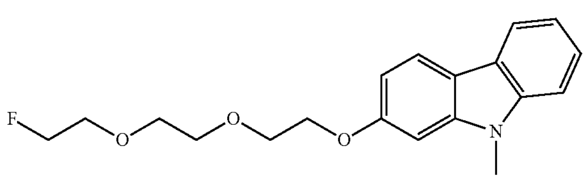 | $C_{19}H_{22}FNO_3$ | 331.38 | CB-006 |

TABLE 3-continued

Examples of radiolabeled analogs useful for detecting AD biomarkers in vivo.

| Name | Structure | Chemical Formula | MW | Code |
|---|---|---|---|---|
| 7-(2-(2-(2-fluoroethoxy-ethoxy)ethoxy)-N,N-dimethyl-9H-carbazol-2-amine | 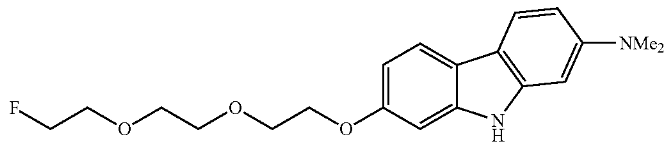 | $C_{20}H_{25}FN_2O_3$ | 360.42 | CB-007 |
| N-(7-(2-(2-(2-fluoroethoxy)-ethoxy)ethoxy)-9H-carbazol-2-yl)acetamide | 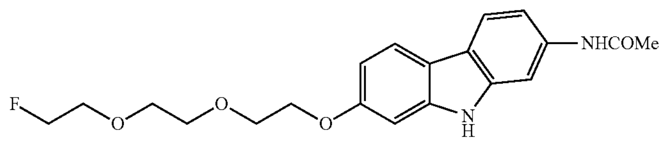 | $C_{20}H_{23}FN_2O_4$ | 374.41 | CB-009 |
| 7-(2-(2-(2-fluoroethoxy)-ethoxy)ethoxy)-9H-pyrido[2,3-b]indole | 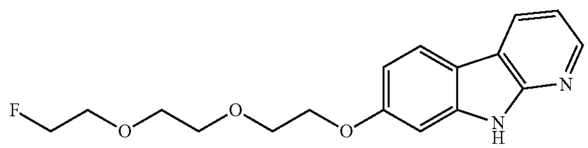 | $C_{17}H_{19}FN_2O_3$ | 318.34 | CB-028 |
| 2-(2-(2-(2-fluoroethoxy)-ethoxy)ethoxy)-9H-carbazole | 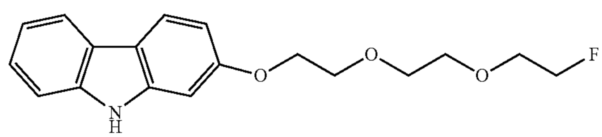 | $C_{18}H_{20}FNO_3$ | 317.35 | CB-003 |
| 7-(2-(2-(2-fluoroethoxy)-ethoxy)ethoxy)-N-methyl-9H-carbazol-2-amine | 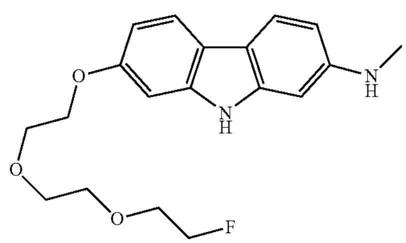 | $C_{19}H_{23}FN_2O_3$ | 346.40 | CB-004 |
| N-(7-(2-(2-(2-fluoroethoxy)-ethoxy)ethoxy)-9H-carbazol-2-yl)formamide | 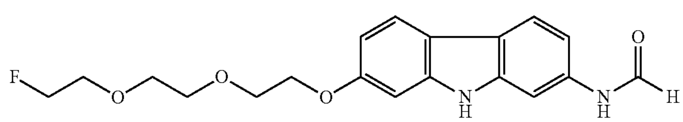 | $C_{19}H_{21}FN_2O_4$ | 360.38 | CB-010 |
| 6-(2-(2-(2-fluoroethoxy)-ethoxy)ethoxy)-9-(methoxymethyl)-N,N-dimethyl-9H-carbazol-3-amine | 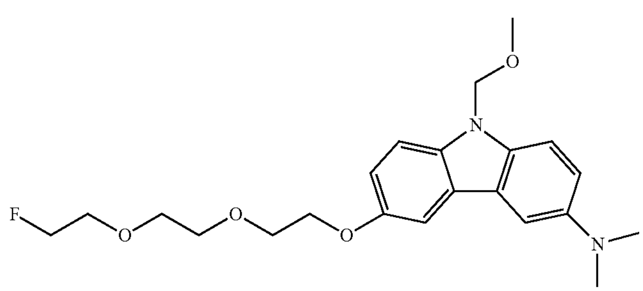 | $C_{22}H_{29}FN_2O_4$ | 404.48 | CB-011 |
| N-(7-(2-fluoroethoxy)-9H-carbazol-2-yl)formamide | 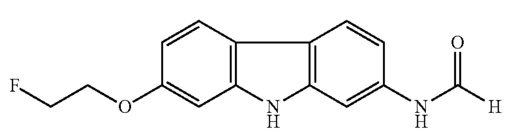 | $C_{15}H_{13}FN_2O_2$ | 272.27 | CB-012 |
| N-(7-(2-(2-fluoroethoxy)ethoxy)-9H-carbazol-2-yl)formamide | | $C_{17}H_{17}FN_2O_3$ | 316.33 | CB-024 |

TABLE 3-continued

Examples of radiolabeled analogs useful for detecting AD biomarkers in vivo.

| Name | Structure | Chemical Formula | MW | Code |
|------|-----------|------------------|-----|------|
| N-(2-fluoroethyl)-6-methoxy-9H-carbazol-3-amine | 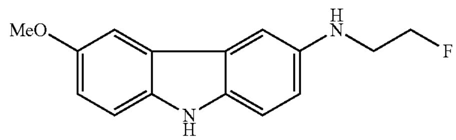 | $C_{15}H_{15}FN_2O$ | 258.29 | CB-013 |
| 7-((4-fluorobutyl)-(methyl)amino)-9H-carbazol-2-ol | 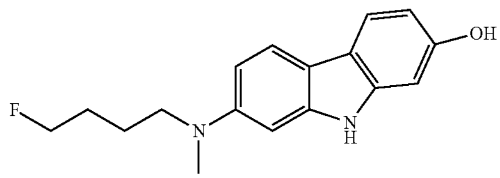 | $C_{17}H_{19}FN_2O$ | 286.34 | CB-014 |
| 7-((2-fluoroethyl)-(methyl)amino)-9H-carbazol-2-ol | 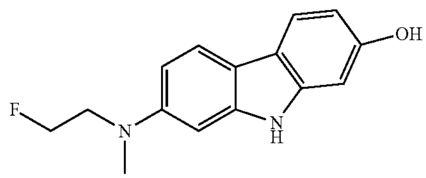 | $C_{15}H_{15}FN_2O$ | 258.29 | CB-015 |
| 7-(2-fluoro-ethylamino)-9H-carbazol-2-ol | 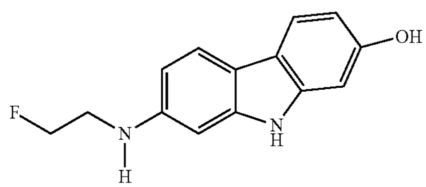 | $C_{14}H_{13}FN_2O$ | 244.26 | CB-016 |
| 7-((2-(2-(2-fluoroethoxy)-ethoxy)ethyl)-(methyl)amino)-9H-carbazol-2-ol | 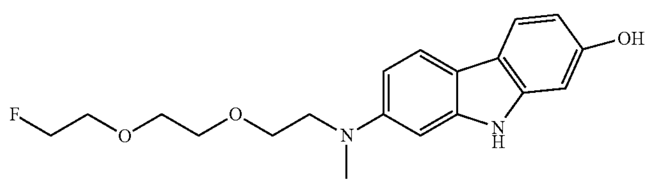 | $C_{19}H_{23}FN_2O_3$ | 346.40 | CB-019 |
| 7-(2-fluoroethoxy)-N-methyl-9H-carbazol-2-amine | 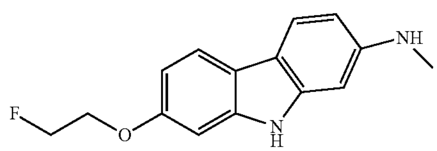 | $C_{15}H_{15}FN_2O$ | 258.29 | CB-020 |
| 7-(2-fluoro-ethoxy)-9H-carbazol-2-ol | 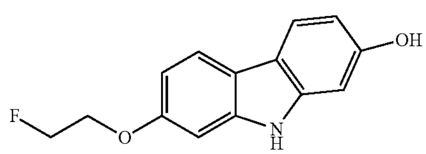 | $C_{14}H_{12}FNO_2$ | 245.25 | CB-025 |
| 7-(2-(2-(2-fluoroethoxy)-ethoxy)ethoxy)-9H-carbazol-2-ol | 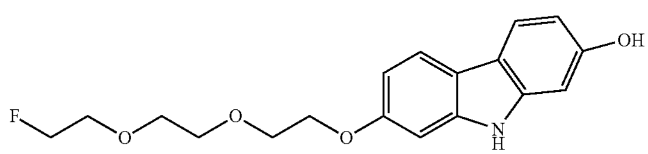 | $C_{18}H_{20}FNO_4$ | 333.35 | CB-026 |
| N-(4-(7-amino-9H-carbazol-2-yloxy)phenyl)-2-fluoropropanamide | 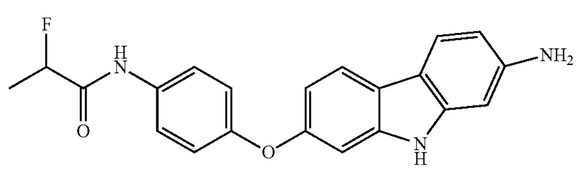 | $C_{21}H_{18}FN_3O_2$ | 363.38 | CB-027 |

TABLE 3-continued

Examples of radiolabeled analogs useful for detecting AD biomarkers in vivo.

| Name | Structure | Chemical Formula | MW | Code |
|---|---|---|---|---|
| 1-(2-(2-(2-(2-fluoroethoxy)ethoxy)ethoxy)-9H-carbazol-9-yl)ethanone | | $C_{20}H_{22}FNO_4$ | 359.39 | CB-017 |
| (2-(2-(2-(2-fluoroethoxy)ethoxy)ethoxy)-9H-carbazol-9-yl)(phenyl)methanone | | $C_{25}H_{24}FNO_4$ | 421.46 | CB-021 |
| 2-fluoro-N-(4-(7-(methylamino)-9H-carbazol-2-yloxy)phenyl)propanamide | | $C_{22}H_{20}FN_3O_2$ | 377.41 | CB-029 |
| N-(7-(4-fluorobutoxy)-9H-carbazol-2-yl)formamide | | $C_{17}H_{17}FN_2O_2$ | 300.33 | CB-030 |
| tert-butyl 2-(2-(2-(2-fluoroethoxy)ethoxy)ethoxy)-9H-pyrido[2,3-b]indol-7-ylcarbamate | | $C_{22}H_{28}FN_3O_5$ | 433.47 | CB-031 |
| 2-(2-(2-(2-fluoroethoxy)ethoxy)ethoxy)-9H-pyrido[2,3-b]indol-7-amine | | $C_{17}H_{20}FN_3O_3$ | 333.36 | CB-032 |
| 7-(benzyloxy)-N-(2-fluoroethyl)-N-methyl-9H-carbazol-2-amine | | $C_{22}H_{21}FN_2O$ | 348.41 | CB-033 |
| 2-(2-(2-(2-fluoroethoxy)ethoxy)ethoxy)-N-methyl-9H-pyrido[2,3-b]indol-7-amine | | $C_{18}H_{22}FN_3O_3$ | 347.38 | CB-034 |
| 6-bromo-9H-carbazol-2-ol | | $C_{12}H_8BrNO$ | 262.10 | |

TABLE 3-continued
Examples of radiolabeled analogs useful for detecting AD biomarkers in vivo.
| Name | Structure | Chemical Formula | MW | Code |
|---|---|---|---|---|
| 8-(2-fluoroethoxy)-7-hydroxy-4-phenyl-2H-chromen-2-one | 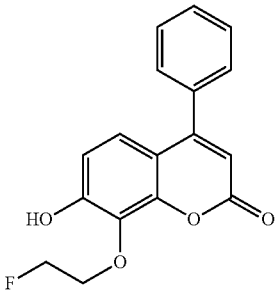 | $C_{17}H_{13}FO_4$ | 300.28 | |
| 2-(4-(2-fluoroethoxy)-3-hydroxyphenyl)-3,7-dihydroxy-4H-chromen-4-one | 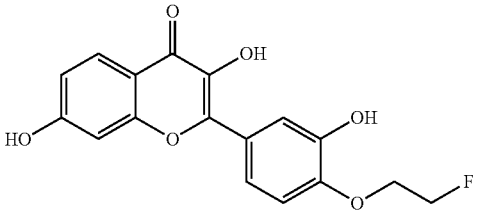 | $C_{17}H_{13}FO_6$ | 332.28 | |
| 7-(2-fluoroethoxy)-8-hydroxy-4-phenyl-2H-chromen-2-one | 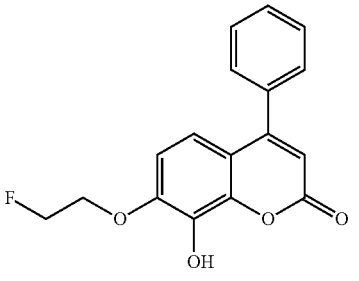 | $C_{17}H_{13}FO_4$ | 300.28 | |
| 4-(4-(2-fluoroethoxy)phenyl)-7,8-dihydroxy-2H-chromen-2-one | 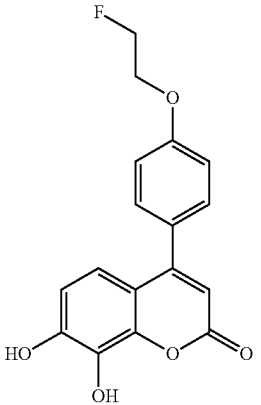 | $C_{17}H_{13}FO_5$ | 316.28 | |

TABLE 3-continued

Examples of radiolabeled analogs useful for detecting AD biomarkers in vivo.

| Name | Structure | Chemical Formula | MW | Code |
|---|---|---|---|---|
| 4-(4-(2-fluoroethylamino)-phenyl)-7,8-dihydroxy-2H-chromen-2-one | 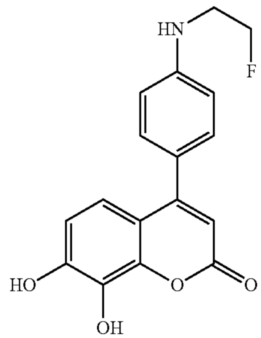 | $C_{17}H_{14}FNO_4$ | 315.30 | |
| 4-(3,4-dihydroxy-phenyl)-7-(2-fluoroethoxy)-8-hydroxy-2H-chromen-2-one | 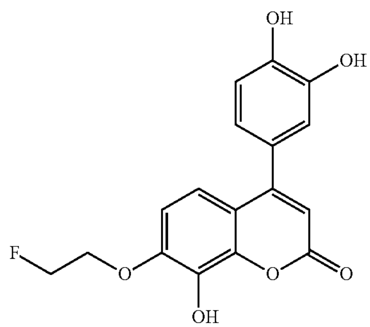 | $C_{17}H_{13}FO_6$ | 332.28 | |
| 7-(2-(2-(2-fluoro-ethoxy)ethoxy)-8-hydroxy-4-(4-hydroxyphenyl)-2H-chromen-2-one | 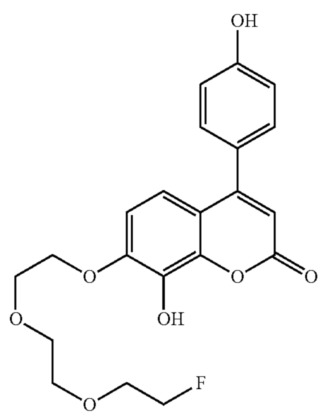 | $C_{21}H_{21}FO_7$ | 404.39 | |
| 6-(2-fluoroethoxy)-3-hydroxy-2-phenylquinolin-4(1H)-one | 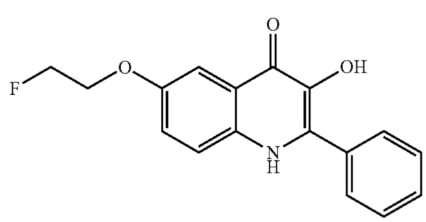 | $C_{17}H_{14}FNO_3$ | 299.30 | |
| 1-(2-fluoroethyl)-3,6-dihydroxy-2-phenylquinolin-4(1H)-one | 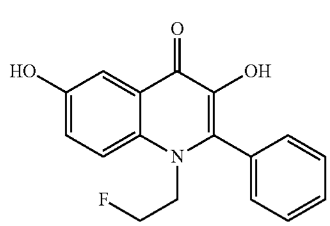 | $C_{17}H_{14}FNO_3$ | 299.30 | |

TABLE 3-continued

Examples of radiolabeled analogs useful for detecting AD biomarkers in vivo.

| Name | Structure | Chemical Formula | MW | Code |
|---|---|---|---|---|
| 2-(3-(2-fluoroethoxy)-4-hydroxyphenyl)-3,6-dihydroxy-quinolin-4(1H)-one | 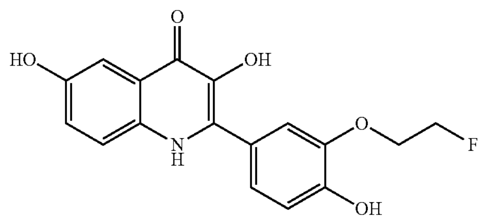 | $C_{17}H_{14}FNO_5$ | 331.30 | |
| 2-(4-(2-(2-(2-fluoroethoxy)ethoxy)ethoxy)-3-hydroxyphenyl)-3,6-dihydroxy-quinolin-4(1H)-one | | $C_{21}H_{22}FNO_7$ | 419.40 | |
| 2-(3,4-dihydroxyphenyl)-3-hydroxy-6-(methylamino)-quinolin-4(1H)-one | | $C_{16}H_{14}N_2O_4$ | 298.29 | |
| 1-(2-fluoroethyl)-3,6-dihydroxy-2-(4-hydroxyphenyl)quinolin-4(1H)-one | 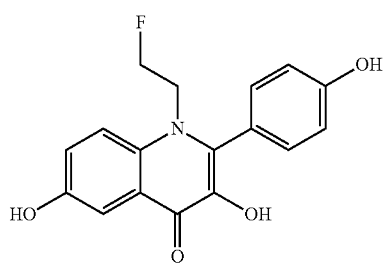 | $C_{17}H_{14}FNO_4$ | 315.30 | |
| 7-(2-(4-(2-fluoroethyl)-1H-1,2,3-triazol-1-yl)ethoxy)-8-hydroxy-4-phenyl-2H-chromen-2-one | 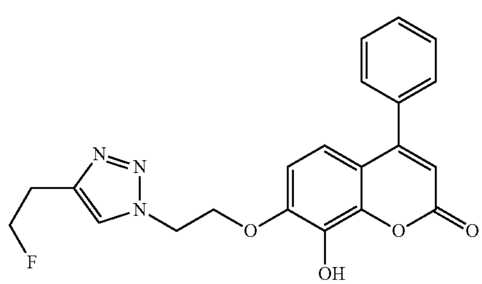 | $C_{21}H_{18}FN_3O_4$ | 395.38 | |
| 1-(2,4-dimethylphenyl)-4-(3-fluoro-5-methylphenyl)-1H-1,2,3-triazole | 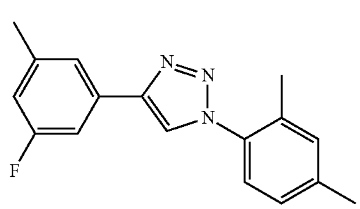 | $C_{17}H_{16}FN_3$ | 281.33 | |

Synthesis of Ligands and their Labeling Precursors:
Halogenation and Radiohalogenation:

As disclosed herein, for a number of different AD ligands, such as flavones, coumarins, carbazoles, quinolinones, chromenones, trisubstituted imidazoles and their derivatives as disclosed herein, the radiolabeled atom, such as a halogen atom, for example, may be readily introduced into the ligand using a number of different methods well known in the art. Accordingly, the radiolabeled compounds of the Formula I to Formula VI of the present application may be prepared using standard methods known in the art for preparing such radiolabeled compounds having a particular substituent, wherein the compound may be incorporated with a particular radionuclide selected from the group consisting of $^{11}$C, $^{13}$N, $^{15}$O, $^{18}$F, $^{123}$I, $^{124}$I, $^{125}$I, $^{131}$I and $^{77}$Br.

In one particular example, the halogen may be introduced by a method using a tin for halogen exchange process. For example, a non-radioactive halogen such as iodine, may be replaced by an organo tin compound via a metal, such as a palladium composition, to form the radiolabeling tin precursor, as represented below. This precursor is then subjected to radioactive halogenation via displacement with Na$^{125}$I source, for example, to afford the radioactive ligand.

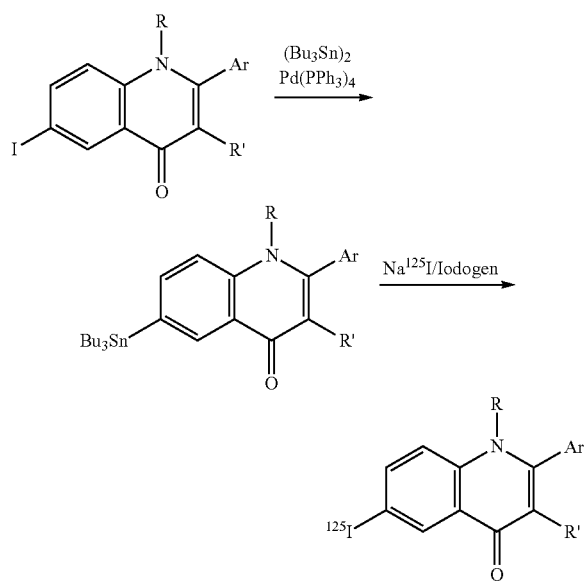

Alternatively, the radio labeled halogen may be readily introduced via direct halogenation. For example, for a ligand comprising an aromatic ring as part of the scaffold, or an aromatic substituent of a ligand, the aromatic ring may be directly iodinated using well-established radioiodination procedure. One such example is represented below using a carbazole ligand.

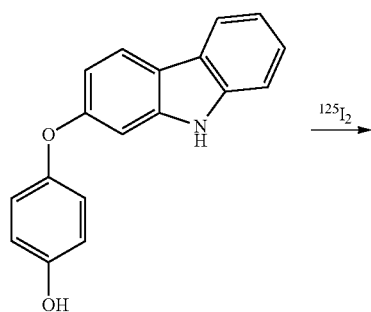

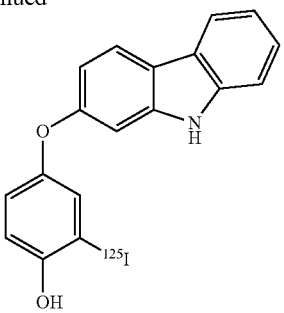

For $^{11}$C-labeled compounds, the labeled compound may be prepared by the alkylation or methylation of a hydroxyl group, such as with [$^{11}$C]CH$_3$I to provide the corresponding C-11 labeled methoxy derivative. For example, such a process is represented by the reaction of the flavone derivative shown below.

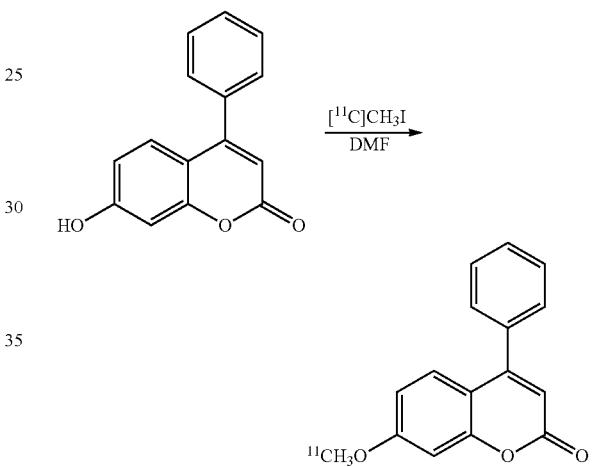

Other methods of preparing radiolabeled ligands are well known in the art. Example of such methods are disclosed in, for example: 1) Jewett, D. M. (1992) A Simple Synthesis of [$^{11}$C]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}$C] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost, J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-$^{11}$C and formaldehyde-$^{11}$C Appl. Radiat. Isot. 28, 49-52; 6) Watkins, G., Jewett, D., Mulholland, G., Kitbourn, M., and Toorongian, S. (1988) A Captive Solvent Method for Rapid N-[$^{11}$C]Methylation of Secondary Amides: Application to the Benzodiazepine, 4'-Chlorodiazepam (RO5-4864) Appl. Radiat. Isot. 39, 441-444; and 7) Wilson, A. A., DaSilva, J. N., and Houle, S. (1996) In vivo evaluation of [$^{11}$C] and [$^{15}$F]-labelled cocaine analogues as potential dopamine transporter ligands for positron emission tomography Nucl. Med. Biol. 23, 141-146. The subject matter of all references cited herein are incorporated herein by reference in their entirety.

Synthesis of AD-CB-WZ01013

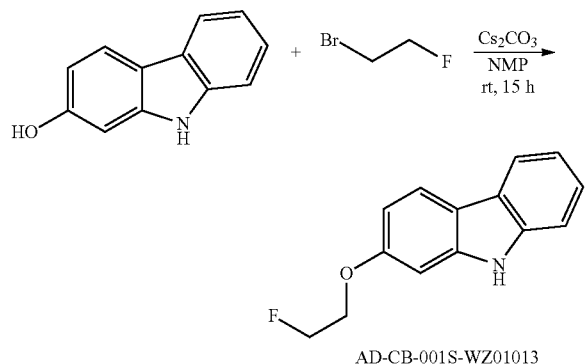

AD-CB-001S-WZ01013

To hydroxycarbazole (73 mg, 0.4 mmol) in 1 mL of NMP was added Cs$_2$CO$_3$ (130 mg, 0.4 mmol) and bromofluoroethane (51 mg, 0.4 mmol). The mixture was stirred at rt for 15 h and diluted with Et$_2$O (50 mL). It was washed with 1 M HCl (30 mL) and water (2×40 mL), dried over MgSO$_4$ and concentrated. The crude product was purified with silica chromatography (4% EtOAc in hexane to 25%) to afford the desired product (36 mg) as an off-white solid.

$^1$H NMR (400 MHz, CDCl$_3$/acetone-d$_6$) δ 9.98 (s, 1H), 7.95 (t, J=8.8 Hz, 2H), 7.40 (d, J=8.0 Hz, 1H), 7.28 (t, J=8 Hz, 1H), 7.13 (t, J=8.0 Hz, 1H), 7.00 (d, J=2 Hz, 1H), 6.83 (dd, J=8.8, 2.0 Hz, 1H), 4.85 (t, J=4 Hz, 1H), 4.73 (t, J=4 Hz, 1H), 4.35 (t, J=4 Hz, 1H), 4.28 (t, J=4 Hz, 1H); MS (ESI) m/z 230 (M+H$^+$).

Synthesis of AD-C-WZ01011

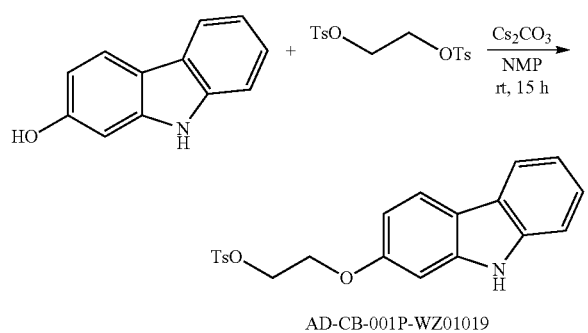

AD-CB-001P-WZ01019

To hydroxycarbazole (183 mg, 1 mmol) in 4 mL of NMP was added Cs$_2$CO$_3$ (326 mg, 1 mmol) and ethylenedi-tosylate (370 mg, 1 mmol). The mixture was stirred at rt for 15 h and diluted with Et$_2$O (80 mL). It was washed with 1 M HCl (50 mL) and water (2×50 mL), dried over MgSO$_4$ and concentrated. The crude product was purified with silica chromatography (50% DCM in hexane to 100% DCM) to afford the desired product (75 mg) as an off-white solid.

$^1$H NMR (400 MHz, acetone-d$_6$) δ 10.21 (s, 1H), 8.00 (d, J=8.0 Hz, 1H), 7.95 (d, J=8.4 Hz, 1H), 7.84 (d, J=8.4 Hz, 2H), 7.45 (m, 3H), 7.30 (t, J=8.0 Hz, 1H), 7.13 (t, J=8.0 Hz, 1H),); 6.98 (s, 1H), 6.73 (d, J=8.4 Hz, 1H), 4.44 (t, J=4.0 Hz, 2H), 4.30 (t, J=4.0 Hz, 2H), 2.42 (s, 3H); MS (ESI) m/z 382 (M+H$^+$), 404 (M+Na$^+$).

Synthesis of 18F-labeled AD-CB-001P-WZ-01019 ([$^{18}$F]2-(2-Fluoro-ethoxy)-9H-carbazole)

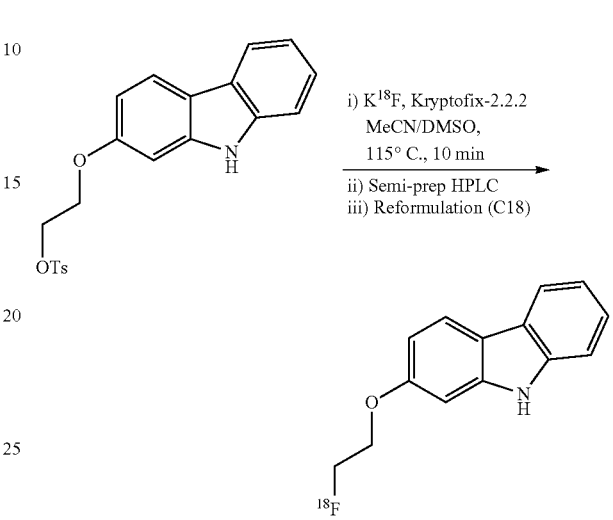

[$^{18}$F]Fluoride (600-900 mCi) as an enriched solution in H$_2$$^{18}$O was delivered to the synthesis module. The [$^{18}$F]fluoride was trapped on an ion-exchange column and then eluted into the reaction vessel using aqueous potassium carbonate (3.0 mg in 0.4 mL H$_2$O). Kryptofix-2.2.2 phase transfer reagent was added (20.0 mg in 1.0 mL MeCN) and the water-acetonitrile azeotrope was evaporated to dryness. Toluene-4-sulfonic acid 2-(9H-carbazol-2-yloxy)-ethyl ester precursor (4 mg in 0.9 mL MeCN/0.1 mL DMSO) was added to the reactor and then the fluorination reaction was heated at 115° C. for 10 min. The crude reaction mixture was then purified by semi-preparative HPLC (Column: Phenomenex Luna C-18, 250 mm×10 mm; Mobile-Phase Gradient 95:5 H$_2$0 (+0.05% TFA): MeCN (+0.05% TFA) to 100% MeCN (+0.05% TFA); Flow rate: 5 mL/min).

The peak corresponding to [$^{18}$F]2-(2-fluoro-ethoxy)-9H-carbazole was collected and simultaneously diluted with sterile water (10 mL). The resulting mixture was passed over a C-18 Sep-Pak so that the product was trapped and residual acetonitrile was washed away with further water (10 mL). [$^{18}$F]2-(2-Fluoro-ethoxy)-9H-carbazole was then eluted into the product vial with USP grade ethanol (0.5 mL) and diluted with sterile water (9.5 mL) to provide a final formulation (19-34 mCi in 10 mL) suitable for injection (7.5% decay corrected yield, 100% radiochemical purity).

Figure 3A:
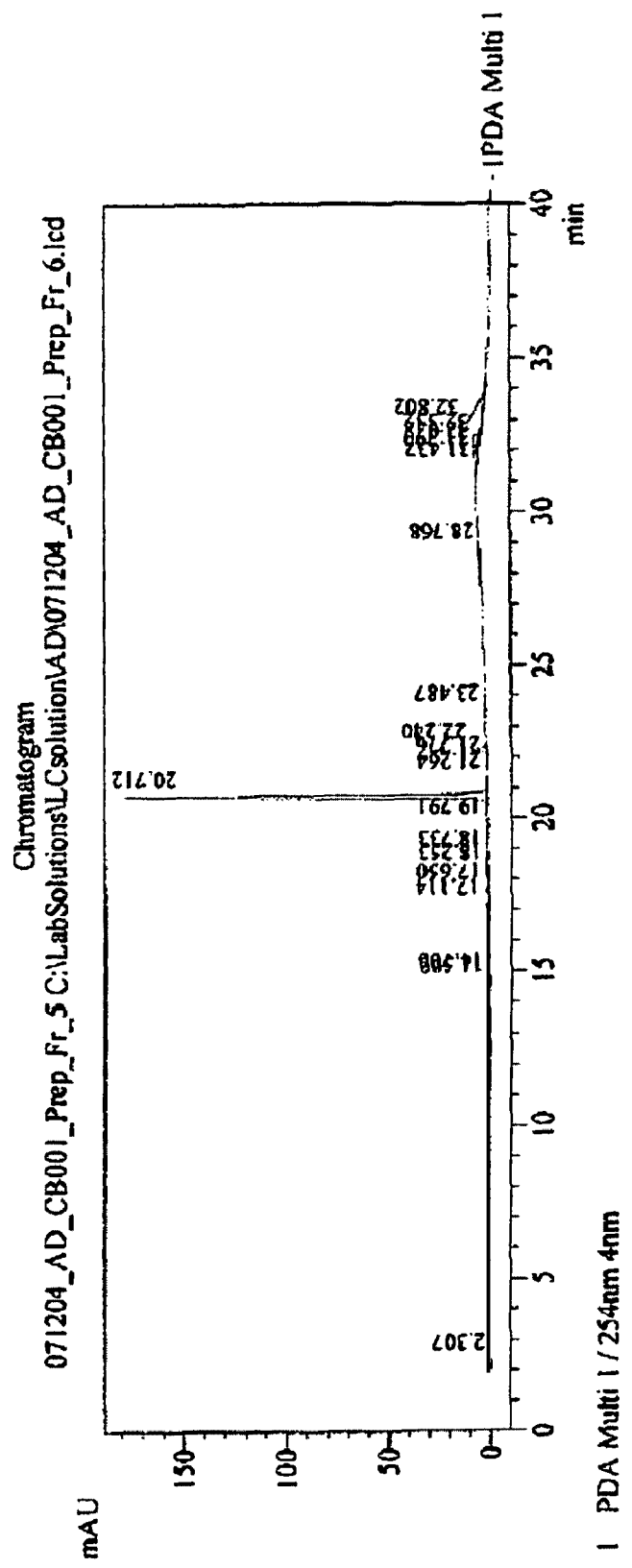
FIG. 3A shows UV HPLC analysis of AD-CB-001P-WZ-01019 synthesis of AD-CB-002P-WZ01031.
Figure 3B:
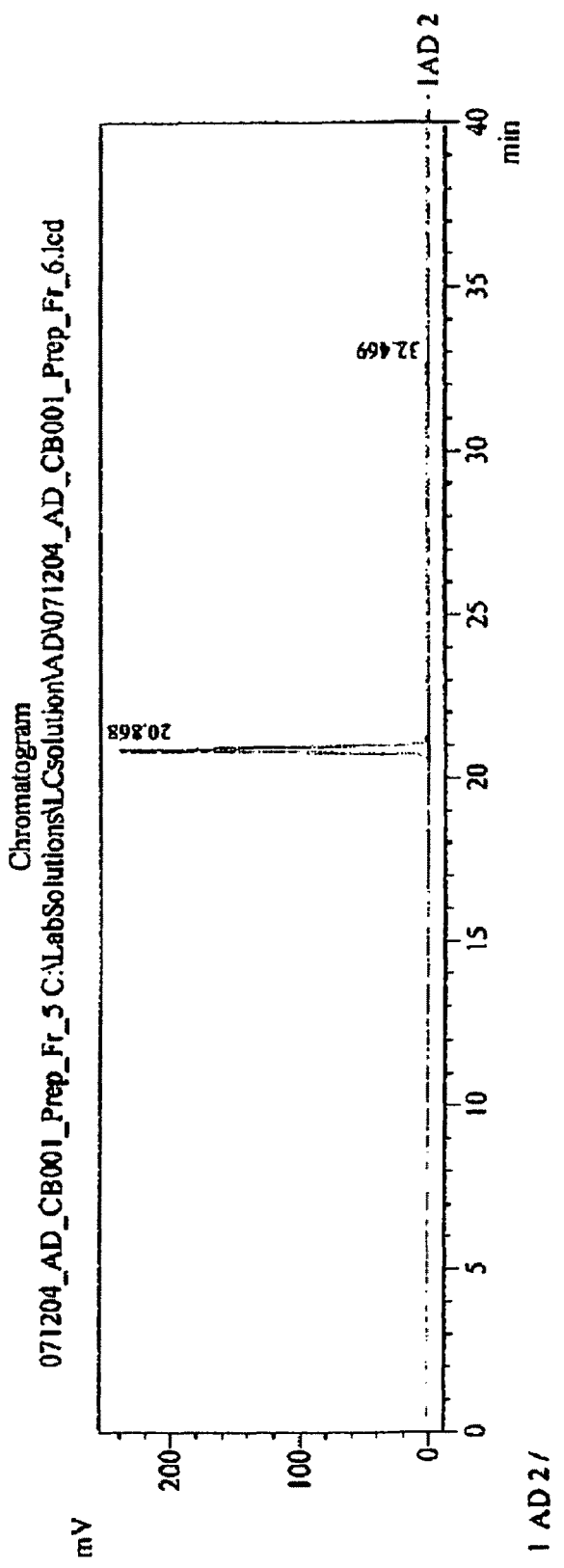
FIG. 3B shows Gamma HPLC analysis of AD-CB-001P-WZ-01019 synthesis of AD-CB-002P-WZ01031.

Purity was determined by analytical HPLC equipped with a radioactivity detector and identity was confirmed by comparison with HPLC data for the corresponding unlabeled reference standard (FIG. 3A and FIG. 3B).

Synthesis of AD-CB-002P-WZ01031

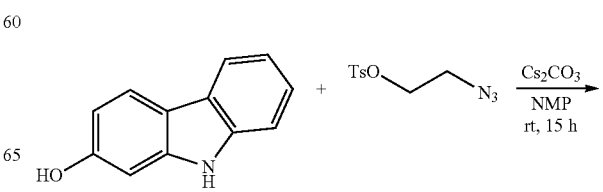

-continued

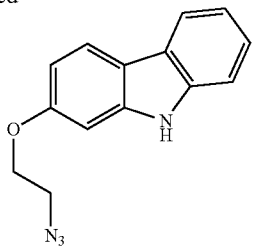

AD-CB-002P-WZ01031

To hydroxycarbazole (92 mg, 0.5 mmol) in 2 mL of NMP was added Cs$_2$CO$_3$ (163 mg, 0.5 mmol) and azido ethyltosylate (121 mg, 0.5 mmol). The mixture was stirred at rt for 15 h and diluted with Et$_2$O (50 mL). It was washed with 0.5 M HCl (50 mL) and water (2×50 mL), dried over MgSO$_4$ and concentrated. The crude product was purified with silica chromatography (80% DCM in hexane to 100% DCM) to afford the desired product (76 mg) as a white solid.

$^1$H NMR (400 MHz, CDCl$_3$/acetone-d$_6$) δ 9.98 (s, 1H), 7.95 (m, 2H), 7.41 (d, J=8.4 Hz, 1H), 7.29 (t, J=8.0 Hz, 1H), 7.14 (t, J=8.0 Hz, 1H),); 7.01 (s, 1H), 6.84 (d, J=8.4 Hz, 1 H), 4.28 (t, J=4.8 Hz, 2H), 3.67 (t, J=4.8 Hz, 2H); MS (ESI) m/z 253 (M+H$^+$).

Synthesis of AD-CB-002S-WZ01033

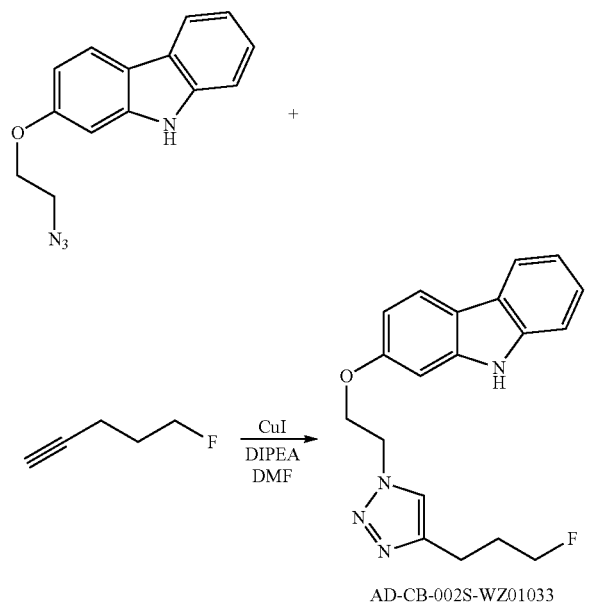

AD-CB-002S-WZ01033

To azido carbazole (32 mg, 0.127 mmol) in 0.5 mL of DMF was added CuI (7.6 mg, 0.04 mmol), DIPEA (16.4 mg, 0.127 mmol), and fluoropentyne (16.4 mg, 0.19 mmol). The reaction mixture was vigorously stirred for 1 h and diluted with EtOAc (30 mL). It was washed with water (50 mL), 0.5 M HCl (30 mL), water (2×50 mL), dried over MgSO$_4$ and concentrated. The crude product was pre-absorbed on silica (3 g) and loaded on a 4 g silica column and eluted with 30% EtOAc in hexane to 50% to afford the desired compound (20 mg).

$^1$H NMR (400 MHz, CDCl$_3$/CD$_3$OD) δ 7.95 (d, J=7.6 Hz, 1H), 7.91 (d, J=8.4 Hz, 1 H), 7.76 (s, 1H), 7.40 (d, J=8.0 Hz, 1H), 7.31 (t, J=7.6 Hz, 1H), 7.14 (t, J=7.6 Hz, 1H), 6.94 (d, J=2.4 Hz, 1H), 6.78 (dd, J=8.8, 2.4 Hz, 1H), 4.83-4.78 (m, 2H), 4.53-4.48 (m, 3H), 4.40 (t, J=6.0 Hz, 1H), 2.85 (t, J=7.6 Hz, 2H), 2.10-1.99 (m, 2H); MS (ESI) m/z 339 (M+H$^+$).

Synthesis of 18F-labeled AD-CB-002S-WZ01033:

Preparation of [$^{18}$F] 5-Fluoro-pent-1-yne

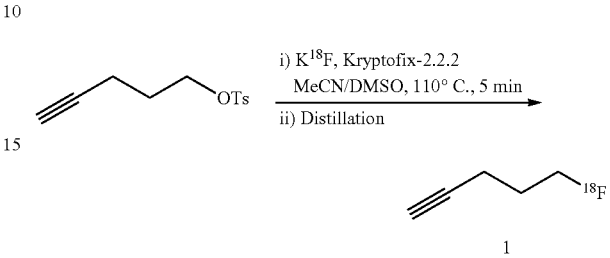

[$^{18}$F]Fluoride (600-900 mCi) as an enriched solution in H$_2$$^{18}$O is delivered to the synthesis module. The [$^{18}$F]fluoride is trapped on an ion-exchange column and then eluted into the reaction vessel using aqueous potassium carbonate (3.0 mg in 0.4 mL H$_2$O). Kryptofix-2.2.2 phase transfer reagent is added (20.0 mg in 1.0 mL MeCN) and the water-acetonitrile azeotrope is evaporated to dryness.

Toluene-4-sulfonic acid pent-4-ynyl ester (20 mg in 0.8 mL MeCN) is added to the reactor and the fluorination reaction is heated at 110° C. for 5 min. Following fluorination, the crude reaction mixture is purified by distillation and yields [$^{18}$F] 5-fluoro-pent-1-yne as a solution in acetonitrile (trapped at −78° C. due to the volatility of the product).

Preparation of Triazole:

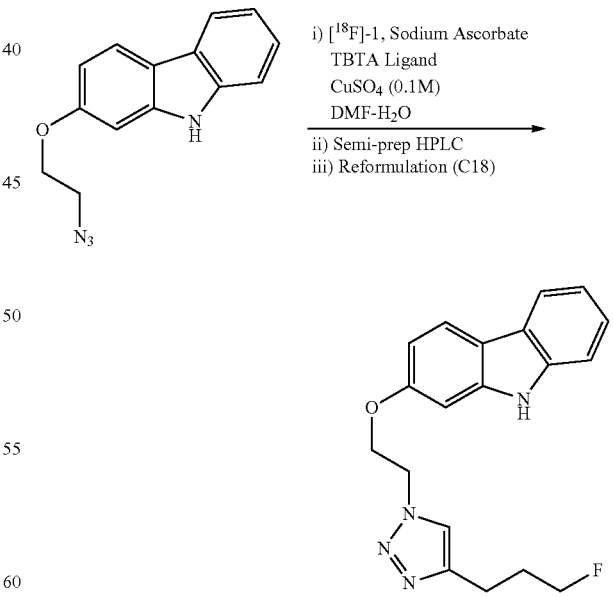

A mixture of azide precursor (5 mg), sodium ascorbate (40 mg), tris-(benzyltriazolylmethyl)amine (TBTA, 25 mg) and aqueous copper sulfate solution (0.1 M, 0.25 mL) in DMF (0.4 mL) and water (0.1 mL) is added to the cooled pentyne solution described above. The reaction mixture is then warmed to rt and stirred for 30 min. After this time, the reaction is purified by semi-preparative HPLC. The peak corresponding to the product is collected and simultaneously diluted with sterile water (10 mL). The resulting mixture is passed over a C-18 Sep-Pak and residual acetonitrile is washed away with additional water (10 mL). The product is eluted into the product vial with USP grade ethanol (0.5 mL) and diluted with sterile water (9.5 mL) providing a final formulation suitable for injection.

Purity is determined by analytical HPLC equipped with a radioactivity detector and identity is confirmed by comparison with HPLC data for the corresponding unlabeled reference standard.

Synthesis of $^{18}$F-Labeled CB-003 was cooled to 55° C. and most of the acetonitrile was evaporated under vacuum and a stream of argon as before. To the crude Boc-protected product was added aqueous hydrochloric acid (1.0 m, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 H$_2$0 (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed

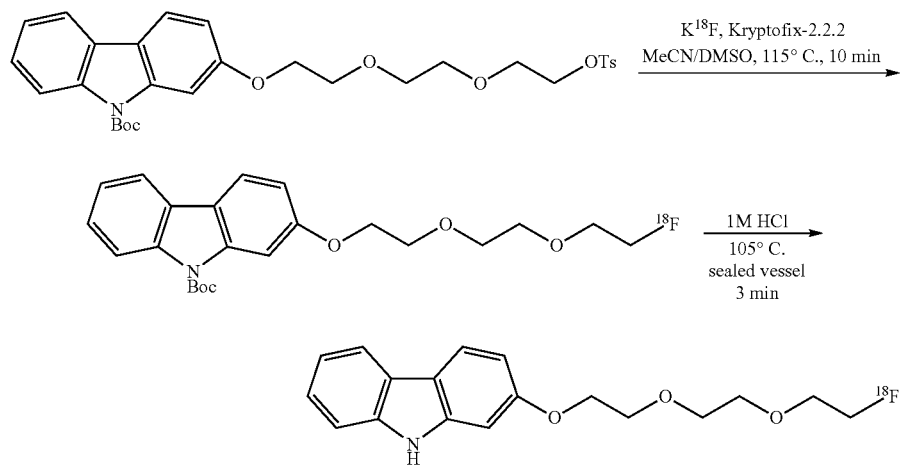

[$^{18}$F]Fluoride (600-900 mCi) as an enriched solution in H$_2$$^{18}$O is delivered to the synthesis module. The [$^{18}$F]fluoride is trapped on an ion-exchange column and then eluted into the reaction vessel using aqueous potassium carbonate (3.0 mg in 0.4 mL H$_2$O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture away with further water (10 mL). The product is then eluted into the product vial with USP grade ethanol (0.5 mL) and diluted with sterile water (9.5 mL) providing a final formulation suitable for injection (31% decay uncorrected yield, 100% radiochemical purity). Purity was determined by analytical HPLC equipped with a radioactivity detector and identity was confirmed by comparison with HPLC data for the corresponding unlabeled reference standard.

Synthesis of $^{18}$F-Labeled CB-004

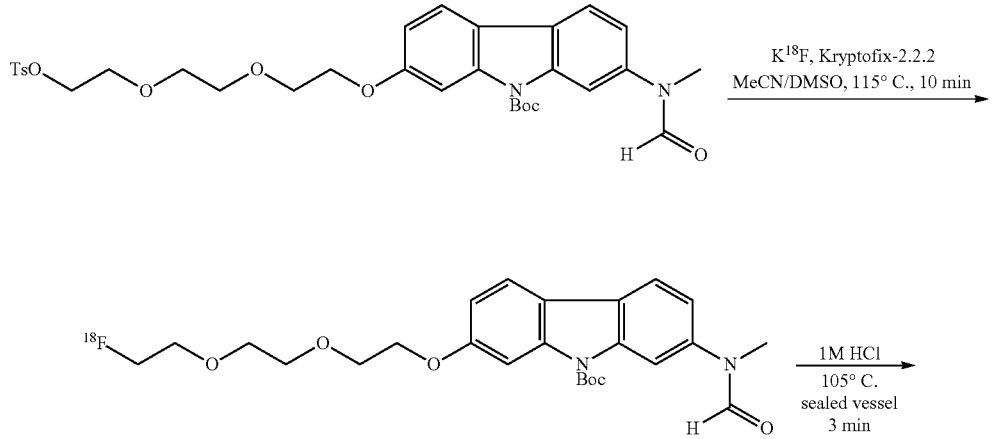

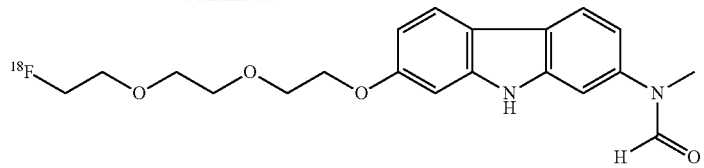

[$^{18}$F]Fluoride (600-900 mCi) as an enriched solution in H$_2$$^{18}$O is delivered to the synthesis module. The [$^{18}$F]fluoride is trapped on an ion-exchange column and then eluted into the reaction vessel using aqueous potassium carbonate (3.0 mg in 0.4 mL H$_2$O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture was cooled to 55° C. and most of the acetonitrile was evaporated under vacuum and a stream of argon as before. To the crude Boc-protected product was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 H$_2$0 (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection (3% decay uncorrected yield, 100% radiochemical purity). Purity was determined by analytical HPLC equipped with a radioactivity detector and identity was confirmed by comparison with HPLC data for the corresponding unlabeled reference standard.

Synthesis of $^{18}$F-Labeled CB-007

[$^{18}$F]Fluoride (600-900 mCi) as an enriched solution in H$_2$$^{18}$O is delivered to the synthesis module. The [$^{18}$F]fluoride is trapped on an ion-exchange column and then eluted into the reaction vessel using aqueous potassium carbonate (3.0 mg in 0.4 mL H$_2$O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture was cooled to 55° C. and most of the acetonitrile was evaporated under vacuum and a stream of argon as before. To the crude Boc-protected product was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 H$_2$0 (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection (1.2% decay uncorrected yield, 100% radiochemical purity). Purity was determined by analytical HPLC equipped with a radioactivity detector and identity was confirmed by comparison with HPLC data for the corresponding unlabeled reference standard.

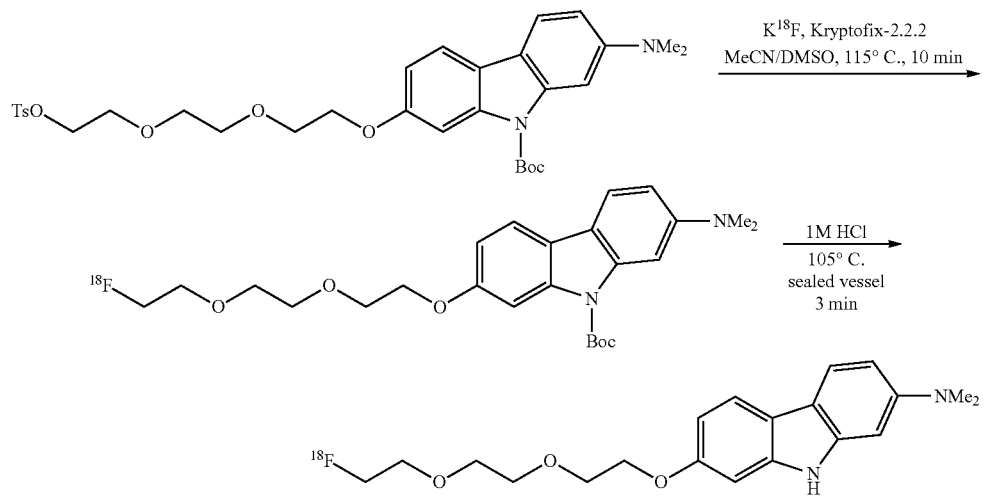

Synthesis of $^{18}$F-Labeled CB-012

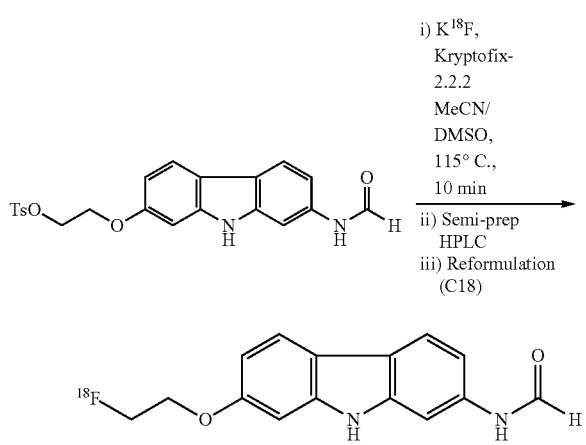

[$^{18}$F]Fluoride (600-900 mCi) as an enriched solution in H$_2$$^{18}$O was delivered to the synthesis module. The [$^{18}$F]fluoride was trapped on an ion-exchange column and then eluted into the reaction vessel using aqueous potassium carbonate (3.0 mg in 0.4 mL H$_2$O). Kryptofix-2.2.2 phase transfer reagent was added (20.0 mg in 1.0 mL MeCN) and the water-acetonitrile azeotrope was evaporated to dryness. Toluene-4-sulfonic acid 2-(9H-carbazol-2-yloxy)-ethyl ester precursor (4 mg in 0.9 mL MeCN/0.1 mL DMSO) was added to the reactor and then the fluorination reaction was heated at 115° C. for 10 min. The crude reaction mixture was then purified by semi-preparative HPLC (Column: Phenomenex Luna C-18, 250 mm×10 mm; Mobile-Phase Gradient 95:5 H$_2$O (+0.05% TFA): MeCN (+0.05% TFA) to 100% MeCN (+0.05% TFA); Flow rate: 5 mL/min). The peak corresponding to the product was collected and simultaneously diluted with sterile water (10 mL). The resulting mixture was passed over a C-18 Sep-Pak so that the product was trapped and residual acetonitrile was washed away with further water (10 mL). [$^{18}$F]2-(2-Fluoro-ethoxy)-9H-carbazole was then eluted into the product vial with USP grade ethanol (0.5 mL) and diluted with sterile water (9.5 mL) to provide a final formulation (19-34 mCi in 10 mL) suitable for injection (2% decay uncorrected yield, 100% radiochemical purity). Purity was determined by analytical HPLC equipped with a radioactivity detector and identity was confirmed by comparison with HPLC data for the corresponding unlabeled reference standard.

Assays of Carbazole Derivatives:

From the Biacore assay, two carbazole derivatives displayed promising binding affinities to oligomers/polymers and fibrils (Table 4). The beta-carboline Harmol, a member of the harmala alkaloids, is the urinary metabolite of harmine. The harmala alkaloids are MAO inhibitors and are commonly found in Syrian rue, *Peganum harmala*, and the South American vine *Banisteriopsis caapi*, both of which are purported to possess strong hallucinogenic effects. The beta-carbolenes have a varied effect on the central nervous system including binding to the 5-HT$_2$, 5-HT$_{1a}$, glutamate NMDA and imidazoline receptors; inhibiting MAO-A enzyme and interfering with dopaminergic transmission. And while beta-carbolines are thought to be cytotoxic, they also maintain neuroprotective properties supposedly offering neuroprotection against dopamine and glutamate and, additionally, by scavenging reactive oxygen species. A recent report demonstrated that beta-carboline alkyloids induce a facilitation of short and long term memory in object recognition tasks in mice, although the means by which the alkyloids are exerting their effect is unclear. Moura, D. J., et al., *Effects of b-carboline alkaloids in the object recognition task in mice*. Life Sciences, 2006, 79: p. 2099-2104.

The second active carbazole discovered in the assay is 2-hydroxycarbazole. 2-Hydroxycarbazole has been recently shown to release Ca$^{2+}$ ion from skeletal and cardiac muscle through a distinct pharmacological pathway. The generic carbazole scaffold exists in several therapeutics including the non-steroidal anti-inflammatory carprofen, carazolol (a beta-blocker) and YM-53601 (a squalene synthase inhibitor). Recent work has shown that carbazole derivatives can act as γ-secretase modulators. [Narlawar, R., et al., *N-Substituted carbazolyloxyacetic acids modulate Alzheimer associated g-secretas*. Bioorganic & Medicinal Chemistry Letters, 2007, 17: p. 176-182] In another AD related project, Howlett discovered highly elaborated carbazoles, such as carvedilol, inhibit fibril formation, albeit the binding affinities to the fibrils were not determined. [Howlett, D. R., et al., *Common Structural Features Determine the Effectiveness of Carvedilol, Daunomycin and Rotiletracycline as Inhibitors of Alzheimer b-Amyloid Fibril Formation*. Biochemical Journal, 1999, 343: p. 419-423] Interestingly, an article intending to determine the practicality of using carbazoles as fibril inhibitors based on cell permeability suggests that carbazoles are unlikely to cross the blood brain barrier, as they are PGP substrates, precluding their use as therapeutics for fibril inhibition. [Saengkhae, C., et al., *Ability of Carbazole Salts, Inhibitors of Alzheimer b-Amyloid Fibril Formation, to Cross Cellular Membranes*. European Journal of Pharmacology, 2007, 559: p. 124-131]

Figure 6:
FIG. 6 shows coronal slices of a white rat brain using 1 min framing. After 2 minutes, the tracer concentration reaches a maximum level in the brain and is completely washed out after 7 minutes.

By using an appropriate imaging modality, a tracer's biodistribution pattern becomes instantly visible and accessible. For example, by using $^{18}$F-labeled tracers one can easily quantify a tracer's uptake into, and washout from, the brain using positron emission tomography (PET). Tracers with high uptake and slow washout in normal brains generate low signal to noise ratios. Tracers with high uptake and fast washout in normal brains have high signal to noise rations and are considered ideal. $^{18}$F-labeled carbazoles possess ideal brain imaging properties. For example, an $^{18}$F-labeled carbazole was prepared and administered to a normal, white Sprague-Dawley rat (FIG. 6). Within minutes, the tracer entered into the brain and washed out over several minutes.

The non-radioactive carbazole also successfully competes off both Thioflavin T and FDDNP in brain tissue sections suggesting that the tracer binds to similar binding sites (FIGS. 4 and 5).

TABLE 4

Carbazole-based hits from the Biacore assay.

| | Binding to oligomers/polymers (A(β-42)) | Binding to fibrils (Aβ1-42) |
|---|---|---|
| #54: Harmol 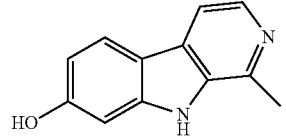 | ++ | + |
| #55: 2-Hydroxycarbazole 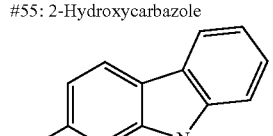 | +++ | + |
| #73: 7,8-Dihydroxy-4-phenylcoumarin | | |

A "+" sign represents a hit and the increase in "+" signs relates to increasing binding affinity.
A "−" sign represents no binding.

A list of examples of carbazole-based imaging agents are shown in Table 5. Many of the compounds are either $^{18}$F- or $^{11}$C-labeled.

TABLE 5

Examples of carbazole-based imaging agents

| Compound Name | Structure | Formula | Mol. Weight |
|---|---|---|---|
| 2-(2-fluoroethoxy)-9H-carbazole | 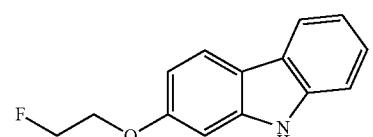 | $C_{14}H_{12}FNO$ | 229.25 |
| 9-(2-fluoroethyl)-9H-carbazol-2-ol | 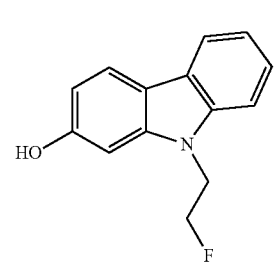 | $C_{14}H_{12}FNO$ | 229.25 |
| N-(2-fluoroethyl)-7-(2-(2-(2-methoxyethoxy)ethoxy)ethoxy)-9H-carbazol-3-amine | 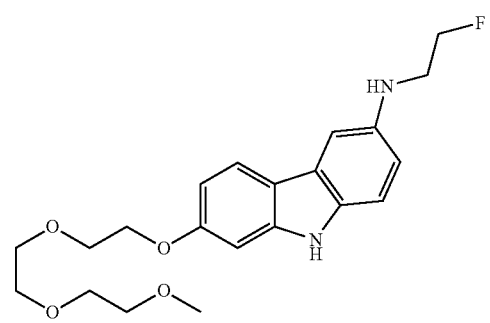 | $C_{21}H_{27}FN_2O_4$ | 390.45 |

TABLE 5-continued

Examples of carbazole-based imaging agents

| Compound Name | Structure | Formula | Mol. Weight |
|---|---|---|---|
| 7-(2-fluoroethoxy)-N,N-dimethyl-9H-carbazol-2-amine | 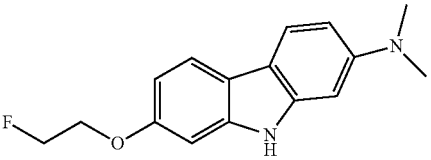 | $C_{16}H_{17}FN_2O$ | 272.32 |
| 7-(2-(2-(2-fluoroethoxy)ethoxy)ethoxy)-N-methyl-9H-carbazol-3-amine | 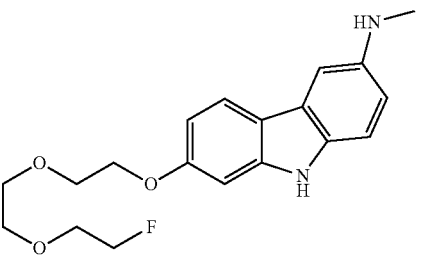 | $C_{19}H_{23}FN_2O_3$ | 346.40 |
| 1-(3,6-diamino-9H-carbazol-9-yl)-3-(2-(2-(2-fluoroethoxy)ethoxy)ethoxy)propan-1-one | 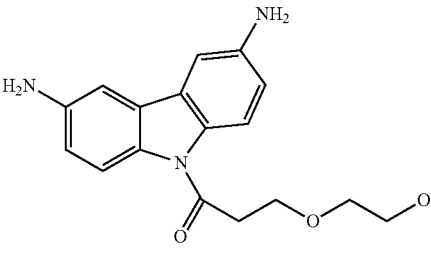 | $C_{21}H_{26}FN_3O_4$ | 403.45 |
| N-(2-fluoroethyl)-2-hydroxy-11H-benzo[a]carbazole-3-carboxamide | 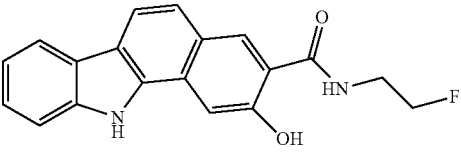 | $C_{19}H_{15}FN_2O_2$ | 322.33 |
| 2-(6-chloro-9H-carbazol-2-yl)-N-(2-fluoroethyl)propanamide | 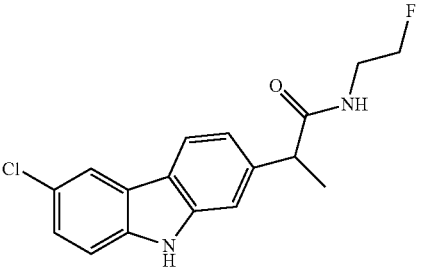 | $C_{17}H_{16}ClFN_2O$ | 318.77 |
| 2-(6-fluoro-9H-carbazol-2-yl)-N,N-dimethylpropanamide | 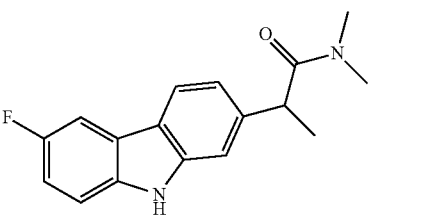 | $C_{17}H_{17}FN_2O$ | 284.33 |
| 2-methoxy-9H-carbazole | 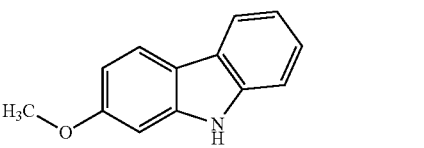 | $C_{13}H_{11}NO$ | 197.23 |

TABLE 5-continued

Examples of carbazole-based imaging agents

| Compound Name | Structure | Formula | Mol. Weight |
|---|---|---|---|
| 6-iodo-2-methoxy-9H-carbazole | 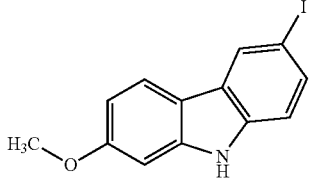 | $C_{13}H_{10}INO$ | 323.13 |

Detailed Biacore Assay Protocol:

β-Amyloid (Aβ42) soluble aggregates (oligomers/soluble polymers). Biotin-LC-Aβ42 was mixed with Aβ42 at a ratio of 3:2. After dissolving in 1% $NH_4OH$ and $dH_2O$, the mixture (40 uM concentration) was incubated in 1×PBS (pH 7.4) buffer at RT for 6-hours to form oligomers/soluble polymers. The free monomer of Aβ42 in the sample was removed using a Microcon centrifugal filter tube with a 10 KDa of MW cutoff. The Biotin-LC-Aβ42 oligomers/polymers were immobilized onto SA chip by streptavidin-biotin capture.

β-Amyloid (Aβ42) insoluble aggregates (fibrils). Fibrils were prepared according to methods published previously (Agdeppa E D et al. 2001). Briefly, 0.5 mg of Aβ42 (Biotin-LC-Aβ42:Aβ42=1:1) was dissolved in 1 ml of PBS, pH 7.4, and mixed with a magnetic stir bar for 3 d at 37° C., resulting in a visibly cloudy solution. The fibril pellet was collected by centrifugation. The Biotin-LC-Aβ42 fibrils were immobilized onto SA chip by streptavidin-biotin capture.

Screening of amyloid binding compounds with Biacore (Surface Plasmon Resonance Analysis). Aβ42 oligomers/soluble polymers or fibrils were immobilized on Flow Cell 2 (Fc2) or Flow Cell 3 (Fc3) of the Sensor Chip, with Fc1 serving as the control. Screening compounds at 10 uM concentration was flown through Fc1, Fc2, and Fc3 for 2 minutes at a flow rate of 30 ul/minute. The Flow Cells were then washed with running buffer (1×PBS) for 2 minute, and regenerated with 50 mM of NaOH for 30 seconds. The real time interaction between the screening compound and the amyloid aggregates immobilized on the chip surface was recorded in the sensorgram.

Immunostaining of brain sections with Thioflavin T. Brain samples from donors with Alzheimer disease were paraffin wax infiltrated after fixation. Paraffin blocks with embedded brain samples were mounted onto microtome and sectioned. Sections were then deparaffinized and hydrated, followed by incubation with or without AD-CB-001S-WZ01013. Staining was carried out with 1 uM Thioflavin T. Images were obtained with a fluorescence microscope (FIG. 4).

Immunostaining of brain sections with FDDNP. Brain samples from donors with Alzheimer disease were paraffin wax infiltrated after fixation. Paraffin blocks with embedded brain samples were mounted onto microtome and sectioned. Sections were then deparaffinized and hydrated, followed by incubation with or without AD-CB-001S-WZ01013. Staining was carried out with 1 uM FDDNP. Images were obtained with a fluorescence microscope (FIG. 5).

Imaging Results of AD-CB-001

A white Sprague-Dawley rat was injected via tail vein with ~850 uCi AD-CB-001, formulated in 10% EtOH:water. A dynamic scan was conducted for 30 min on a R4 microPET scanner. The data was reconstructed using 1 min framing. Within minutes, the tracer entered the rat brain and quickly washed out (FIG. 6).

Preparation of Coumarin Derivatives:

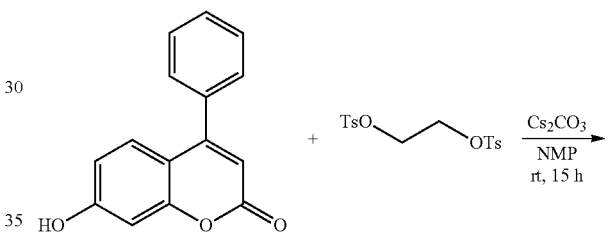

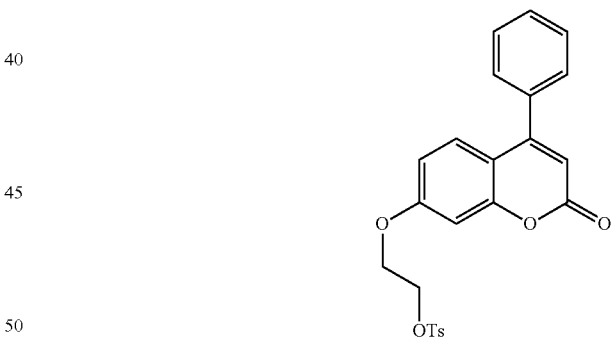

AD-C-003P-WZ01043

To coumarin (120 mg, 0.5 mmol) in 2 mL of NMP was added $Cs_2CO_3$ (163 mg, 0.5 mmol) and ethylenedi-tosylate (185 mg, 0.5 mmol). The mixture was stirred at rt for 15 h and diluted with $Et_2O$ (50 mL). It was washed with 1 M HCl (50 mL) and water (2×50 mL), dried over $MgSO_4$ and concentrated. The crude product was purified with silica chromatography (DCM 100% and then 0.3% MeOH in DCM) to afford the desired product (51 mg) as a clear oil.

$^1$H NMR (400 MHz, $CDCl_3$) δ 7.82 (d, J=8.4 Hz, 2H), 7.52 (m, 3H), 7.43 (m, 2H), 7.37 (m, 3H), 6.75 (s, 1H), 6.71 (d, J=9.2 Hz, 1H), 6.23 (s, 1H), 4.41 (t, J=4.4 Hz, 2H), 4.22 (t, J=4.4 Hz, 2H), 2.46 (s, 3H); MS (ESI) m/z 437 (M+H$^+$).

Synthesis of AD-C-003S-WZ01041

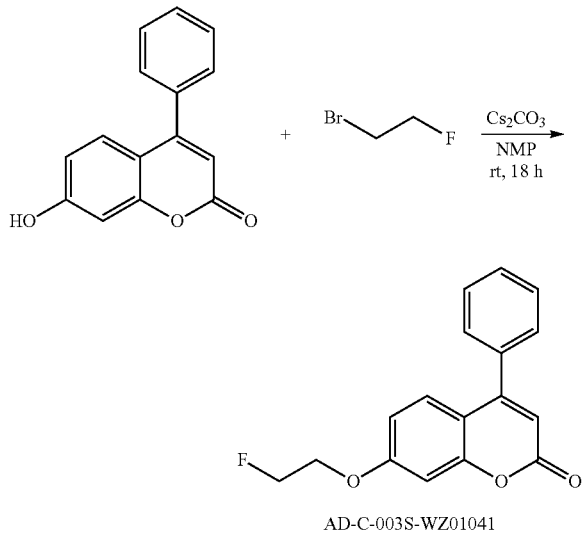

To coumarin (238 mg, 1 mmol) in 4 mL of NMP was added Cs$_2$CO$_3$ (326 mg, 1 mmol) and bromofluoroethane (152 mg, 1.2 mmol). The mixture was stirred at rt for 15 h and diluted with Et$_2$O (50 mL). It was washed with 1 M HCl (50 mL) and water (2×50 mL), dried over MgSO$_4$ and concentrated. The crude product was purified with silica chromatography (DCM 80% in hexane to 100%) to afford the desired product (160 mg) as a white solid.

$^1$H NMR (400 MHz, acetone-d6) δ 7.60-7.56 (m, 5H), 7.43 (d, J=8.8 Hz, 1H), 7.03 (d, J=2.4 Hz, 1H), 6.96 (dd, J=8.8, 2.4 Hz, 1H), 6.18 (s, 1H), 4.91-4.89 (m, 1H), 4.79-4.77 (m, 1 H), 4.49-4.47 (m, 1H), 4.42-4.40 (m, 1H); MS (ESI) m/z 285 (M+H$^+$).

Synthesis of $^{18}$F-Labeled AD-C-003S-WZ01041

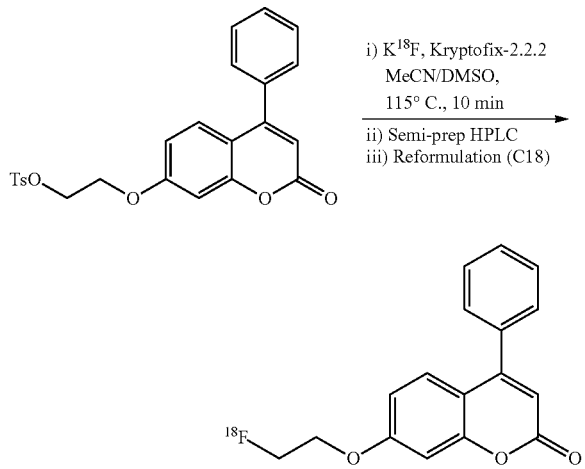

[$^{18}$F]Fluoride (600-900 mCi) as an enriched solution in H$_2$$^{18}$O is delivered to the synthesis module. The [$^{18}$F]fluoride is trapped on an ion-exchange column and then eluted into the reaction vessel using aqueous potassium carbonate (3.0 mg in 0.4 mL H$_2$O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The crude reaction mixture is then purified by semi-preparative HPLC (Column: Phenomenex Luna C-18, 250 mm×10 mm; Mobile-Phase Gradient 95:5 H$_2$0 (+0.05% TFA): MeCN (+0.05% TFA) to 100% MeCN (+0.05% TFA); Flow rate: 5 mL/min; time=25 min).

The peak corresponding to the product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection.

Purity is determined by analytical HPLC equipped with a radioactivity detector and identity is confirmed by comparison with HPLC data for the corresponding unlabeled reference standard.

Synthesis of AD-C-002P-WZ01029

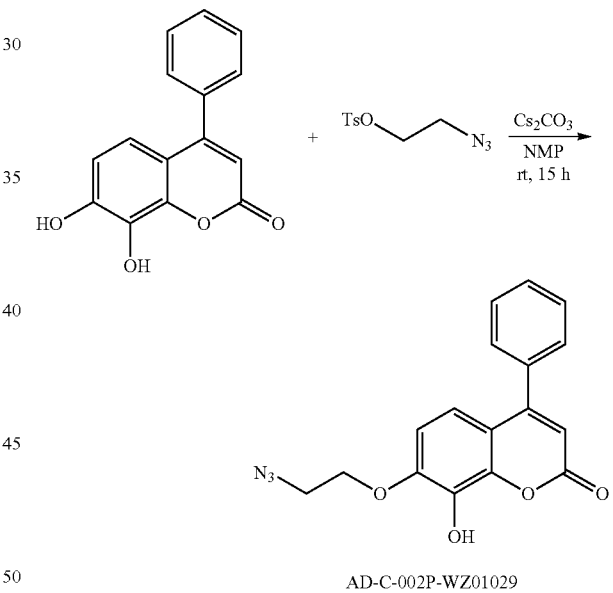

To dihydroxy coumarin (254 mg, 1 mmol) in 4 mL of NMP was added Cs$_2$CO$_3$ (326 mg, 1 mmol) and ethylazido tosylate (241 mg, 1 mmol). The mixture was stirred at rt for 15 h and diluted with Et$_2$O (50 mL). It was washed with 1 M HCl (50 mL) and water (2×50 mL), dried over MgSO$_4$ and concentrated. The crude product was purified with silica chromatography (DCM in hexane from 80% to 100%) to afford the desired mono-alkylated product (72 mg) as an off-white solid.

$^1$H NMR (400 MHz, CDCl$_3$) δ 7.53-7.50 (m, 3H), 7.45-7.43 (m, 2H), 7.00 (d, J=8.8 Hz, 1H), 6.82 (d, J=8.8 Hz, 1H), 6.26 (s, 1H), 5.92 (s, 1H), 4.31 (t, J=5.0 Hz, 2H), 3.72 (t, J=5.0 Hz, 2H); MS (ESI) m/z 324 (MAT).

Synthesis of AD-C-002S-WZ01035

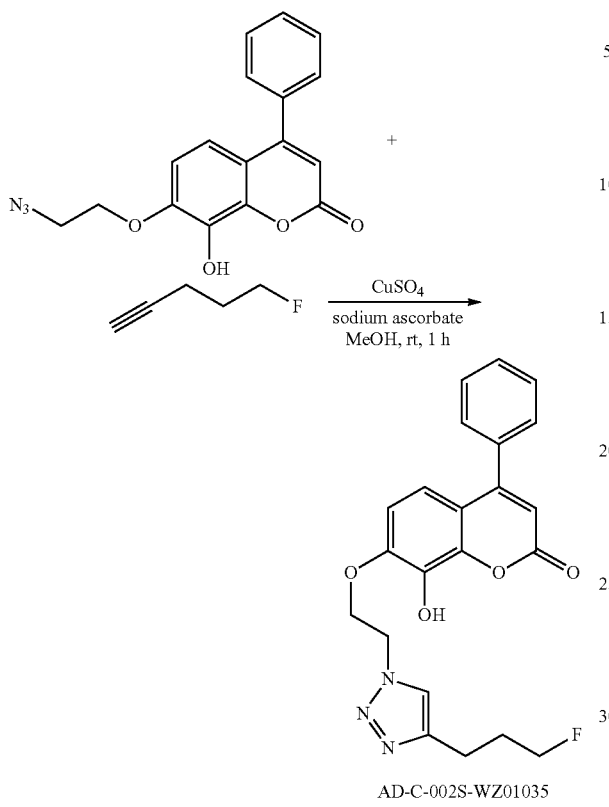

To azidoethyl coumarin (42 mg, 0.13 mmol) in 1 mL of methanol was added CuSO$_4$ (21 mg, 0.13 mmol), sodium ascorbate (28 mg, 0.13 mmol), and fluoropentyne (16.3 mg, 0.19 mmol). The reaction mixture was vigorously stirred for 1 h and diluted with EtOAc (30 mL). It was washed with water (2×50 mL), dried over MgSO$_4$ and concentrated. The crude product was purified with silica chromatography (eluted with 5% EtOAc in hexane to 60%) to afford the desired compound (42 mg).

$^1$H NMR (400 MHz, CDCl$_3$/CD$_3$OD) δ 7.95 (s, 1H), 7.54-7.52 (m, 3H), 7.48-7.44 (m, 2H), 6.94 (d, J=8.8 Hz, 1H), 6.86 (d, J=8.8 Hz, 1H), 4.86 (t, J=4.8 Hz, 2H), 4.55-4.51 (m, 3H), 4.41 (t, J=6.0 Hz, 1H), 2.83 (t, J=7.2 Hz, 2H), 2.14-2.02 (m, 2H); MS (ESI) m/z 410 (M+H$^+$).

Synthesis of 18F-Labeled AD-C-002S-WZ-01035

Preparation of [$^{18}$F] 5-Fluoro-pent-1-yne

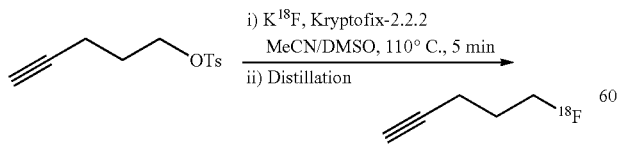

[$^{18}$F]Fluoride (600-900 mCi) as an enriched solution in H$_2$$^{18}$O was delivered to the synthesis module. The [$^{18}$F]fluoride was trapped on an ion-exchange column and then eluted into the reaction vessel using aqueous potassium carbonate (3.0 mg in 0.4 mL H$_2$O). Kryptofix-2.2.2 phase transfer reagent was added (20.0 mg in 1.0 mL MeCN) and the water-acetonitrile azeotrope was evaporated to dryness. Toluene-4-sulfonic acid pent-4-ynyl ester (20 mg in 0.8 mL MeCN) was added to the reactor and then the fluorination reaction was heated at 110° C. for 5 min. Following fluorination, the crude reaction mixture was purified by distillation to yield [$^{18}$F] 5-fluoro-pent-1-yne as a solution in acetonitrile (trapped at −78° C. due to the volatility of the product).

Preparation of Triazole:

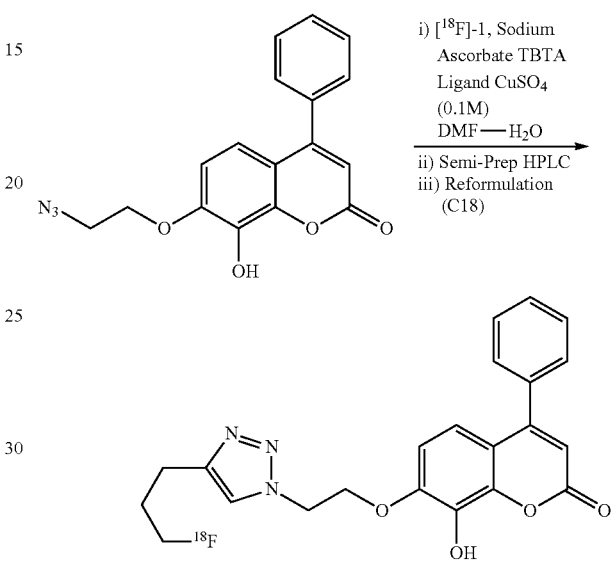

A mixture of azide precursor (5 mg), sodium ascorbate (40 mg), tris-(benzyltriazolylmethyl)amine (TBTA, 25 mg) and aqueous copper sulfate solution (0.1 M, 0.25 mL) in DMF (0.4 mL) and water (0.1 mL) was added to the cooled pentyne solution described above. The reaction mixture was then warmed to rt and stirred for 30 min. After this time, the reaction was purified by semi-preparative HPLC. The peak corresponding to the product was collected and simultaneously diluted with sterile water (10 mL). The resulting mixture was passed over a C-18 Sep-Pak so that the product was trapped and residual acetonitrile was washed away with further water (10 mL). The product was then eluted into the product vial with USP grade ethanol (0.5 mL) and diluted with sterile water (9.5 mL) to provide a final formulation (19 mCi in 10 mL) suitable for injection (10% decay corrected yield, 100% radiochemical purity).

Purity was determined by analytical HPLC equipped with a radioactivity detector and identity was confirmed by comparison with HPLC data for the corresponding unlabeled reference standard.

Synthesis of AD-CB-002P-WZ01031

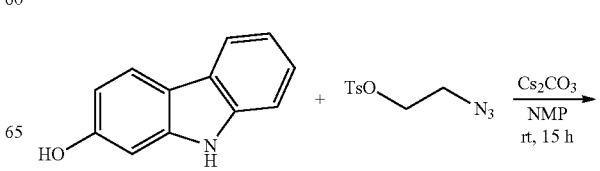

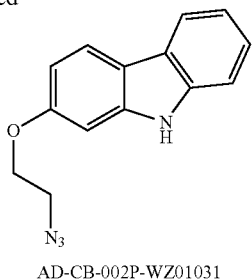

AD-CB-002P-WZ01031

To hydroxycarbazole (92 mg, 0.5 mmol) in 2 mL of NMP was added Cs$_2$CO$_3$ (163 mg, 0.5 mmol) and ethylazido tosylate (121 mg, 0.5 mmol). The mixture was stirred at rt for 15 h and diluted with Et$_2$O (50 mL). It was washed with 0.5 M HCl (50 mL) and water (2×50 mL), dried over MgSO$_4$ and concentrated. The crude product was purified with silica chromatography (80% DCM in hexane to 100% DCM) to afford the desired product (76 mg) as a white solid.

$^1$H NMR (400 MHz, CDCl$_3$/acetone-d6) δ 9.98 (s, 1H), 7.95 (m, 2H), 7.41 (d, J=8.4 Hz, 1H), 7.29 (t, J=8.0 Hz, 1H), 7.14 (t, J=8.0 Hz, 1H),); 7.01 (s, 1H), 6.84 (d, J=8.4 Hz, 1 H), 4.28 (t, J=4.8 Hz, 2H), 3.67 (t, J=4.8 Hz, 2H); MS (ESI) m/z 253 (M+H$^+$).

Synthesis of AD-CB-002S-WZ01033

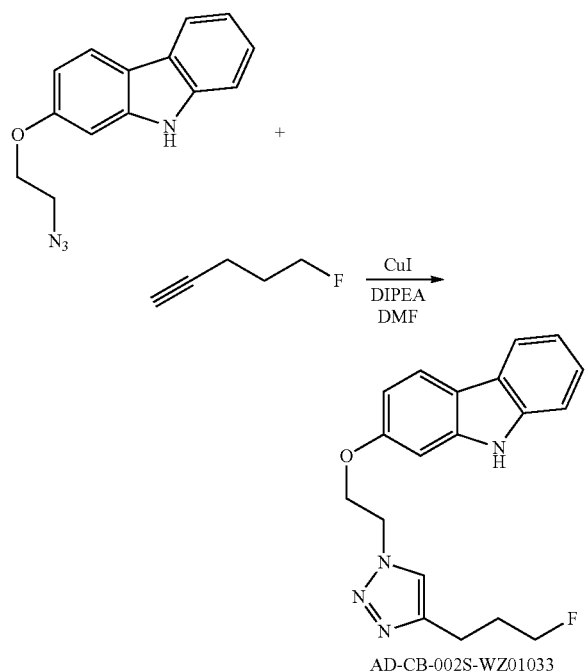

AD-CB-002S-WZ01033

To ethylazido carbazole (32 mg, 0.127 mmol) in 0.5 mL of DMF was added CuI (7.6 mg, 0.04 mmol), DIPEA (16.4 mg, 0.127 mmol), and fluoropentyne (16.4 mg, 0.19 mmol). The reaction mixture was vigorously stirred for 1 h and diluted with EtOAc (30 mL). It was washed with water (50 mL), 0.5 M HCl (30 mL), water (2×50 mL), dried over MgSO$_4$ and concentrated. The crude product was pre-absorbed on silica (3 g) and loaded on a 4 g silica column and eluted with 30% EtOAc in hexane to 50% to afford the desired compound (20 mg).

$^1$H NMR (400 MHz, CDCl$_3$/CD$_3$OD) δ 7.95 (d, J=7.6 Hz, 1H), 7.91 (d, J=8.4 Hz, 1H), 7.76 (s, 1H), 7.40 (d, J=8.0 Hz, 1H), 7.31 (t, J=7.6 Hz, 1H), 7.14 (t, J=7.6 Hz, 1H); 6.94 (d, J=2.4 Hz, 1H), 6.78 (dd, J=8.8, 2.4 Hz, 1H), 4.83-4.78 (m, 2H), 4.53-4.48 (m, 3H), 4.40 (t, J=6.0 Hz, 1H), 2.85 (t, J=7.6 Hz, 2H), 2.10-1.99 (m, 2H); MS (ESI) m/z 339 (M+H$^+$).

Synthesis of 18F-Labeled AD-CB-002S-WZ01033

Preparation of Triazole

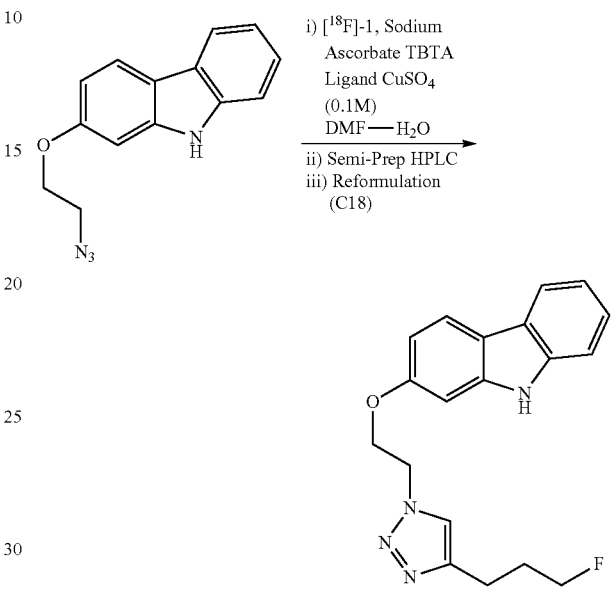

A mixture of azide precursor (5 mg), sodium ascorbate (40 mg), tris-(benzyltriazolylmethyl)amine (TBTA, 25 mg) and aqueous copper sulfate solution (0.1 M, 0.25 mL) in DMF (0.4 mL) and water (0.1 mL) is added to the cooled pentyne solution described above. The reaction mixture is then warmed to rt and stirs for 30 min. After this time, the reaction is purified by semi-preparative HPLC. The peak corresponding to the product is collected and simultaneously diluted with sterile water (10 mL). The resulting mixture is passed over a C-18 Sep-Pak and residual acetonitrile is washed away with additional water (10 mL). The product is eluted into the product vial with USP grade ethanol (0.5 mL) and diluted with sterile water (9.5 mL) providing a final formulation suitable for injection.

Purity is determined by analytical HPLC equipped with a radioactivity detector and identity is confirmed by comparison with HPLC data for the corresponding unlabeled reference standard.

Synthesis of AD-C-WZ01011

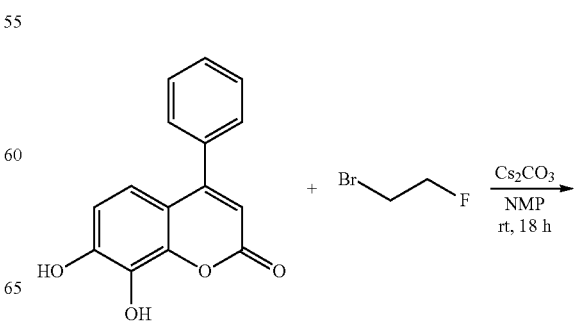

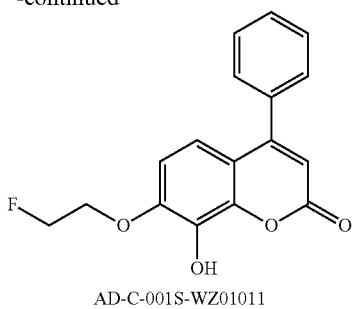

AD-C-001S-WZ01011

To dihydroxy coumarin (100 mg, 0.4 mmol) in 2.5 mL of NMP was added Cs$_2$CO$_3$ (130 mg, 0.4 mmol) and bromofluoroethane (46 mg, 0.36 mmol). The mixture was stirred at rt for 18 h and diluted with Et$_2$O (50 mL). It was washed with 1 M HCl (50 mL) and water (2×50 mL) and dried over MgSO$_4$ and concentrated. The crude product was purified with silica chromatography (MeOH in DCM from 0% to 1%) to afford the desired mono-alkylated product (25 mg) as a white solid.

$^1$H NMR (400 MHz, CDCl$_3$/CD$_3$OD) δ 7.55-7.48 (m, 5H), 6.96 (q, J=7.6 Hz, 2H), 6.19 (s, 1H), 4.86 (m, 1H), 4.75 (m, 1H), 4.43 (m, 1H), 4.37 (m, 1H); MS (ESI) m/z 301 (M+H$^+$).

General Procedure for Carbazole N-Boc Protection:

To a round bottomed flask equipped with a magnetic stir bar, rubber septum, and argon inlet containing THF (40 vol) was placed carbazole (1.0 equiv). To this solution was added NaH (60% dispersion in oil, 3 equiv) at 0° C. and the reaction was allowed to stir at 0° C. for 30 min. To this reaction was added (Boc)$_2$O (1.2 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Procedure for Carbazole N-Methylation:

To a round bottomed flask equipped with a magnetic stir bar, rubber septum, and argon inlet containing THF (50 vol) was placed carbazole (1.0 equiv). To this solution was added NaH (60% dispersion in oil, 3 equiv) at 0° C. and the reaction was allowed to stir at 0° C. for 30 min. To this reaction was added MeOTf (1.0 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Phenolic Alkylation:

To a round bottomed flask equipped with a magnetic stir bar containing DMF (20 vol) was placed phenol (1 equiv). To this solution was added alkylating agent (1.0 equiv), Cs$_2$CO$_3$ (1.2 equiv) and the reaction was allowed to stir at 60° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Suzuki Coupling Reaction:

To a round bottomed flask equipped with a magnetic stir bar rubber septum, and argon inlet containing toluene:H$_2$O (1:1, 40 vol) was placed chloro compound (1 equiv). To this solution was added boronic acid (1.5 equiv), Pd(PPh$_3$)$_4$ (0.02 equiv), K$_2$CO$_3$ and the reaction was allowed to stir at 110° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Carbazole Formation Using P(OEt)$_3$:

To a round bottomed flask equipped with a magnetic stir bar containing P(OEt)$_3$ (25 vol) was placed biaryl (1 equiv). The reaction was allowed to stir at 150° C. for 16 h. After the reaction was complete, P(OEt)$_3$ was removed in vacuo. The residue was purified over silica gel using Hexanes:EtOAc as the eluent to afford the final compound.

Synthesis of CB1-Nosylate Precursor:

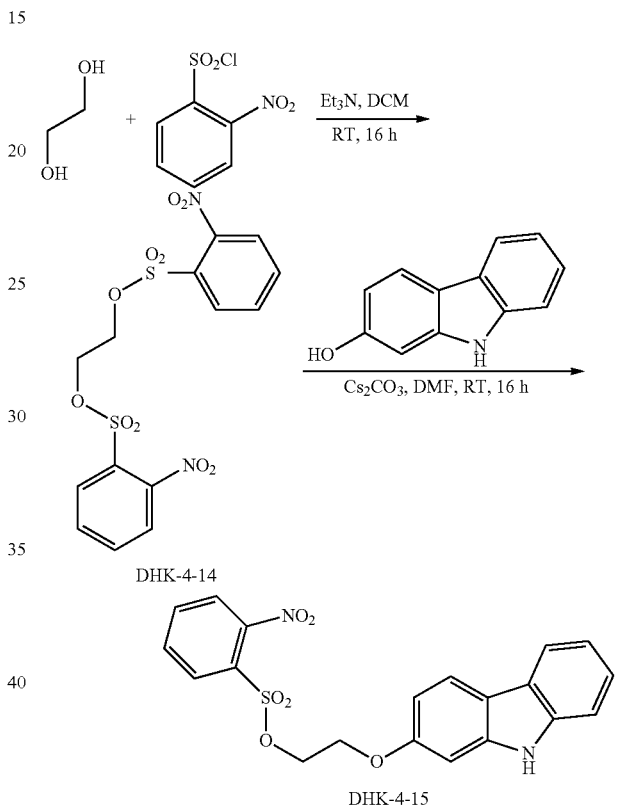

Preparation of Ethane-1,2-diyl bis(2-nitrobenzenesulfonate) (DHK-4-14)

To a 50 mL round bottomed flask equipped with a magnetic stir bar containing DCM (10 mL) was placed 1,2-ethanediol (0.25 g, 4.0 mmol). To this solution was added nosyl chloride (1.9 g, 8.5 mmol) and Et$_3$N (0.90 g, 8.9 mmol) at 0° C. and the reaction was allowed to stir at room temperature for 16 h. After the reaction was complete, the white solid was filtered, washed with DCM (100 mL) and dried in vacuo to afford DHK-4-14 (1.3 g, 75%) as a colorless solid. MS: [M+Na]$^+$: 455.0

Preparation of 2-(9H-carbazol-2-yloxy)ethyl 2-nitrobenzenesulfonate (DHK-4-15)

To a 25 mL round bottomed flask equipped with a magnetic stir bar containing DMF (5 vol) was placed carbazole (0.2 g, 1.1 mmol). To this solution was added the DHK-4-14 (0.52 g, 1.2 mmol), Cs$_2$CO$_3$ (0.43 g, 1.3 mmol) and the reaction was allowed to stir at room temperature for 16 h. The reaction was then poured into water (25 mL) and extracted into EtOAc (4×50 mL). The combined organic extracts were dried (Na$_2$SO$_4$) and concentrated in vacuo. The crude residue was purified by flash chromatography using Hexanes:EtOAc (50:50) on a Combiflash purification system to yield DHK-4-15 as a white solid (0.28 g, 62%). MS: [M+Na]$^+$: 435.0

Synthesis of CB-5:

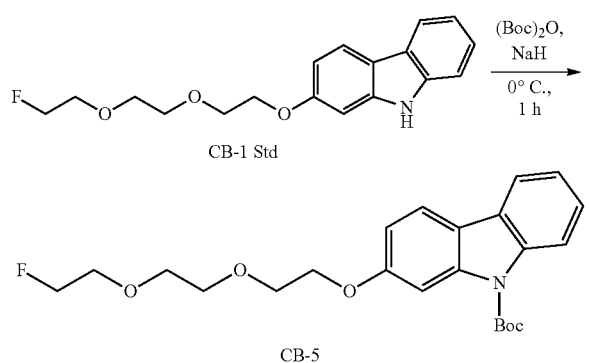

Preparation of tert-butyl 2-(2-(2-(2-fluoroethoxy)ethoxy)ethoxy)-9H-carbazole-9-carboxylate: CB-5: DHK-4-27

General experimental procedure for carbazole N-Boc protection was followed. Reaction was performed on a 0.03 g scale. Product eluted out in 30-35% EtOAc:Hexanes mixture in a gradient elution on a Combiflash purification system. Isolated 0.03 g (74%) of CB-5 as a colorless oil. MS: [M+H]$^+$: 418.0

Synthesis of CB-6: DHK-4-28

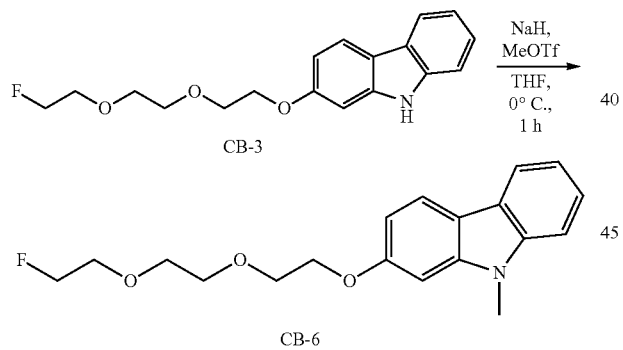

Preparation of 2-(2-(2-(2-fluoroethoxy)ethoxy)ethoxy)-9-methyl-9H-carbazole: CB-6

General experimental procedure for carbazole N-methylation was followed. Reaction was performed on a 0.05 g scale. Product eluted out in 40-45% EtOAc:Hexanes mixture in a gradient elution on a Combiflash purification system. Isolated 0.04 g (78%) of CB-6 as a white solid. MS: [M+H]$^+$: 332.1.

Synthesis of N-Boc-Protected CB-3 Precursor:

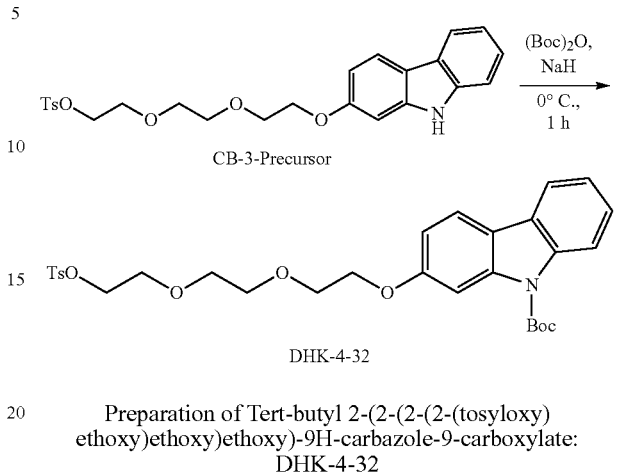

Preparation of Tert-butyl 2-(2-(2-(2-(tosyloxy)ethoxy)ethoxy)ethoxy)-9H-carbazole-9-carboxylate: DHK-4-32

General experimental procedure for carbazole N-Boc protection was followed. Reaction was performed on a 0.07 g scale. Product eluted out in 40% EtOAc:Hexanes mixture in a gradient elution on a Combiflash purification system. Isolated 0.07 g (82%) of DHK-4-32 as white solid. MS: [M+Na]$^+$: 592.

Synthesis of N-methyl CB-3 Precursor:

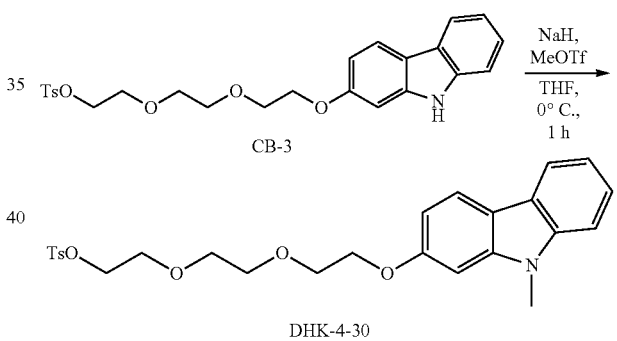

Preparation of 2-(2-(2-(9-methyl-9H-carbazol-2-yloxy)ethoxy)ethoxy)ethyl 4-methylbenzenesulfonate: DHK-4-30

General experimental procedure for carbazole N-methylation was followed. Reaction was performed on a 0.075 g scale. Product eluted out in 40% EtOAc:Hexanes mixture in a gradient elution on a Combiflash purification system. Isolated 0.07 g (91%) of DHK-4-30 as a white solid. MS: [M+H]$^+$: 484.2

Synthesis of CB-7 Std:

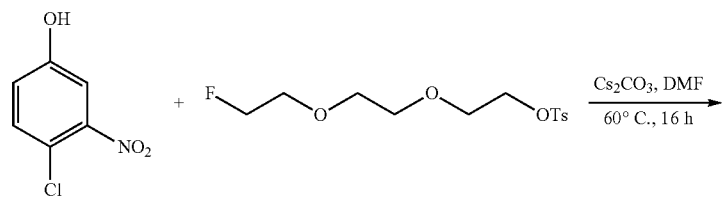

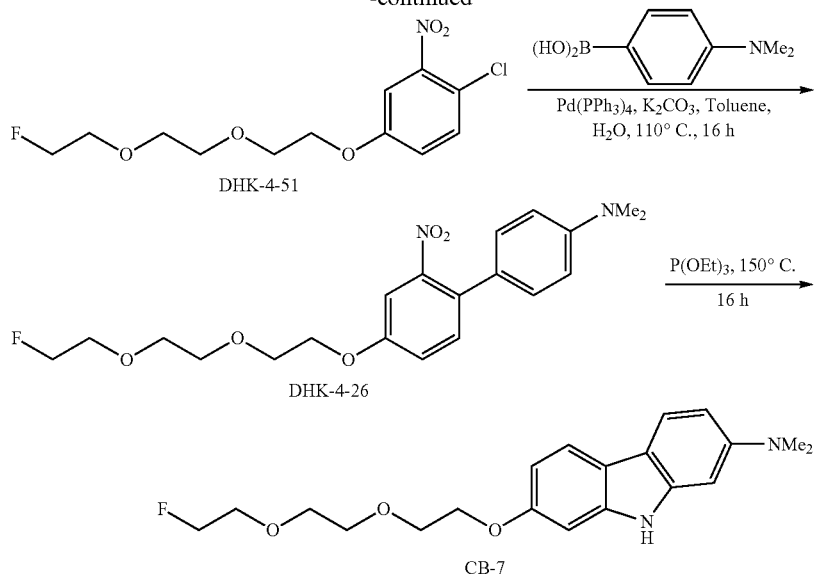

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: [M+H]$^+$: 308.0.

Preparation of 4'-(2-(2-(2-fluoroethoxy)ethoxy)ethoxy)-N,N-dimethyl-2'-nitrobiphenyl-4-amine: DHK-4-26

General experimental procedure for Suzuki coupling reaction was followed. Reaction was performed on a 0.11 g scale. Product eluted out in 50-60% EtOAc:Hexanes mixture in a gradient elution on a Combiflash purification system. Isolated 0.06 g (43%) of DHK-4-26 as yellow oil. MS: [M+H]$^+$: 393.1

Preparation of 7-(2-(2-(2-fluoroethoxy)ethoxy)ethoxy)-N,N-dimethyl-9H-carbazol-2-amine: DHK-4-29: CB-7

General experimental procedure for carbazole formation using P(OEt)$_3$ was followed. Reaction was performed on a 0.06 g scale. Product eluted out in 70-80% EtOAc:Hexanes mixture in a gradient elution on a Combiflash purification system. Isolated 0.03 g (49%) of DHK-4-29 CB-7 as white solid. MS: [M+H]$^+$: 361.1.

Synthesis of CB-9 Std:

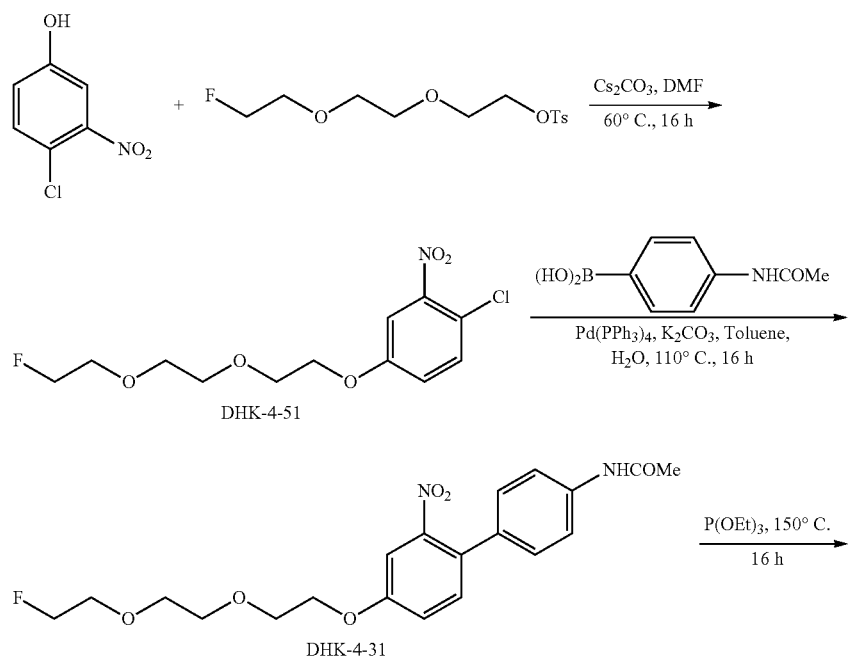

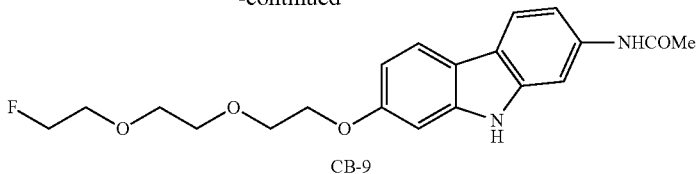

CB-9

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: [M+H]$^+$: 308.0.

Preparation of N-(4'-(2-(2-(2-fluoroethoxy)ethoxy)ethoxy)-2'-nitrobiphenyl-4-yl)acetamide: DHK-4-31

General experimental procedure for Suzuki coupling reaction was followed. Reaction was performed on a 0.11 g scale. Product eluted out in 80-90% EtOAc:Hexanes mixture in a gradient elution on a Combiflash purification system. Isolated 0.14 g (100%) of DHK-4-31 as yellow oil. MS: [M+H]$^+$: 407.0.

Preparation of N-(7-(2-(2-(2-fluoroethoxy)ethoxy)ethoxy)-9H-carbazol-2-yl)acetamide: DHK-4-33: CB-9

General experimental procedure for carbazole formation using P(OEt)$_3$ was followed. Reaction was performed on a 0.15 g scale. Product eluted out in 90% EtOAc:Hexanes mixture in a gradient elution on a Combiflash purification system. Isolated 0.03 g (49%) of CB-9 as white solid. MS: [M+H]$^+$: 375.1.

Synthesis of CB-28 Std:

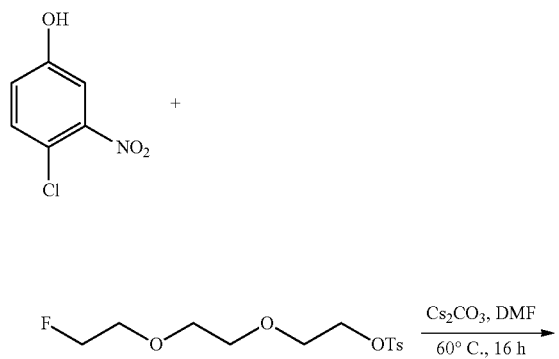

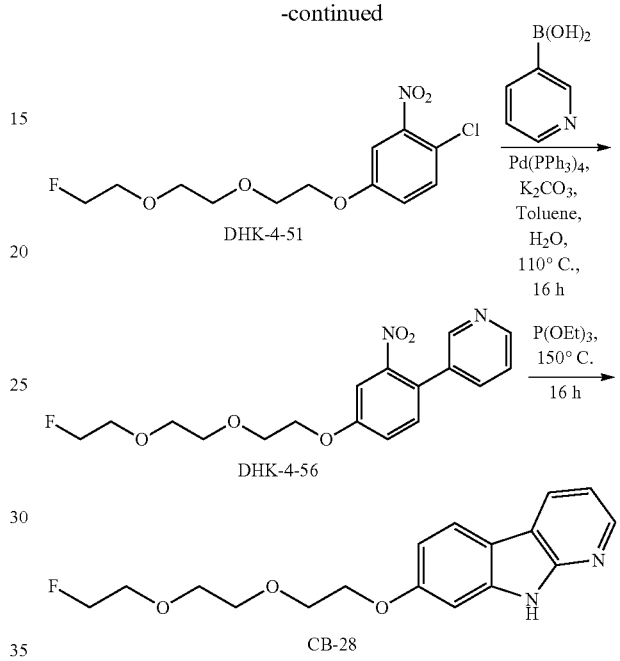

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: [M+H]$^+$: 308.0.

Preparation of 3-(4-(2-(2-(2-fluoroethoxy)ethoxy)ethoxy)-2-nitrophenyl)pyridine: DHK-4-56

General experimental procedure for Suzuki coupling reaction was followed. Reaction was performed on a 0.095 g scale. Product eluted out in 40-50% EtOAc:Hexanes mixture in a gradient elution on a Combiflash purification system. Isolated 0.01 g (9%) of DHK-4-56 as yellow oil. MS: [M+H]$^+$: 351.1.

Preparation of 7-(2-(2-(2-fluoroethoxy)ethoxy)ethoxy)-9H-pyrido[2,3-b]indole DHK-4-58: CB-28

General experimental procedure for carbazole formation using P(OEt)$_3$ was followed. Reaction was performed on a 0.01 g scale. Product eluted out in 50% EtOAc:Hexanes mixture in a gradient elution on a Combiflash purification system. Isolated 0.002 g (22%) of CB-28 as white solid. MS: [M+H]$^+$: 319

Synthesis of CB-7-Precursor

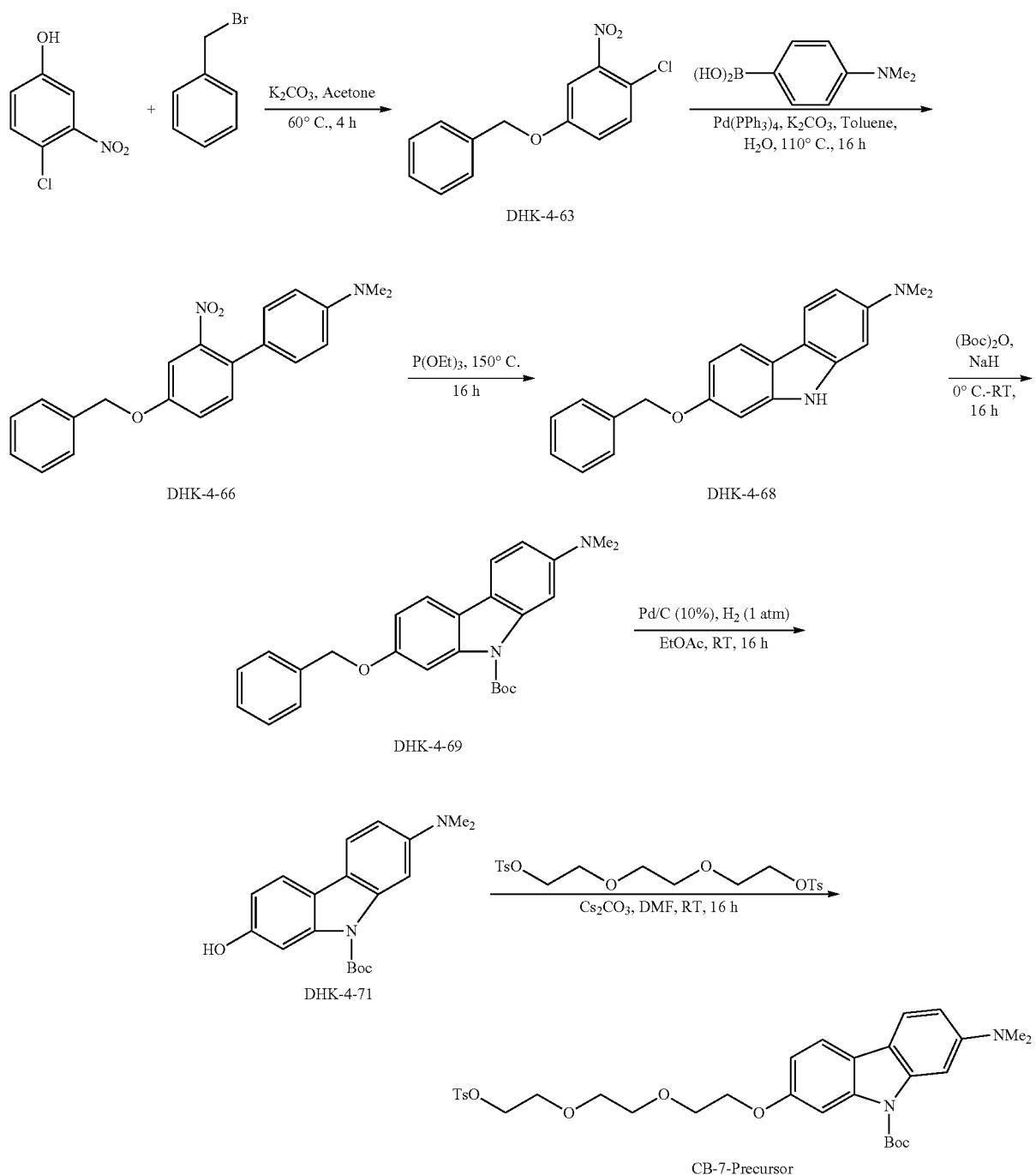

Preparation of 4-(benzyloxy)-1-chloro-2-nitrobenzene: DHK-4-63

General experimental procedure for phenolic alkylation was followed. Reaction was performed on a 1 g scale. K$_2$CO$_3$ was used as a base and acetone was used as the solvent. Reaction time was 4 h. Product eluted out in 20-30% EtOAc:Hexanes mixture in a gradient elution on a Combiflash purification system. Isolated 1.45 g (95%) of DHK-4-63 as white crystalline solid. MS: [M+H]$^+$: 264.0

Preparation of 3 4'-(benzyloxy)-N,N-dimethyl-2'-nitrobiphenyl-4-amine: DHK-4-66

General experimental procedure for Suzuki coupling reaction was followed. Reaction was performed on a 0.47 g scale. Product eluted out in 20-30% EtOAc:Hexanes mixture in a gradient elution on a Combiflash purification system. Isolated 0.21 g (34%) of DHK-4-66 as orange solid. MS: [M+H]$^+$: 349.1

Preparation of 7-(benzyloxy)-N,N-dimethyl-9H-carbazol-2-amine DHK-4-68

General experimental procedure for carbazole formation using P(OEt)₃ was followed. Reaction was performed on a 0.21 g scale. Product eluted out in 20-30% EtOAc:Hexanes mixture in a gradient elution on a Combiflash purification system. Isolated 0.13 g (68%) of DHK-4-68 as white solid. MS: [M+H]⁺: 317.1

Preparation of tert-butyl 2-(benzyloxy)-7-(dimethylamino)-9H-carbazole-9-carboxylate: DHK-4-69

General experimental procedure for carbazole N-Boc protection was followed. Reaction was performed on a 0.13 g scale. Reaction temperature was carried at room temperature for 16 h. Product eluted out in 10% EtOAc:Hexanes mixture in a gradient elution on a Combiflash purification system. Isolated 0.12 g (70%) of DHK-4-69 as white solid. MS: [M+H]⁺: 417:2.

Preparation of tert-butyl 2-(dimethylamino)-7-hydroxy-9H-carbazole-9-carboxylate: DHK-4-71

To a 50 mL round bottomed flask equipped with a magnetic stir bar containing EtOAc (50 mL) was placed DHK-4-69 (0.11 g, 0.19 mmol). To this solution was added Pd/C (10%, 20 mg) and the reaction was allowed to stir under H₂ (1 atm) at RT for 16 h. After the reaction was complete, the reaction mixture was filtered through celite and the volatiles were removed in vacuo to afford DHK-4-71 (0.09 g, 100%) as white solid.

Preparation of Tert-butyl 2-(dimethylamino)-7-(2-(2-(2-(tosyloxy)ethoxy)ethoxy)ethoxy)-9H-carbazole-9-carboxylate: DHK-4-72: CB-7 precursor General experimental procedure for phenolic alkylation was followed. Reaction was performed on a 0.09 g scale. Product eluted out in 45% EtOAc:Hexanes mixture in a gradient elution on a Combiflash purification system. Isolated 0.07 g (41%) of CB-7 precursor as white solid. MS: [M+H]⁺: 613.2.

Synthesis of AD-CB-003S-WZ0129

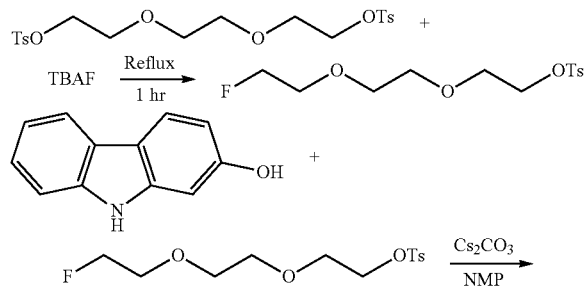

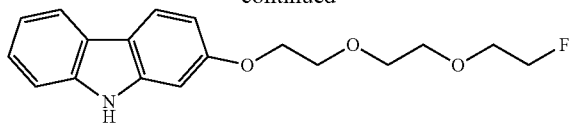

AD-CB-003S-WZ0129

To 2,2'-(ethane-1,2-diylbis(oxy))bis(ethane-2,1-diyl)bis (4-methylbenzenesulfonate) (8.7 g, 19 mmol) was added TBAF (22.8 mL, 1.0 M THF solution, 22.8 mmol). The mixture was heated to reflux for 1 h under Ar atmosphere and cooled to rt and concentrated under reduced pressure. The crude material was purified with silica chromatography (5% to 40% THF in hexane) to afford 2-(2-(2-fluoroethoxy) ethoxy)ethyl 4-methylbenzenesulfonate as a clear oil (2.5 g, 43%). ¹H NMR (400 MHz, CDCl₃) δ 7.80 (d, J=8.4 Hz, 2H), 7.34 (d, J=8.4 Hz, 2H), 4.61 (m, 1H), 4.49 (m, 1H), 4.16 (m, 2H), 3.75 (m, 1H), 3.71-3.67 (m, 3H), 3.62 (m, 4H); MS (ESI) m/z 307 (M+H⁺).

To 2-hydroxycarbazole (45 mg, 0.25 mmol) and 2-(2-(2-fluoroethoxy)ethoxy)ethyl 4-methylbenzenesulfonate (82 mg, 0.27 mmol) in 0.5 mL NMP was added Cs₂CO₃ (82 mg, 0.25 mmol). The mixture was stirred at rt for 15 h under Ar atmosphere and diluted with Et₂O (50 mL). It was washed with water (3×50 mL) and dried over MgSO₄. Solvent was removed under reduced pressure and the crude product was purified with silica chromatography (5% to 50% EtOAc in hexane) to afford the desired product as white solid (37 mg, 47%). ¹H NMR (400 MHz, CDCl₃) δ 8.02 (s, 1H), 7.96 (d, J=7.2 Hz, 1H), 7.91 (d, J=8.4 Hz, 1H), 7.38-7.33 (m, 2H), 7.20 (m, 1H), 6.91 (d, J=2.4 Hz, 1H), 6.86 (dd, J=8.8, 2.4 Hz, 1H), 4.63 (m, 1H), 4.51 (m, 1 H), 4.21 (m, 2H), 3.90 (m, 2H), 3.80-3.76 (m, 3H), 3.74-3.71 (m, 3H); MS (ESI) m/z 318 (M+H⁺).

Synthesis of AD-CB-003P-WZ0141

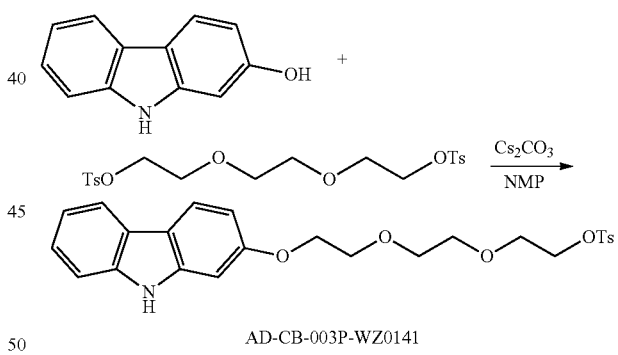

AD-CB-003P-WZ0141

To 2-hydroxycarbazole (183 mg, 1 mmol) and 2-(2-(2-fluoroethoxy)ethoxy)ethyl 4-methylbenzenesulfonate (687 mg, 1.5 mmol) in 5 mL NMP was added Cs₂CO₃ (326 mg, 1 mmol). The mixture was stirred at rt for 15 h under Ar atmosphere and diluted with Et₂O (100 mL). It was washed with water (3×100 mL) and dried over MgSO₄. Solvent was removed under reduced pressure and the crude product was purified with silica chromatography (5% to 60% EtOAc in hexane) to afford the desired product as white solid (165 mg, 35%). NMR (400 MHz, CDCl3) 8.21 (s, 1H), 7.95 (d, J=7.2 Hz, 1H), 7.91 (d, J=8.4 Hz, 1H), 7.77-7.75 (m, 2H), 7.37-7.30 (m, 2H), 7.28 (s, 1H), 7.25 (m, 1H), (td, J=7.6, 1.2 Hz, 1H), 6.92 (d, J=2.4 Hz, 1H), 6.83 (dd, J=8.8, 2.4 Hz, 1H), 4.15 (m, 4H), 3.84 (m, 2H), 3.69-3.65 (m, 4H), 3.62-3.59 (m, 2H), 2.38 (s, 3H); MS (ESI) m/z 470 (MAT), 492 (M+Na⁺).
AD-CB-004S-WZ01165

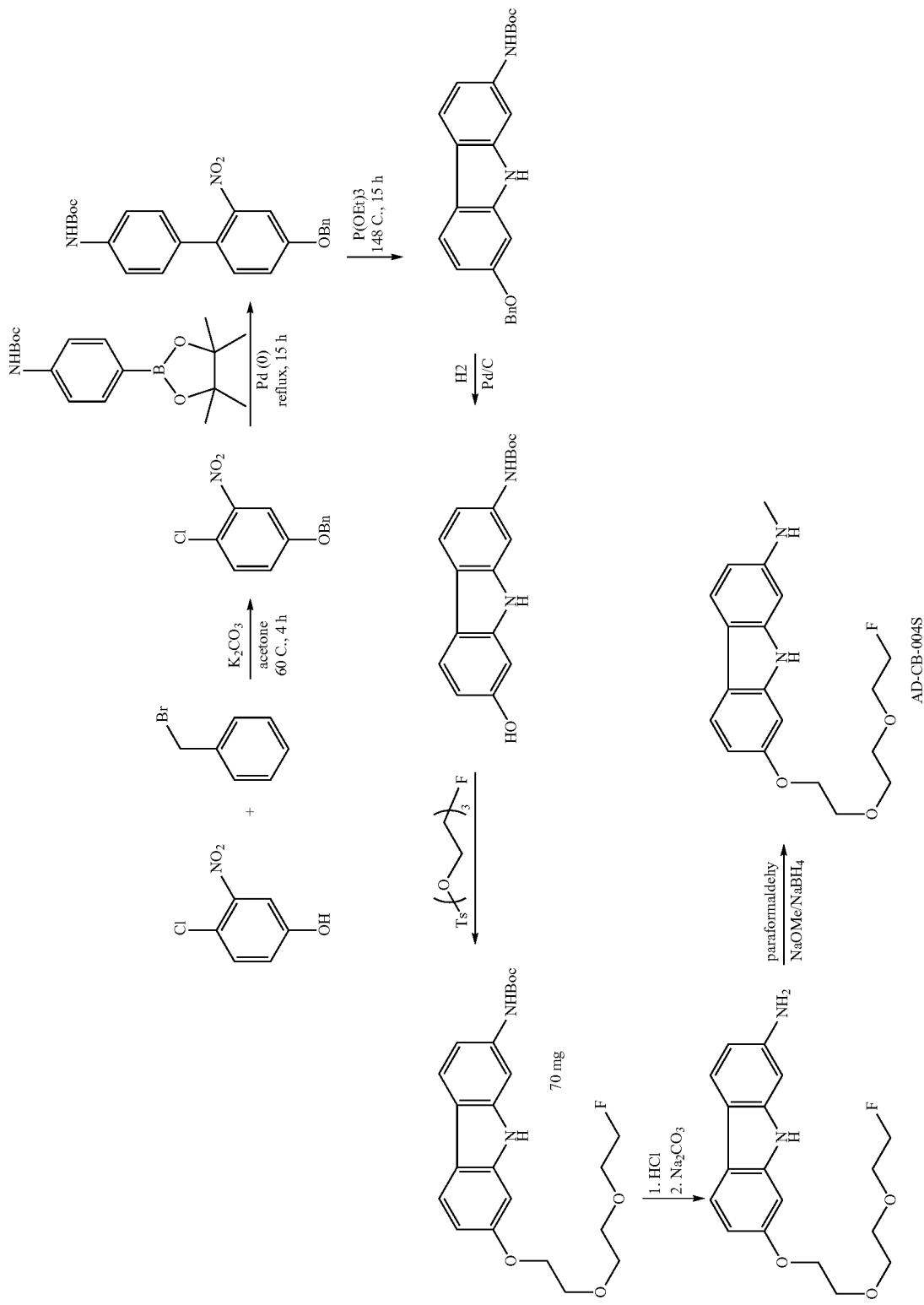

To 4-chloro-3-nitrophenol (1.74 g, 10 mmol) and benzyl bromide (2.05 g, 12 mmol) in 25 mL of acetone was added $K_2CO_3$ (2.76 g, 20 mmol). The mixture was heated at 60° C. for 4 h under Ar atmosphere and cooled to rt. It was filtered and the solid was washed with ether (80 mL) and the combined filtrate was concentrated and chromatographed (EtOAc in hexane, 3% to 30% gradient) to afford 4-(benzyloxy)-1-chloro-2-nitrobenzene as a light-yellow solid (2.5 g, 95%). $^1$H NMR (400 MHz, $CDCl_3$) δ 7.46 (d, J=2.8 Hz, 1H), 7.42-7.34 (m, 5H), 7.11 (dd, J=8.8, 2.8 Hz, 1H), 5.08 (s, 2H); MS (ESI) m/z 264 $(M+H^+)$.

To 4-(benzyloxy)-1-chloro-2-nitrobenzene (526 mg, 2 mmol) and tert-butyl 4-(4,4,5,5-tetramethyl-1,3,2-dioxaborolan-2-yl)phenylcarbamate (670 mg, 2.1 mmol) in 12 mL dioxane was added 4 mL of a 1 M $Na_2CO_3$ (aq) solution and Tetrakis(triphenylphosphine)palladium (69 mg, 0.06 mmol). The suspension was heated at reflux for 15 h under Ar atmosphere and cooled to rt. It was added EtOAc (100 mL) and washed with brine (80 mL), water (80 mL), and dried over $MgSO_4$. After solvent removal, the residue was chromatographed (hexane/EtOAc) to afford tert-butyl 4'-(benzyloxy)-2'-nitrobiphenyl-4-ylcarbamate as a yellow solid (740 mg, 88%). $^1$H NMR (400 MHz, $CDCl_3$) δ 7.44-7.34 (m, 8H), (d, J=8.4 Hz, 1H), 7.20-7.16 (m, 3H), 6.50 (s, 1H), 5.12 (s, 2H), 1.51 (s, 9H); MS (ESI) m/z 443 $(M+Na^+)$.

A suspension of tert-butyl 4'-(benzyloxy)-2'-nitrobiphenyl-4-ylcarbamate (740 mg, 1.67 mmol) in 2 mL of triethyl phosphite was heated at 145° C. for 15 h under Ar atmosphere and cooled to rt. It was added 10 mL of hexane and let sit for 10 min. Solid was collected via filtration and washed with ether/hexane (v:v 1/1, 10 mL) and dried under high vacuum to afford tert-butyl 7-(benzyloxy)-9H-carbazol-2-ylcarbamate as a off-white solid (480 mg, 74%). $^1$H NMR (400 MHz, $CDCl_3$) δ 7.89 (s, 1H), 7.83-7.78 (m, 3H), 7.46 (d, J=7.2 Hz, 2H), 7.38 (m, 2H), 7.32 (d, J=7.2 Hz, 1H), 6.94 (d, J=2.0 Hz, 1H), 6.88 (dd, J=8.8, 2.4 Hz, 1H), 6.83 (dd, J=8.4, 2.0 Hz, 1H), 6.60 (s, 1H), 5.15 (s, 2H), 1.52 (s, 9H); MS (ESI) m/z 389 $(M+H^+)$.

To tert-butyl 7-(benzyloxy)-9H-carbazol-2-ylcarbamate (220 mg, 0.56 mmol) in 50 mL MeOH was added Palladium on activated carbon (80 mg). The mixture was stirred at rt under H2 atmosphere for 3 h. Solid was filtered off and the filtrate was concentrated to afford tert-butyl 7-hydroxy-9H-carbazol-2-ylcarbamate as a brown solid (165 mg, 100%). This material was used directly for the next reaction without purification. MS (ESI) m/z 619 $(2M+Na^+)$.

To tert-butyl 7-hydroxy-9H-carbazol-2-ylcarbamate (165 mg, 0.55 mmol) and 2-(2-(2-fluoroethoxy)ethoxy)ethyl 4-methylbenzenesulfonate (202 mg, 0.66 mmol) in 2 mL of NMP was added $Cs_2CO_3$ (179 mg, 0.55 mmol). The mixture was stirred at rt for 15 h under Ar atmosphere and diluted with EtOAc (50 mL). It was washed with water (3×50 mL) and dried over $MgSO_4$. After solvent removal, the residue was chromatographed (hexane/EtOAc) to afford tert-butyl 7-(2-(2-(2-fluoroethoxy)ethoxy)ethoxy)-9H-carbazol-2-ylcarbamate as a white solid (130 mg, 55%). $^1$H NMR (400 MHz, $CDCl_3$) δ 7.94 (s, 1H), 7.83-7.79 (m, 3H), 6.91 (d, J=2.0 Hz, 1H), 6.86 (dd, J=8.4, 2.0 Hz, 1H), 6.83 (dd, J=8.8, 2.4 Hz, 1H), 6.63 (s, 1H), 4.64 (m, 1H), 4.51 (m, 1 H), 4.21 (m, 2H), 3.91 (m, 2H), 3.81-3.71 (m, 6H), 1.55 (s, 9H); MS (ESI) m/z 433 $(M+H^+)$.

To tert-butyl 7-(2-(2-(2-fluoroethoxy)ethoxy)ethoxy)-9H-carbazol-2-ylcarbamate (130 mg, 0.3 mmol) was added 10 mL of a 4 M HCl in dioxane solution. The mixture was stirred at rt for 5 h and concentrated under reduced pressure. The residue was washed with ether (15 mL) and suspended in EtOAc (50 mL). To this suspension was added 10 mL of a $NaHCO_3$ (sat.) and the mixture was stirred for 5 min. The organic layer was dried over $MgSO_4$ and concentrated to afford 7-(2-(2-(2-fluoroethoxy)ethoxy)ethoxy)-9H-carbazol-2-amine as a brown solid (95 mg, 95%). MS (ESI) m/z 333 $(M+H^+)$.

A mixture of 7-(2-(2-(2-fluoroethoxy)ethoxy)ethoxy)-9H-carbazol-2-amine (95 mg, 0.28 mmol), paraformaldehyde (43 mg, 1.43 mmol), and NaOMe (492 mg, 25% MeOH solution, 2.3 mmol) in 8 mL of MeOH was heated at reflux for 1.5 h under Ar atmosphere and cooled to rt. To this mixture was added $NaBH_4$ (54 mg, 1.43 mmol) and the mixture was heated at reflux for 2 h. After cooling to rt, the mixture was quenched onto ice. It was extracted with ether (3×30 mL) and the combined organic phase was dried over $MgSO_4$ and concentrated. The crude product was purified with chromatography (hexane/EtOAc) to afford 7-(2-(2-(2-fluoroethoxy)ethoxy)ethoxy)-N-methyl-9H-carbazol-2-amine (AD-CB-003P-WZ0141) as a light-brown solid (55 mg, 56%).

$^1$H NMR (400 MHz, $CDCl_3$) δ 7.76 (s, 1H), 7.77 (t, J=8.8 Hz, 2H), 6.78 (dd, J=8.0, 2.0 Hz, 1 H), 6.77 (s, 1H), 6.53 (dd, J=8.4, 2.0 Hz, 1H), 6.46 (s, 1H), 4.62 9m, 1H), 4.50 (m, 1H), 4.13 (t, J=5.2 Hz, 2H), 3.85 (t, J=5.2 Hz, 2H), 3.83 (s, 1H), 3.79-3.67 (m, 6H), 2.87 (s, 3H); MS (ESI) m/z 347 $(M+H^+)$. AD-CB-004 Pa-WZ01179

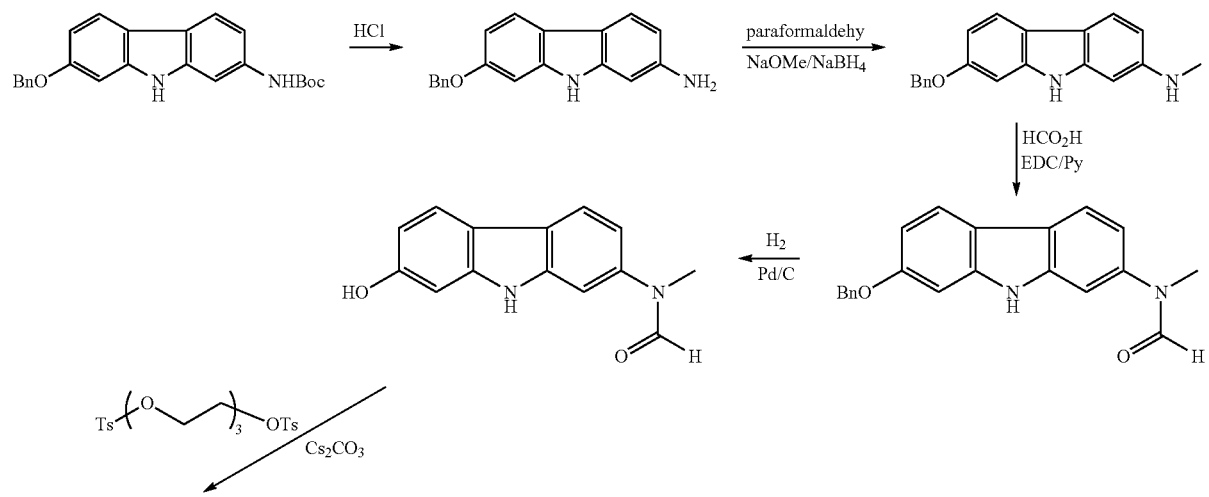

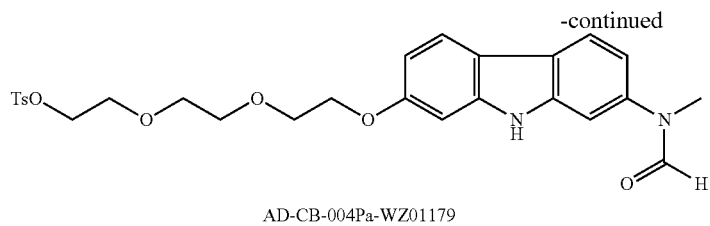

AD-CB-004Pa-WZ01179

To tert-butyl 7-(benzyloxy)-9H-carbazol-2-ylcarbamate (200 mg, 0.51 mmol) was added 10 mL of a 4 M HCl in dioxane solution. The mixture was stirred at rt for 4 h and concentrated under reduced pressure. The residue was washed with ether (15 mL) and suspended in EtOAc (50 mL). To this suspension was added 10 mL of a NaHCO₃ (sat.) and the mixture was stirred for 5 min. The organic layer was dried over MgSO₄ and concentrated to afford 7-(benzyloxy)-9H-carbazol-2-amine as a brown solid (150 mg, 100%). $^1$H NMR (400 MHz, DMSO-d6) δ 11.33 (s, 1H), 7.99 (d, J=8.4 Hz, 1H), 7.92 (d, J=8.8 Hz, 1H), 7.42 (d, J=6.8 Hz, 2H), 7.34-7.21 (m, 3H), 7.27-7.23 (m, 1H), 7.00-6.97 (m, 2H), 6.81 (dd, J=8.8, 2.4 Hz, 1 H), 5.12 (s, 2H); MS (ESI) m/z 289 (M+H$^+$).

A mixture of 7-(benzyloxy)-9H-carbazol-2-amine (150 mg, 0.52 mmol), paraformaldehyde (78 mg, 2.6 mmol), and NaOMe (900 mg, 25% MeOH solution, 4.16 mmol) in 15 mL of MeOH was heated at reflux for 2 h under Ar atmosphere and cooled to rt. To this mixture was added NaBH₄ (98 mg, 2.6 mmol) and the mixture was heated at reflux for 2 h. After cooling to rt, the mixture was quenched onto ice (30 g). It was extracted with EtOAc (3×50 mL) and the combined organic phase was dried over MgSO₄ and concentrated. The crude product was purified with chromatography (hexane/EtOAc) to afford 7-(benzyloxy)-N-methyl-9H-carbazol-2-amine as a light-brown solid (130 mg, 82%). $^1$H NMR (400 MHz, acetone-d6) δ 9.78 (s, 1H), 7.72 (d, J=8.4 Hz, 1H), 7.66 (d, J=8.8 Hz, 1H), 7.49 (d, J=7.2 Hz, 2H), 7.37 (m, 2H), 7.32-7.28 (m, 1H), 6.98 (d, J=2.4 Hz, 1H), 6.78 (dd, J=8.4, 2.4 Hz, 1H), 6.56 (d, J=2.0 Hz, 1H), 6.49 (dd, J=8.4, 2.4 Hz, 1H), 5.13 (s, 2H), 4.96 (s, 1H), 2.82 (s, 3H); MS (ESI) m/z 303 (M+H$^+$).

To 7-(benzyloxy)-N-methyl-9H-carbazol-2-amine (120 mg, 0.4 mmol), formic acid (55 mg, 1.2 mmol) and DMAP (5 mg, 0.04 mmol) in 3 mL of pyridine was added portionwise EDC (230 mg, 1.2 mmol). The mixture was stirred at rt for 3 h under Ar atmosphere and concentrated under reduced pressure. The residue was diluted with EtOAc (50 mL) and washed with water (2×50 mL), 0.5 M HCl(2×50 mL), and brine (50 mL), and dried over MgSO₄. After solvent removal, the crude product was purified with chromatography (hexane/EtOAc) to afford N-(7-(benzyloxy)-9H-carbazol-2-yl)-N-methylformamide as a white solid (110 mg, 83%). $^1$H NMR (400 MHz, acetone-d6) δ 10.34 (s, 1H), 8.49 (s, 1H), 8.02 (d, J=8.4 Hz, 1H), 7.98 (d, J=8.8 Hz, 1H), 7.51 (d, J=7.2 Hz, 2H), 7.39 (m, 2H), 7.34-7.28 (m, 1H), 7.13 (d, J=2.4 Hz, 1H), 7.08 (dd, J=8.4, 2.4 Hz, 1H), 6.91 (dd, J=8.4, 2.4 Hz, 1H), 5.19 (s, 2H), 3.31 (s, 3H); MS (ESI) m/z 331 (M+H$^+$).

To N-(7-(benzyloxy)-9H-carbazol-2-yl)-N-methylformamide (110 mg, 0.33 mmol) in 50 mL MeOH was added Palladium on activated carbon (50 mg). The mixture was stirred at rt under H2 atmosphere for 15 h. Solid was filtered off and the filtrate was concentrated to afford N-(7-hydroxy-9H-carbazol-2-yl)-N-methylformamide as a brown solid (75 mg, 94%). This material was used directly for the next reaction without purification. MS (ESI) m/z 241 (M+H$^+$).

To N-(7-hydroxy-9H-carbazol-2-yl)-N-methylformamide (45 mg, 0.187 mmol) and 2-(2-(2-fluoroethoxy)ethoxy)ethyl 4-methylbenzenesulfonate (172 mg, 0.38 mmol) in 0.5 mL NMP was added Cs₂CO₃ (65 mg, 0.2 mmol). The mixture was stirred at rt for 15 h under Ar atmosphere and diluted with EtOAc (50 mL). It was washed with water (2×50 mL), 0.5 M HCl (50 mL) and brine (50 mL), and dried over MgSO₄. Solvent was removed under reduced pressure and the crude product was purified with silica chromatography (hexane/EtOAc) to afford 2-(2-(2-(7-(N-methylformamido)-9H-carbazol-2-yloxy)ethoxy)ethoxy)ethyl 4-methylbenzenesulfonate (AD-CB-004 Pa-WZ01179) as a light-brown oil (48 mg, 48%). $^1$H NMR (400 MHz, CDCl₃) δ 8.52 (s, 1 H), 8.45 (s, 1H), 7.95 (d, J=8.4 Hz, 1H), 7.90 (d, J=8.8 Hz, 1H), 7.80-7.77 (m, 2H), 7.30 (d, J=8.0 Hz, 2H), 7.17 (d, J=2.4 Hz, 1H), 7.02 (d, J=2.0 Hz, 1H), 7.01 (dd, J=8.0, 2.0 Hz, 1H), 6.89 (dd, J=8.8, 2.4 Hz, 1H), 4.23 (m, 1H), 4.17 (m, 2H), 3.88 (m, 2H), 3.72-3.68 (m, 4H), 3.66-3.61 (m, 2H), 3.39 (s, 3H), 2.41 (s, 3H); MS (ESI) m/z 527 (M+H$^+$).

AD-CB-004Pb-WZ01191

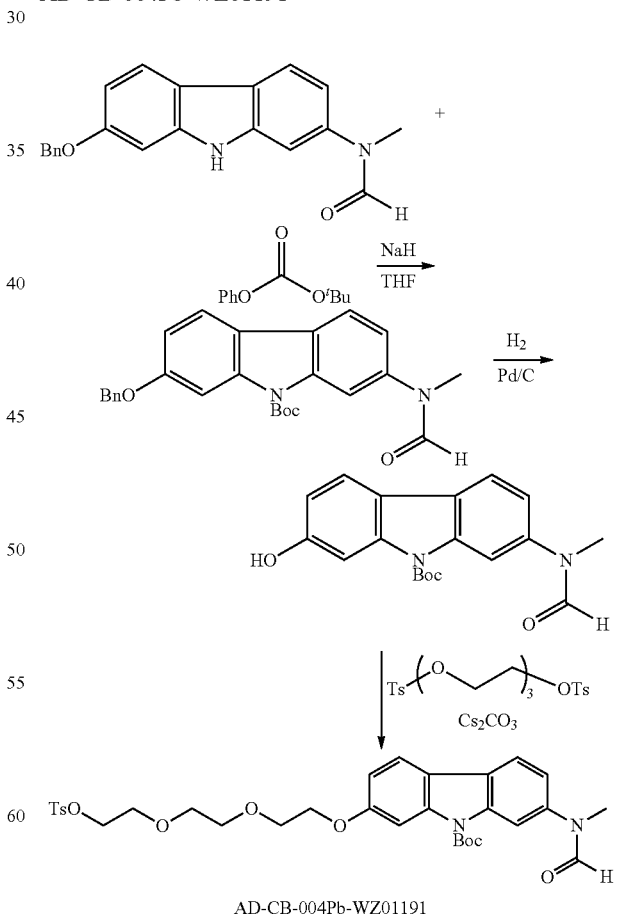

AD-CB-004Pb-WZ01191

To N-(7-(benzyloxy)-9H-carbazol-2-yl)-N-methylformamide (140 mg, 0.42 mmol) in 5 mL dry THF at 0° C. under Ar atmosphere was added NaH (50 mg, 60% in oil, 1.26 mmol) in 4 portions. The mixture was then stirred at rt for 20 min followed by the addition of tert-butyl phenyl carbonate (244 mg, 1.26 mmol) with a syringe. The reaction was allowed to stir at rt for 3 h and quenched onto ice (30 g). The mixture was extracted with EtOAc (2×40 mL) and the combined organic phase was dried over MgSO$_4$. After solvent removal, the residue was chromatographed to afford tert-butyl 2-(benzyloxy)-7-(N-methylformamido)-9H-carbazole-9-carboxylate as a white solid (120 mg, 66%). $^1$H NMR (400 MHz, CDCl$_3$) δ 8.56 (s, 1H), 8.15 (s, 1H), 7.98 (s, 1H), 7.86 (d, J=8.4 Hz, 1H), 7.83 (d, J=8.4 Hz, 1H), 7.50-7.49 (m, 2H), 7.43-7.39 (m., 2H), 7.37-7.32 (m, 1H), 7.13 (dd, J=8.4, 2.0 Hz, 1H), 7.05 (dd, J=8.8, 2.4 Hz, 1H), 5.18 (s, 2H), 3.41 (s, 3H), 1.75 (s, 9H); MS (ESI) m/z 431 (M+H$^+$).

To tert-butyl 2-(benzyloxy)-7-(N-methylformamido)-9H-carbazole-9-carboxylate (120 mg, 0.28 mmol) in 50 mL MeOH was added Palladium on activated carbon (50 mg). The mixture was stirred at rt under H2 atmosphere for 3 h. Solid was filtered off and the filtrate was concentrated to afford tert-butyl 2-hydroxy-7-(N-methylformamido)-9H-carbazole-9-carboxylate as a brown solid (95 mg, 100%). This material was used directly for the next reaction without purification. MS (ESI) m/z 341 (M+H$^+$).

To tert-butyl 2-hydroxy-7-(N-methylformamido)-9H-carbazole-9-carboxylate (65 mg, 0.19 mmol) and 2-(2-(2-fluoroethoxy)ethoxy)ethyl 4-methylbenzenesulfonate (174 mg, 0.38 mmol) in 0.5 mL NMP was added Cs$_2$CO$_3$ (68 mg, 0.21 mmol). The mixture was stirred at rt for 15 h under Ar atmosphere and diluted with EtOAc (80 mL). It was washed with water (3×50 mL), and dried over MgSO$_4$. Solvent was removed under reduced pressure and the crude product was purified with silica chromatography (hexane/EtOAc) to afford tert-butyl 2-(N-methylformamido)-7-(2-(2-(2-(tosyloxy)ethoxy)ethoxy)ethoxy)-9H-carbazole-9-carboxylate (AD-CB-004Pb-WZ01191) as a clear oil (75 mg, 63%). $^1$H NMR (400 MHz, CDCl$_3$) δ 8.56 (s, 1H), 8.14 (s, 1H), 7.89 (s, 1H), 7.87 (d, J=8.0 Hz, 1H), 7.83 (d, J=8.8 Hz, 1H), 7.79 (m, 2H), 7.32 (d, J=8.4 Hz, 2H), 7.15 (dd, J=8.4, 2.0 Hz, 1H), 7.00 (dd, J=8.8, 2.4 Hz, 1H), 4.23 (m, 1H), 3.89 (m, 2H), 3.88 (m, 2H), 3.73-3.68 (m, 4H), 3.66-3.63 (m, 2H), 3.41 (s, 3H), 2.42 (s, 3H), 1.76 (s, 9H); MS (ESI) m/z 527 (M+H$^+$).

AD-CB-010S-WZ01183

To 4-(benzyloxy)-1-chloro-2-nitrobenzene (394 mg, 1.5 mmol) N-(4-(4,4,5,5-tetramethyl-1,3,2-dioxaborolan-2-yl)phenyl)formamide (370 mg, 1.5 mmol) in 6 mL dioxane was added 3 mL of a 1 M Na$_2$CO$_3$ (aq) solution and Tetrakis (triphenylphosphine)palladium (52 mg, 0.045 mmol). The suspension was headed at reflux for 15 h under Ar atmosphere and cooled to rt. It was added EtOAc (80 mL) and washed with brine (50 mL), water (2×80 mL), and dried over MgSO$_4$. After solvent removal, the residue was chromatographed (hexane/EtOAc) to afford N-(4'-(benzyloxy)-2'-nitrobiphenyl-4-yl)formamide as a yellow solid (395 mg, 75%). MS (ESI) m/z 349 (M+H$^+$).

A suspension of N-(4'-(benzyloxy)-2'-nitrobiphenyl-4-yl)formamide (350 mg, 1 mmol) in 2 mL of triethyl phosphite was heated at 145 C for 15 h under Ar atmosphere and cooled to rt. It was added 10 mL of hexane and let sit for 10 min. Solid was collected via filtration and washed with ether/hexane (v:v 1/1, 10 mL) and dried under high vacuum to N-(7-(benzyloxy)-9H-carbazol-2-yl)formamide as a light-brown solid (280 mg, 88%). MS (ESI) m/z 317 (M+H$^+$).

To N-(7-(benzyloxy)-9H-carbazol-2-yl)formamide (250 mg, 0.79 mmol) in 50 mL MeOH was added Palladium on activated carbon (60 mg). The mixture was stirred at rt under H2 atmosphere for 15 h. The mixture was concentrated under reduced pressure and dried under high vacuum to afford N-(7-hydroxy-9H-carbazol-2-yl)formamide mixed with the catalyst as a black solid (240 mg). This material was used directly for the next reaction without purification. MS (ESI) m/z 227 (M+H$^+$).

To N-(7-hydroxy-9H-carbazol-2-yl)formamide (30 mg) and 2-(2-(2-fluoroethoxy)ethoxy)ethyl 4-methylbenzenesulfonate (48 mg, 0.156 mmol) in 0.3 mL of NMP was added Cs$_2$CO$_3$ (42 mg, 0.13 mmol). The mixture was stirred at rt for 15 h under Ar atmosphere and diluted with EtOAc (30 mL). It was washed with water (3×30 mL) and dried over MgSO$_4$. After solvent removal, the residue was chromatographed (hexane/EtOAc) to N-(7-(2-fluoroethoxy)-9H-carbazol-2-yl)formamide (AD-CB-010S-WZ01183) as a white solid (17 mg, 36%). For the major rotomer: $^1$H NMR (400 MHz, acetone-d6) δ 10.10 (s, 1H), 9.28 (s, 1H), 8.39 (d, J=1.6 Hz, 1H), 8.11 (d, J=2.0 Hz, 1H), 7.91 (s, 1H), 7.87 (d, J=8.4, Hz, 2H), 7.17 (dd, J=8.4, 2.0 Hz, 1H), 7.01 (d, J=2.0 Hz, 1H), 6.80

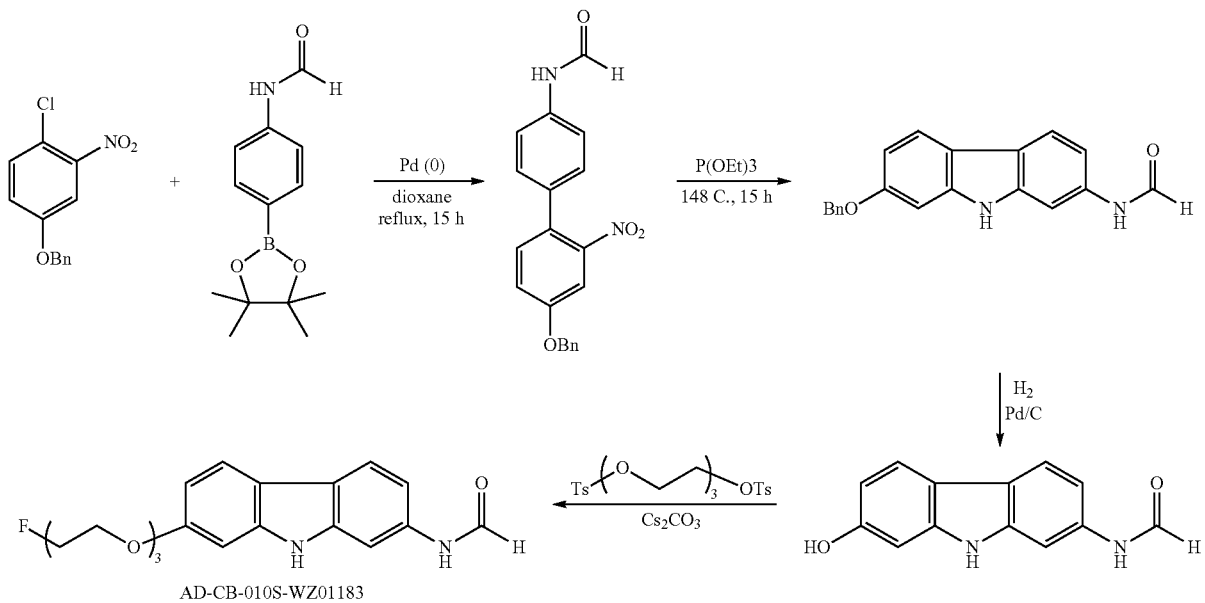

AD-CB-010S-WZ01183

(dd, J=8.4, 2.0 Hz, 1H), 4.58 (m, 1H), 4.46 (m, 1H), 4.21 (m, 2H), 3.88 (m, 2H), 3.77 (m, 1H), 3.73-3.66 (m, 5H); MS (ESI) m/z 361 (M+H$^+$).
AD-CB-012S-WZ01185

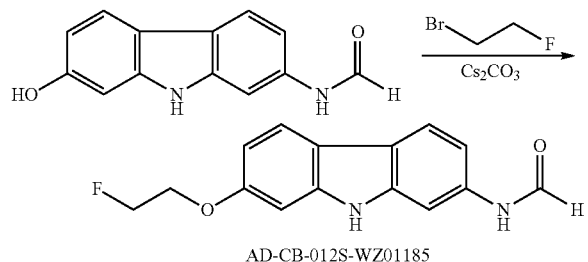

AD-CB-012S-WZ01185

Compound AD-CB-012S-WZ01185 was prepared using the same procedure for the preparation of AD-CB-010S-WZ01183. For the major rotomer: $^1$H NMR (400 MHz, acetone-d6) δ 10.08 (s, 1H), 9.19 (s, 1H), 8.26 (d, J=1.6 Hz, 1H), 8.00 (d, J=2.0 Hz, 1H), 7.84-7.77 (m, 3H), 7.07 (dd, J=8.4, 2.0 Hz, 1H), 6.93 (d, J=2.0 Hz, 1H), 6.69 (dd, J=8.4, 2.0 Hz, 1H), 4.73 (m, 1H), 4.61 (m, 1H), 4.24 (m, 1H), 4.17 (m, 1H); MS (ESI) m/z 273 (M+H$^+$).
AD-CB-024S-WZ02033

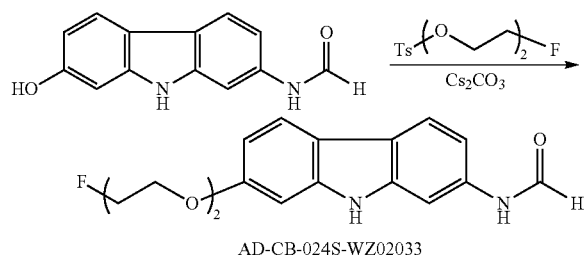

AD-CB-024S-WZ02033

Compound AD-CB-024S-WZ02033 was prepared using the same procedure for the preparation of AD-CB-010S-WZ01183. For the major rotomer: $^1$H NMR (400 MHz, acetone-d6) δ 10.19 (s, 1H), 9.31 (s, 1H), 8.38 (d, J=1.6 Hz, 1H), 8.11 (d, J=2.0 Hz, 1H), 7.88 (d, J=8.2 Hz, 2H), 7.19 (dd, J=8.4, 2.0 Hz, 1H), 7.03 (d, J=2.0 Hz, 1H), 6.79 (dd, J=8.4, 2.0 Hz, 1H), 4.62 (m, 1H), 4.50 (m, 1H), 4.20 (m, 2H), 3.88 (m, 2H), 3.83 (m, 1H), 3.75 (m, 1H); MS (ESI) m/z 317 (M+H$^+$).
AD-CB-013S-WZ-02001

A mixture of palladium acetate (37 mg, 0.165 mmol) and BINAP (154 mg, 0.248 mmol) in 5 mL dioxane was stirred for 10 min under Ar atmosphere. To this mixture was added 1-bromo-4-nitrobenzene (1.11 g, 5.5 mmol), 4-methoxyaniline (745 mg, 6.07 mmol), CsCO$_3$ (2.5 g, 7.73 mmol), and 10 mL of dioxane. The mixture was heated at reflux for 15 h and cooled and diluted with ether (80 mL). The solid was removed through filtration and the filtrate was concentrated. The residue was chromatographed (hexane/EtOAc) to afford 4-methoxy-N-(4-nitrophenyl)aniline as a yellow solid (786 mg, 58%). MS (ESI) m/z 245 (M+H$^+$).

To 4-methoxy-N-(4-nitrophenyl)aniline (785 mg, 3.2 mmol) in 5 mL of AcOH was added Pd(OAc)$_2$ (1.43 g, 6.4 mmol). The mixture was heated at 100° C. for 15 h under air atmosphere and cooled to rt and concentrated under reduced pressure. The residue was taken up in EtOAc (100 mL) and washed with NaHCO$_3$ (2×100 mL) and water (100 mL). After solvent removal, the crude was purified with chromatography (hexane/EtOAc) to afford 3-methoxy-6-nitro-9H-carbazole as a orange solid (495 mg, 64%). $^1$H NMR (400 MHz, acetone-d6) δ 10.90 (s, 1H), 9.09 (d, J=2.4 Hz, 1H), 8.27 (dd, J=9.2, 2.4 Hz, 1H), 7.96 (d, J=2.4 Hz, 1H), 7.62 (d, J=9.2 Hz, 1H), 7.53 (d, J=8.8 Hz, 1H), 7.14 (dd, J=8.8, 2.8 Hz, 1H), 3.92 (s, 3H); MS (ESI) m/z 243 (M+H$^+$).

To 3-methoxy-6-nitro-9H-carbazole (100 mg, 0.41 mmol) in 40 mL MeOH was added Palladium on activated carbon (50 mg). The mixture was stirred at rt under H2 atmosphere for 5 h. Solid was filtered off and the filtrate was concentrated to afford 6-methoxy-9H-carbazol-3-amine as a brown solid (80 mg, 92%). This material was used directly for the next reaction without purification. MS (ESI) m/z 213 (M+H$^+$).

To 6-methoxy-9H-carbazol-3-amine (16 mg, 0.075 mmol) and 1-bromo-2-fluoroethane (48 mg, 0.375 mmol) in 0.3 mL of NMP was added Cs$_2$CO$_3$ (30 mg, 0.09 mmol). The mixture was stirred at rt for 72 h under Ar atmosphere and diluted with EtOAc (30 mL). It was washed with water (3×30 mL) and dried over MgSO$_4$. After solvent removal, the residue was purified by reversed-phase HPLC (buffer A: 0.05% aqueous TFA; buffer B: 0.05% TFA in MeCN) to afford a light-brown wax (5 mg, 26%). $^1$H NMR (400 MHz, acetone-d6) δ 7.75 (s, 1H), 7.67 (s, 1H), 7.52 (d, J=2.4 Hz, 1H), 7.35 (t, J=9.6 Hz, 2H), 7.14 (d, J=8.0 Hz, 1H), 7.00 (dd, J=8.8, 2.4 Hz, 1H), 4.81 (t, J=5.2 Hz, 1H), 4.69 (t, J=4.8 Hz, 1H), 3.89 (s, 3H); MS (ESI) m/z 259 (M+H$^+$).

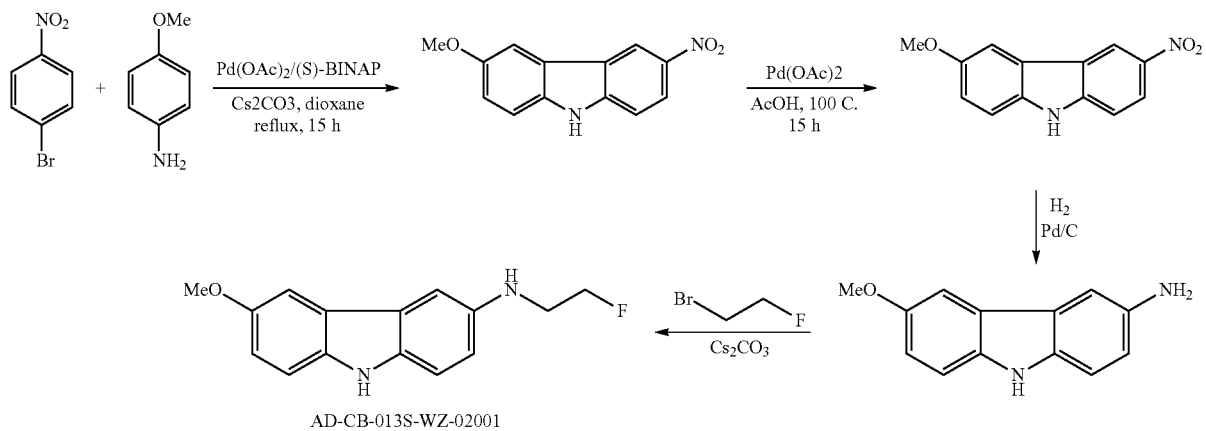

AD-CB-013S-WZ-02001

AD-C-004S-WZ01055

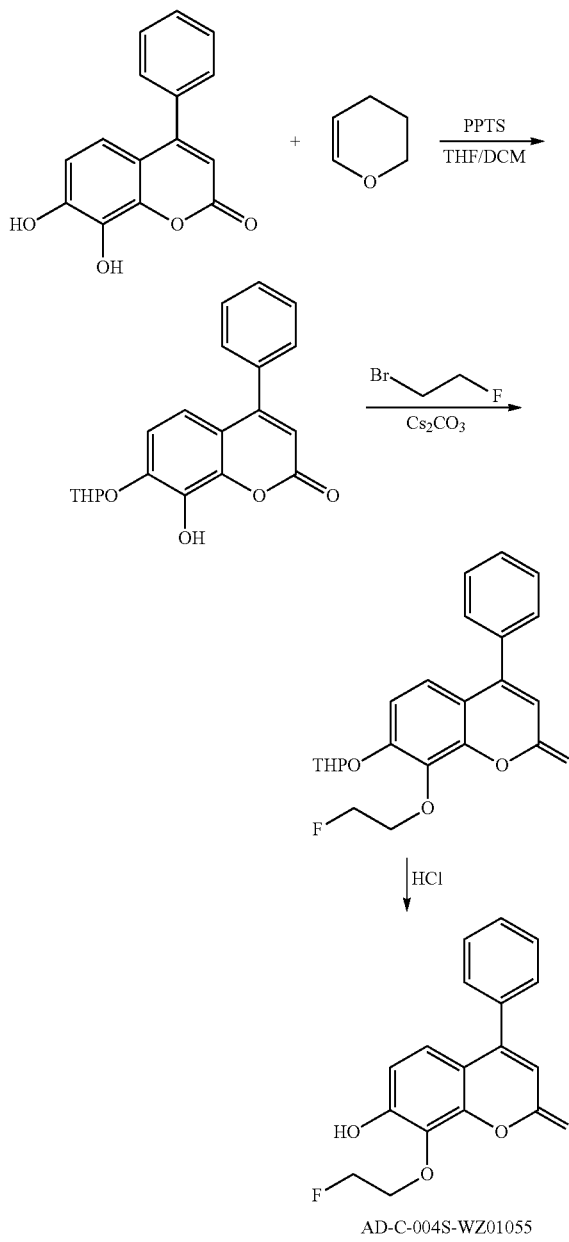

AD-C-004S-WZ01055

To 7,8-dihydroxy-4-phenyl-2H-chromen-2-one (500 mg, 2 mmol) and 3,4-dihydro-2H-pyran in 4 mL THF and 4 mL DCM was added pyridinium paratoluene sulfonate (PPTS, 8 mg). The mixture was stirred at rt for 15 h under Ar atmosphere and diluted with EtOAc (50 mL). It was washed with NaHCO$_3$ (sat. 30 mL) and water (50 mL) and dried over MgSO$_4$ and concentrated under reduced pressure. The residue was chromatographed (hexane/EtOAc) to afford 8-hydroxy-4-phenyl-7-(tetrahydro-2H-pyran-2-yloxy)-2H-chromen-2-one as a yellow solid (180 mg, 26%). MS (ESI) m/z 339 (M+H$^+$).

To 8-hydroxy-4-phenyl-7-(tetrahydro-2H-pyran-2-yloxy)-2H-chromen-2-one (40 mg, 0.12 mmol) and 1-bromo-2-fluoroethane (22 mg, 0.17 mmol) in 0.4 mL NMP was added Cs$_2$CO$_3$ (46 mg, 0.14 mmol). The mixture was stirred at rt for 5 h under Ar atmosphere and diluted with ether (40 mL). It was washed with water (3×30 mL) and dried over MgSO$_4$ and concentrated. The crude product was purified with chromatography (hexane/EtOAc) to afford 8-(2-fluoroethoxy)-4-phenyl-7-(tetrahydro-2H-pyran-2-yloxy)-2H-chromen-2-one as a white solid (34 mg, 73%). MS (ESI) m/z 385 (M+H$^+$).

To 8-(2-fluoroethoxy)-4-phenyl-7-(tetrahydro-2H-pyran-2-yloxy)-2H-chromen-2-one was added 1.5 mL of a 4 M HCl dioxane solution. The mixture was stirred at rt for 30 min under Ar atmosphere and concentrated. The crude product was purified with chromatography (hexane/EtOAc) to afford 8-(2-fluoroethoxy)-7-hydroxy-4-phenyl-2H-chromen-2-one (AD-C-004S-WZ01055) as a white solid (24 mg, 90%). $^1$H NMR (400 MHz, CDCl$_3$) δ 8.96 (s, 1H), 7.57-7.54 (m, 3H), 7.52-7.49 (m, 2H), 7.08 (dd, J=8.8, 1.2 Hz, 1H), 6.87 (dd, J=8.8, 1.2 Hz, 1H), 6.11 (d, J=1.2 Hz, 1H), 4.86 (m, 1H), 4.74 (m, 1H), 4.50 (m, 1H), 4.43 (m, 1H); MS (ESI) m/z 301 (M+H$^+$), 323 (M+H$^+$).

AD-C-004P-WZ01051

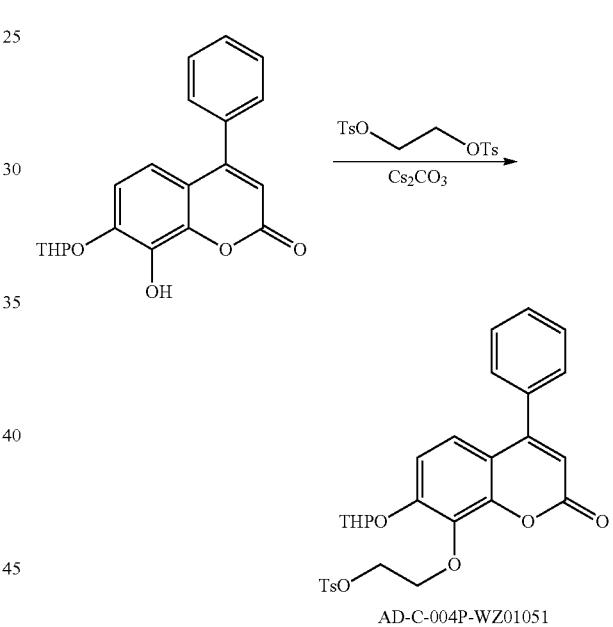

AD-C-004P-WZ01051

To 8-hydroxy-4-phenyl-7-(tetrahydro-2H-pyran-2-yloxy)-2H-chromen-2-one (115 mg, 0.34 mmol) and ethane-1,2-diylbis(4-methylbenzenesulfonate) (188 mg, 0.51 mmol) in 1 mL NMP was added Cs$_2$CO$_3$ (133 mg, 0.41 mmol). The mixture was stirred at rt for 15 h under Ar atmosphere and diluted with ether (50 mL). It was washed with water (3×50 mL) and dried over MgSO$_4$ and concentrated. The crude product was purified with chromatography (hexane/EtOAc) to 2-(2-oxo-4-phenyl-7-(tetrahydro-2H-pyran-2-yloxy)-2H-chromen-8-yloxy)ethyl 4-methylbenzenesulfonate as a white wax (97 mg, 53%). $^1$H NMR (400 MHz, CDCl$_3$) δ 7.83 (d, J=8.4 Hz, 1H), 7.53-7.50 (m, 3H), 7.43-7.41 (m, 2 h), 7.36 (d, J=8.0 Hz, 1H), 7.16 (d, J=8.8 Hz, 1H), 7.06 (d, J=9.2 Hz, 1H), 6.22 (s, 1H), 5.56 (t, J=2.8 Hz, 1H), 4.41 (m, 4H), 3.86 (td, J=10.8, 2.8 Hz, 1H), 3.61 (m, 1H), 2.08-1.86 (m, 3H), 1.76-1.63 (m, 3H); MS (ESI) m/z 537 (M+H$^+$).

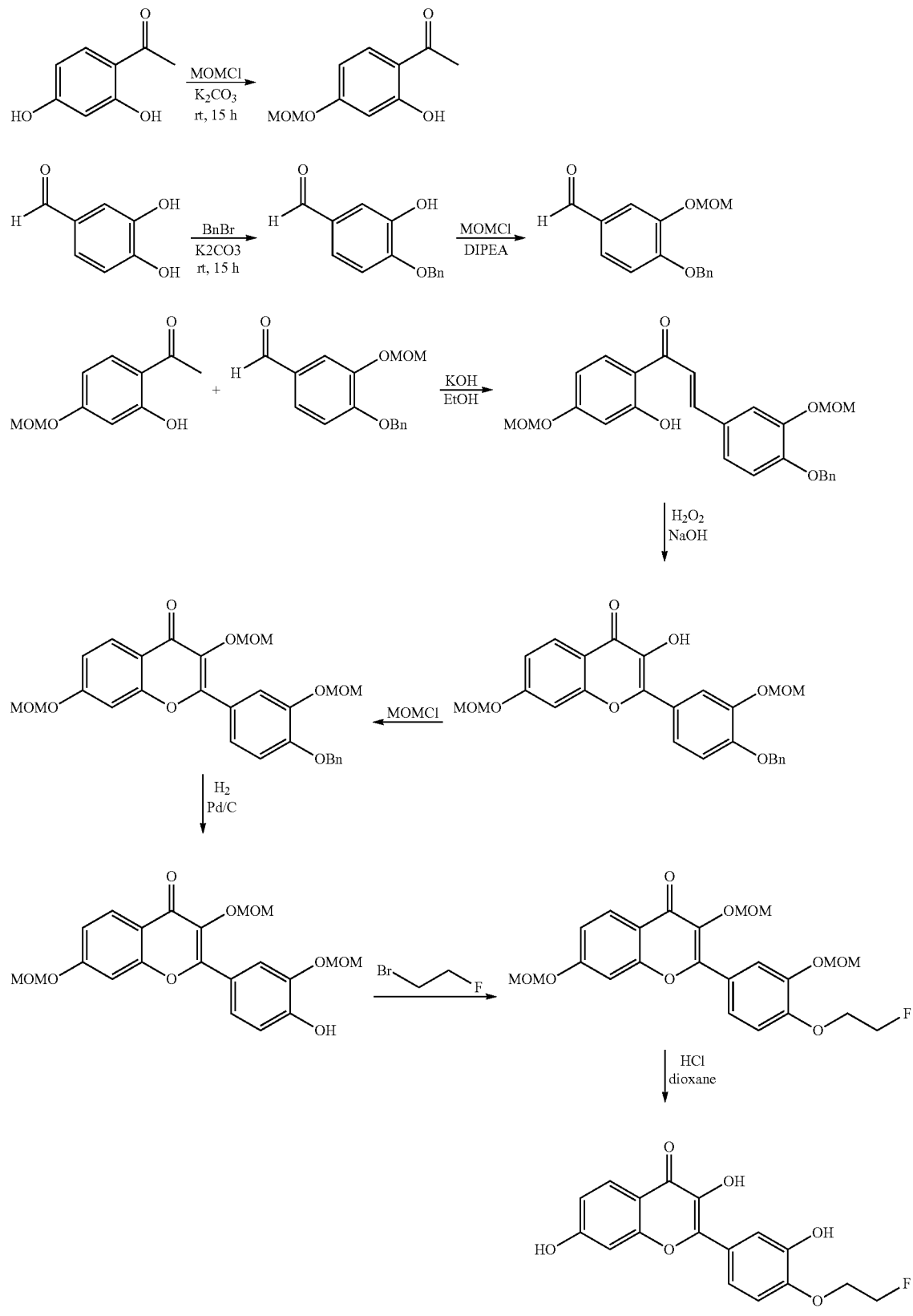

To 1-(2,4-dihydroxyphenyl)ethanone (1.52 g, 10 mmol) in 12 mL acetone was added K2CO3 (1.38 g, 10 mmol) followed by slow addition of chloro(methoxy)methane (885 mg, 11 mmol) with stirring under Ar atmosphere at rt. The reaction mixture was stirred at rt for 4 h and filtered. Solid was washed with EtOAc (80 mL) and the combined filtrate was washed with $NaH_2PO_4$ (sat. 50 mL) and water (80 mL) and dried over $MgSO_4$ and concentrated. The crude product was purified with silica chromatography (hexane/EtOAc) to afford 1-(2-hydroxy-4-(methoxymethoxy)phenyl)ethanone as a off-white solid (1.2 g, 61%). MS (ESI) m/z 197 (M+H$^+$).

A mixture of 3,4-dihydroxybenzaldehyde (1.38 g, 10 mmol), benzyl bromide (1.71 g, 10 mmol), and $K_2CO_3$ (1.24 g, 9 mmol) in 20 mL acetone was stirred at rt for 15 h under Ar atmosphere. Solid was filtered off and the filtrated was diluted with EtOAc (100 mL) and washed with $NaH_2PO_4$ (sat. 100 mL), and dried over $MgSO_4$ and concentrated. The residue was chromatographed (hexane/EtOAc) to afford 4-(benzyloxy)-3-hydroxybenzaldehyde as a white solid (1.15 g, 50%). $^1$H NMR (400 MHz, CDCl$_3$) δ 9.84 (s, 1H), 7.46 (d, J=2.0 Hz, 1H), 7.44-7.40 (m, 6H), 7.04 (d, J=8.0 Hz, 1H), 5.80 (s, 1H), 5.21 (s, 2H); MS (ESI) m/z 229 (M+H$^+$).

A mixture of 4-(benzyloxy)-3-hydroxybenzaldehyde (912 mg, 4 mmol), chloro(methoxy)methane (480 mg, 6 mmol), and DIPEA (1.03 g, 8 mmol) in 20 mL DCM was stirred at rt under Ar atmosphere for 15 h. It was diluted with ether (100 mL) and washed with 0.5 M HCl(2×50 mL) and water (2×80 mL), dried over $MgSO_4$ and concentrated. The crude product was purified with silica chromatography (hexane/EtOAc) to afford 4-(benzyloxy)-3-(methoxymethoxy)benzaldehyde as a clear oil (960 mg, 88%). MS (ESI) m/z 273 (M+H$^+$).

To 1-(2-hydroxy-4-(methoxymethoxy)phenyl)ethanone (618 mg, 3.15 mmol) and 4-(benzyloxy)-3-(methoxymethoxy)benzaldehyde (816 mg, 3 mmol) in a 25-mL round-bottom flask under Ar atmosphere was added 2.5 mL of a freshly made 5% KOH in EtOH solution. The mixture was vigorously stirred at rt until it solidified and kept at rt for 6 days. It was taken up in ether (100 mL) and added 0.5 M HCl to pH=5, and stirred for 3 min. The mixture was washed with water (2×100 mL) and dried over $MgSO_4$ and concentrated. The residue was chromatographed (hexane/EtOAc) to afford (E)-3-(4-(benzyloxy)-3-(methoxymethoxy)phenyl)-1-(2-hydroxy-4-(methoxymethoxy)phenyl)prop-2-en-1-one as a clear oil (780 mg, 58%). MS (ESI) m/z 451 (M+H$^+$).

To (E)-3-(4-(benzyloxy)-3-(methoxymethoxy)phenyl)-1-(2-hydroxy-4-(methoxymethoxy)phenyl)prop-2-en-1-one (450 mg, 1 mmol) in 1.5 mL MeOH was added 4 mL of a 15% NaOH solution, followed by hydrogen peroxide (113 mg, 30% solution). The mixture was stirred at rt for 2 h and additional 226 mg of hydrogen peroxide was added. The reaction was stirred for 15 and quenched onto $NaH_2PO_4$ (sat. 50 mL). It was extracted with EtOAc (3×50 mL) and the combined organic phase was dried over $MgSO_4$ and concentrated. The residue was chromatographed (hexane/EtOAc) to afford 2-(4-(benzyloxy)-3-(methoxymethoxy)phenyl)-3-hydroxy-7-(methoxymethoxy)-4H-chromen-4-one as a off-white solid (55 mg, 12%). MS (ESI) m/z 465 (M+H$^+$).

To 2-(4-(benzyloxy)-3-(methoxymethoxy)phenyl)-3-hydroxy-7-(methoxymethoxy)-4H-chromen-4-one (55 mg, 0.12 mmol) in 2 mL of DCM was added DIPEA (31 mg, 0.24 mmol), followed by slow addition of chloro(methoxy)methane (15 mg, 0.18 mmol). The reaction mixture was stirred at rt under Ar atmosphere for 3 h and diluted with ether (30 mL). It was washed with water (3×30 mL) and dried over $MgSO_4$ and concentrated. The crude product was purified with silica chromatography (hexane/EtOAc) to afford 2-(4-(benzyloxy)-3-(methoxymethoxy)phenyl)-3,7-bis(methoxymethoxy)-4H-chromen-4-one as a white solid (55 mg, 90%). $^1$H NMR (400 MHz, CDCl$_3$) δ 8.14 (d, J=8.8 hz, 1H), 7.91 (d, J=2.0 Hz, 1H), 7.71 (dd, J=8.4 Hz, 2.0 Hz, 1H), 7.46-7.44 (m, 2H), 7.39 (m, 2H), 7.34-7.31 (m, 1H), 7.12 (d, J=2.4 Hz, 1H), 7.05 (dd, J=8.8, 2.4 Hz, 1H), 7.03 (d, J=8.4 Hz, 1H), 5.30 (s, 2H), 5.28 (s, 2H), 5.24 (s, 2H), 5.21 (s, 2H), 3.55 (s, 3H), 3.51 (s, 3H), 3.18 (s, 3H); MS (ESI) m/z 509 (M+H$^+$).

To 2-(4-(benzyloxy)-3-(methoxymethoxy)phenyl)-3,7-bis(methoxymethoxy)-4H-chromen-4-one (55 mg, 0.108 mmol) in 10 mL MeOH was added Palladium on activated carbon (20 mg). The mixture was stirred at rt under $H_2$ atmosphere for 2 h. Solid was filtered off and the filtrate was concentrated to afford 2-(4-hydroxy-3-(methoxymethoxy)phenyl)-3,7-bis(methoxymethoxy)-4H-chromen-4-one as a yellow solid (45 mg, 99%). This material was used directly for the next reaction without purification. MS (ESI) m/z 419 (M+H$^+$).

To 2-(4-hydroxy-3-(methoxymethoxy)phenyl)-3,7-bis(methoxymethoxy)-4H-chromen-4-one (20 mg, 0.048 mmol) and 1-bromo-2-fluoroethane (18 mg, 0.14 mmol) in 0.3 mL NMP was added $Cs_2CO_3$ (39 mg, 0.12 mmol). The mixture was stirred at rt for 15 h under Ar atmosphere and diluted with ether (30 mL). It was washed with $NaH_2PO_4$ (sat. 30 mL) and water (2×30 mL) and dried over $MgSO_4$ and concentrated. The crude product was purified with chromatography (hexane/EtOAc) to afford 2-(4-(2-fluoroethoxy)-3-(methoxymethoxy)phenyl)-3,7-bis(methoxymethoxy)-4H-chromen-4-one as a white solid (19 mg, 85%). $^1$H NMR (400 MHz, CDCl$_3$) δ 8.15 (d, J=8.8 Hz, 1H), 7.91 (d, J=2.0 Hz, 1H), 7.76 (dd, J=8.4 Hz, 2.0 Hz, 1H), 7.13 (d, J=2.4 Hz, 1H), 7.05 (dd, J=8.8, 2.4 Hz, 1H), 7.03 (d, J=8.4 Hz, 1H), 5.29 (s, 4H), 5.22 (s, 2H), 4.89 (m, 1H), 4.78 (m, 1H), 4.40 (m. 1H), 4.32 (m, 1H), 3.56 (s, 3H), 3.51 (s, 3 H) 3.20 (s, 3H); MS (ESI) m/z 465 (M+H$^+$).

To 2-(4-(2-fluoroethoxy)-3-(methoxymethoxy)phenyl)-3,7-bis(methoxymethoxy)-4H-chromen-4-one (19 mg, 0.041 mmol) was added 1 mL of 4 M HCl solution in dioxane. The mixture was stirred at rt for 3 h. Volatiles were removed under reduced pressure and the residue was washed with ether (2×1 mL) and dried under high vacuum to afford 2-(4-(2-fluoroethoxy)-3-hydroxyphenyl)-3,7-dihydroxy-4H-chromen-4-one (AD-F-001S-WZ01067) as a yellow solid (11 mg, 81%). $^1$H NMR (400 MHz, DMSO-d6) δ 10.73 (s, 1H), 9.39 (s, 1H), 9.17 (s, 1H), 7.89 (d, J=9.6 Hz, 1H), 7.69 (d, J=2.0 Hz, 1H), 7.59 (dd, J=8.4 Hz, 2.0 Hz, 1H), 7.06 (d, J=8.8 Hz, 1H), 6.87 (m, 2H), 4.80 (m, 1H), 4.68 (m, 1H), 4.30 (m, 1H), 4.23 (m, 1H); MS (ESI) m/z 333 (M+H+), 355 (M+Na+).

AD-C-001P-WZ01079

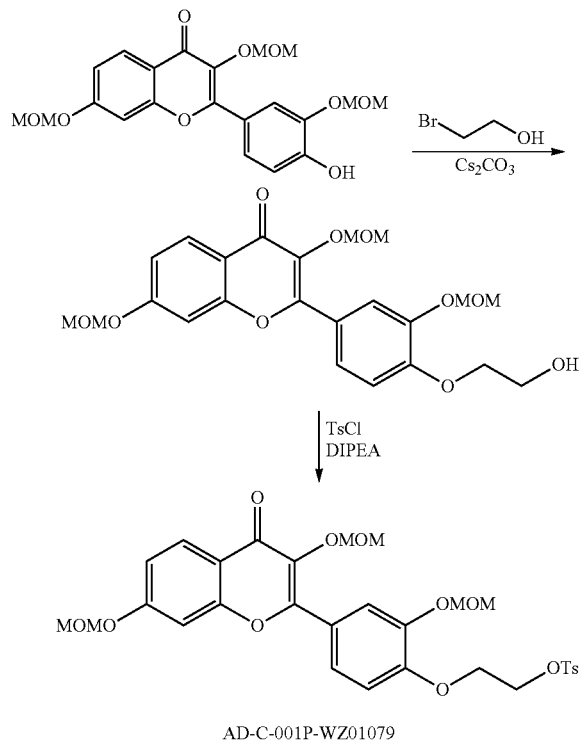

AD-C-001P-WZ01079

To 2-(4-hydroxy-3-(methoxymethoxy)phenyl)-3,7-bis(methoxymethoxy)-4H-chromen-4-one (19 mg, 0.045 mmol) and 2-bromoethanol (44 mg, 0.36 mmol) in 0.2 mL NMP was added Cs$_2$CO$_3$ (29 mg, 0.09 mmol). The mixture was stirred at rt for 15 h under Ar atmosphere and diluted with ether (30 mL). It was washed with NaH$_2$PO$_4$ (sat. 30 mL) and water (2×30 mL) and dried over MgSO$_4$ and concentrated. The crude product was purified with chromatography (hexane/EtOAc) to 2-(4-(2-hydroxyethoxy)-3-(methoxymethoxy)phenyl)-3,7-bis(methoxymethoxy)-4H-chromen-4-one (18 mg, 86%). MS (ESI) m/z 463 (M+H+).

To 2-(4-(2-hydroxyethoxy)-3-(methoxymethoxy)phenyl)-3,7-bis(methoxymethoxy)-4H-chromen-4-one (18 mg, 0.039 mmol) and DIPEA (15 mg, 0.11 mmol) was added 4-methylbenzene-1-sulfonyl chloride (11 mg, 0.058 mmol). The mixture was stirred at rt for 15 h under Ar atmosphere and diluted with ether (30 mL). It was washed with 0.5 M HCl (2×30 mL) and water (50 mL), and dried over MgSO$_4$ and concentrated. The crude product was chromatographed to afford 2-(4-(3,7-bis(methoxymethoxy)-4-oxo-4H-chromen-2-yl)-2-(methoxymethoxy)phenoxy)ethyl 4-methylbenzenesulfonate (AD-C-001P-WZ01079) as a yellow wax (20 mg, 83%). $^1$H NMR (400 MHz, CDCl$_3$) δ 8.15 (dd, J=8.8, 2.0 Hz, 1H), 7.89 (d, J=2.0 Hz, 1H), 7.76 (dd, J=8.4 Hz, 2.0 Hz, 2H), 7.73 (dd, J=8.4, 2.0 Hz, 1H), 7.36 (d, J=6.8 Hz, 2H), 7.27 (d, J=2.0 Hz, 1H), 7.14 (d, J=2.4 Hz, 1H), 7.05 (dd, J=8.8, 2.0 Hz, 1H), 6.94 (dd, J=8.8, 2.0 Hz, 1H), 5.29 (d, J=1.6 Hz, 2H), 5.22 (d, J=2.0 Hz, 4H), 4.42 (t, J=3.0 Hz, 2H), 4.32 (t, J=3.0 Hz, 2H), 3.53 (d, J=2.4 Hz, 3H), 3.52 (d, J=2.0 Hz, 3H), 3.20 (d, J=2.4 Hz, 3H), 2.46 (s, 3H); MS (ESI) m/z 617 (M+H+).

Synthetic Scheme of CB 14-16, 19 and 20

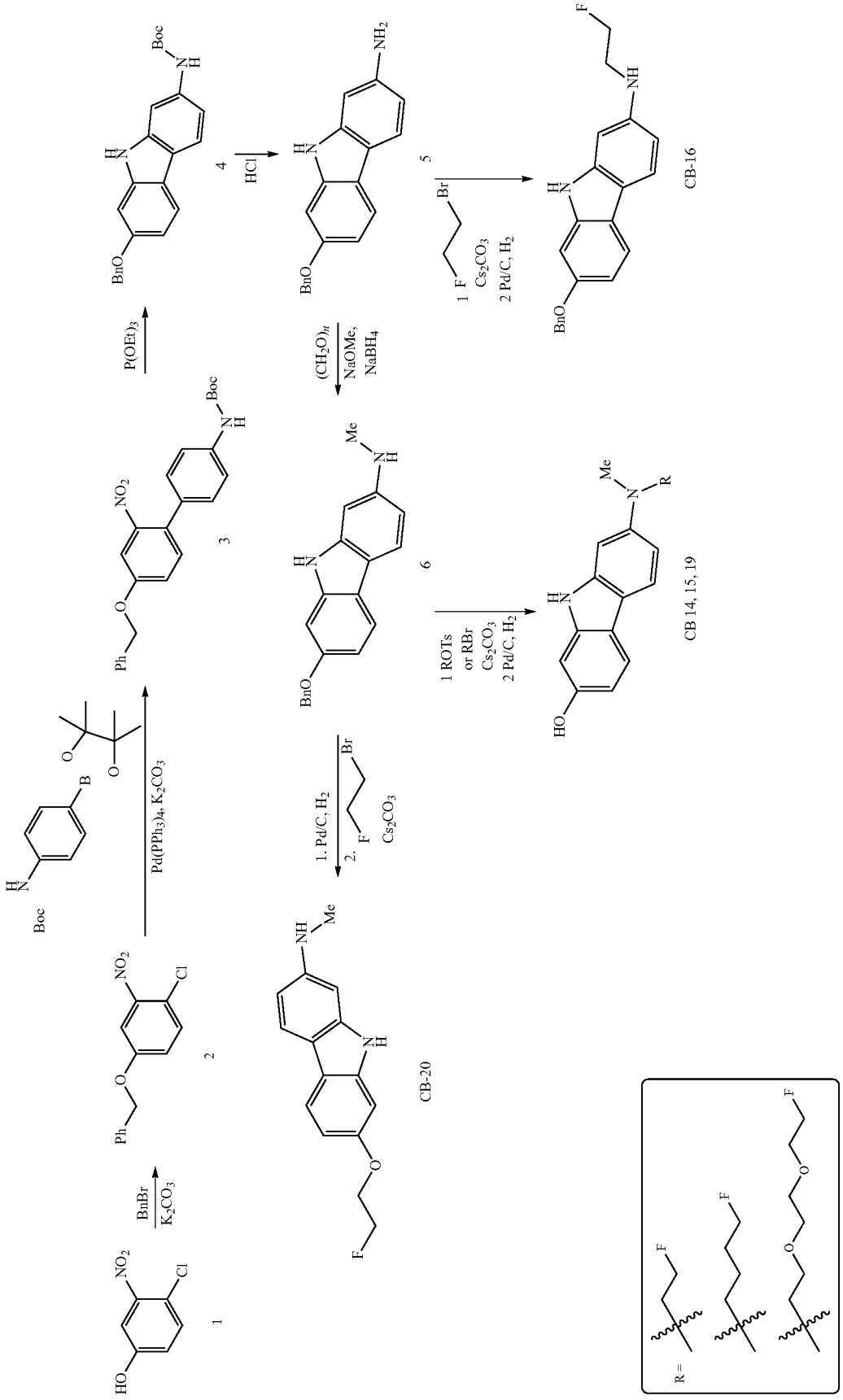

7-((4-fluorobutyl)(methyl)amino)-9H-carbazol-2-ol (CB-14)

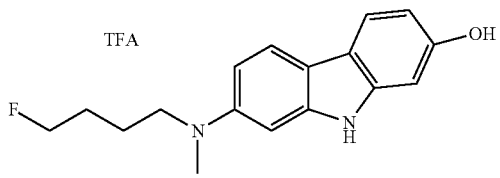

To a round bottom flask containing Compound 6 (21 mg, 0.073 mmol) in DMF (1 ml), were added cesium carbonate (28.5 mg, 0.087 mmol) and 1-bromo-4-fluorobutane (56.4 mg, 0.364 mmol). The reaction was stirred at rt for 30 min. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (22 mg). The mixture was stirred at rt overnight under hydrogen (1 atm). The reaction was filtered through a celite plug, concentrated in vacuo and purified on HPLC to afford CB-14 (11 mg, 0.029 mmol, 40.3% yield). $^1$H-NMR (400 MHz, CD$_3$OD) δ: 8.74 (d, J=8.4 Hz, 1H), 7.85 (d, J=8.4 Hz, 1H), 7.53 (s, 1H), 7.25 (d, J=8.0 Hz, 1H), 6.85 (s, 1H), 6.73 (d, J=8.4 Hz, 1H), 4.44 (m, 1H), 4.32 (m, 1H), 3.70 (m, 2H), 3.35 (s, 3H), 1.74-1.67 (m, 4H); LRMS for C$_{19}$H$_{19}$F$_4$N$_2$O$_2$+H$^+$, calc'd: 384.1. found: 287.2 (M+H$^+$-TFA).

7-((2-fluoroethyl)(methyl)amino)-9H-carbazol-2-ol (CB-15)

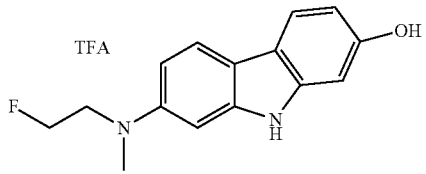

To a round bottom flask containing Compound 6 (37 mg, 0.122 mmol) in DMF (0.5 ml), were added cesium carbonate (47.8 mg, 0.147 mmol) and 1-bromo-2-fluoroethane (78 mg, 0.612 mmol). The reaction was stirred at rt for 30 min. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (22 mg). The mixture was stirred at rt overnight under hydrogen (1 atm). The reaction was filtered through a celite plug, concentrated in vacuo and purified on HPLC to afford CB-15 (5 mg, 0.019 mmol, 7.3% yield). $^1$H-NMR (400 MHz, CD$_3$CN) δ: 7.96 (d, J=8.0 Hz, 1H), 7.87 (d, J=8.4 Hz, 1H), 7.31 (d, J=2.0 Hz, 1H), 7.05 (dd, J=8.0 Hz, 2.0 Hz, 1H), 6.90 (d, J=2.0 Hz, 1H), 6.76 (dd, J=8.0 Hz, 2.0 Hz, 1H), 4.86 (m, 1H), 4.74 (m, 1H), 4.60-4.52 (m, 2H), 3.28 (br, 1H), 3.03 (s, 3H); LRMS for C$_{17}$H$_{15}$F$_4$N$_2$O$_2$+H$^+$, calc'd: 356.1. found: 259.2 (M+H$^+$-TFA).

7-(2-fluoroethylamino)-9H-carbazol-2-ol (CB-16)

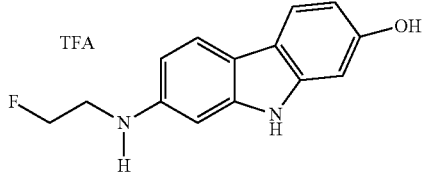

To a round bottom flask containing Compound 5 (21 mg, 0.073 mmol) in DMF (1 ml), were added cesium carbonate (28.5 mg, 0.087 mmol) and 1-bromo-2-fluoroethane (46 mg, 0.36 mmol). The reaction was stirred at rt for 72 hours. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (20 mg). The mixture was stirred at rt overnight under hydrogen (1 atm). The reaction was filtered through a celite plug, concentrated in vacuo and purified on HPLC to afford CB-16 (5 mg, 0.015 mmol, 20% yield). $^1$H-NMR (400 MHz, CD$_3$CN) δ: 9.00 (br, 1H), 7.77-7.73 (m, 2H), 6.82 (s, 1H), 6.81 (s, 1H), 6.72-6.65 (m, 2H), 4.71 (m, 1H), 4.60 (m, 1H), 3.60-3.50 (m, 2H); LRMS for C$_{16}$H$_{13}$F$_4$N$_2$O$_2$+H$^+$, calc'd: 342.3. found: 245.1 (M+H$^+$-TFA).

7((2-(2-(2-fluoroethoxy)ethoxy)ethyl)(methyl)amino)-9H-carbazol-2-ol (CB-19)

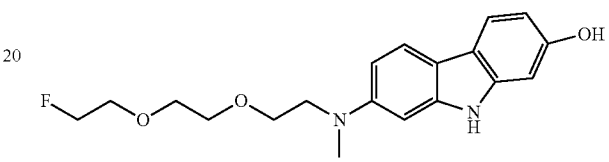

To a round bottom flask containing Compound 6 (41 mg, 0.14 mmol) in DMF (0.5 ml), were added cesium carbonate (53 mg, 0.16 mmol) and 2-(2-(2-fluoroethoxy)ethoxy)ethyl 4-methylbenzenesulfonate (125 mg, 0.407 mmol). The reaction was stirred at rt for 4 weeks. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (20 mg). The mixture was stirred at rt overnight under hydrogen atmosphere (1 atm). The reaction was filtered through a celite plug, concentrated in vacuo and purified on HPLC to afford CB-19 (7 mg, 0.020 mmol, 14% yield). $^1$H-NMR (400 MHz, CD$_3$CN) δ: 9.43 (br, 1H), 8.07 ((d, J=8.4 Hz, 1H), 7.91 (d, J=8.4 Hz, 1H), 7.58 (d, J=2.4 Hz, 1H), 7.24 (dd, J=8.0 Hz, 2.0 Hz, 1H), 6.93 (d, J=2.0 Hz, 1H), 6.77 (dd, J=8.0 Hz, 2.0 Hz, 1H), 4.59 (m, 1H), 4.52 (m, 1H), 3.74-3.50 (m, 10H), 3.28 (s, 3H); LRMS for C$_{21}$H$_{23}$F$_4$N$_2$O$_4$+Na$^+$, calc'd: 444.2. found: 347.2 (M+H$^+$-TFA).

7-(2-fluoroethoxy)-N-methyl-9H-carbazol-2-amine (CB-20)

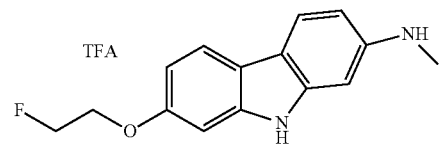

To a round bottom flask containing Compound 6 (90 mg, 0.29 mmol) in MeOH (10 ml), were added Pd/C (20 mg). The reaction was purged with hydrogen and stirred at rt for 2 h under hydrogen atmosphere (1 atm). The reaction was filtered through a celite plug concentrated in vacuo to afford a dark solid (60 mg, 0.28 mmol, 95% yield). To a round bottom flask containing the above dark solid (15 mg, 0.071 mmol) in DMF (0.5 mL), was added cesium carbonate (21 mg, 0.65 mmol) and 2-bromo-1-fluoroethane (8.1 mg, 0.065 mmol). The reaction was stirred at rt overnight. The reaction was concentrated in vacuo via MeCN co-evaporation. The residue was purified on HPLC to afford CB-20 (7.0 mg, 0.027 mmol, 38% yield). $^1$H NMR (400 MHz, CD$_3$CN) δ: 9.52 (br, 1H), 7.91-7.86 (m, 2H), 7.13 (s, 1H), 7.02 (s, 1H), 6.88 (d, J=7.6 Hz, 1H), 6.82 (dd, J=7.6 Hz, J=2.4 Hz 1H), 4.85 (m, 1H), 4.72 (m, 1H), 4.34-4.25 (m, 2H), 2.96 (s, 3H); LRMS for $C_{17}H_{15}N_2O_2+H^+$, calc'd: 356.1. found: 259.1 (M+H$^+$-TFA).

Synthetic Scheme of CB 25, 26:

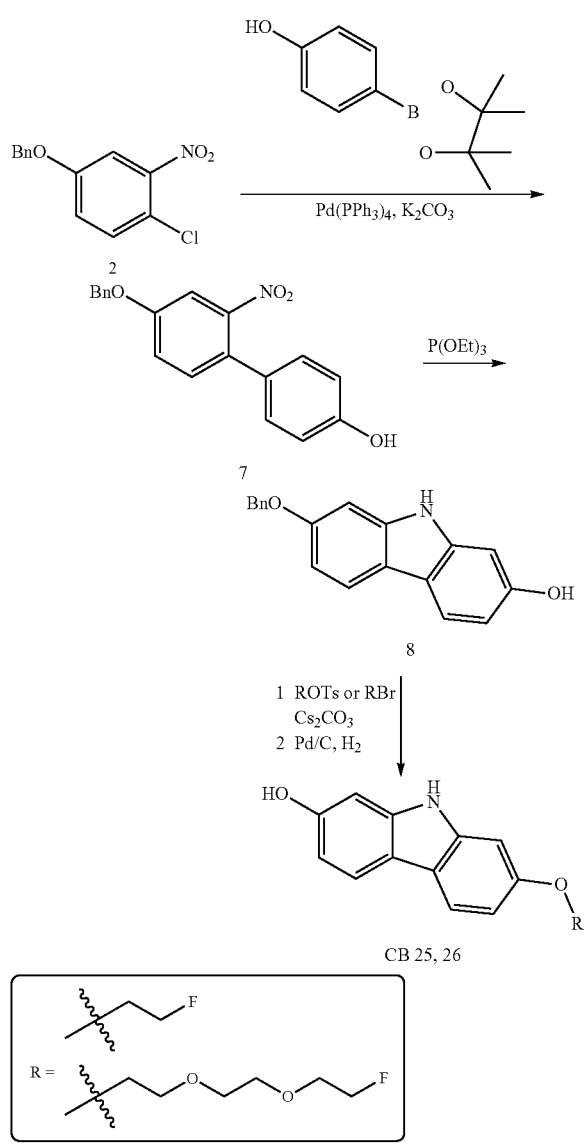

4'-(benzyloxy)-2'-nitrobiphenyl-4-ol (Compound 7)

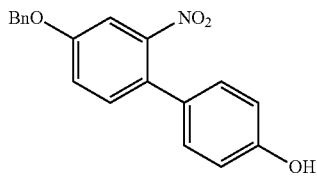

A round bottom flask charged with Compound 2 (1.96 g, 7.44 mmol), 4-Hydroxyphenylboronic acid pinacol ester (1.56 g, 7.09 mmol), terakis(triphenylphosphine) palladium (0.410 g, 0.354 mmol), were purged with Argon. To the mixture, was added DME (10 ml) and potassium carbonate (1.96 g, 14.2 mmol) in Water (2 ml). The mixture was heated for 60 hours. The reaction was diluted with HCl (1N, 10 mL) and brine (40 mL), then extracted with EtOAc (50 mL×3). The combined organic layer were washed with Brine (50 mL), dried (MgSO$_4$) and concentrated in vacuo. The residue was purified on a silica gel column (EtOAc: Hexanes=1:4) to afford Compound 7 as a yellow solid (2 g, 6.22 mmol, 88% yield). $^1$H-NMR (400 MHz, CDCl$_3$) δ: 7.45-7.33 (m, 7H), 7.37-7.15 (m, 3H), 6.88-6.85 (m, 2H), 5.14 (s, 2H), 5.03 (s, 1H); LRMS for $C_{19}H_{15}NO_4+H^+$, calc'd: 322.1. found: 322.1 (M+H$^+$).

7-(benzyloxy)-9H-carbazol-2-ol (Compound 8)

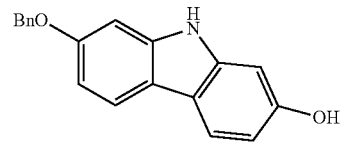

To a pressure resistant vial, was added Compound 7 (2.00 g, 6.22 mmol and Triethyl phosphite (6.53 ml, 37.3 mmol. The mixture was heated to 160° C. overnight. The reaction mixture was concentrated in vacuo. The residue was suspended in chloroform (20 mL), solid precipitate formed and was filtered and washed with ether (10 mL×2) to afford Compound 8 (900 mg, 3.11 mmol, 50.0% yield). $^1$H-NMR (400 MHz, DMSO) δ: 10.81 (br, 1H), 9.25 (br, 1H), 7.80 (d, J=8.4 Hz, 1H), 7.72 (d, J=8.4 Hz, 1H), 7.50-7.33 (m, 5H), 6.95 (s, 1H), 6-78-6.76 (m, 2H), 6.56 (dd, J=8.4, 2.0 Hz 1H), 5.16 (s, 2H); LRMS for $C_{19}H_{15}NO_2+H^+$, calc'd: 290.1. found: 290.1 (M+H$^+$).

7-(2-fluoroethoxy)-9H-carbazol-2-ol (CB-25)

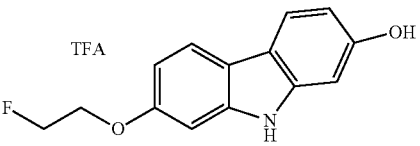

To a round bottom flask containing Compound 8 (50 mg, 0.17 mmol) in DMF (1 ml), was added cesium carbonate (62 mg, 0.19 mmol) and 1-bromo-2-fluoroethane (33 mg, 0.26 mmol). The reaction was stirred at rt for 15 h and then diluted with water (15 mL). White precipitate (50 mg) was collected via filtration and dried in vacu. The solid was dissolved in MeOH (10 mL). To the reaction, was added Pd/C (30 mg) and acetic acid (5 drops). The mixture was stirred under hydrogen (1 atm) atmosphere for 20 h and then filtered through a celite plug, concentrated in vacuo. The residue was purified on HPLC to afford CB-25 (18 mg, 0.053 mmol, 31% yield). $^1$H NMR (400 MHz, CD$_3$CN) δ: 8.99 (br, 1H), 7.72 (d, J=8.4 Hz, 1H), 7.67 (d, J=8.4 Hz, 1H), 6.88 (d, J=2.0 Hz, 1H), 6.76 (d, J=2.0 Hz, 1H), 6.67 (dd, J=8.0 Hz, 2.0 Hz, 1H), 6.58 (dd, J=8.0 Hz, 2.0 Hz, 1H), 4.75-4.74 (m, 1H), 4.63-4.61 (m, 1H), 4.23-4.13 (m, 2H); LRMS for $C_{16}H_{12}F_4NO_3+H^+$, calc'd: 343.1. found: 246.0 (M+H$^+$-TFA).

7-(2-(2-(2-fluoroethoxy)ethoxy)ethoxy)-9H-carbazol-2-ol (CB-26)

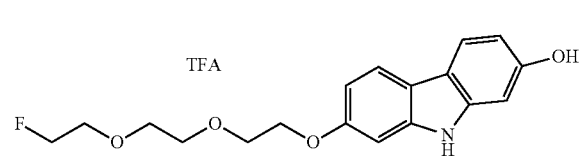

To a round bottom flask containing Compound 8 (50 mg, 0.17 mmol) in DMF (1 ml), was added cesium carbonate (56 mg, 0.17 mmol) and 2-(2-(2-fluoroethoxy)ethoxy)ethyl 4-methylbenzenesulfonate (53 mg, 0.17 mmol). The reaction was stirred at rt for 15 h and then diluted with water (15 mL). White precipitate (72 mg) was collected via filtration and dried in vacou. The solid was dissolved in MeOH (10 mL). To the reaction, was added Pd/C (20 mg) and acetic acid (5 drops). The mixture was stirred under hydrogen (1 atm) atmosphere for 20 h and then filtered through a celite plug and concentrated in vacuo. The residue was purified on HPLC to afford CB-26 (20 mg, 0.046 mmol, 27% yield). $^1$H NMR (400 MHz, CD$_3$CN) δ: 9.03 (br, 1H), 7.81-7.75 (m, 2H), 6.96 (d, J=2.4 Hz, 1H), 6.84 (d, J=2.4 Hz, 1H), 6.76 (dd, J=7.6 Hz, 2.0 Hz, 1H), 6.67 (dd, J=7.6 Hz, 2.0 Hz, 1H), 4.59-4.57 (m, 1H), 4.47-4.45 (m, 1H), 4.17-4.15 (m, 2H), 3.83-3.63 (m, 8H); LRMS for C$_{20}$H$_{20}$NO$_5$+H$^+$, calc'd: 431.1. found: 334.1 (M+H$^+$-TFA).

Synthetic Scheme of CB 27:

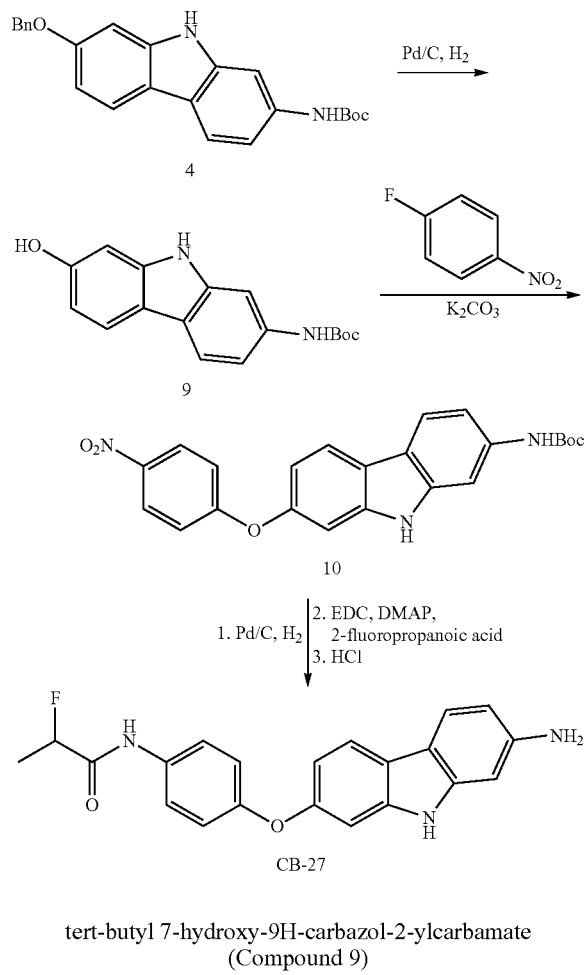

tert-butyl 7-hydroxy-9H-carbazol-2-ylcarbamate (Compound 9)

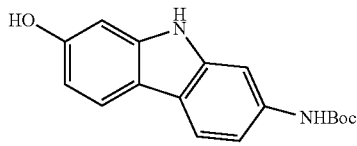

To a round bottom flask containing Compound 4 (1.0 g, 2.6 mmol) in MeOH (150 mL), was added palladium on charcoal (400 mg). The flask was purged with hydrogen gas and stirred under hydrogen atmosphere overnight. The reaction mixture was filtered through a celite plug and concentrated to afford Compound 9 as a grey solid (700 mg, 2.34 mmol, 90% yield). $^1$H NMR (400 MHz, (CD$_3$)$_2$CO) δ: 9.99 (br, 1H), 8.41 (br, 1H), 8.24 (s, 1H), 7.86 (s, 1H), 7.81-7.78 (m, 2H), 7.18 (dd, J=8.4 Hz, 2.0 Hz, 1H), 6.90 (d, J=2.0 Hz, 1H), 6.70 (dd, J=8.4 Hz, 2.0 Hz, 1H), 1.51 (s, 9H).

tert-butyl 7-(4-nitrophenoxy)-9H-carbazol-2-ylcarbamate (Compound 10)

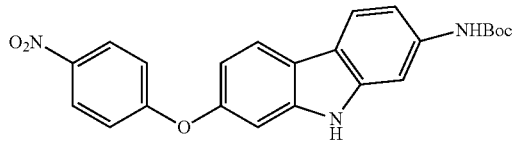

To a round bottom flask containing Compound 9 (80 mg, 0.268 mmol) in DMF (2 mL) was added potassium carbonate (74.1 mg, 0.536 mmol) and 4-fluoro-nitrobenzene (41.6 mg, 0.295 mmol). The reaction mixture was heated for 20 min at 140° C. After cooling down to rt, the mixture was diluted with water (20 mL) and extracted with EtOAc (20 mL×3). The organic layers were dried, concentrated. The residue was purified on a silica gel column (EtOAc: Hexanes=3:7) to afford Compound 10 as a yellow solid (50 mg, 0.12 mmol, 44% yield). $^1$H NMR (400 MHz, CDCl$_3$) δ: 8.22 (d, J=9.2 Hz, 2H), 8.10 (br, 1H), 8.00-7.90 (m, 3H), 7.12 (s, 1H), 7.06-6.90 (m, 4H), 6.70 (br, 1H), 1.56 (s, 9H); LRMS for C$_{23}$H$_{21}$N$_3$O$_5$+H$^+$, calc'd: 420.2. found: 420.2 (M+H$^+$).

Tert-butyl 7-(4-nitrophenoxy)-9H-carbazol-2-ylcarbamate (CB-27)

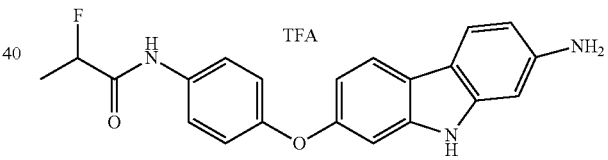

To a round bottom flask containing Compound 10 (35 mg, 0.083 mmol) in MeOH (5 mL), was added palladium on charcoal (10 mg). The flask was purged with hydrogen gas and stirred under hydrogen atmosphere overnight. The reaction mixture was filtered through a silica gel plug and concentrated to afford the amine intermediate (23 mg). To a vial containing 2-fluoropropanoic acid (10.87 mg, 0.118 mmol) in DCM (1 mL), was added EDC (22.64 mg, 0.118 mmol) and DMAP (1 mg). The mixture was stirred at rt for 5 min. The above amine intermediate was dissolved in DCM (1 ml) and added into the reaction vial dropwise. The reaction mixture was stirred at rt from 3 hour. The reaction mixture was then washed with water (3 mL) and concentrated. The residue was redissolved in HCl (4.0 M in dioxane, 5 mL) and stirred overnight. The mixture was concentrated and purified on HPLC to afford CB-27 (12 mg, 0.026 mmol, 31% yield). $^1$H NMR (400 MHz, CD$_3$CN) δ: 9.42 (br, 1H), 8.69 (br, 1H), 7.92 (d, J=8.4 Hz, 1H), 7.87 (d, J=8.4 Hz, 1H), 7.60 (m, 2H), 7.04-7.01 (m, 4H), 6.86 (d, J=8.0 Hz, 1H), 6.84 (d, J=8.0 Hz, 1H), 5.11 (dt, J=49.2, 6.8 Hz, 1H), 1.58 (dd, J=24.8, 6.8 Hz, 3H); LRMS for C$_{23}$H$_{18}$F$_4$N$_3$O$_3$+H$^+$, calc'd: 460.1. found: 364.1 (M+H$^+$-TFA).

Experimental Section for the Preparation of Carbazole Derivatives

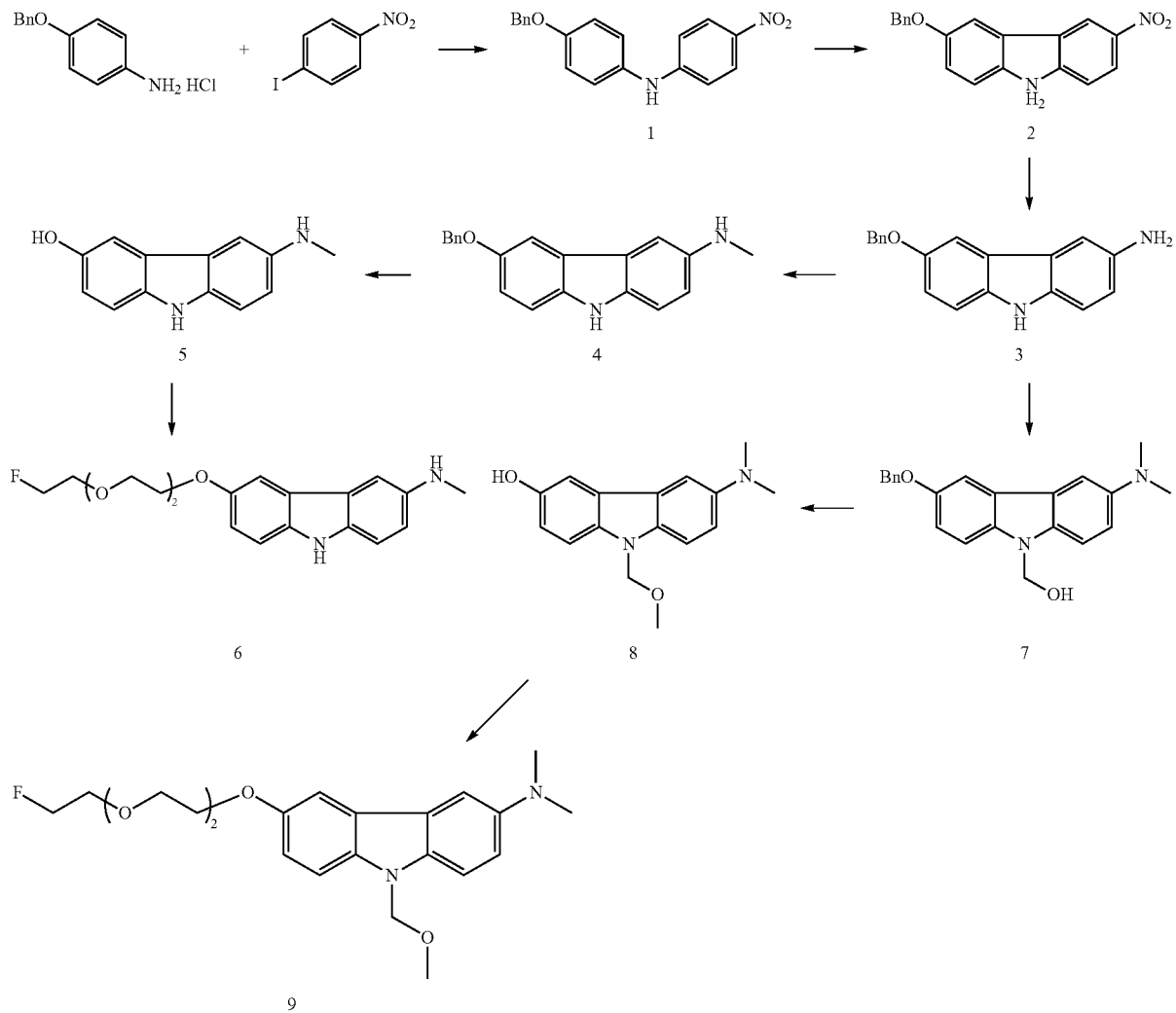

4-(Benzyloxy)-N-(4-nitrophenyl)aniline 1: To a oven dried flask was charged with Pd(OAc)$_2$ (81 mg, 0.36 mmol) and (S)-(−)-BINAP (336 mg, 0.54 mmol), followed by toluene (10 mL). The mixture was stirred under Ar at room temperature for 5 min. To this mixture was added 4-nitroiodobenzene (3.0 g, 12 mmol), 4-benzyloxyaniline hydrochloride (3.39 g, 14.4 mmol), Cs$_2$CO$_3$ (9.8 g, 30 mmol) and toluene (40 mL). The resulting mixture was heated under Ar at 100° C. for 16 hrs, and then cooled to room temperature and poured into H$_2$O (100 mL). The layers were separated. The aqueous layer was extracted with EtOAc (3×20 mL). The combined organic layers were washed with brine (2×20 mL), dried (MgSO$_4$) and filtered. The filtrate was concentrated. The residue was purified via column chromatography (silica gel, 5-40% EtOAc/hexane) to give the desired product as an orange solid (1.2 g, 31%). $^1$H NMR (CDCl$_3$, 400 MHz) δ: 8.09 (d, J=9.2 Hz, 2H), 7.30-7.49 (m, 5H), 7.15 (d, J=9.2 Hz, 2H), 7.01 (d, J=9.2 Hz, 2H), 6.77 (d, J=8.8 Hz, 2H), 6.10 (br s, 1H), 5.09 (s, 2H). MS: m/z=321 (M+H$^+$)$^+$.

3-(Benzyloxy)-9-nitro-9H-carbazole 2: A mixture of 4-(benzyloxy)-N-(4-nitrophenyl)aniline 1 (0.5 g, 1.56 mmol) and Pd(OAc)$_2$ (0.8 g, 3.56 mmol) in acetic acid (20 mL) was refluxed and monitored by TLC. After refluxing for 2 hrs, TLC showed that no starting material was present. It was concentrated in vacuo to remove acetic acid. The residue was diluted with EtOAc (30 mL), washed with H$_2$O (20 mL), sat. NaHCO$_3$ solution (2×20 mL), brine (20 mL), and then dried (MgSO$_4$) and filtered. The filtrate was concentrated in vacuo. The residue was purified via column chromatography (silica gel, 5-40% EtOAc/hexane) to give the desired product 2 as a dark yellow solid (100 mg, 20%). $^1$H NMR (acetone-d$_6$, 400 MHz) δ: 10.92 (br s, 1H), 9.08 (d, J=2.0 Hz, 1H), 8.28 (dd, J=8.8, 2.4 Hz, 1H), 8.07 (d, J=2.4 Hz, 1H), 7.63 (d, J=9.2 Hz, 1H), 7.55 (d, J=8.8 Hz, 3H), 7.40 (t, J=7.2 Hz, 2H), 7.33 (t, J=7.2 Hz, 1H), 7.24 (dd, J=8.8, 2.4 Hz, 1H), 5.26 (s, 2H). MS: m/z=319 (M+H$^+$)$^+$.

3-Amino-6-(benzyloxy)-9H-carbazole 3: To a suspension of 3-(benzyloxy)-9-nitro-9H-carbazole 2 (100 mg, 0.31 mmol) and Cu(OAc)$_2$ (57 mg, 0.31 mmol) in EtOH (20 mL) was added NaBH$_4$ (240 mg, 6.3 mmol). The resulting mixture was stirred at room temperature for 3 hrs, and then concentrated in vacuo. The residue was dissolved in H$_2$O (30 mL), extracted with EtOAc (2×30 mL). The combined organic layers were dried (MgSO$_4$), filtered and concentrated in vacuo to give a solid (90 mg). It was used directly in the next step without any further purification. ¹H NMR (acetone-d₆, 400 MHz) δ: 9.67 (br s, 1H), 7.57 (d, J=2.4 Hz, 1H), 7.52 (d, J=6.8 Hz, 2H), 7.39 (t, J=6.8 Hz, 2H), 7.26-7.33 (m, 3H), 7.19 (d, J=8.8 Hz, 1H), 7.03 (dd, J=8.8, 2.4 Hz, 1H), 6.81 (dd, J=8.8, 2.4 Hz, 1H), 5.17 (s, 2H), 4.24 (br s, 2H). MS: m/z=289 (M+H)⁺.

6-(Benzyloxy)-N-methyl-9H-carbazol-3-amine 4: To a suspension of 3-amino-6-(benzyloxy)-9H-carbazole 3 (90 mg, 0.31 mmol) and paraformaldehyde (47 mg, 1.57 mmol) in MeOH (20 mL) was added a solution of NaOMe in MeOH (0.32 mL, 1.56 mmol). The resulting mixture was heated at 80° C. for 1 h, then NaBH₄ (59 mg, 1.55 mmol) was added. The resulting mixture was heated at 80° C. for 2 hrs, and then cooled to room temperature. To this solution was added NaOH (1 N, 30 mL). The mixture was then extracted with CH₂Cl₂ (3×20 mL). The combined organic layers were dried (MgSO₄), filtered. The filtrate was concentrated in vacuo to give a brown solid (93 mg, 100%). It was used directly in the next step without any further purification. ¹H NMR (acetone-d₆, 400 MHz) δ: 9.68 (br s, 1H), 7.67 (d, J=2.4 Hz, 1H), 7.53 (d, J=7.6 Hz, 2H), 7.20-7.42 (m, 6H), 7.03 (dd, J=8.8, 2.4 Hz, 1H), 6.79 (dd, J=8.4, 2.4 Hz, 1H), 5.17 (s, 2H), 2.85 (s, 3H). MS: m/z=303 (M+H⁺)⁺.

6-(Methylamino)-9H-carbazol-3-ol 5: A mixture of 6-(benzyloxy)-N-methyl-9H-carbazol-3-amine 4 (93 mg, 0.31 mmol), Pd/C (10 mg) and acetic acid (10 drops) in MeOH (10 mL) was hydrogenated at room temperature for 1.5 hrs. It was passed through a short Celite pad. The filtrate was concentrated in vacuo to give the desired product 5 (66 mg). It was used directly in the next step without any further purification. MS: m/z=213 (M+H⁺)⁺.

[3-(Benzyloxy)-6-(dimethylamino)-9H-carbazol-9-yl] methanol 7: To a solution of 6-(benzyloxy)-N-methyl-9H-carbazol-3-amine 4 (110 mg, 0.38 mmol) and aqueous formaldehyde solution (37%, 1.0 mL) in acetonitrile (30 mL) was added NaB(OAc)₃ (323 mg, 1.52 mmol). The resulting mixture was stirred at room temperature for 6 hrs, and then concentrated. The residue was dissolved in H₂O (30 mL), extracted with CH₂Cl₂ (2×30 mL). The combined organic layers were dried (MgSO₄), filtered. The filtrate was concentrated in vacuo to give the desired product (0.12 g). It was used directly in the next step without any further purification. MS: m/z=347 (M+H⁺)⁺.

6-(Dimethylamino)-9-(methoxymethyl)-9H-carbazol-3-ol 8: A mixture of [3-(benzyloxy)-6-(dimethylamino)-9H-carbazol-9-yl]methanol 7 (120 mg), Pd/C (100 mg) and acetic acid (cat. amount) in MeOH (15 mL) was hydrogenated at room temperature for 4 hrs. It was filtered through a short Celite pad. The filtrate was concentrated in vacuo to give the desired product (94 mg, 100%). NMR (acetone-d₆, 400 MHz) δ: 7.38-7.50 (m, 4H), 7.05 (dd, J=8.8, 2.4 Hz, 1H), 6.97 (dd, J=8.4, 2.4 Hz, 1H), 5.62 (s, 2H), 3.20 (s, 3H), 2.94 (s, 6H). MS: m/z=271 (M+H⁺)⁺.

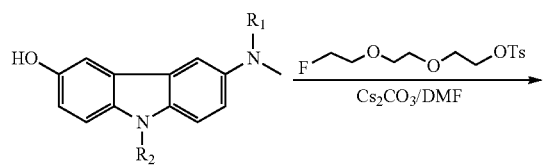

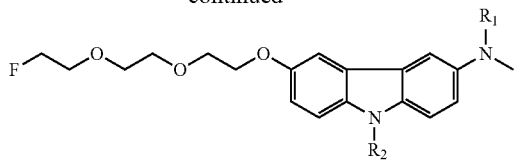

General procedures for the preparation of O-alkylated carbazole derivatives: To a solution of carbazol-3-ol derivatives (1 eq.) and Cs₂CO₃ (1.5 eq.) in DMF (10 mL) was added a solution of 2-(2-(2-fluoroethoxy)ethoxy)ethyl-4-methylbenzenesulfonate (1.2 eq.) in DMF (1.0 mL). The resulting mixture was stirred at room temperature overnight, and then concentrated in vacuo. The residue was purified via column chromatography (silica gel, 5-50% EtOAc/hexane) to provide the desired products.

6-(2-(2-(2-Fluoroethoxy)ethoxy)ethoxy)-N-methyl-9H-carbazol-3-amine 6: (3 mg, 5%). ¹H NMR (acetone-d₆, 400 MHz) δ: 7.59 (d, J=2.4 Hz, 1H), 7.28-7.33 (m, 2H), 7.26 (d, J=8.4 Hz, 1H), 6.97 (dd, J=8.8, 2.4 Hz, 1H), 6.85 (dd, J=8.8, 2.0 Hz, 1H), 4.51 (dt, J=48, 4.0 Hz, 2H), 4.19 (t, J=4.4 Hz, 2H), 3.61-3.88 (m, 8H), 3.87 (s, 3H). MS: m/z=347 (M+H⁺)⁺.

6-(2-(2-(2-Fluoroethoxy)ethoxy)ethoxy)-9-(methoxymethyl)-N,N-dimethyl-9H-carbazol-3-amine 9: (50 mg, 36%). NMR (acetone-d₆, 400 MHz) δ: 7.68 (d, J=2.4 Hz, 1H), 7.46-7.52 (m, 3H), 7.04-7.08 (m, 2H), 5.66 (s, 2H), 4.52 (dt, J=48.4, 4.4 Hz, 2H), 4.21 (t, J=4.8 Hz, 2H), 3.63-3.87 (m, 8H). MS: m/z=405 (M+H⁺)⁺.

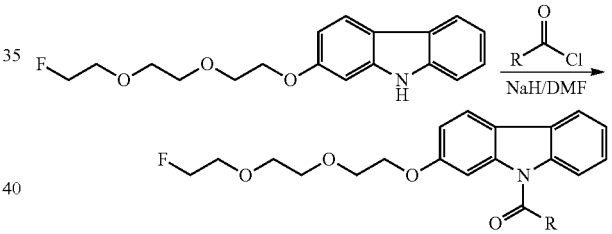

General procedures for the preparation of acylated carbazole derivatives: To a solution of 2-(2-(2-(2-fluoroethoxy) ethoxy)ethoxy)-9H-carbazole (1.0 eq.) in DMF (3.0 mL) was added NaH (excess). After stirring at room temperature for 5 min, an acyl halide (excess) was added. The resulting mixture was stirred at room temperature overnight, and then concentrated in vacuo. The residue was purified via column chromatography (silica gel, 0-40% EtOAc/hexane) to give the desired product.

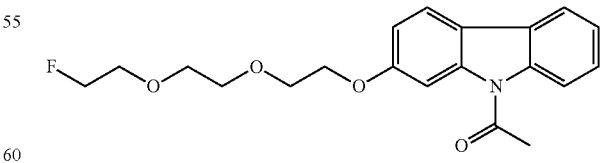

1-(2-(2-(2-(2-Fluoroethoxy)ethoxy)ethoxy)-9H-carbazol-9-yl)ethanone: (4 mg, 36%). ¹H NMR (CDCl₃, 400 MHz) δ: 8.21 (d, J=8.0 Hz, 1H), 7.99-8.25 (m, 2H), 7.94 (d, J=2.4 Hz, 1H), 7.36-7.46 (m, 2H), 7.06 (dd, J=8.4, 2.4 Hz, 1H), 4.52 (dt, J=48, 4.4 Hz, 2H), 4.27 (t, J=4.4 Hz, 2H), 3.89 (t, J=8.8 Hz, 2H), 3.64-3.78 (m, 6H), 2.91 (s, 3H). MS: m/z=360 (M+H⁺)⁺.

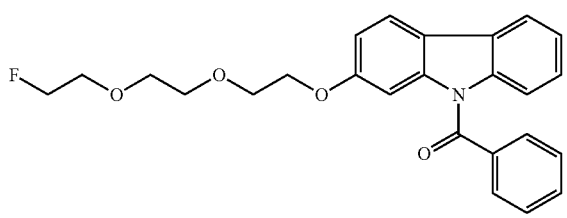

1-(2-(2-(2-(2-Fluoroethoxy)ethoxy)ethoxy)-9H-carbazol-9-yl)phenylmethanone: (51 mg, 78%). ¹H NMR (CDCl₃, 400 MHz) δ: 7.84-7.92 (m, 2H), 7.62-7.74 (m, 3H), 7.53 (t, J=8.0 Hz, 2H), 7.27-7.33 (m, 2H), 7.17-7.23 (m, 1H), 6.99 (dd, J=8.4, 2.4 Hz, 1H), 4.57 (dt, J=47.6, 4.4 Hz, 2H), 4.06 (t, J=4.8 Hz, 2H), 3.70-3.87 (m, 8H). MS: m/z=422 (M+H⁺)⁺.

Preparation of 2-(7-formamido-9H-carbazol-2-yloxy)ethyl 4-methylbenzenesulfonate: AD-CB-012P-WZ02039

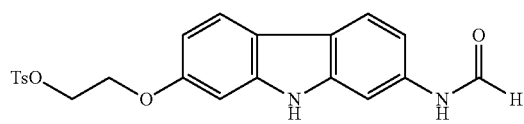

Compound 2-(7-formamido-9H-carbazol-2-yloxy)ethyl 4-methylbenzenesulfonate (AD-CB-012P-WZ02039) was prepared using the same procedure for the preparation of AD-CB-012S-WZ01185) from N-(7-hydroxy-9H-carbazol-2-yl)formamide (100 mg) and ethane-1,2-diyl bis(4-methylbenzenesulfonate) (325 mg). (white solid, 22 mg, 12%). For the major rotomer: ¹H NMR (400 MHz, acetone-d6) δ 10.19 (s, 1H), 9.31 (s, 1H), 8.38 (d, J=1.6 Hz, 1H), 8.11 (d, J=2.0 Hz, 1H), 7.90-7.81 (m, 4H), 7.45 (d, J=8.4 Hz, 2H), 7.19 (dd, J=8.4, 2.0 Hz, 1H), 6.95 (d, J=2.0 Hz, 1H), 6.69 (dd, J=8.4, 2.0 Hz, 1H), 4.43-4.41 (m, 2H), 4.29-4.27 (m, 2H); MS (ESI) m/z 425 (M+H⁺).

Preparation of N-(7-(4-fluorobutoxy)-9H-carbazol-2-yl)formamide: AD-CB-30S-WZ02055

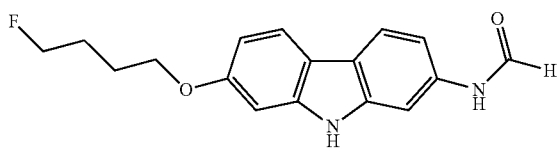

Compound N-(7-(4-fluorobutoxy)-9H-carbazol-2-yl)formamide (AD-CB-30S-WZ02055) was prepared using the same procedure for the preparation of AD-CB-012S-WZ01185) from N-(7-hydroxy-9H-carbazol-2-yl)formamide (20 mg) and 1-bromo-4-fluorobutane (27 mg). (white solid, 11 mg, 42%). ¹H NMR (400 MHz, acetone-d6) δ 10.18 (s, 1H), 9.31 (s, 1 H), 8.39 (d, J=2.0 Hz, 1H), 8.11 (d, J=2.0 Hz, 1H), 7.95 (d, J=1.6 Hz, 2H), 7.88 (d, J=2.0 Hz, 1H), 7.20 (dd, J=8.4, 2.0 Hz, 1H), 7.03 (d, J=2.4 Hz, 1H), 6.79 (dd, J=8.4, 2.4 Hz, 1H), 4.61 (m, 1H), 4.49 (m, 1H), 4.11 (m, 2H), 1.97-1.88 (m, 4H); MS (ESI) m/z 301 (M+H⁺).

Preparation of 2-(2-(2-(2-fluoroethoxy)ethoxy)ethoxy)-9H-pyrido[2,3-b]indol-7-amine hydrochloride

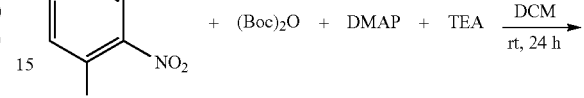
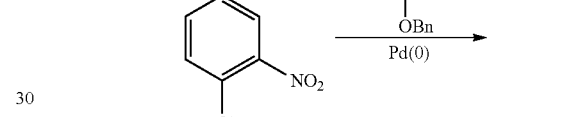
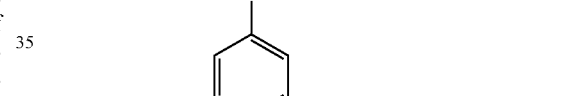
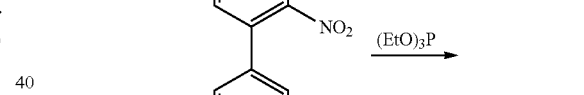
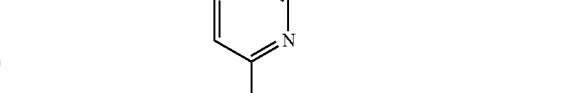
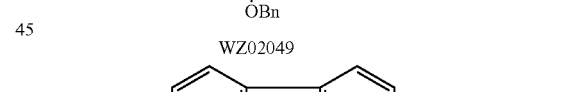
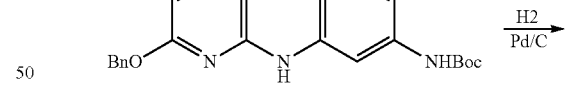
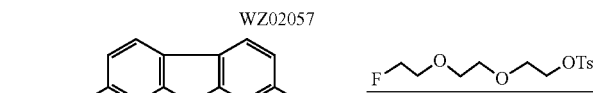
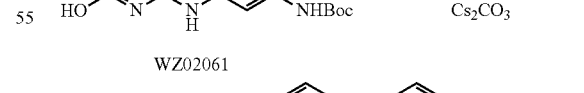
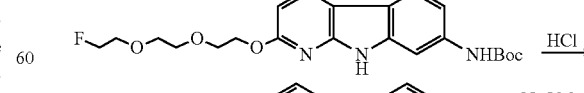
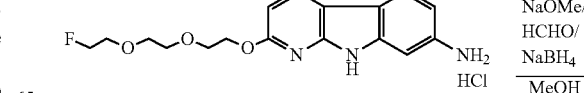
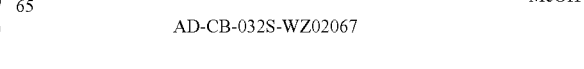

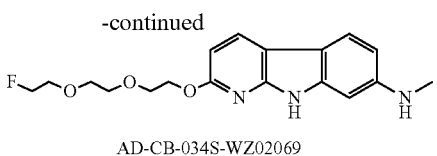

AD-CB-034S-WZ02069

Preparation of WZ02045:

To 4-chloro-3-nitroaniline (2.5 g, 14.5 mmol) in 40 mL DCM was added TEA (2.9 g, 29 mmol), DMAP (177 mg, 1.45 mmol), and di-tert-butyl dicarbonate (4.7 g, 21.7 mmol). The mixture was stirred at rt for 24 h and concentrated. The residue was diluted with Et2O (100 mL), washed with brine (100 mL), water (100 mL), 0.5 M HCl (2×100 mL), and brine (100 mL), dried over $MgSO_4$ and concentrated. The crude product was purified by silica chromatography (EtOAc/hexane) to afford tert-butyl 4-chloro-3-nitrophenylcarbamate (WZ02045) as a yellow solid (1.5 g, 38%). MS (ESI) m/z 295 (M+Na$^+$).

Preparation of WZ02049:

A mixture of tert-butyl 4-chloro-3-nitrophenylcarbamate (818 mg, 3 mmol), 2-(benzyloxy)-5-(4,4,5,5-tetramethyl-1,3,2-dioxaborolan-2-yl)pyridine (933 mg, 3 mmol), tetrakis(triphenylphosphine)palladium (104 mg, 0.09 mmol), 10 mL of dioxane, and 6 mL of 1 M $Na_2CO_3$ was heated at reflux for 15 h. It was diluted with 50 mL $Et_2O$ and washed with brine (2×50 mL) and dried over $MgSO_4$ and concentrated. The crude product was purified by silica chromatography (EtOAc/hexane) to afford tert-butyl 4-(6-(benzyloxy)pyridin-3-yl)-3-nitrophenylcarbamate (WZ02049) as a yellow wax (1.2 g, 95%). MS (ESI) m/z 444 (M+Na$^+$).

Preparation of WZ02057:

A suspension of above compound (800 mg, 1.9 mmol) in 2 mL of triethyl phosphite was heated at 148° C. for 15 h. After cooling, it was concentrated under reduced pressure to remove volatiles. The crude product was purified by silica chromatography (EtOAc/hexane) to afford tert-butyl 2-(benzyloxy)-9H-pyrido[2,3-b]indol-7-ylcarbamate (WZ02057) as a off-white solid (400 mg, 54%). MS (ESI) m/z 390 (M+H$^+$).

Preparation of WZ02061:

To above compound (220 mg, 0.56 mmol) dissolved in 80 mL MeOH was added Palladium on activated carbon (80 mg). The mixture was stirred at rt under $H_2$ atmosphere for 15 h. Solid was filtered off and the filtrate was concentrated to afford tert-butyl 2-hydroxy-9H-pyrido[2,3-b]indol-7-ylcarbamate (WZ02061) as a white solid (105 mg, 100%). This material was used directly for the next reaction without purification. MS (ESI) m/z 300 (M+H$^+$).

Preparation of WZ02063:

To above compound (50 mg, 0.167 mmol) in 1 mL of NMP was added 2-(2-(2-fluoroethoxy)ethoxy)ethyl 4-methylbenzenesulfonate (76 mg, 0.25 mmol), and $Cs_2CO_3$ (65 mg, 0.2 mmol). The mixture was stirred at rt for 15 h and diluted with Et2O (40 mL), washed with water (3×30 mL), and dried over $MgSO_4$ and concentrated. The crude product was purified by silica chromatography (EtOAc/hexane) to afford tert-butyl 2-(2-(2-(2 fluoroethoxy)ethoxy)ethoxy)-9H-pyrido[2,3-b]indol-7-ylcarbamate (WZ02063) as a clear wax (45 mg, 62%). MS (ESI) m/z 434 (M+H$^+$).

Preparation of AD-CB-032S-WZ02067:

The above compound (45 mg, 0.1 mmol) was treated with 2 mL of a 4 M HCl in dioxane solution at rt for 5 h and concentrated under reduced pressure. The residue was washed with ether (5 mL) and dried under high vacuum to afford 2-(2-(2-(2-fluoroethoxy)ethoxy)ethoxy)-9H-pyrido[2,3-b]indol-7-amine hydrochloride (AD-CB-032S-WZ02067) as a light-yellow solid (23 mg, 62%). $^1$H NMR (400 MHz, methanol-d$_4$) δ 8.42 (d, J=8.4 Hz, 1H), 8.12 (d, J=8.4 Hz, 1 H), 7.53 (d, J=2.0 Hz, 1H), 7.21 (dd, J=8.4, 2.0 Hz, 1H), 6.77 (d, J=8.4 Hz, 1H), 4.58-4.54 (m 3H), 4.43 (m, 1H), 3.91 (m, 2H), 3.76-3.72 (m, 3H), 3.70-3.66 (m, 3H); MS (ESI) m/z 334 (M+H$^+$).

Preparation of 2-(2-(2-(2-fluoroethoxy)ethoxy)ethoxy)-N-methyl-9H-pyrido[2,3-b]indol-7-amine: AD-CB-034S-WZ02069

Compound AD-CB-034S-WZ02069 was prepared using the same procedure for the preparation of AD-CB-004S from 2-(2-(2-(2-fluoroethoxy)ethoxy)ethoxy)-9H-pyrido[2,3-b]indol-7-amine hydrochloride (AD-CB-032S-WZ02067, 20 mg) (10 mg, 53%). $^1$H NMR (400 MHz, methanol-d4) δ 8.06 (d, J=8.0 Hz, 1H), 7.66 (d, J=8.4 Hz, 1H), 6.65 (d, J=2.0 Hz, 1H), 6.58 (dd, J=8.4, 2.0 Hz, 1H), 6.53 (d, J=8.0 Hz, 1H), 4.58 (m 1H), 4.53-4.45 (m, 3H), 3.88 (m, 2 H), 3.76 (m, 1H), 3.73-3.67 (m, 5H), 3.03 (s, 3H); MS (ESI) m/z 348 (M+H$^+$).

Preparation of 6-bromo-9H-carbazol-2-ol: W138

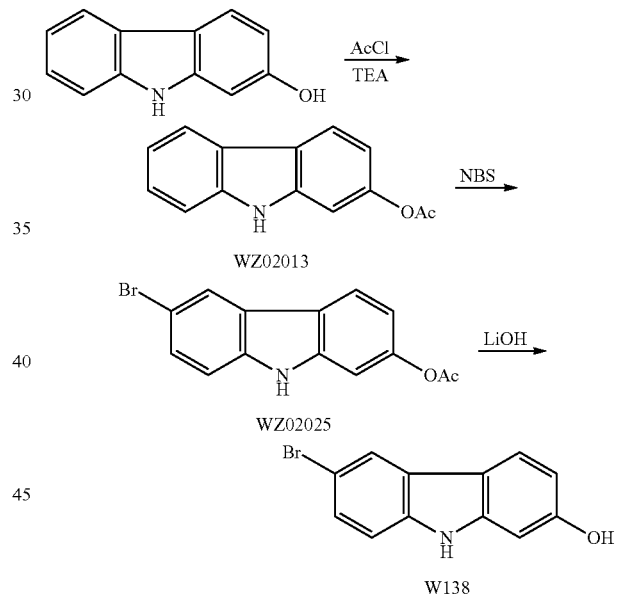

Preparation of WZ02013:

To 9H-carbazol-2-ol (915 mg, 5 mmol) in 10 mL DMF and 20 mL DCM was added TEA (1.0 g, 10 mmol), followed by acetyl chloride (589 mg, 7.5 mmol) at 0° C. The reaction mixture was then stirred at rt for 1 h and poured onto ice (50 g). The mixture was extracted with EtOAc (2×60 mL) and combined organic phase was dried over $MgSO_4$ and concentrated. The crude product was purified by silica chromatography to afford 9H-carbazol-2-yl acetate (WZ02013) as an off-white solid (800 mg, 71%). MS (ESI) m/z 348 (M+H$^+$).

Preparation of WZ02025:

To a solution of 9H-carbazol-2-yl acetate (500 mg, 2.2 mmol) in DCM (40 mL) was added a solution of NBS in 25 mL of DCM dropwise at rt. The reaction mixture was stirred in the dark for 5 h. It was washed with water (3×50 mL) and dried over $MgSO_4$ and concentrated. The crude product was purified by silica chromatography (EtOAc/hexane) to afford 6-bromo-9H-carbazol-2-yl acetate (WZ02025) as an off-white solid (250 mg, containing 17% dibrominated product). MS (ESI) m/z 305 (M+H$^+$).

Preparation of W138:

A suspension of 6-bromo-9H-carbazol-2-yl acetate (200 mg, 0.65 mmol) in 30 mL MeOH and 4 mL of 1.0 M aqueous LiOH was stirred for 5 h. It was neutralized with 1 M HCl and concentrated. The crude product was purified by silica chromatography (EtOAc/hexane) to afford 6-bromo-9H-carbazol-2-ol (W138) as an off-white solid (125 mg, containing 15% dibrominated product). $^1$H NMR (400 MHz, acetone-d6) δ 8.58 (s, 1H), 8.10 (d, J=2.0 Hz, 1 H), 1H), 7.92 (d, J=8.8 Hz, 1H), 7.42 (dd, J=8.4, 2.0 Hz, 1H), 7.35 (s, 1H), 7.13 (d, J=8.4 Hz, 1H), 6.92 (d, J=2.0 Hz, 1H), 6.76 (dd, J=8.8, 2.0 Hz, 1H); MS (ESI) m/z 263 (M+H$^+$).

Ex Vivo Competition Assay Using Amyloid (Ad Patient's Brain Slice) Autoradiography Staining The carbazole series of AD imaging agents display surprisingly good qualities when compared to previously established results performed by others. Data from prior art suggests that compounds with higher LogP values have higher amyloid affinities, yet these same compounds can also suffer from high non-specific binding, i.e poor brain washout (J. Molecular Neuroscience 2003, 20, 255-260). For the disclosed studies in this application, cLogP values were used in place of LogP values.

Figure 7:
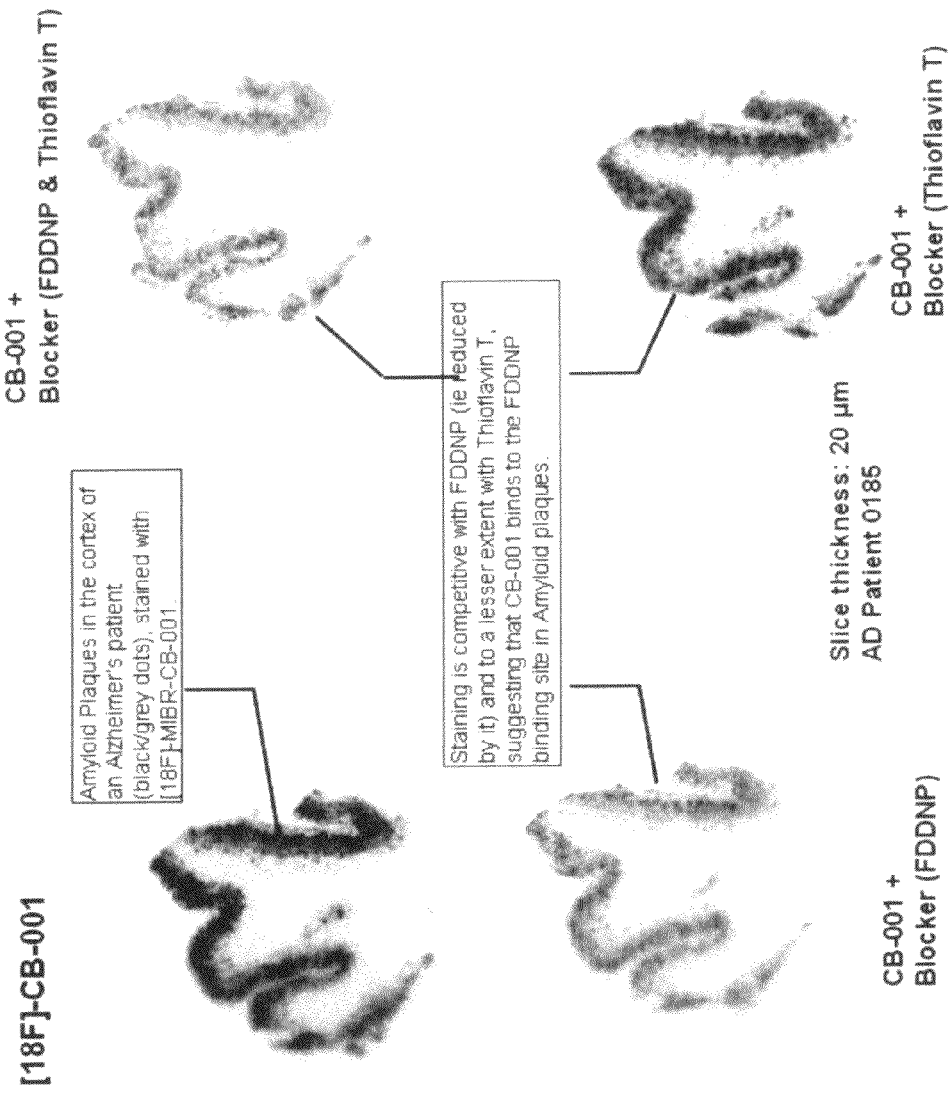
FIG. 7 shows amyloid autoradiography staining (ex vivo) of an AD patient's brain with [18F]-CB-001 shows good amyloid binding and little/no white matter binding.
Figure 8:
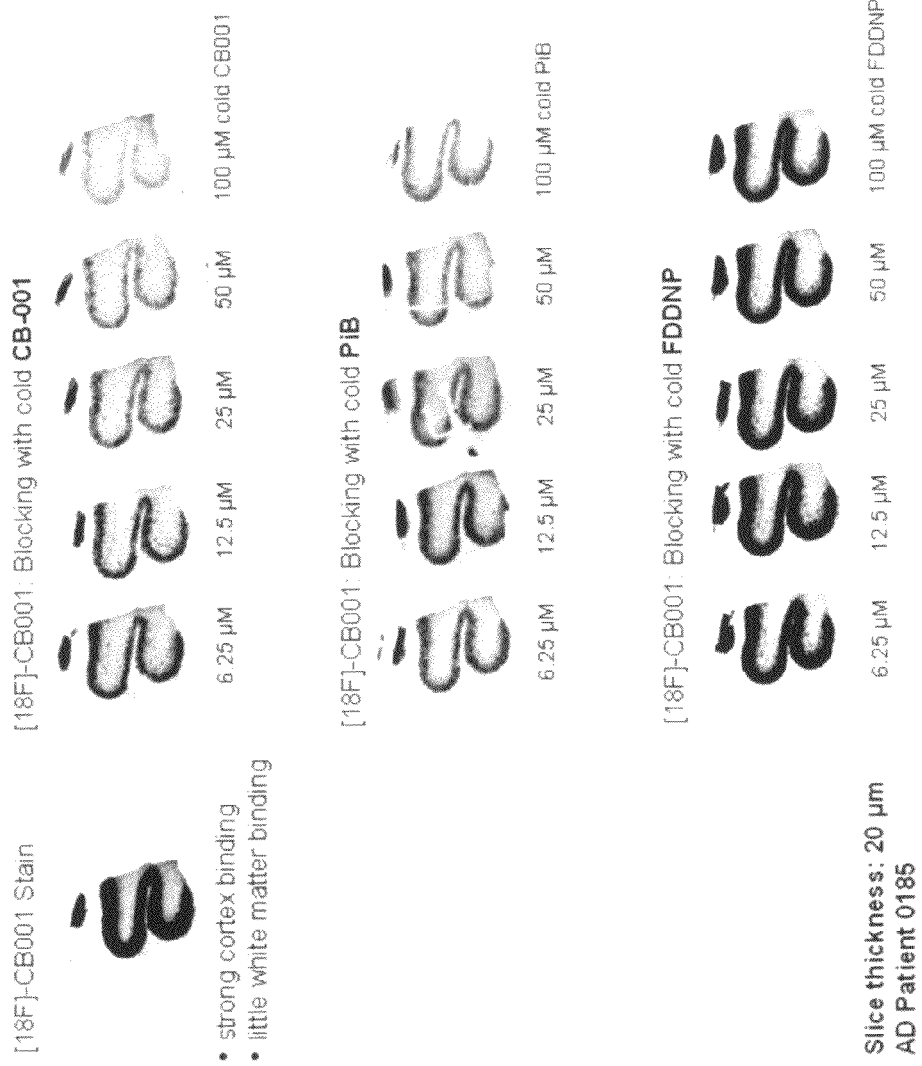
FIG. 8 shows [18F]-CB001 competition studies on AD Brain slices demonstrate reversible plaque binding and competition with PiB, and little/no white matter binding.
Figure 9:
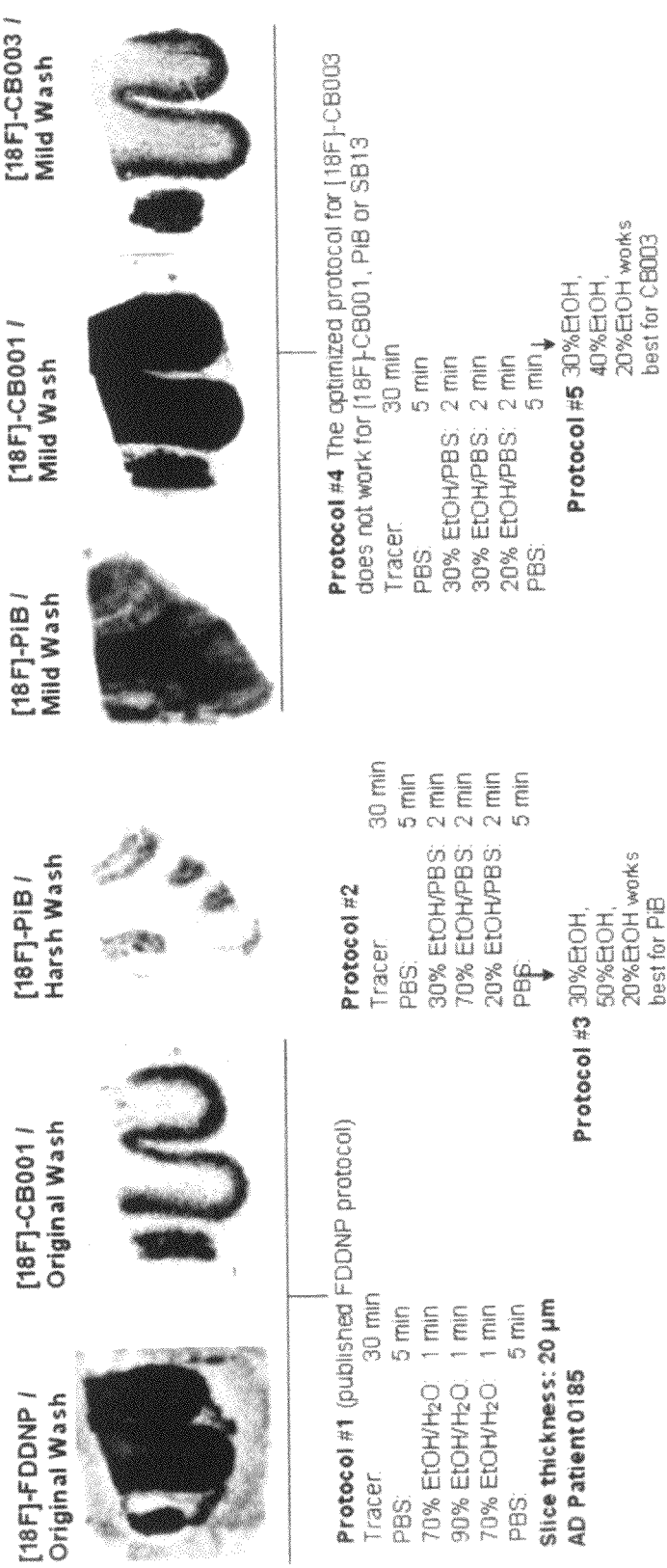
FIG. 9 shows the optimal staining and wash protocol indicating tracer specific.

A study was conducted to examine the grey to white matter binding ratios for 4 different tracers: CB-001, CB-003, FDDNP and F-PiB (FIG. 7 and FIG. 8). A known carbazole containing imaging agent, 18F-fluorocarazolol, was not examined in this study because of its relatively low cLogP value (2.77) compared to FDDNP and PiB, and its competing specific uptake into the beta-adrenoceptors. In addition, there is no prior art data suggesting that 18F-fluorocarazolol binds to AD plaques. After the human brain slices from AD patients were incubated with a given tracer for 30 min, the slices were washed with various EtOH:water solutions in an attempt to optimize the grey to white matter ratios (FIG. 9). The results were surprising and unexpected in view of previous work performed by other researchers. CB-001 has a slightly higher cLogP than FDDNP (3.8 vs 3.4) and would be expected to have poorer washout than FDDNP based on these values. However, despite the difference in cLogP values, CB-001 has a lower non-specific binding propensity and displays a much better grey to white matter ratio compared to FDDNP (see section above, "original wash"). More specifically, the white matter binding of FDDNP is several shades darker than CB-001's white matter binding, indicating low non-specific binding of CB-001. In contrast, F-PiB, which has a cLogP value of 3.99, also displays reasonable, binding ratios similar to CB-001, albeit displaying a very weak overall signal. The washing data suggests that the carbazoles are a viable and novel target for imaging AD-related targets due to their unique binding and washout properties.

To expand on these results, CB-003, a tracer with a cLogP value similar to FDDNP, was prepared and tested. Using washing conditions that were far milder than the harsh washing conditions (FIG. 9), CB-003 displayed excellent grey to white matter binding ratios that are far superior to the results taken from FDDNP, PiB and CB-001. These favorable and unique results suggest that CB-003 would have a more favorable brain washout in living systems, leading to more specific uptake and lowered non-specific binding, leading to a clear advantage over FDDNP and PiB imaging.

Summary of Washing Results:

| Name | Structure | cLogP | Grey/white matter binding ratio using harsh FDDNP wash conditions* | Grey/white matter binding ratio using mild wash conditions** |
|---|---|---|---|---|
| CB-001 | 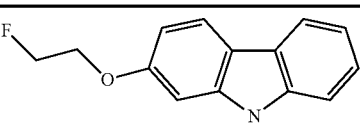 | 3.789 | Excellent | Poor |
| CB-003 | 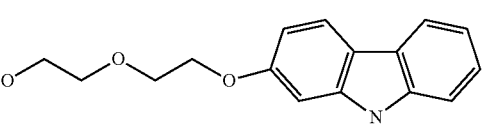 | 3.4032 | N/A | Excellent |
| FDDNP | 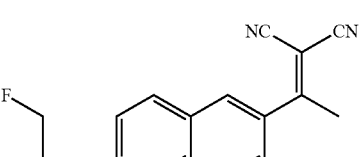 | 3.422 | Fair | Poor |
| PiB | 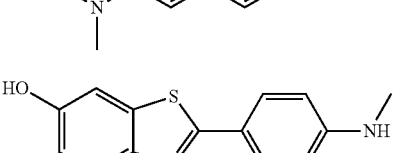 | 3.9907 | Poor (signal is washed away) | Poor |

*published FDDNP wash conditions: 30 min incubation of CB-1 or CB-3 tracer, PBS wash (5 min), 70% EtOH:water (1 min), 90% EtOH:water (1 min), 70% EtOH:water (1 min), PBS (5 min). The brain slices were 20 um thick.
**mild wash conditions: 30 min incubation of CB-1 or CB-3 tracer, PBS wash (5 min), 30% EtOH:water (2 min), 40% EtOH:water (2 min), 20% EtOH:water (2 min), PBS (5 min). The brain slices were 20 um thick.

The results demonstrate that 1) PiB blocks [18F]-CB001 staining with increasing concentrations, suggesting the two compounds to compete for the same amyloid binding pockets; 2) PiB appears to block tracer binding with the same strength as cold CB001, suggesting both to have similar binding affinities; 3) FDDNP is much less capable of blocking [18F]-CB001 staining, due to its lower amyloid binding affinity.

This data suggests the following order of (non-specific) white matter binding: FDDNP>CB001>[18F]-PiB>CB003

| Compound | IC50 Determination with [18F]-PiB by ex vivo competition assay using autoradiography staining |||||||||||||| Average |||
|---|---|---|---|---|---|---|---|---|---|---|---|---|---|---|---|---|
| Code | 1 | 2 | 3 | 4 | 5 | 6 | 7 | 8 | 9 | 10 | 11 | 12 | 13 | IC50 | SD | SD % |
| F-PiB |  |  |  |  |  | 43 |  | 43 | 40 | 50 | 55 | 41 |  | 45 | 6 | 13 |
| PiB | 80 | 40 | 40 | 48 | 60 | 43 | 50 |  |  |  |  |  | 280 | 52 | 14 | 28 |
| CB7 | 260 |  | 170 |  | 200 | 290 |  |  |  |  |  |  | 300 | 244 | 57 | 23 |
| CB4 | 260 |  | 350 |  | 300 | 300 |  |  |  |  |  |  | 400 | 322 | 54 | 17 |
| CB12 |  |  |  | 610 | 300 | 450 | 390 |  |  |  |  |  |  | 438 | 130 | 30 |
| CB24 |  |  |  |  |  |  | 540 |  |  |  |  |  |  | 540 |  |  |
| CB1 | 1000 | 480 |  |  |  |  |  |  |  |  |  |  |  | 740 | 368 | 50 |
| CB10 |  |  |  | 900 |  |  |  |  |  |  |  |  |  | 900 |  |  |
| CB3 | 1100 |  |  |  |  | 900 |  |  |  |  |  |  | 920 | 973 | 110 | 11 |

To further demonstrate the efficiency of employing these CB-related tracers as AD imaging agents, CB-003 was used to clearly differentiate between a healthy brain and an AD brain (FIG. 10). More specifically, by using the mild wash protocol, the amyloid deposits were clearly visible in the grey matter with little white matter uptake. The results were corroborated by both antibody IHC and thioflaving T amyloid staining, confirming the specificity of uptake. These surprising results demonstrate that this tracer possess the unique quality of rapid washout from white matter and significant high uptake in grey matter that is specific for AD plaques.

Figure 11A:
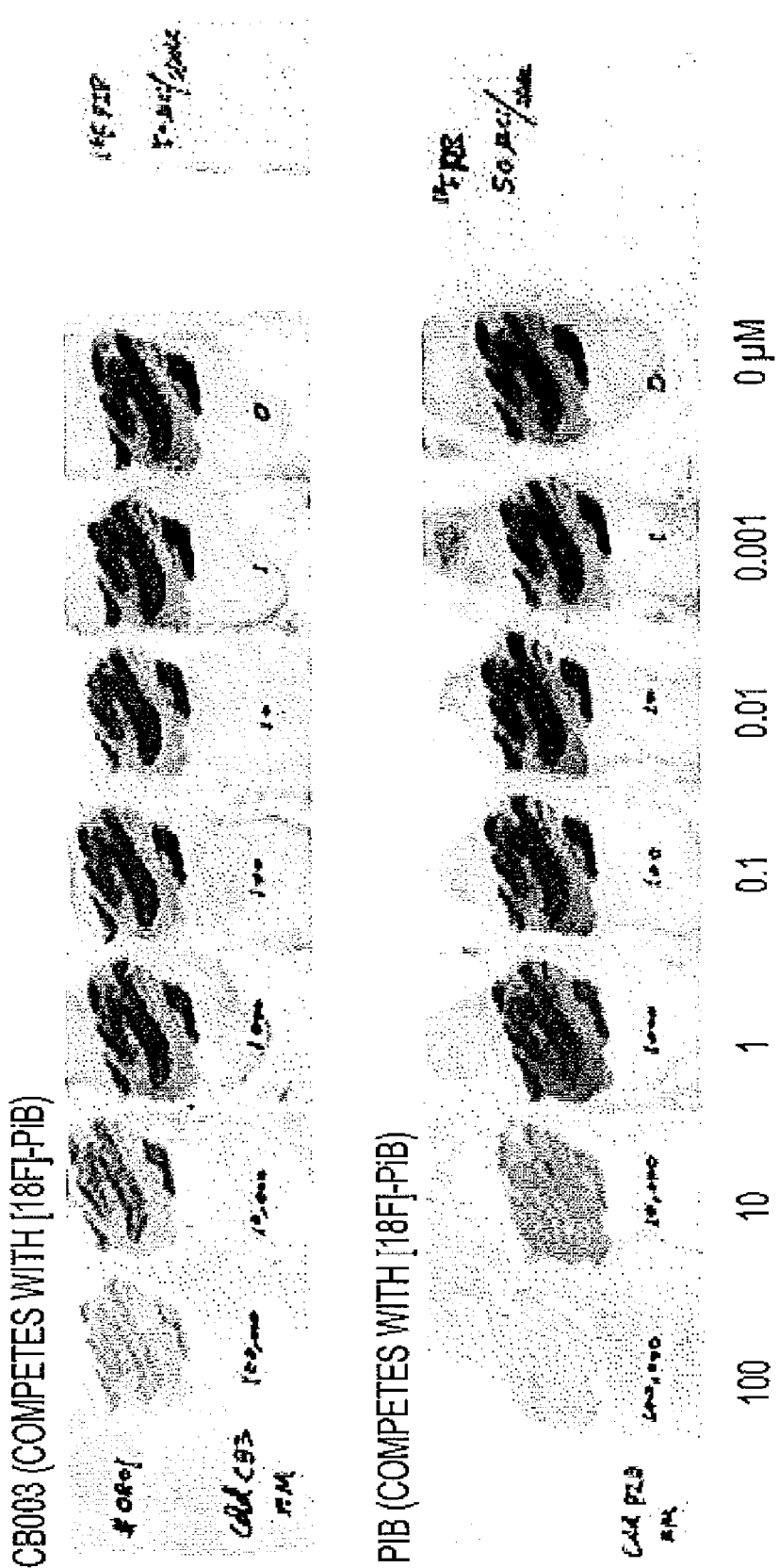
FIG. 11 shows concentration-dependent blocking of [18F]-PiB tissue binding with PiB and CB003.
Figure 11B:
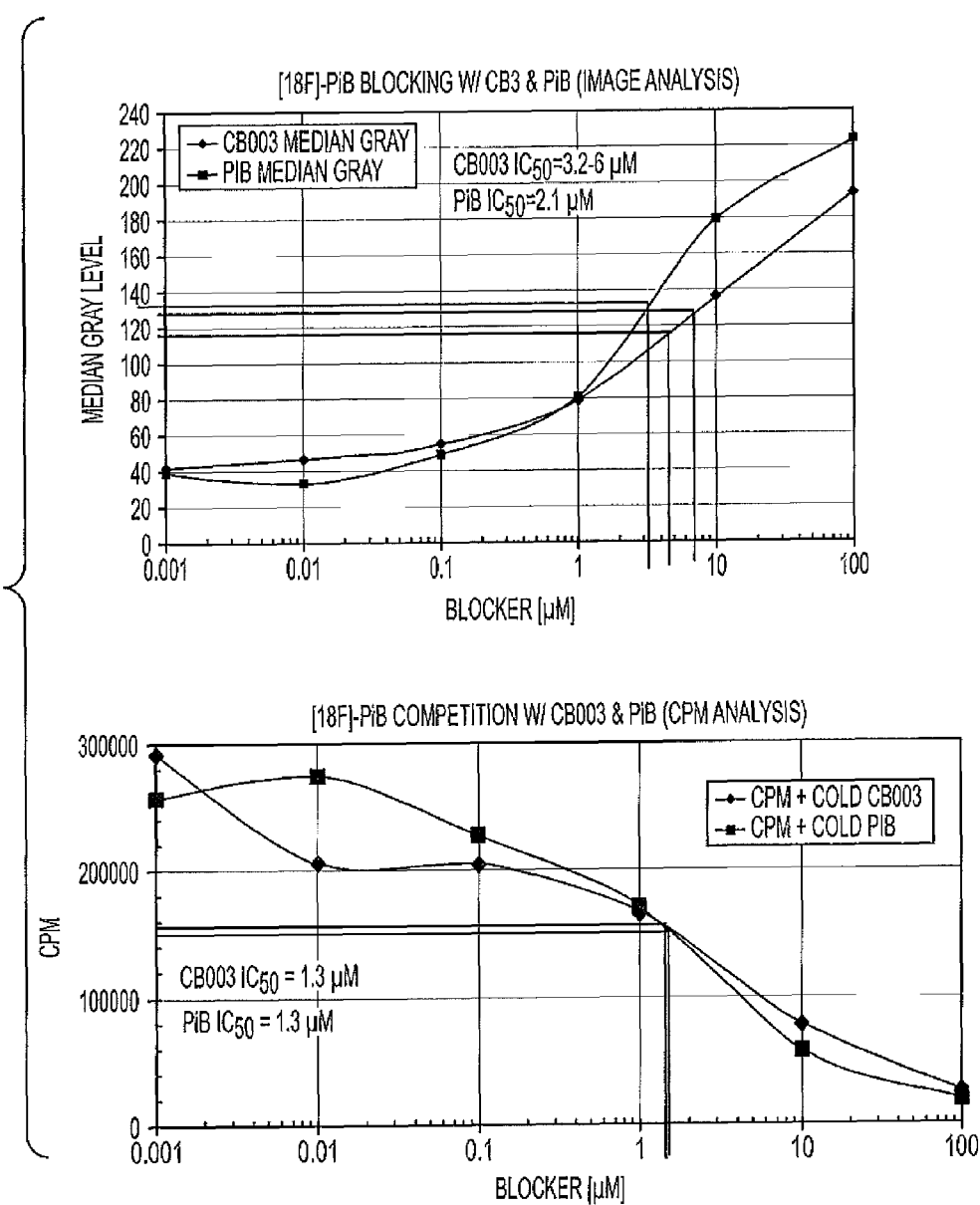

The carbazoles compete directly against 18F-PiB for the same binding sites in human AD brains (FIG. 11). This surprising result could not have been predicted given their dissimilar structures and CB-003's lack of a phenolic OH and terminal NH-Me group, which are deemed essential for binding to AD plaques. Despite CB-003 lacking both of these functional groups, it still competes with 18F-PiB for binding sites in human AD brains. Because of the simplicity of its structure, the labeling yields of CB-001 and CB-003 are exceptionally high and better than the labeling yields of 18F-PiB.

Surface Plasmon Resonance (SPR) Assay

An assay was developed using a Biacore instrument that introduced the ligands over gold-surface immobilized target proteins and measured the resultant rates of association and disassociation in order to test various compounds that bind to soluble AD oligomers, polymers and fibrils (FIGS. 12 to 17).

Figure 12:
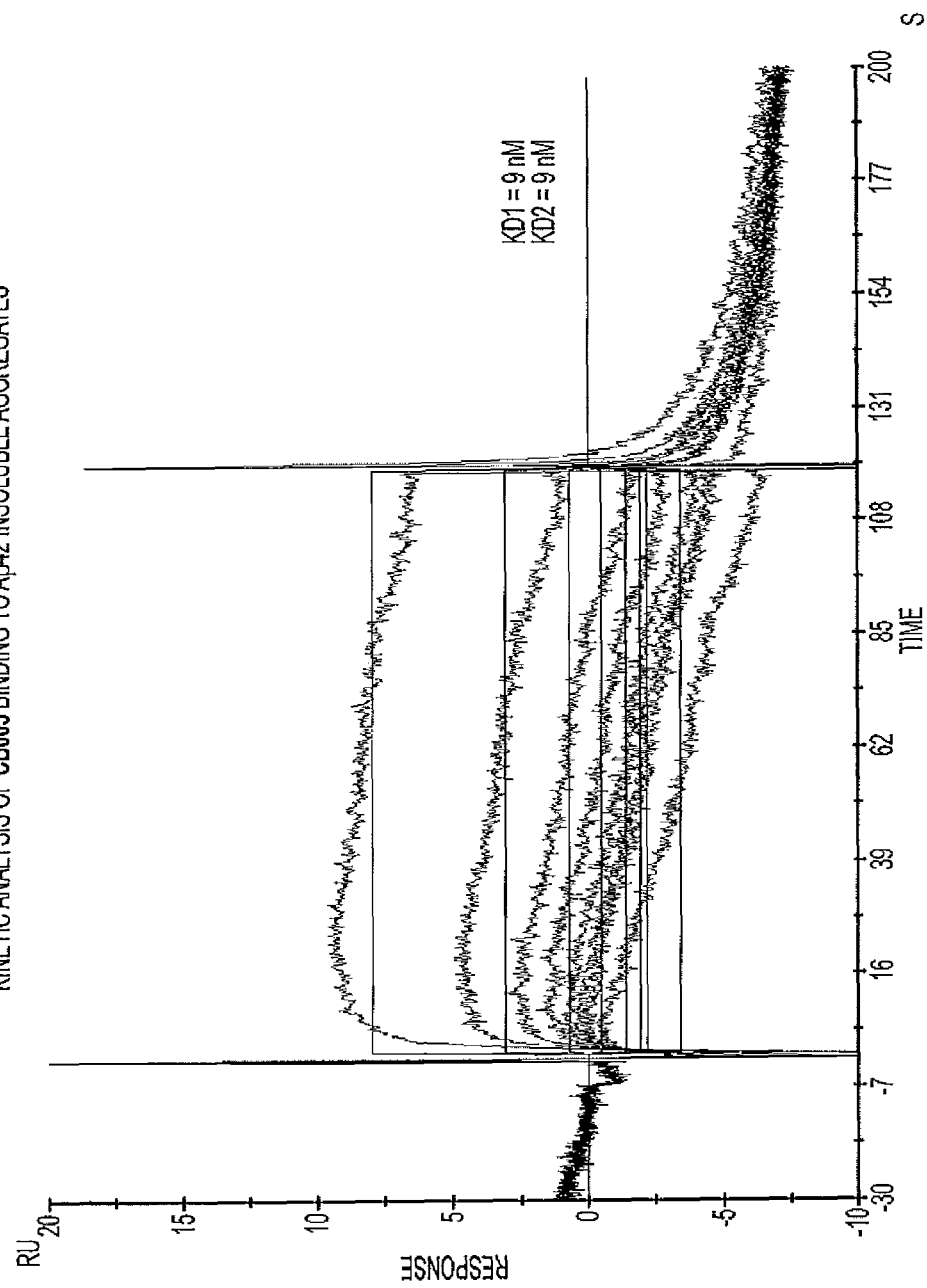
FIG. 12 shows surface plasmon resonance assay results of CB003 binding to Aβ42 insoluble aggregates.
Figure 13:
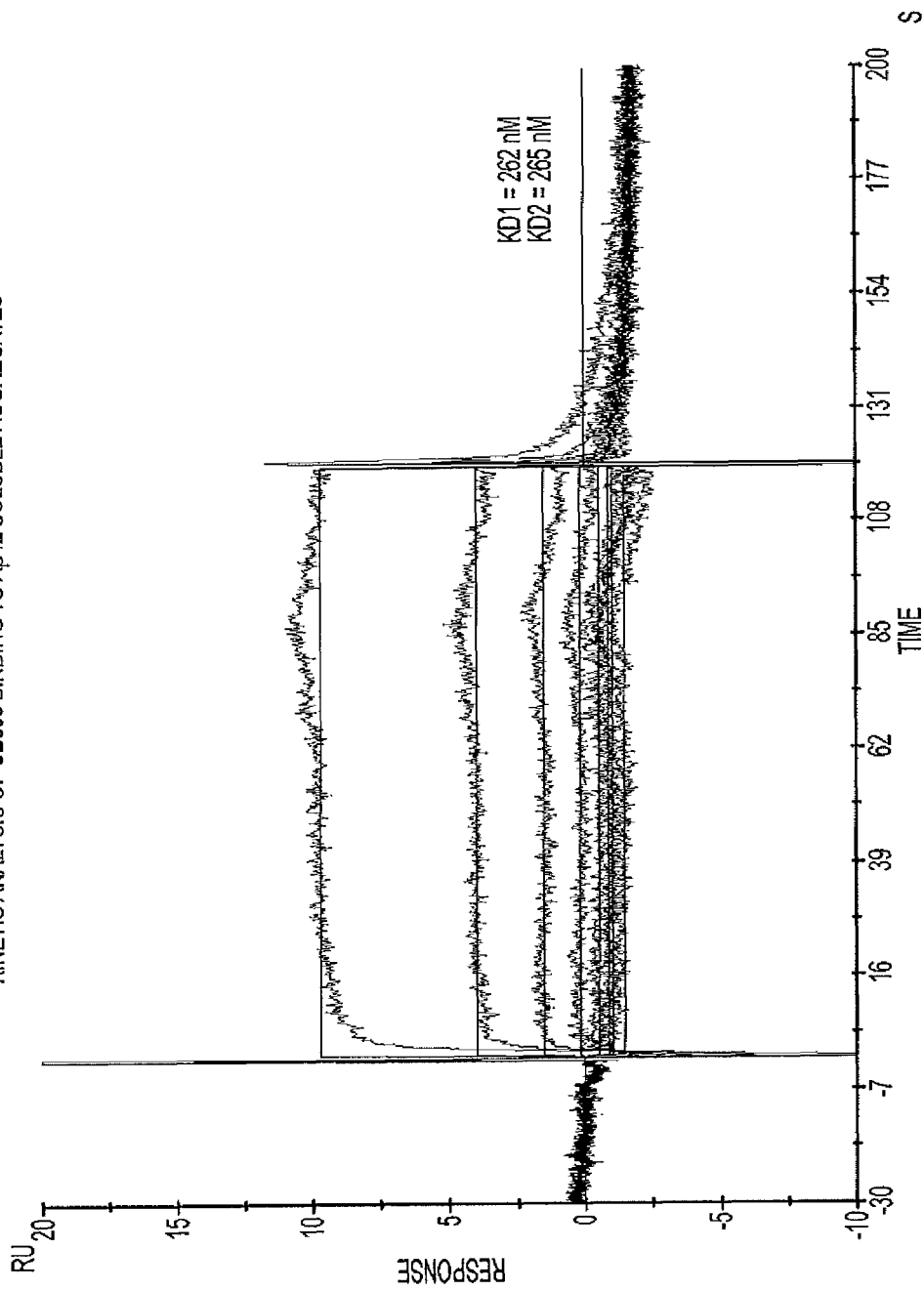
FIG. 13 shows surface plasmon resonance assay results of CB003 binding to Aβ42 soluble aggregates.
Figure 14:
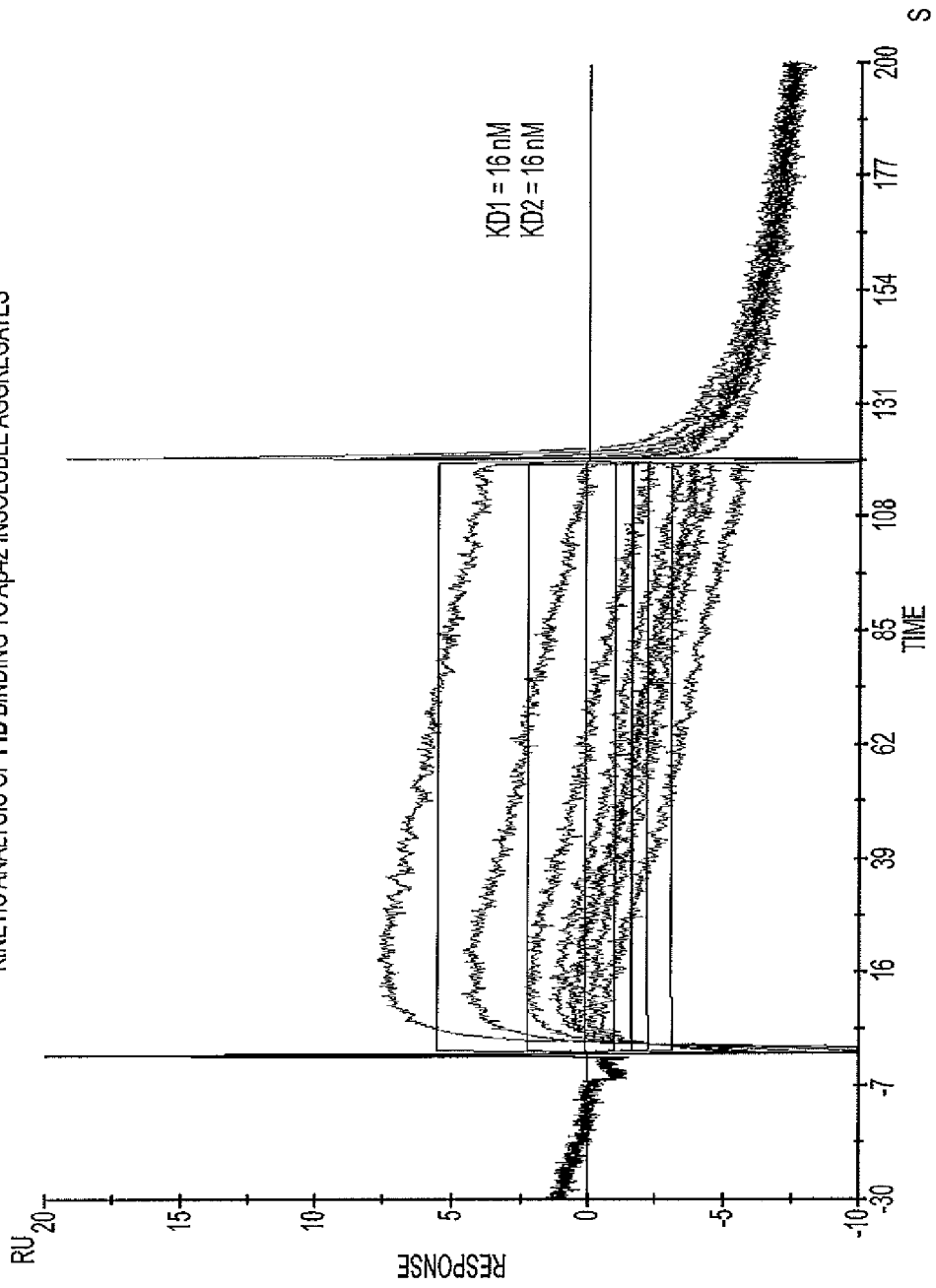
FIG. 14 shows surface plasmon resonance assay results of PiB binding to Aβ42 insoluble aggregates.
Figure 15:
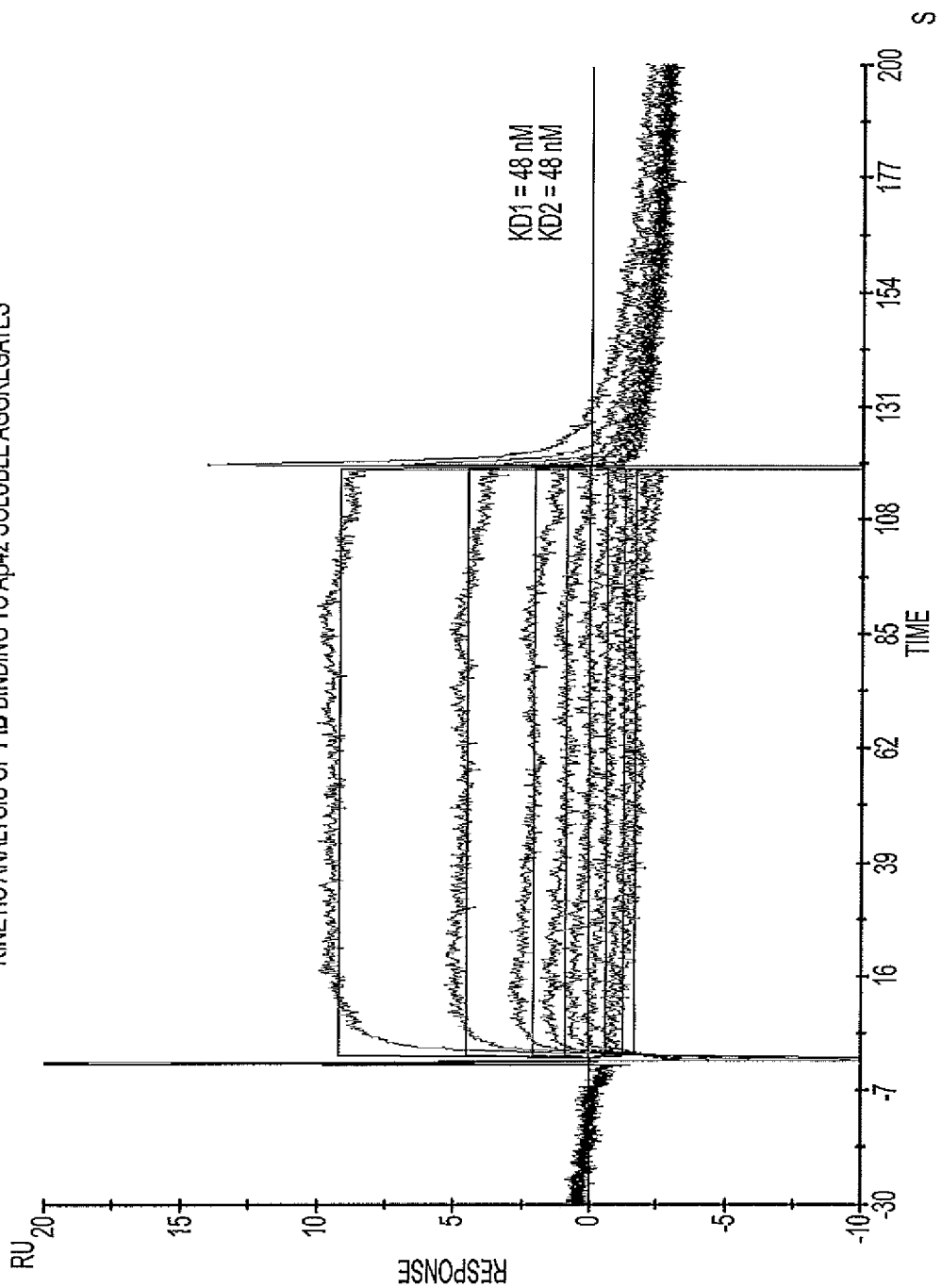
FIG. 15 shows surface plasmon resonance assay results of PiB binding to Aβ42 soluble aggregates.
Figure 16:
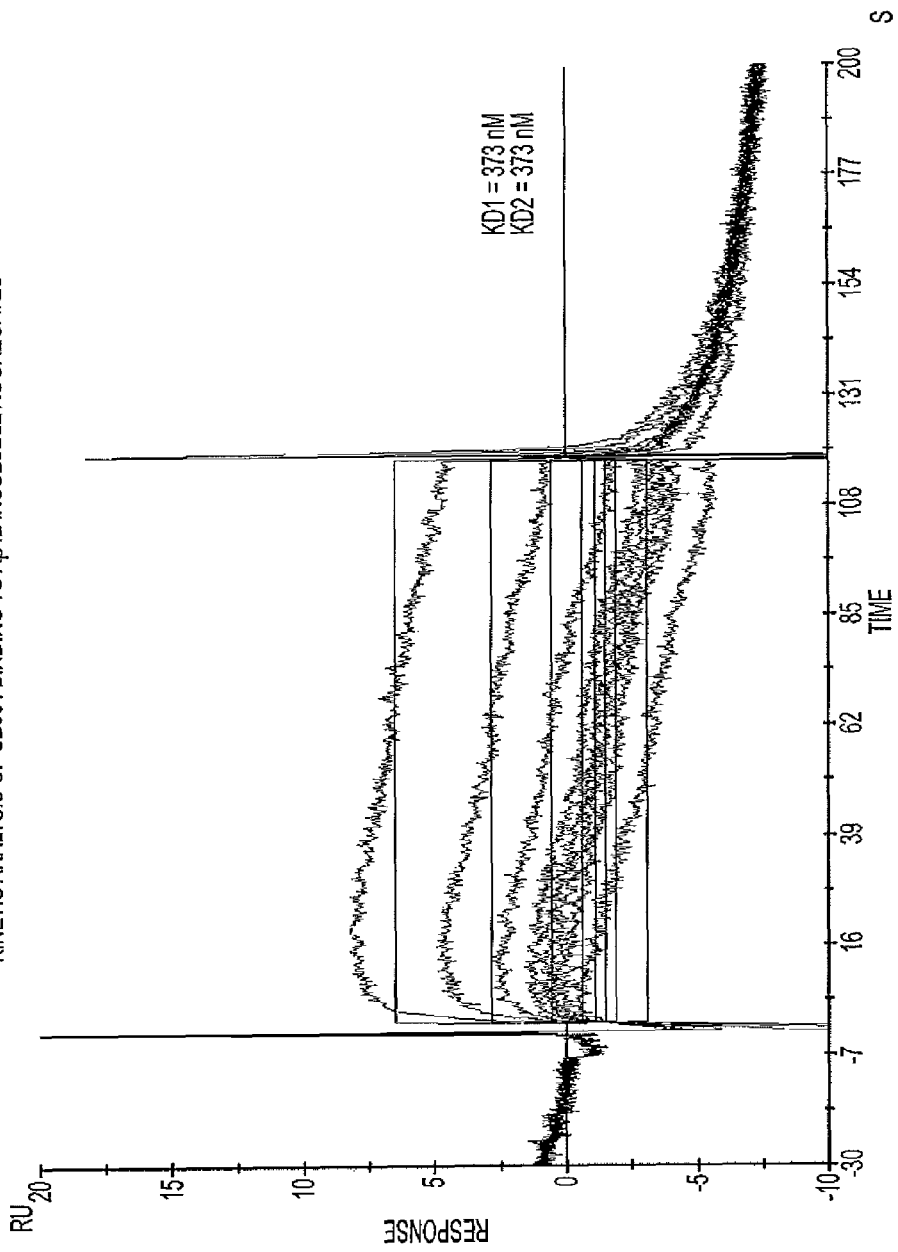
FIG. 16 shows surface plasmon resonance assay results of CB004 binding to Aβ42 insoluble aggregates.

The carbazole series also demonstrated a unique and surprising ability to bind favorably and preferentially to insoluble aggregates (9 nM) over soluble aggregates (262 nM) (FIG. 12 and FIG. 13). PiB also binds well to insoluble aggregates (16 nM) but also binds essentially equally as well to soluble aggregates (48 nM) (FIG. 14 and FIG. 15). For imaging applications where it is favorable to distinguish between a tracer's binding to insoluble versus soluble aggregates, CB-003 provides a larger binding ratio of 29:1, whereas PiB only provides a ratio 3:1. Thus, CB-003 may provide more selective binding information relative to PiB.

The results indicate that 1) for soluble aggregate binding, PIB>CB3>CB4; and 2) for insoluble aggregate binding, PIB=CB3>CB4.

MicroPET Imaging with [18F]-CB-001 or [18F]-CB-003 in WT and App MICE

Figure 18A:
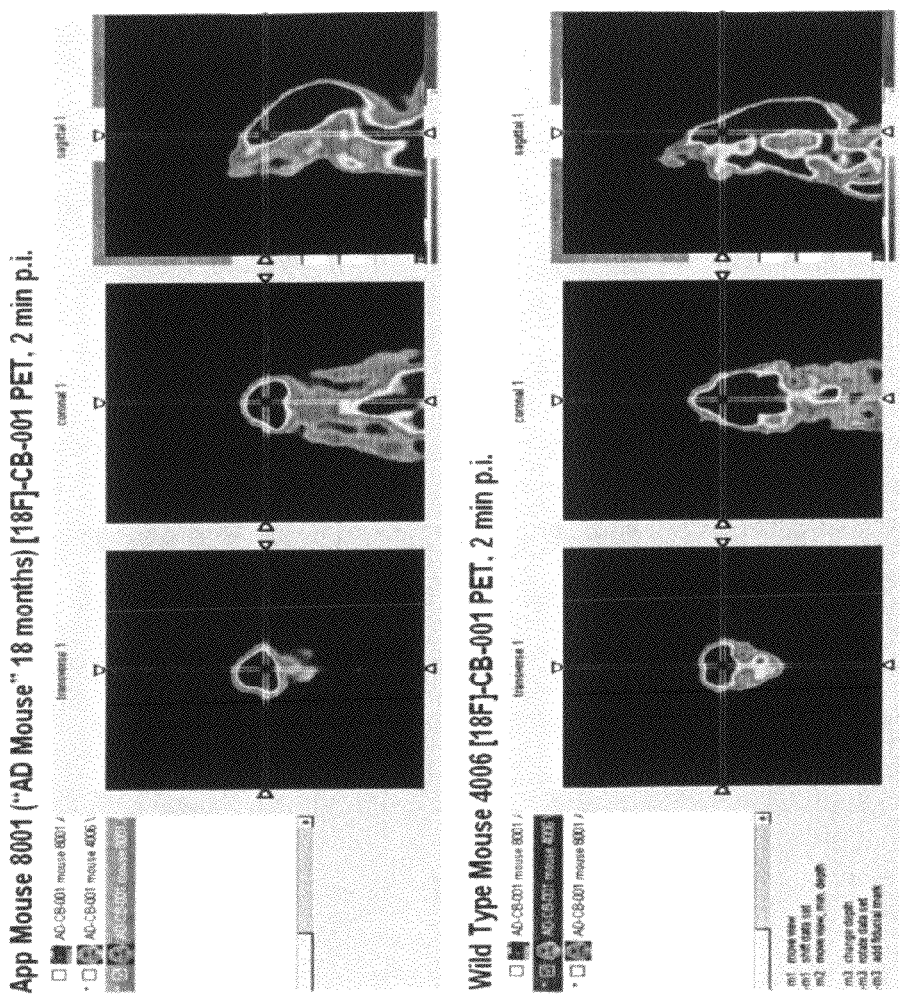
FIG. 18A shows MicroPET imaging, 2 min p.i., with [18F]-CB-001 in App and WT mice demonstrates very good brain uptake.
Figure 18B:
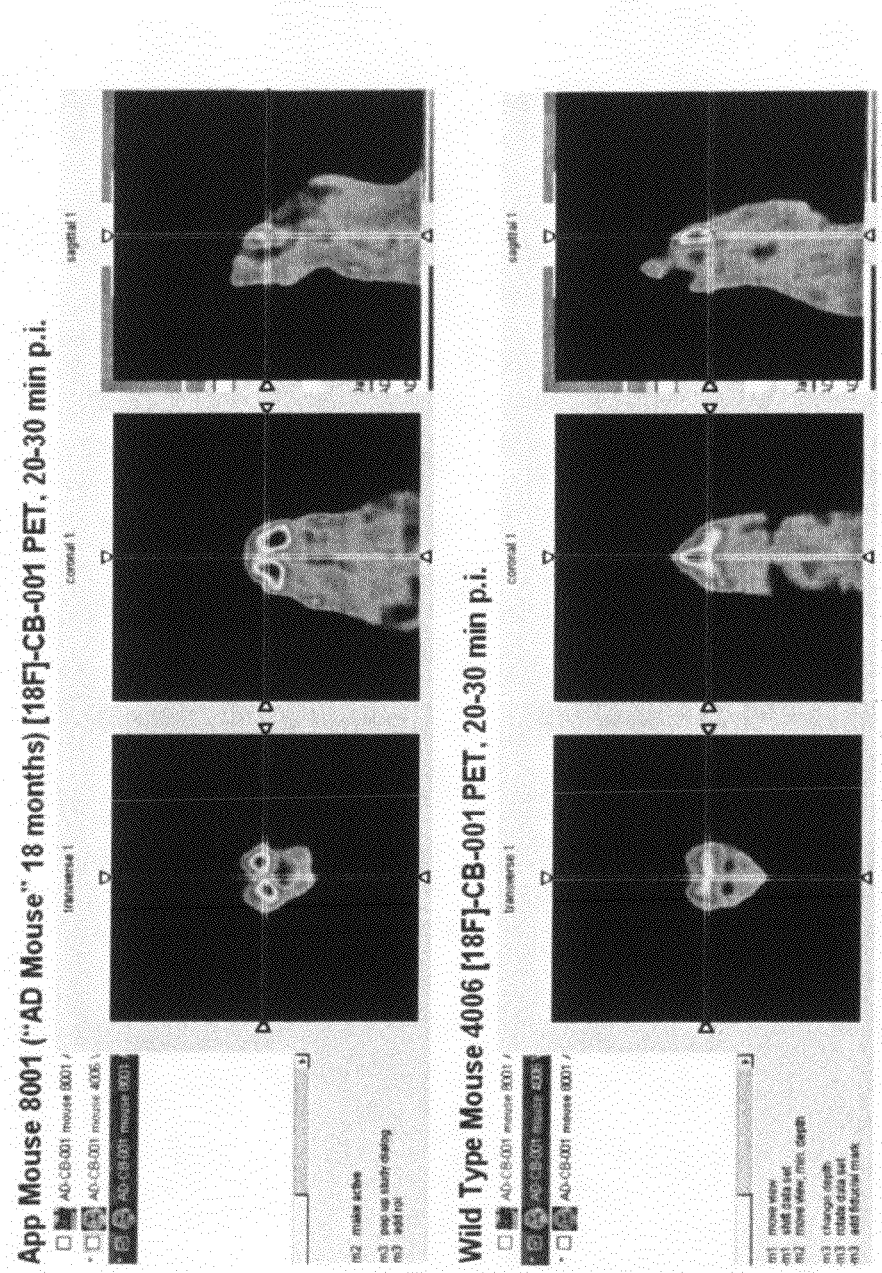
FIG. 18B shows MicroPET imaging, 20-30 min p.i., with [18F]-CB-001 in App and WT mice demonstrates very good brain uptake.
Figure 19:
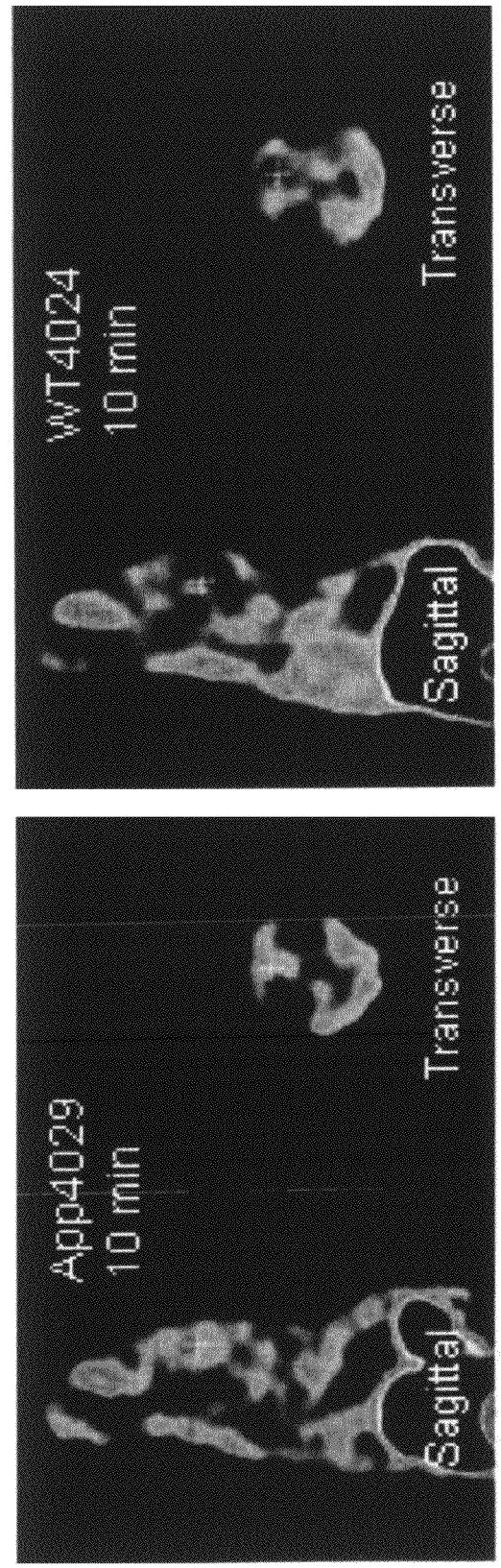
FIG. 19 shows MicroPET imaging, 10 min, with [18F]-CB003 in WT and App mice.
Figure 20:
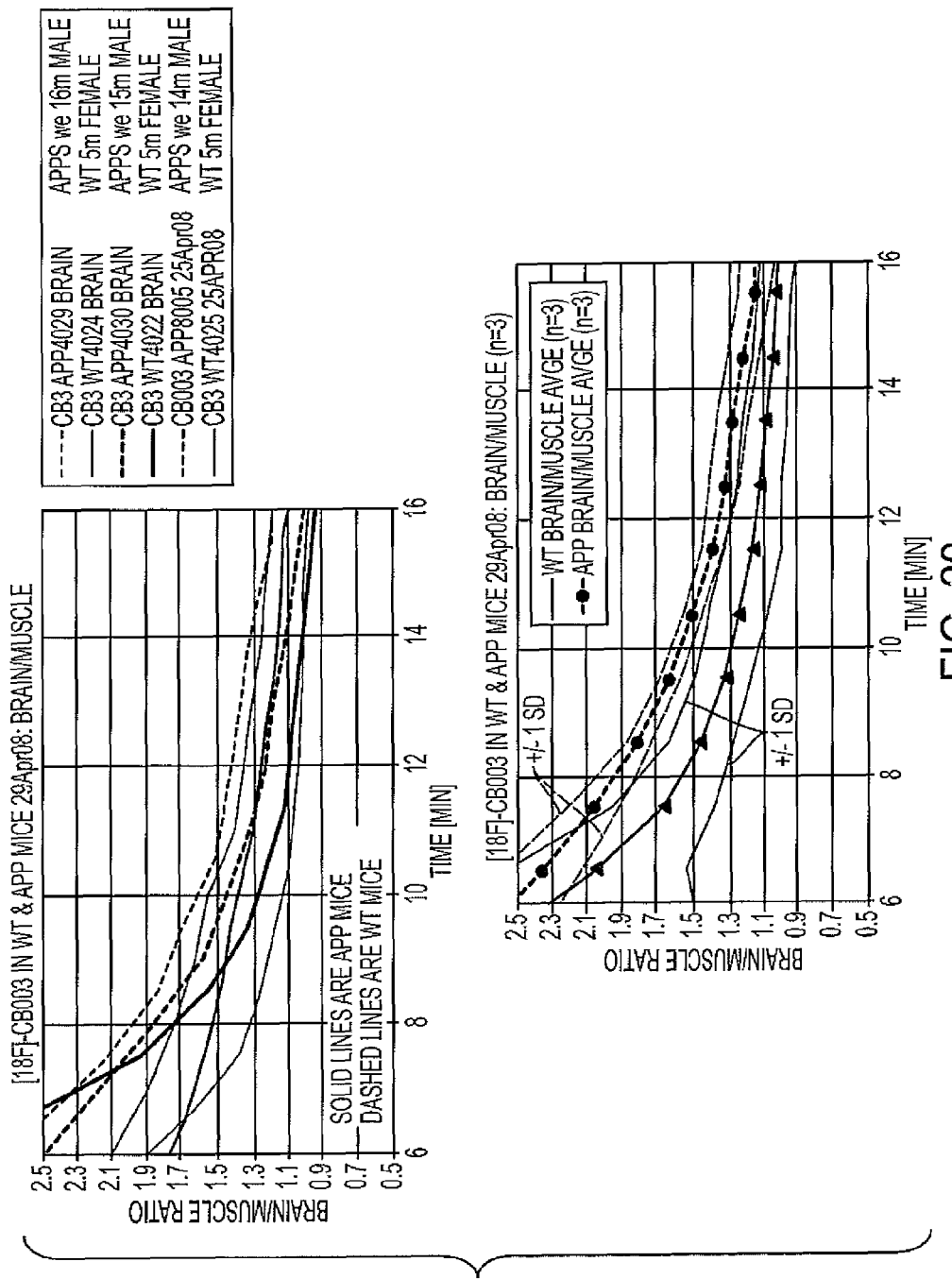
FIG. 20 left panel shows MicroPET imaging analysis with [18F]-CB003 in individual WT and App mice. Right panel shows combined MicroPET imaging analysis with [18F]-CB003 in WT and App mice.
Figure 21:
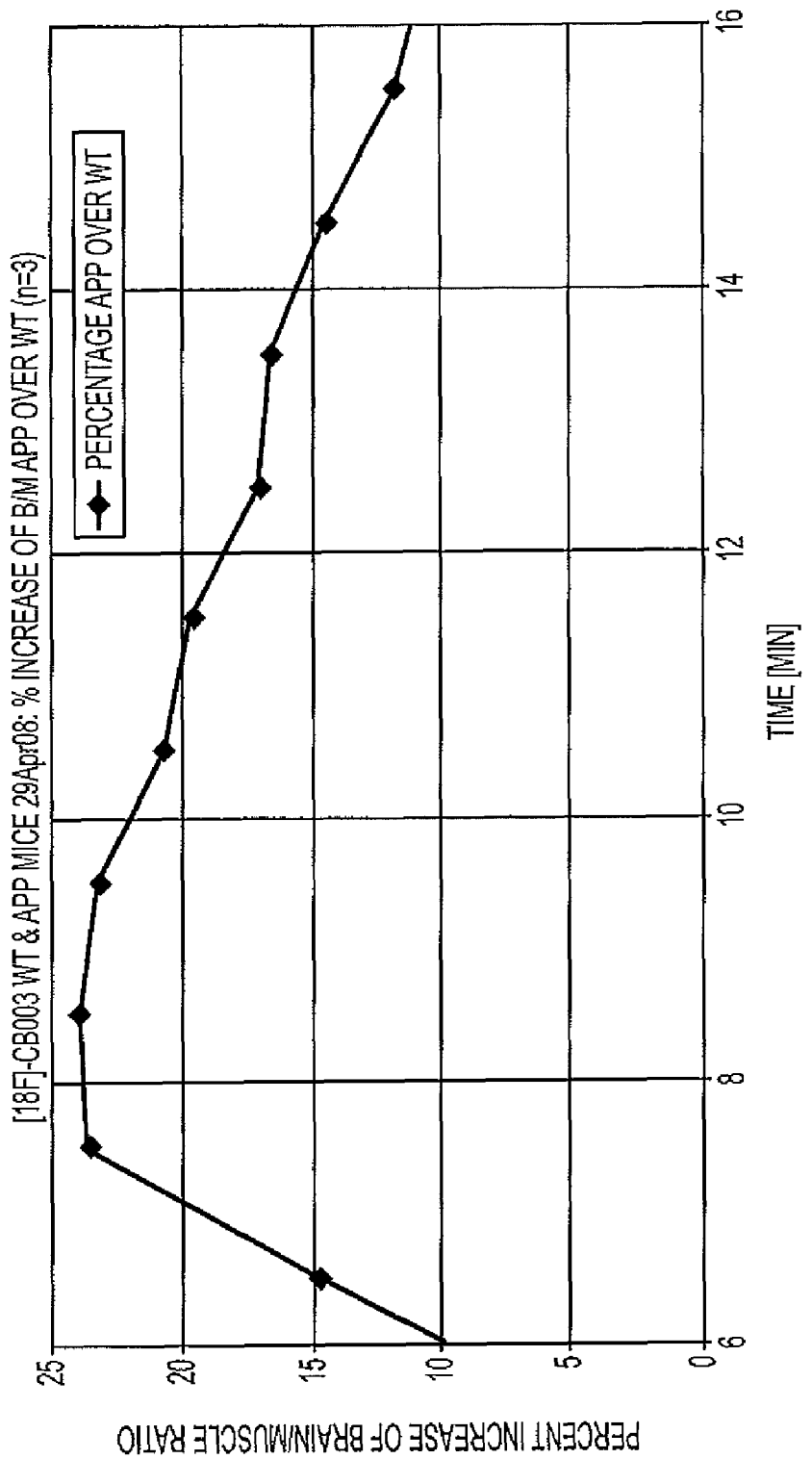
FIG. 21 shows percent increase of brain/muscle (B/M) ratio for MicroPET imaging analysis with [18F]-CB003 in WT and App mice.
Figure 22:
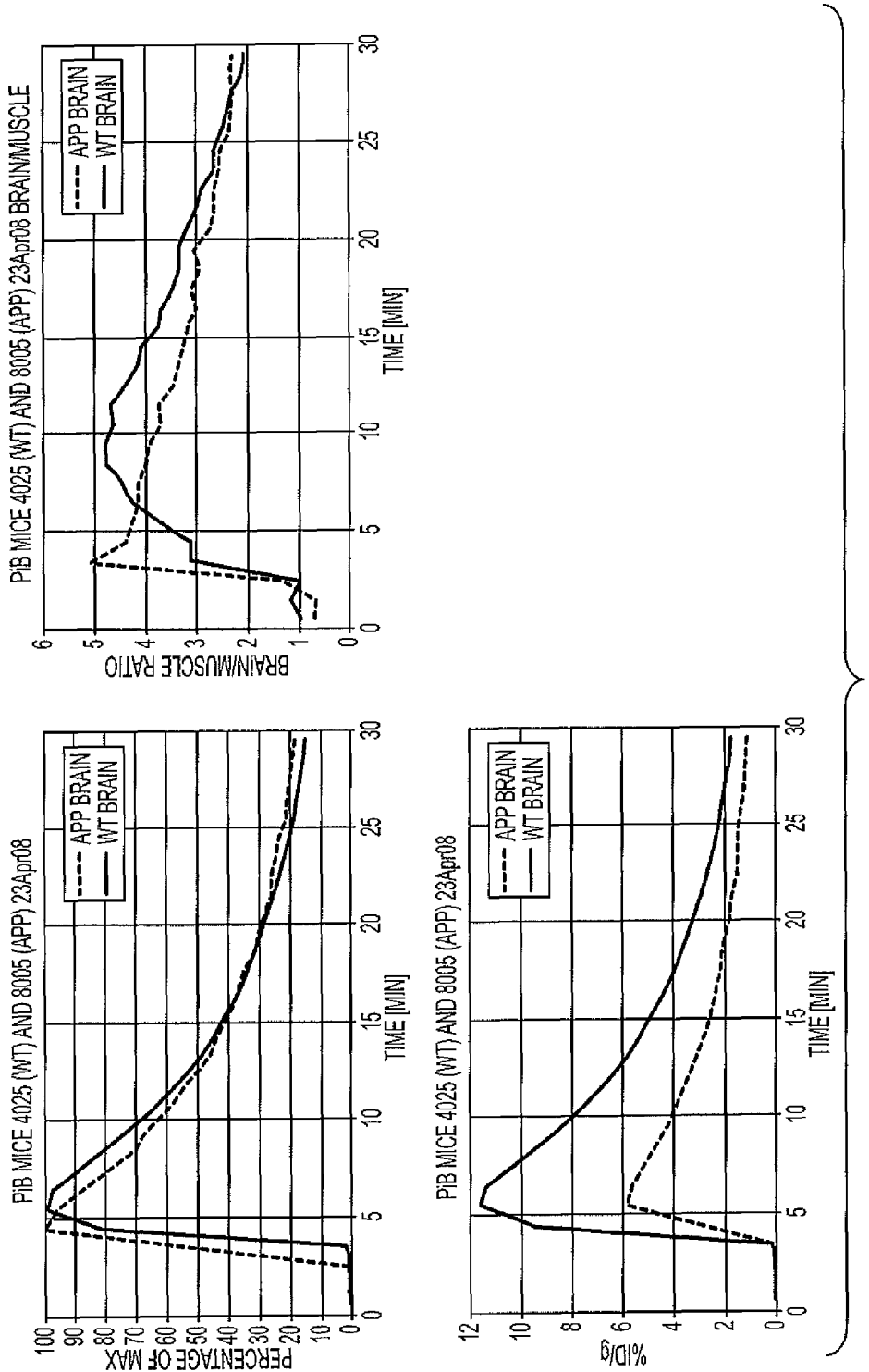
FIG. 22 shows clearance of [18F]PiB in WT and App mice brain.
Figure 23:
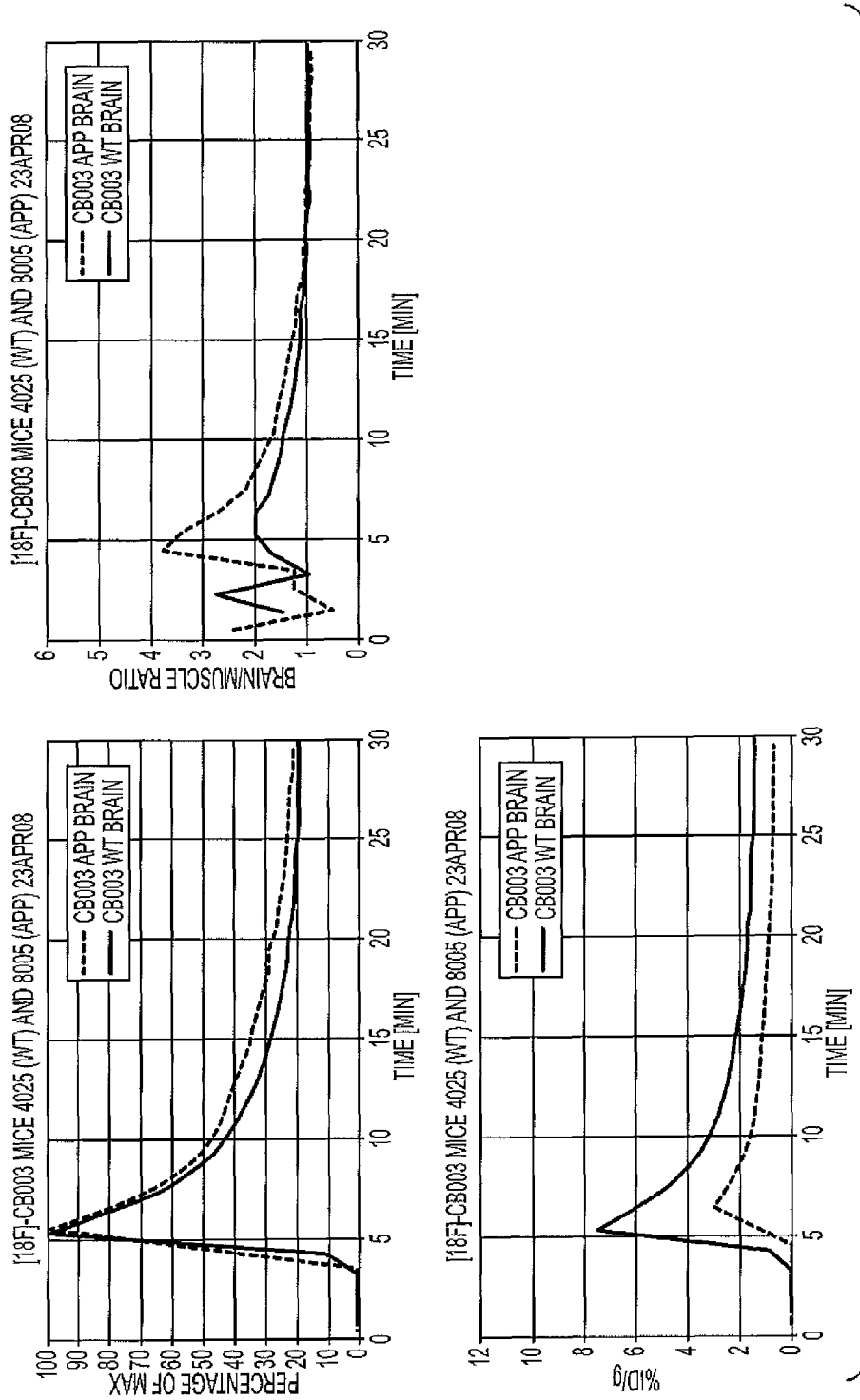
FIG. 23 shows clearance of [18F]-CB003 in WT and App mice brain indicates that brain clearance of [18F]-CB003 is much faster than with [18F]PiB.

The results demonstrate that 1) WT and App mice show statistically significant differences in tracer retention in the brain (FIG. 18A, FIG. 18B and FIG. 19); 2) App mice show up to 25% larger brain/muscle ratios compared to WT mice (FIG. 20 and FIG. 21). The carbazoles display both a surprising high uptake in mice brains (both WT and APP) and sufficiently slow washout such that one can distinguish WT from APP mice (FIG. 22 and FIG. 23). Without being bound by any theory proposed herein, we speculate that the reason behind these results may be that CB-003 possesses a faster washout rate than 18F-PiB, which is consistent with consistent with the staining data: 18F-PiB requires harsher wash conditions in order to give reasonable grey to white matter ratios. The rapid washout of CB-003 is presumably a major factor for its low non-specific binding, yet the washout is slow enough to distinguish WT from APP. This suggests that the carbazoles display a unique combination of excellent washout and retention properties in human AD brains that are not obvious from prior art data. CB-003, being a neutral compound, would also potentially possess greater uptake values versus zwitterionic-based imaging agents such as methylene blue.

What is claimed:

1. A compound or a pharmaceutically acceptable salt thereof represented by the formula Ic:

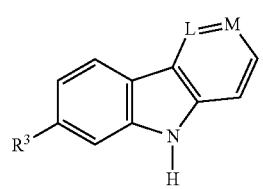

Ic wherein
L is N or CR⁵ where R⁵ is H;
M is N or CR⁶ where R⁶ is H;
R³ is alkylamino, arylamino, cycloalkylamino, heteroarylamino, halo-$C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, H(OCH$_2$CH$_2$)$_{1-6}$O, $C_{1-3}$alkyl(OCH$_2$CH$_2$)$_{1-6}$O, halo-$C_{1-5}$alkoxy, halo-$C_{1-3}$alkyl(OCH$_2$CH$_2$)$_{1-6}$O, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, or heteroaryloxy;

wherein at least one hydrogen of $R^3$ is replaced with, or a radionuclide selected from the group consisting of $^{18}$F, $^{77}$Br, $^{123}$I, $^{125}$I, and $^{131}$I.

2. The compound or a pharmaceutically acceptable salt thereof according to claim 1, wherein M is N and L is $CR^5$.

3. The compound or a pharmaceutically acceptable salt thereof according to claim 2, wherein $R^3$ is amino, halo-$C_{1-6}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, $H(OCH_2CH_2)_{1-6}O$, $C_{1-3}$alkyl$(OCH_2CH_2)_{1-6}O$, halo-$C_{1-5}$alkoxy, halo-$C_{1-3}$alkyl$(OCH_2CH_2)_{1-6}O$, $C_{3-6}$cycloalkoxy, $C_{3-12}$cycloalkyl$C_{1-5}$alkoxy, heteroaryl$C_{2-5}$alkoxy, $C_{6-14}$aryloxy, $C_{6-10}$aryl$C_{1-4}$alkoxy, or heteroaryloxy.

4. The compound or a pharmaceutically acceptable salt thereof according to claim 3, wherein:

$R^3$ is a pyridine having at least one hydrogen replaced by halo or a radionuclide selected from the group consisting of $^{18}$F, $^{123}$I, $^{125}$I, and $^{131}$.

5. The compound or a pharmaceutically acceptable salt thereof according to claim 4, wherein the pyridine has at least one hydrogen replaced by halo or a radionuclide selected from the group consisting of $^{18}$F, $^{77}$Br, $^{123}$I, $^{125}$I, and $^{131}$I.

6. A pharmaceutical composition for in vivo imaging of amyloid deposits and tau tangles, comprising (a) the compound or a pharmaceutically acceptable salt thereof according to claim 1 and (b) a pharmaceutically acceptable carrier.

7. A method of diagnosing Alzheimer's Disease or a predisposition thereto in a mammal, the method comprising:

a) administering to the mammal a diagnostically effective amount of the compound or a pharmaceutically acceptable salt according to claim 1;

b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

8. The method of claim 7, wherein the compound or a pharmaceutically acceptable salt thereof binds to tau tangles.

9. The method of claim 7, which further comprises imaging by employing a fluorescence imaging technique or a nuclear imaging technique selected from the group consisting of positron emission tomography (PET) and single photon emission computed tomography (SPECT), the fluorescence imaging technique and/or nuclear imaging technique for monitoring or visualizing a distribution of the radiolabeled or tagged compound within the brain or within a portion thereof.

* * * * *